(12) United States Patent
Mao et al.

(10) Patent No.: US 9,097,667 B2
(45) Date of Patent: Aug. 4, 2015

(54) FLUORESCENT COMPOUNDS

(75) Inventors: Fei Mao, Fremont, CA (US); Wai-Yee Leung, San Ramon, CA (US); Ching-Ying Cheung, San Ramon, CA (US); Hye Eun Hoover, Alameda, CA (US)

(73) Assignee: BIOTIUM, INC., Hayward, CA (US)

( * ) Notice: Subject to any disclaimer, the term of this patent is extended or adjusted under 35 U.S.C. 154(b) by 131 days.

(21) Appl. No.: 12/334,387

(22) Filed: Dec. 12, 2008

(65) Prior Publication Data

US 2009/0305410 A1 Dec. 10, 2009

Related U.S. Application Data

(60) Provisional application No. 61/013,956, filed on Dec. 14, 2007.

(51) Int. Cl.
| | |
|---|---|
| C09B 23/08 | (2006.01) |
| C07K 2/00 | (2006.01) |
| C07K 16/00 | (2006.01) |
| C07H 17/02 | (2006.01) |
| C07H 21/00 | (2006.01) |
| C12N 5/07 | (2010.01) |
| G01N 21/64 | (2006.01) |
| C09B 11/08 | (2006.01) |
| C09B 11/24 | (2006.01) |
| C09B 23/01 | (2006.01) |
| C09B 23/06 | (2006.01) |
| C09B 57/00 | (2006.01) |
| C09B 57/02 | (2006.01) |
| C09B 69/00 | (2006.01) |
| G01N 33/58 | (2006.01) |

(52) U.S. Cl.
CPC ............ *G01N 21/6428* (2013.01); *C09B 11/08* (2013.01); *C09B 11/24* (2013.01); *C09B 23/0066* (2013.01); *C09B 23/06* (2013.01); *C09B 23/083* (2013.01); *C09B 23/086* (2013.01); *C09B 57/001* (2013.01); *C09B 57/02* (2013.01); *C09B 69/00* (2013.01); *G01N 33/582* (2013.01)

(58) Field of Classification Search
None
See application file for complete search history.

(56) References Cited

U.S. PATENT DOCUMENTS

| | | | |
|---|---|---|---|
| 4,520,110 A | 5/1985 | Stryer et al. | |
| 4,711,955 A | 12/1987 | Ward et al. | |
| 4,813,973 A | 3/1989 | Winnik et al. | |
| 4,877,411 A | 10/1989 | Hines et al. | |
| 5,047,519 A | 9/1991 | Hobbs, Jr. et al. | |
| 5,082,934 A | 1/1992 | Saga et al. | |
| 5,234,903 A | 8/1993 | Nho et al. | |
| 5,268,486 A | 12/1993 | Waggoner et al. | |
| 5,298,643 A | 3/1994 | Greenwald | |
| 5,321,095 A | 6/1994 | Greenwald | |
| 5,324,844 A | 6/1994 | Zalipsky | |
| 5,349,001 A | 9/1994 | Greenwald et al. | |
| 5,405,877 A | 4/1995 | Greenwald et al. | |
| 5,436,134 A | 7/1995 | Haugland et al. | |
| 5,478,805 A | 12/1995 | Shorr et al. | |
| 5,567,422 A | 10/1996 | Greenwald | |
| 5,585,235 A | 12/1996 | Brocia | |
| 5,605,976 A | 2/1997 | Martinez et al. | |
| 5,612,460 A | 3/1997 | Zalipsky | |
| 5,625,048 A | 4/1997 | Tsien et al. | |
| 5,637,749 A | 6/1997 | Greenwald | |
| 5,650,388 A | 7/1997 | Shorr et al. | |
| 5,681,567 A | 10/1997 | Martinez et al. | |
| 5,686,110 A | 11/1997 | Greenwald et al. | |
| 5,696,157 A | 12/1997 | Wang et al. | |
| 5,714,386 A | 2/1998 | Roederer | |
| 5,756,593 A | 5/1998 | Martinez et al. | |

(Continued)

FOREIGN PATENT DOCUMENTS

| | | | |
|---|---|---|---|
| EP | 1535969 A2 | 6/2005 | |
| EP | 1535969 A3 | 6/2005 | |

(Continued)

OTHER PUBLICATIONS

Adams et al. Journal of Biomedical Optics, 12(2), Mar./Apr. 2007, pp. 0204017-1 through 0204017-9.*

(Continued)

*Primary Examiner* — Alicia L Otton
(74) *Attorney, Agent, or Firm* — Wilson, Sonsini, Goodrich & Rosati

(57) ABSTRACT

The present invention relates to fluorescent dyes. The present invention provides a wide range of fluorescent dyes and kits containing the same, which are applicable for labeling a variety of biomolecules, cells and microorganisms. In one aspect, the invention provides a compound having a maximal fluorescence excitation wavelength, wherein the compound has a structure of Formula II:

$$F-Y=\Psi \qquad \text{Formula II}$$

and wherein Z— is a counterion, Y is a bridge unit permitting electron delocalization between F and Ψ, and F is a moiety having the structure:

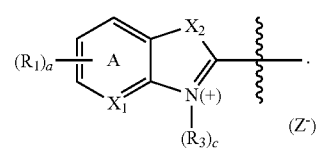

The present invention also provides various methods of using the fluorescent dyes for research and development, forensic identification, environmental studies, diagnosis, prognosis, and/or treatment of disease conditions.

30 Claims, 24 Drawing Sheets

(56) References Cited

U.S. PATENT DOCUMENTS

| | | | |
|---|---|---|---|
| 5,777,079 | A | 7/1998 | Tsien et al. |
| 5,808,044 | A | 9/1998 | Brush et al. |
| 5,808,096 | A | 9/1998 | Zalipsky |
| 5,866,366 | A | 2/1999 | Kallender |
| 5,880,131 | A | 3/1999 | Greenwald et al. |
| 5,880,287 | A * | 3/1999 | Dandliker et al. ............ 548/156 |
| 5,968,479 | A | 10/1999 | Ito et al. |
| 5,981,747 | A | 11/1999 | Mujumdar et al. |
| 5,986,093 | A | 11/1999 | Mujumdar et al. |
| 6,013,283 | A | 1/2000 | Greenwald et al. |
| 6,037,137 | A | 3/2000 | Komoriya et al. |
| 6,046,925 | A | 4/2000 | Tsien et al. |
| 6,066,475 | A | 5/2000 | Mcclaren et al. |
| 6,077,707 | A | 6/2000 | Tsien et al. |
| 6,124,128 | A | 9/2000 | Tsien et al. |
| 6,130,101 | A | 10/2000 | Mao et al. |
| 6,133,445 | A | 10/2000 | Waggoner et al. |
| 6,251,382 | B1 | 6/2001 | Greenwald et al. |
| 6,319,669 | B1 | 11/2001 | Tsien et al. |
| 6,387,672 | B1 | 5/2002 | Arimori et al. |
| 6,399,392 | B1 | 6/2002 | Haugland et al. |
| 6,479,303 | B1 | 11/2002 | Waggoner et al. |
| 6,485,703 | B1 | 11/2002 | Cote et al. |
| 6,512,097 | B1 | 1/2003 | Marks et al. |
| 6,662,040 | B1 | 12/2003 | Henrichs et al. |
| 6,716,979 | B2 | 4/2004 | Diwu et al. |
| 6,766,183 | B2 | 7/2004 | Walsh et al. |
| 6,824,782 | B2 | 11/2004 | Whitlow et al. |
| 6,974,873 | B2 | 12/2005 | Leung et al. |
| 6,977,305 | B2 * | 12/2005 | Leung et al. ................ 548/450 |
| 2001/0055567 | A1 | 12/2001 | Licha et al. |
| 2003/0044353 | A1 | 3/2003 | Weissleder et al. |
| 2003/0045717 | A1 | 3/2003 | Czerney et al. |
| 2003/0124576 | A1 | 7/2003 | Kumar et al. |
| 2003/0134790 | A1 | 7/2003 | Langenfeld |
| 2003/0165942 | A1 | 9/2003 | Czerney et al. |
| 2004/0106806 | A1 | 6/2004 | Bhatt et al. |
| 2004/0152084 | A1 | 8/2004 | Slattum et al. |
| 2004/0260093 | A1 | 12/2004 | Czerney et al. |
| 2005/0069962 | A1 | 3/2005 | Archer et al. |
| 2006/0030638 | A1 | 2/2006 | Vonwiller et al. |
| 2006/0246477 | A1 | 11/2006 | Hermans et al. |
| 2007/0128659 | A1 | 6/2007 | Czerney et al. |
| 2007/0154899 | A1 | 7/2007 | Coull et al. |

FOREIGN PATENT DOCUMENTS

| | | |
|---|---|---|
| EP | 1619501 A1 | 1/2006 |
| EP | 1792949 A2 | 6/2007 |
| EP | 1792949 A3 | 3/2008 |
| WO | WO 00/13026 A1 | 3/2000 |
| WO | WO 01/16375 A2 | 3/2001 |
| WO | WO 01/16375 A3 | 10/2001 |
| WO | WO 02/26890 A1 | 4/2002 |
| WO | WO 2004/085539 A2 | 10/2004 |
| WO | WO 2004/085539 A3 | 1/2006 |
| WO | WO 2008/093647 A1 | 8/2008 |

OTHER PUBLICATIONS

Haugland, R.P. The Handbook—A Guide to Fluorescent Probes and Labeling Technologies, Tenth Edition. Molecular Probes, 2005.*

Haugland, Current Protocols in Cell Biology, (2000); 16.5.1-16.5.22.*

Kpl, "Cy3 and Cy5 Conjugates" flyer. Accessed online at <http://www.kpl.com> Obtained on Oct. 6, 2010.*

Lucas et al. (Macromolecules, 2004, 37, pp. 3832-3840).*

Taylor et al. Proceedings of the National Academy of Sciences, vol. 67, No. 1, pp. 164-171, Sep. 1970.*

Balakrishnan, et al. Chemical modification of poly(vinyl chloride) resin using poly(ethylene glycol) to improve blood compatibility. Biomaterials. Jun. 2005;26(17):3495-502.

Brinkley, et al. A brief survey of methods for preparing protein conjugates with dyes, haptens, and cross-linking reagents. Bioconjug Chem. Jan.-Feb. 1992;3(1):2-13.

Cooper, et al. Cy3B: improving the performance of cyanine dyes. J Fluoresc. Mar. 2004;14(2):145-50.

Giaid, et al. Non-isotopic RNA probes. Comparison between different labels and detection systems. Histochemistry. 1989;93(2):191-6.

Haugland, et al. Coupling of monoclonal antibodies with biotin. Chapter 23. Meth. Mol. Biol. 1995; 45:223-233.

Haugland, R. P. Antibody conjugates for cell biology. Current Protocols in Cell Biology. 2000;16.5.1-16.5.22.

Haugland, R. P. Coupling of monoclonal antibodies with enzymes. Chapter 24. Meth. Mol. Biol. 1995; 45:235-243.

Haugland, R. P. Coupling of monoclonal antibodies with fluorophores. Chapter 22. Meth. Mol. Biol. 1995; 45:205-221.

Haugland, R. P. The Handbook—A Guide to Fluorescent Probes and Labeling Technologies, Tenth Edition. Molecular Probes. 2005.

Hu, et al. Bioactivities of ricin retained and its immunoreactivity to anti-ricin polyclonal antibodies alleviated through pegylation. Int J Biochem Cell Biol. Apr. 2002;34(4):396-402.

Kulbersh, et al. Sensitivity and specificity of fluorescent immunoguided neoplasm detection in head and neck cancer xenografts. Arch Otolaryngol Head Neck Surg. May 2007;133(5):511-5.

Mehvar, R. Modulation of the pharmacokinetics and pharmacodynamics of proteins by polyethylene glycol conjugation. J Pharm Pharm Sci. Jan.-Apr. 2000;3(1):125-36.

Molecular Probes, Inc. Optimally labeled fluorescent antibodies for in vivo animal imaging. BioProbes 52. Mar. 2007; 10-11, by Molecular Probes, Inc.

Muhlegger, et al. Non-radioactive labeling and detection of nucleic acids. IV. Synthesis and properties of digoxigenin-modified 2'-deoxyuridine-5'-triphosphates and a photoactivatable analog of digoxigenin (photodigoxigenin). Biol Chem Hoppe Seyler. Oct. 1990;371(10):953-65.

Nimmakayalu, et al. Simple method for preparation of fluor/hapten-labeled dUTP. Biotechniques. 2000;28:518-522.

Panchuk-Voloshina, et al. Alexa dyes, a series of new fluorescent dyes that yield exceptionally bright, photostable conjugates. J Histochem Cytochem. Sep. 1999;47(9):1179-88.

Sambrook, et al. Molecular Cloning: A Laboratory Manual. 2nd ed. 1989.

Veiseh, et al. Tumor paint: a chlorotoxin:Cy5.5 bioconjugate for intraoperative visualization of cancer foci. Cancer Res. Jul. 15, 2007;67(14):6882-8.

International search report dated Mar. 2, 2009 for PCT Application No. US2008/13698.

European search report dated Mar. 25, 2011 for EP 08861025.8.

Holtke, et al. A fluorescent photoprobe for the imaging of endothelin receptors. Bioconjug Chem. May-Jun. 2007;18(3):685-94.

Licha, et al. Synthesis and characterization of cyanine dye poly(ethylene glycol) conjugates as contrast agents for in-vivo fluorescence imaging. Proc. SPIE. 1998; 3196:98-102.

Moon, et al. Enhanced tumor detection using a folate receptor-targeted near-infrared fluorochrome conjugate. Bioconjug Chem. May-Jun. 2003;14(3):539-45.

Narayanan, et al. A New Method for the Synthesis of Heptamethine Cyanine Dyes: Syntheses of New Near-Infrared Fluorescent Labels. J. Org. Chem. 1995; 60(8):2391-2395.

Tokimoto, et al. Probing orientations of single fluorescent labels on a peptide reversibly binding to the human delta-opioid receptor. Appl Spectrosc. Feb. 2007;61(2):130-7.

* cited by examiner

FLUORESCENT COMPOUNDS

This application claims the benefit of U.S. Provisional Application Ser. No. 61/013,956, filed on Dec. 14, 2007, which is hereby incorporated by reference in its entirety.

BACKGROUND OF THE INVENTION

Fluorescent dyes are widely used in biological research and medical diagnostics. Fluorescent dyes are superior to conventional radioactive materials because fluorescent dyes are typically sufficiently sensitive to be detected, less expensive and less toxic. In particular, a diversity of fluorophores with a distinguishable color range has made it more practical to perform multiplexed assays capable of detecting multiple biological targets in parallel. The ability to visualize multiple targets in parallel is often required for delineating the spatial and temporal relationships amongst different biological targets in vitro and in vivo. In addition, the generation of a wide range of fluorescent dyes has opened a new avenue for conducting high-throughput and automated assays, thus dramatically reducing the unit cost per assay. Moreover, the low toxicity of fluorescent dyes provides ease of handling in vitro, and also renders it safer for imaging biological activities in vivo.

Despite the various advantages of fluorescent dyes, conventional dyes have a number of profound limitations. For example, conventional fluorescent dyes are typically prone to inter-dye quenching, a phenomenon known to diminish the effective brightness of the dyes. It is a common practice to conjugate a given target with multiple dye molecules in order to maximize the brightness of the labeled target, e.g., a biomolecule such as protein or DNA. For many conventional fluorescent dyes, the fluorescence intensity of the labeled target is often not directly proportional to the number of attached dye molecules, but rather less than the predicted intensity due to, e.g., quenching amongst the multiple dyes attached to the target. Such quenching effect can be attributed to, in part, the physical interaction amongst the attached dye molecules, which may lead to formation of nonfluorescent dye dimers. Dimer formation may be driven by hydrophobic interaction. Because many traditional fluorescent dyes, such as various rhodamine dyes and cyanine dyes, are highly hydrophobic aromatic compounds, these commonly used dyes are particularly prone to forming dimers on labeled biomolecules. Adding sulfonate groups to a dye has been shown to reduce dimer formation. See, e.g., U.S. Pat. Nos. 5,268,486 and 6,977,305, 6,130,101 and Panchuk-Voloshina, et al. J. Histochem. Cytochem. 47(9), 1179 (1999). However, while sulfonation may reduce dimer formation, it also introduces negative charges into a biomolecule, and thus may increase the risk of disrupting the biological activity of the labeled biomolecule. Furthermore, dyes substituted with sulfonates alone may exhibit a shorter serum half-life when used in vivo in a subject.

Another limiting factor for conventional fluorescent dyes is the low fluorescence brightness intrinsic to individual fluorescent groups. Such property is generally determined by the fluorescence quantum yield of the fluorescent group. A low fluorescence quantum yield is usually due to energy transfer from the excited electronic state to the vibrational and rotational states of the molecule, a process in which the electronic energy is converted to heat, instead of light. One approach to improve the fluorescence quantum yield of a fluorescent group is to rigidify the dye structure so that the dye has limited vibrational and rotational modes. See, e.g., U.S. Pat. Nos. 5,981,747 and 5,986,093, which describe monomethine cyanine dyes that are rigidified by a two-carbon chain that links the two benzazolium nitrogen atoms. Similarly, in U.S. Pat. No. 6,133,445, trimethine cyanine dyes are rigidified by incorporating the bridge moiety into a three fused ring system. The rigidified cyanine dyes all have significantly improved quantum yields compared to the nonrigidified counterpart dyes. However, the improvements in quantum yield are obtained at the expense of other desirable properties. For example, because of their relatively complex structures, these rigidified dyes typically take several more steps to synthesize than regular cyanine dyes, often with low yields. Highly rigidified dyes may also show a higher tendency to aggregate on proteins. For example, a rigidified cyanine dye has been shown to form dimers even when used at a much lower degree of labeling on proteins than a nonrigidified cyanine (Cooper, et al. Journal of Fluorescence 14, 145 (2004)). Furthermore, rigidified trimethine cyanine dyes have shown significantly reduced photostability, compared to regular non-rigidified trimethine cyanine dyes (see, e.g., U.S. Pat. No. 6,133,445).

SUMMARY OF THE INVENTION

Thus there remains a considerable need for improved compositions and methods that would allow convenient and effective labeling of a wide range of molecules in various applications. The present invention addresses this need and provides additional advantages.

Accordingly, the present invention provides fluorescent compounds which may have any or all of the following characteristics. In one aspect, labeled biomolecules prepared using fluorescent compounds of the invention show significantly reduced dimer formation. In other aspects, compounds and labeled biomolecules of the invention show other desirable properties such as higher water solubility, improved fluorescence quantum yield, improved photostability, relatively simple synthesis, improved specificity of the labeled conjugates, and/or improved in vivo half-life.

The invention provides a compound of formula I:

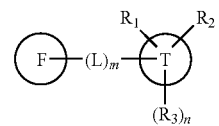

wherein
F is a fluorophore;
T is a joining moiety formed of one or more chemical bonds and connecting three or more distinct moieties, and wherein said joining moiety contains about 1-100 atoms;
m and n are independently integers ranging from 0 to 20;
$R_1$, $R_2$, and $R_3$ are each independently $(R)_p$-$(L)_q$-;
each L of $R_1$, $R_2$, and $R_3$ is independently a linking moiety formed of one or more chemical bond and containing about 1-100 atoms selected such that the group is a stable moiety;
each p of $R_1$, $R_2$, and $R_3$ is an integer ranging from 1 to 20;
each q of $R_1$, $R_2$, and $R_3$ is an integer ranging from 0 to 20;
each R of $R_1$, $R_2$, and $R_3$ is independently: i) a reactive group capable of forming a covalent bond upon reacting with a reaction partner; ii) a radical of a water-soluble polymer; iii) an alkyl group, a trifluoroalkyl group, a halogen group, a sulfonyl group, a sulfonate group, a phosphonate group or a sulfonamido group; or iv) —H; and wherein at least one R of $R_1$, $R_2$, and $R_3$ is a reactive group and at least one other R of $R_1$, $R_2$, and $R_3$ is a radical of a water-soluble polymer.

In some embodiments, the fluorophore is a xanthene dye, a coumarin dye, a pyrene dye or a cyanine dye. The water soluble group may, for example, be a polyalkylene oxide such as a polyethylene oxide. Alternatively, the water soluble polymer group may be a carbohydrate or a polypeptide. The water soluble polymer group may have a molecular weight of greater than about 300 Da, or alternatively greater than about 800 Da, or a molecular weight ranging from about 800 Da to about 3000 Da. The reactive group may form a covalent bond with an amino, a sulfhydryl or a hydroxy nucleophile. For example, the reactive group may be an isothiocyanate, an isocyanate, a monochlorotriazine, a dichlorotriazine, a halogen-substituted pyridine, a halogen-substituted diazine, a phosphoramidite, a maleimide, an aziridine, a sulfonyl halide, an acid halide, a hydroxysuccinimidyl ester, a hydroxysulfosuccinimidyl ester, a tetrafluorophenol ester, an imido ester, a hydrazine, an azidonitrophenyl, an azide, an alkyne, a 3-(2-pyridyl dithio)-propionamide, a glyoxal or an aldehyde.

A fluorescence excitation wavelength of the compound of the invention may range from about 350 to about 1200 nm, while a fluorescence emission wavelength of the compound may range from about 360 to about 1250 nm.

In one embodiment, the compound of Formula I comprises a fluorophore which is a coumarin of the formula:

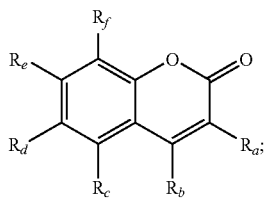

wherein one moiety of $R_a$, $R_b$, $R_c$, $R_d$, $R_e$ and $R_f$ is a bond connecting said fluorophore to said moiety $-(L)_m$- or said moiety

also each remaining moiety of $R_a$, $R_b$, $R_c$, $R_d$, $R_e$ and $R_f$ has the formula $(R)_p$-$(L)_q$-, wherein each R of $R_a$, $R_b$, $R_c$, $R_d$, $R_e$ and $R_f$ is independently i) a reactive group capable of forming a covalent bond upon reacting with a reaction partner; ii) a radical of a water-soluble polymer; iii) an alkyl group, a trifluoroalkyl group, a halogen group, a sulfonyl group, a sulfonate group, a phosphonate group or a sulfonamido group; or iv) —H;

each L of $R_a$, $R_b$, $R_c$, $R_d$, $R_e$ and $R_f$ is a a linking moiety formed of one or more chemical bond and containing about 1-100 atoms selected such that the group is a stable moiety; each p of $R_a$, $R_b$, $R_c$, $R_d$, $R_e$ and $R_f$ is independently an integer ranging from 1 to 20; and each q of $R_a$, $R_b$, $R_c$, $R_d$, $R_e$ and $R_f$ is independently an integer ranging from 0 to 20.

In other embodiments, the compound of Formula I comprises a fluorophore which is a rhodamine of the formula:

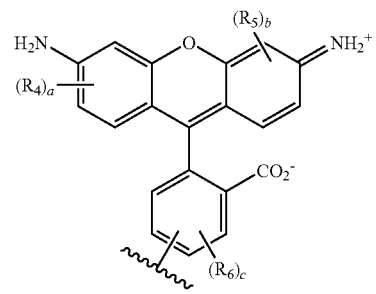

wherein

connects said fluorophore to said moiety $-(L)_m$- or said moiety

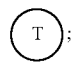

$R_4$, $R_5$, and $R_6$ are each independently $(R)_p$-$(L)_q$-; each R of $R_4$, $R_5$, $R_6$ is independently i) a reactive group capable of forming a covalent bond upon reacting with a reaction partner; ii) a water soluble polymer group; iii) an alkyl group, a trifluoroalkyl group, a halogen group, a sulfonate group or a sulfonamido group; or iv) —H; each L of $R_4$, $R_5$ and $R_6$ is independently a linking moiety formed of one or more chemical bonds and containing about 1-100 atoms; each p of $R_4$, $R_5$, and $R_6$ is independently an integer ranging from 1 to 20; each q of $R_4$, $R_5$, and $R_6$ is independently an integer ranging from 0 to 20; and a, b, and c are independently 0, 1, 2, or 3.

In related embodiments,

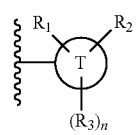

has the formula

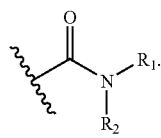

In some embodiments, $R_1$, comprises a water soluble polymer group and $R_2$ comprises a reactive group. For example, $R_1$, comprise a polyethylene glycol. In other embodiments, $R_2$ comprises an N-hydroxysuccinimide group.

In still other embodiments, the fluorophore is substituted by one or more sulfonate groups.

In another aspect, the invention provides a compound having a maximal fluorescence excitation wavelength, wherein the compound has a structure of Formula II:

  Formula II

Wherein F is a moiety having the structure:

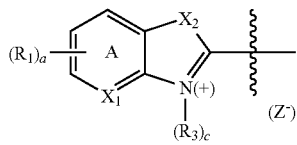

$Z^-$ is a counterion; Y is a bridge unit permitting electron delocalization between F and Ψ;

Ψ is a moiety having one of the following structures:

Formula 1

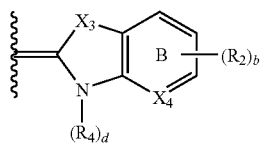

Formula 2

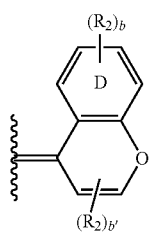

Formula 3

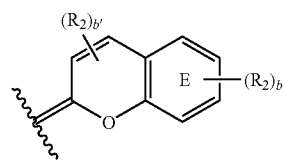

Formula 4

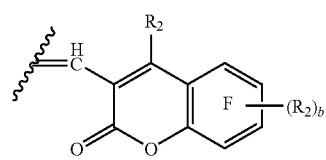

Formula 5

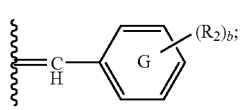

$X_1$ and $X_4$ are independently

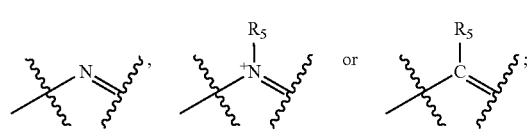

$X_2$ and $X_3$ are independently

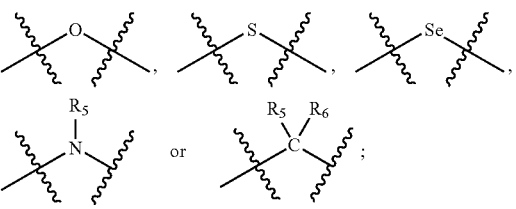

a and b are independently 0, 1, 2, or 3;
b' is 0, 1 or 2;
wherein when Ψ is Formula 1, and the maximal fluorescence excitation wavelength of the compound is less than 660 nm, then $R_5$ and $R_6$ are independently $(R)_p$-$(L)_q$-, wherein $R_5$ and $R_6$ are not combinable to form a substituted ring;
$R_1$, $R_2$, $R_3$, $R_4$, $R_5$, and $R_6$ are each independently $(R)_p$-$(L)_q$-;
each R of each $(R)_p$-$(L)_q$- of the compound is independently i) a reactive group capable of forming a covalent bond upon reacting with a reaction substrate; ii) a water soluble polymer group; iii) an alkyl group, an aryl group, an alkylamino group, a dialkylamino group, an alkoxy group, a trifluoroalkyl group, a halogen group, a sulfonyl group, a sulfonate group or a sulfonamido group; or iv) —H;
each L of each $(R)_p$-$(L)_q$- of the compound is independently a linking moiety formed of one or more chemical bonds and containing about 1-100 atoms;
each p of each $(R)_p$ $(L)_q$- is independently an integer of about 1 to about 20;
each q of each $(R)_p$-$(L)_q$- of $R_1$ or $R_2$ is independently an integer of 0 to about 20;
each q of each $(R)_p$-$(L)_q$- of $R_3$, $R_4$, $R_5$, $R_6$, or $R_7$, is independently an integer of 1 to about 20;
c is 0 or 1; d is 0 or 1;
at least one R of the $(R)_p$-$(L)_q$- of the compound is a reactive moiety; and
at least one R of the $(R)_p$-$(L)_q$- of the compound is a water-soluble polymer.

In some embodiments, the invention provides the compound of Formula II wherein when at least two adjacent $R_1$, and/or two adjacent $R_2$ are present, the two adjacent $R_1$, and/or the two adjacent $R_2$ are combinable to form a 6-membered ring which is unsubstituted or substituted by one or more $(R)_p$ $(L)_q$-. In some embodiments, the invention provides a compound of Formula II wherein when the two adjacent $R_1$, and/or the two adjacent $R_2$ are combinable to form a 6-membered ring, the ring so formed is aromatic.

In some embodiments in the compounds of Formula II, when Ψ is Formula 1, and the maximal fluorescence excitation wavelength of the compound is equal to or greater than 660 nm, or Ψ is other than Formula 1, then $R_5$ and $R_6$ are independently $(R)_p$-$(L)_q$, or $R_5$ and $R_6$ are combinable to form a cyclic moiety which is unsubstituted or substituted by one or more $(R)_p$-$(L)_q$-.

In some embodiments in the compounds of Formula II, Y is:

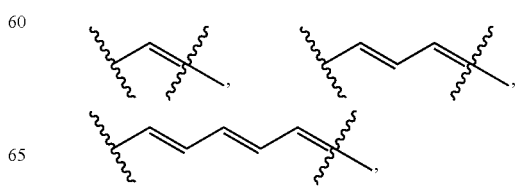

-continued

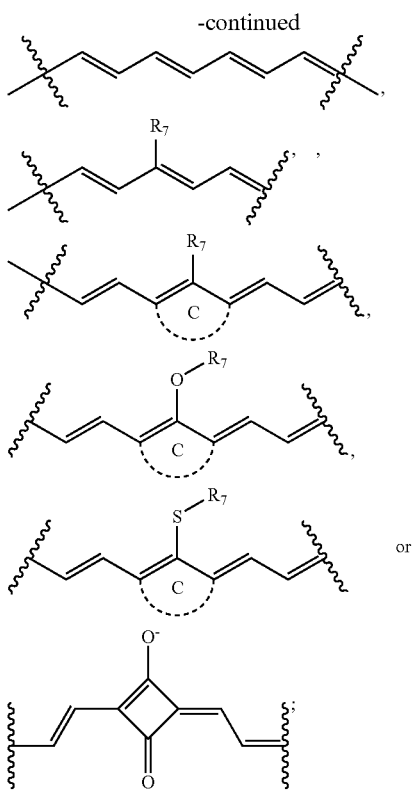

or wherein when C is present, it is a five- or six-membered cyclic group; $R_7$ is $(R)_p\text{-}(L)_q\text{-}$; each R of $(R)_p\text{-}(L)_q\text{-}$ is independently i) a reactive group capable of forming a covalent bond upon reacting with a reaction substrate; ii) a water soluble polymer group; iii) an alkyl group, an aryl group, an alkylamino group, a dialkylamino group, an alkoxy group, a trifluoroalkyl group, a halogen group, a sulfonyl group, a sulfonate group or a sulfonamido group; or iv) —H; each L of $(R)_p\ (L)_q\text{-}$ is independently a linking moiety formed of one or more chemical bonds and containing about 1-100 atoms; p is an integer of about 1 to about 20; and q, is an integer of 1 to about 20.

In some embodiments of the compound of Formula II, at least one R of $R_1$ and $R_2$ is a charged moiety. In other embodiments, at least one R of $R_1$ and $R_2$ comprises a sulfonate group or a phosphonate group. In yet other embodiments, each R of $R_1$ and $R_2$ comprises a sulfonate group or a phosphonate group.

In some embodiments of the compound of Formula II, $X_2$ and $X_3$ are independently

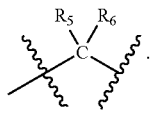

In other embodiments, $X_2$ and $X_3$ are independently

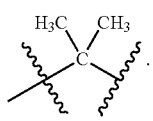

In some embodiments of the compound of Formula II, the water-soluble polymer is a polyalkylene oxide. In other embodiments, the water-soluble polymer is a polyethylene oxide. In some embodiments, the water-soluble polymer has a molecular weight of greater than about 300. In other embodiments, the water-soluble polymer has a molecular weight of greater than about 800. In other embodiments, the water-soluble polymer has a molecular weight ranging from about 800 to about 3000.

In some embodiments of the compound of Formula II, two adjacent $(R_1)_a$ and the atoms in ring A to which it is attached are combined to form a carbocyclic ring. In some embodiments, the carbocyclic ring is aromatic. In other embodiments, two adjacent $(R_2)_b$ and the atoms in ring B to which it is attached are combined to form a carbocyclic ring. In some embodiments, the carbocyclic ring is aromatic.

In some embodiments of the compound of Formula II, the compound has the formula:

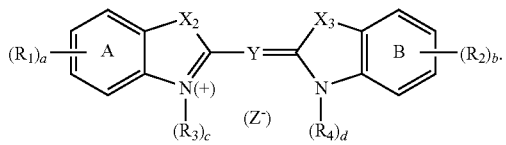

In some embodiments of the compound of Formula II, the compound has the formula:

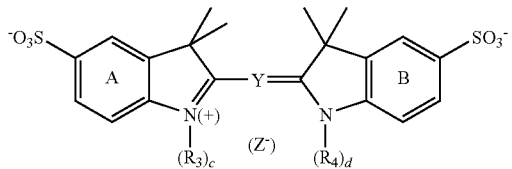

wherein c is 1; d is 1; at least one R of $R_3$ and $R_4$ is a reactive group capable of forming a covalent bond upon reacting with a reaction substrate; and at least one R of $R_3$ and $R_4$ is a water soluble polymer group.

In some embodiments of the compound of Formula II, the compound has the formula:

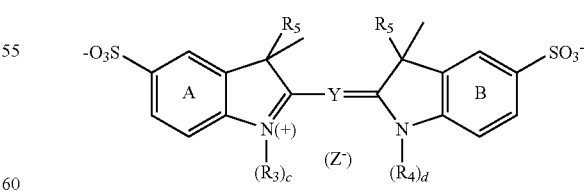

wherein c is 1; d is 1;
at least one R of $R_3$, $R_4$ and $R_5$ is a reactive group capable of forming a covalent bond upon reacting with a reaction substrate; and at least one R of $R_3$, $R_4$ and $R_5$ is a radical of a water-soluble polymer.

In some embodiments of the compound of Formula II, the compound has the formula:

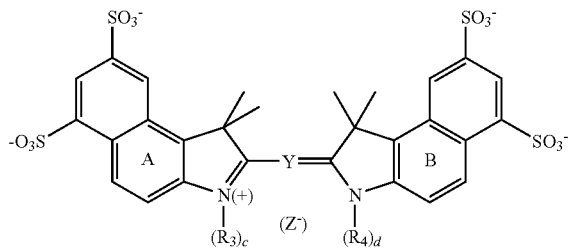

wherein c is 1; d is 1; one R of $R_3$ and $R_4$ is a reactive group capable of forming a covalent bond upon reacting with a reaction substrate; and one R of $R_3$ and $R_4$ is a water soluble polymer group.

In embodiments of the compound of Formula II, the compound has the formula:

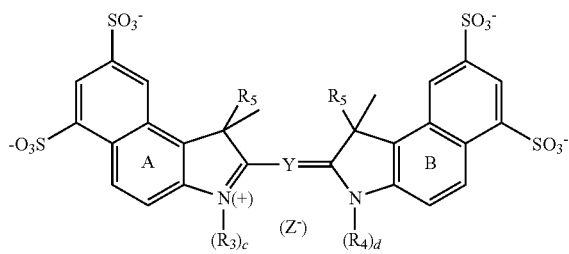

wherein c is 1; d is 1; at least one R of $R_3$, $R_4$ and $R_5$ is a reactive group capable of forming a covalent bond upon reacting with a reaction substrate; and at least one R of $R_3$, $R_4$ and $R_5$ is a radical of a water-soluble polymer.

In some embodiments of the compound of Formula II, the compound has the formula:

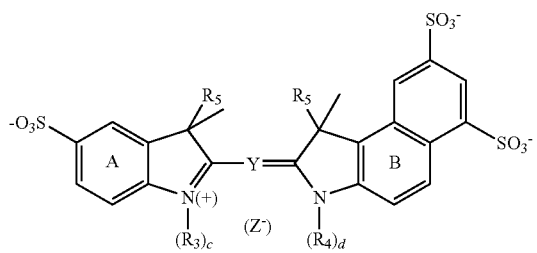

wherein c is 1; d is 1; at least one R of $R_3$, $R_4$ and $R_5$ is a reactive group capable of forming a covalent bond upon reacting with a reaction substrate; and at least one R of $R_3$, $R_4$ and $R_5$ is a radical of a water-soluble polymer.

In some embodiments, the maximal fluorescence excitation wavelength of the compound ranges from about 350 to about 1200 nm. In other embodiments, a maximal fluorescence emission wavelength of the compound ranges from about 360 to about 1250 nm.

In some embodiments, the water-soluble polymer is a polyalkylene oxide. In other embodiments, the water-soluble polymer is a polyethylene oxide. In yet other embodiments, the water-soluble polymer is a carbohydrate. In other embodiments, the water-soluble polymer is a polypeptide. In some embodiments, the water-soluble polymer has a molecular weight of greater than 300. In other embodiments, the water-soluble polymer has a molecular weight of greater than 800.

In some embodiments of the compound of Formula II, the compound is

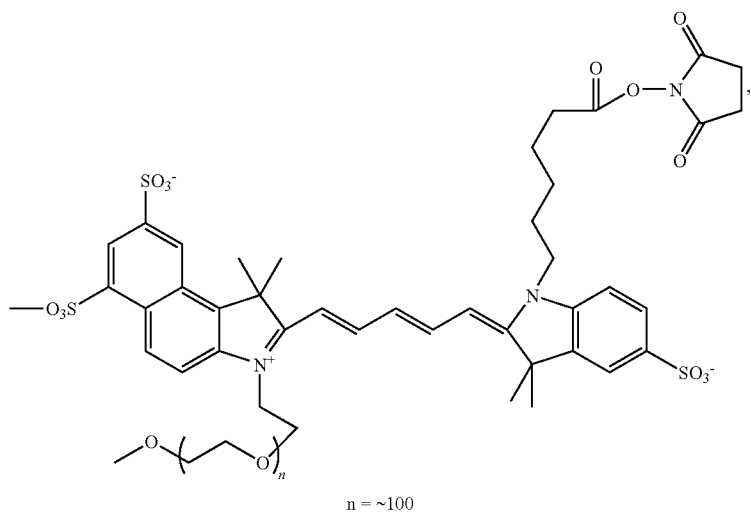

n = ~100

-continued
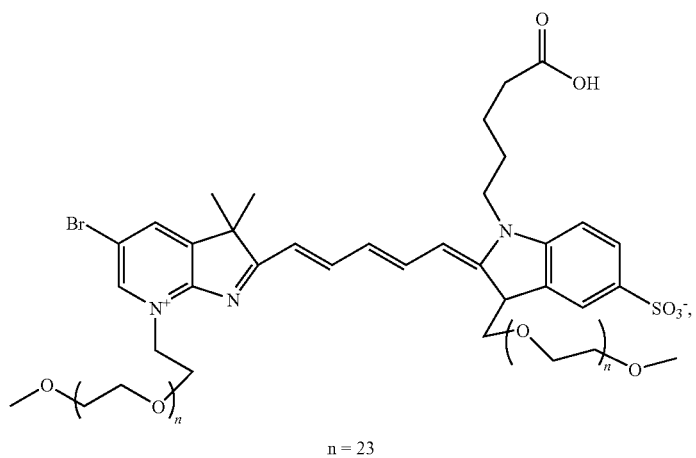
n = 23
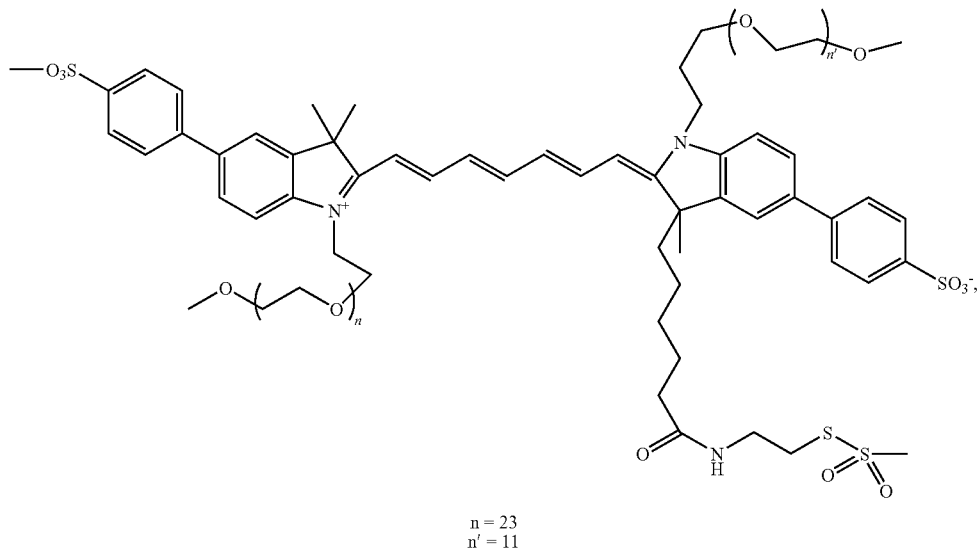
n = 23
n' = 11
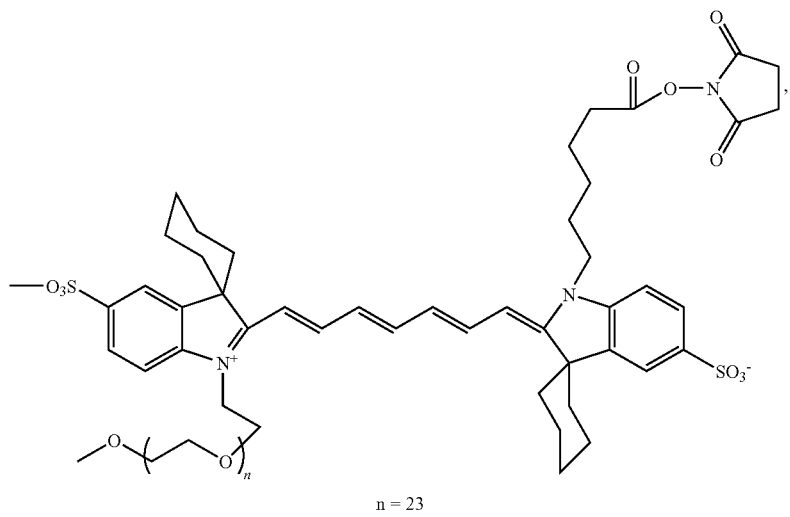
n = 23

-continued
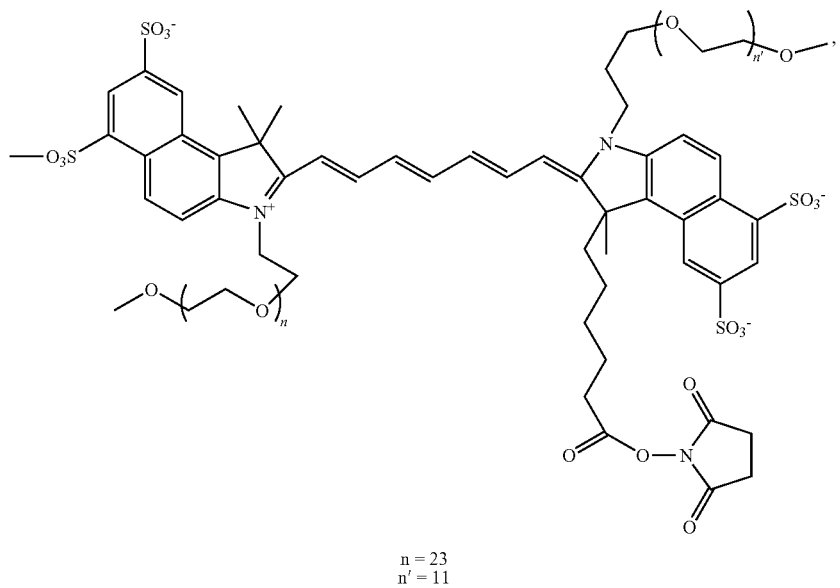
n = 23
n' = 11
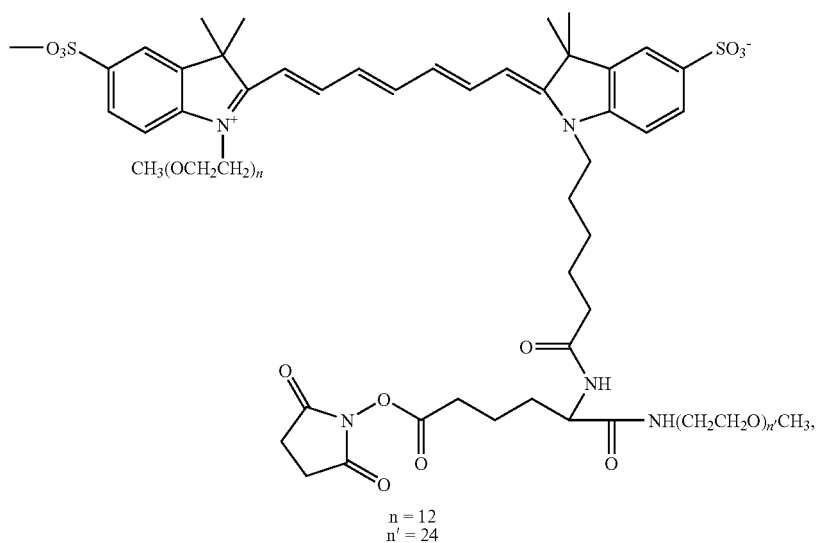
n = 12
n' = 24
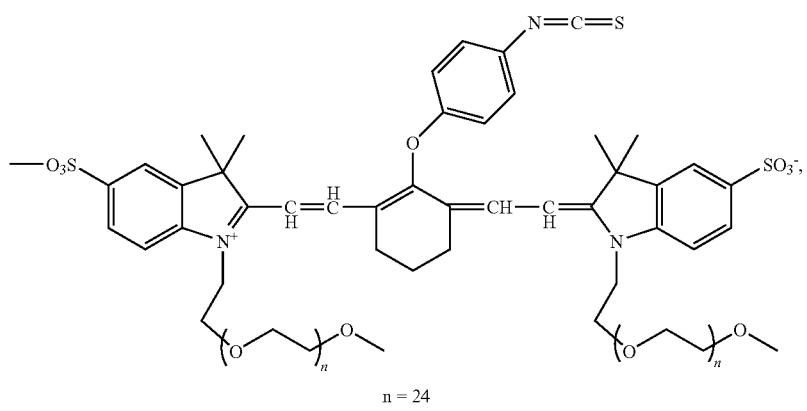
n = 24

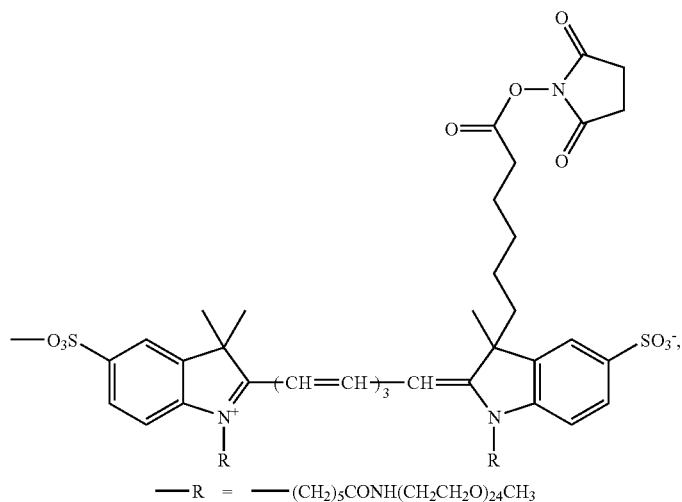
R = —(CH$_2$)$_5$CONH(CH$_2$CH$_2$O)$_{24}$CH$_3$
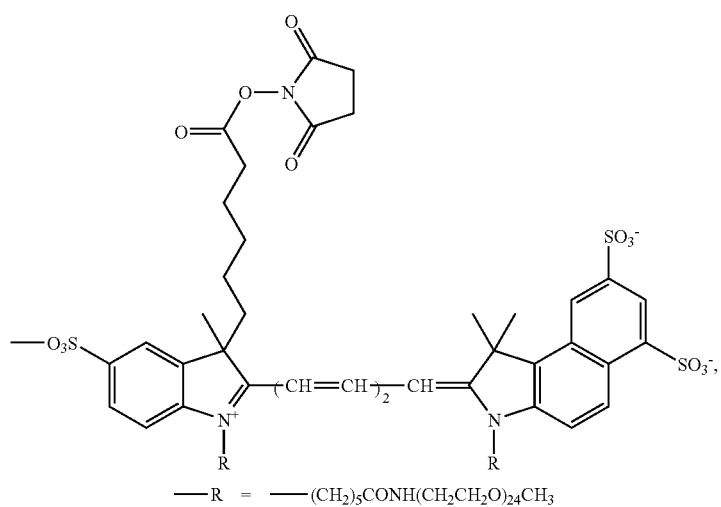
R = —(CH$_2$)$_5$CONH(CH$_2$CH$_2$O)$_{24}$CH$_3$
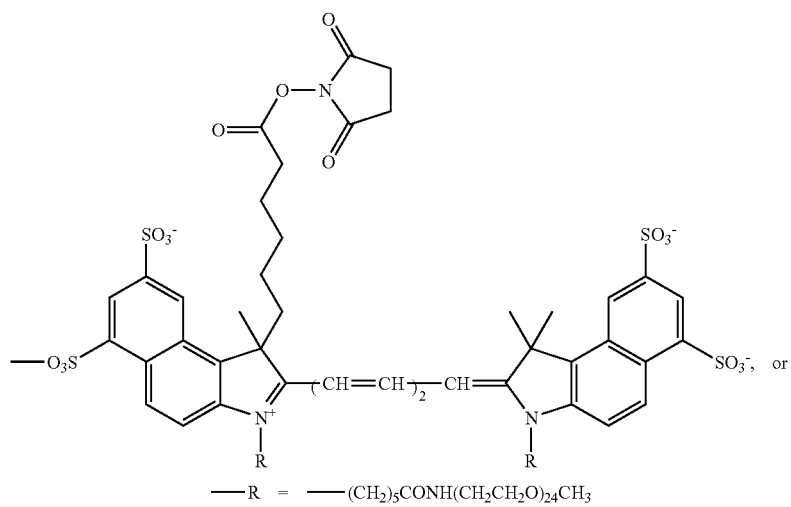
R = —(CH$_2$)$_5$CONH(CH$_2$CH$_2$O)$_{24}$CH$_3$ -continued

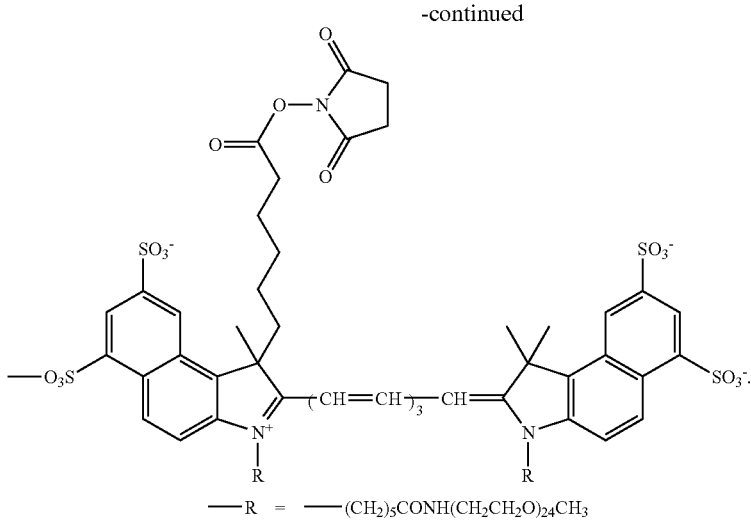

R = —(CH₂)₅CONH(CH₂CH₂O)₂₄CH₃

In another aspect, the invention provides a substituted cyanine dye comprising a reactive group and one or more water soluble polymer groups, wherein the cyanine dye has a maximal fluorescence excitation wavelength of equal to or greater than about 660 nm. In some embodiments, the substituted cyanine dye of claim, the dye is substituted by a non-spiro moiety.

In a further aspect, the invention provides a substituted cyanine dye comprising a reactive group and one or more water soluble polymer groups, wherein the cyanine dye has an absorption maximal wavelength of equal to or greater than about 660 nm. In some embodiments, the substituted cyanine dye of claim, the dye is substituted by a non-spiro moiety.

In yet another aspect, the invention provides a binding agent labeled with a substituted cyanine dye of the invention, wherein the binding agent binds selectively to a target polypeptide to form a complex, and wherein formation of the complex yields a signal to noise ratio of fluorescence that is at least 100. In some embodiments, the binding agent comprises a substituted cyanine dye which is substituted with a non-spiro substituent. In some embodiments, the binding agent is a polypeptide. In other embodiments, the polypeptide is an antibody.

In another aspect, the invention provides a compound of Formula III:

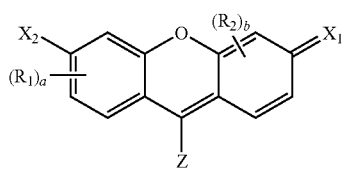

Formula III wherein Z is —H, alkyl, —CF₃, —CN or a radical of the formula:

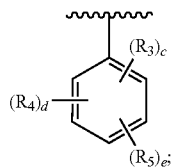

$X_1$ is =O, =$NH_2^+$ or =$NR_6R_7^+$;
$X_2$ is —OH, $NH_2$, or —$NR_8R_9$;
$R_1, R_2, R_3, R_4, R_5, R_6, R_7, R_8$ and $R_9$ are each independently $(R)_p\text{-}(L)_q\text{-}$;
each R of $R_1, R_2, R_3, R_4, R_5, R_6, R_7, R_8$ and $R_9$ is independently i) a reactive group capable of forming a covalent bond upon reacting with a reaction substrate; ii) a water soluble polymer group; iii) an alkyl group, a trifluoroalkyl group, a halogen group, a sulfonate group or a sulfonamido group; or iv) —H;
each L of $R_1, R_2, R_3, R_4, R_5, R_6, R_7, R_8$ and $R_9$ is independently a linking moiety formed of one or more chemical bonds and containing about 1-100 atoms;
each p of $R_1, R_2, R_3, R_4, R_5, R_6, R_7, R_8$ and $R_9$ is independently an integer ranging from 1 to 20;
each q of $R_1, R_2, R_3, R_4, R_5, R_6, R_7, R_8$ and $R_9$ is independently an integer ranging from 0 to 20;
a, b, c, d and e are independently 0, 1, 2, 3 or 4;
at least one R of $R_1, R_2, R_3, R_4, R_5, R_6, R_7, R_8$ and $R_9$ is a reactive moiety; and
at least one R of $R_1, R_2, R_3, R_4, R_5, R_6, R_7, R_8$ and $R_9$ is a water soluble polymer group.

In some embodiments of the compound of Formula III, at least one of $R_6, R_7, R_8$ or $R_9$ is combinable with a neighboring $R_1$ or $R_2$ and any intervening atoms in a ring to which the neighboring $R_1$ or $R_2$ is attached, to form a 5- or 6-membered ring which is unsubstituted or substituted by one or more $(R)_p\text{-}(L)_q\text{-}$. In some embodiments, when the at least one of $R_6, R_7, R_8$ or $R_9$ and a neighboring $R_1$ or $R_2$ are combinable to form a 5- or 6-membered ring, the ring so formed is unsaturated. In other embodiments, when the at least one of $R_6, R_7, R_8$ or $R_9$ and a neighboring $R_1$ or $R_2$ are combinable to form a 5- or 6-membered ring, the ring so formed is saturated.

In some embodiments of the compound of Formula III, $X_1$ is =$NH_2^+$. In other embodiments, $X_1$ is =O. In yet other embodiments, $X_2$ is —OH. In some embodiments $X_2$ is —$NH_2$.

In some embodiments of the compound of Formula III, a maximal fluorescence excitation wavelength of the compound ranges from about 450 to 750 nm. In other embodiments, a maximal fluorescence emission wavelength of the compound ranges from about 470 to 800 nm.

In another aspect, the invention provides a compound of Formula V:

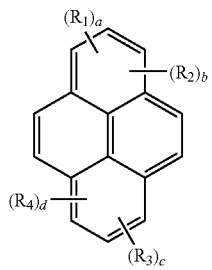

Formula V wherein $R_1$, $R_2$, $R_3$, and $R_4$ are each independently $(R)_p$-$(L)_q$-, each R of $R_1$, $R_2$, $R_3$, and $R_4$ is independently i) a reactive group capable of forming a covalent bond upon reacting with a reaction substrate; ii) a water soluble polymer group; iii) an alkyl group, a trifluoroalkyl group, a halogen group, a phosphonate group, a sulfonate group or a sulfonamido group; or iv) —H;

each L of $R_1$, $R_2$, $R_3$, and $R_4$ is independently a linking moiety formed of one or more chemical bond and containing about 1-100 atoms;

each p of $R_1$, $R_2$, $R_3$, $R_4$, $R_5$, $R_6$ and $R_7$ is independently an integer ranging from 1 to 20;

each q of $R_1$, $R_2$, $R_3$, $R_4$, $R_5$, $R_6$ and $R_7$ is independently an integer ranging from 0 to 20;

a, b, c and d are independently 0, 1, 2 or 3;

at least one R of $R_1$, $R_2$, $R_3$ and $R_4$ is a reactive moiety; and at least one R of $R_1$, $R_2$, $R_3$ and $R_4$ is a water soluble polymer group.

In a further aspect, the invention provides a kit comprising: i) the compound of claim 1, 25, 59, 60, 66, or 76; ii) a buffer; iii) materials or devices for purifying conjugation products; and iv) instructions instructing the use of the compound.

In another aspect, the invention provides a biomolecule comprising a label having a structure of Formula I, II, III, IV, V, a substituted cyanine dye comprising a reactive group and one or more water soluble polymer groups, wherein the cyanine dye has a maximal fluorescence excitation wavelength of equal to or greater than about 660 nm or a substituted cyanine dye comprising a reactive group and one or more water soluble polymer groups, wherein the cyanine dye has an absorption maximal wavelength of equal to or greater than about 660 nm, wherein the at least one reactive moiety of the Formula has undergone a reaction which attaches the label to the biomolecule. In some embodiments, the biomolecule comprises a polynucleotide. In some embodiments, the biomolecule comprises a polypeptide. In some embodiments, the polypeptide further comprises an antigen binding site. In some embodiments, the polypeptide is a whole immunoglobulin. In some embodiments, the polypeptide is a Fab fragment.

In another aspect, the invention provides an immunoglobin comprising a label having a structure of Formula I, II, III, IV, V, a substituted cyanine dye comprising a reactive group and one or more water soluble polymer groups, wherein the cyanine dye has a maximal fluorescence excitation wavelength of equal to or greater than about 660 nm or a substituted cyanine dye comprising a reactive group and one or more water soluble polymer groups, wherein the cyanine dye has an absorption maximal wavelength of equal to or greater than about 660 nm, wherein the at least one reactive moiety of the Formula has undergone a reaction which attaches the label to the immunoglobin, wherein the immunoglobin is an antibody that binds specifically to an antigen on a cancer cell. In some embodiments, the antibody binds to erb2.

In another aspect, the invention provides a method of preparing a labeled biomolecule comprising reacting a compound having a structure of Formula I, II, III, IV, V, a substituted cyanine dye comprising a reactive group and one or more water soluble polymer groups, wherein the cyanine dye has a maximal fluorescence excitation wavelength of equal to or greater than about 660 nm or a substituted cyanine dye comprising a reactive group and one or more water soluble polymer groups, wherein the cyanine dye has an absorption maximal wavelength of equal to or greater than about 660 nm, and a substrate biomolecule under conditions sufficient to effect crosslinking between the compound and the substrate biomolecule. In some embodiments, the substrate biomolecule is a polypeptide, a polynucleotide, a carbohydrate, a lipid or a combination thereof. In other embodiments, the substrate biomolecule is a polynucleotide.

In yet another aspect, the invention provides a method for labeling a cell within a population of cells whereby the cell is differentially labeled relative to neighboring cells within the population, the method comprising contacting the cell with a biomolecule of labeled according to the methods of the invention, wherein the biomolecule comprises a targeting moiety that binds to a binding partner that is indicative of the cell, and thereby differentially labeling the cell relative to neighboring cells within the population. In some embodiments, the method further comprises the step of imaging the cell, the imaging step comprising: i) directing exciting wavelength to the cell; and ii) detecting emitted fluorescence from the cell. In some embodiments, the labeling takes place in vitro. In other embodiments, the labeling takes place in vivo.

In another aspect, the invention provides an immunoglobulin labeled with a fluorescent compound comprising a polyalkylene oxide and a fluorophore that has an absorption maximal wavelength equal to or greater than 685 nm. In some embodiments, the immunoglobulin retains binding specificity to a target upon conjugation to the fluorescent compound. In some embodiments, the immunoglobin is an antibody that binds specifically to an antigen on a cancer cell. In some embodiments, the antibody binds to erb2. In some embodiments, the fluorescent compound is a compound of Formula I, II, III, a substituted cyanine dye comprising a reactive group and one or more water soluble polymer groups, wherein the cyanine dye has a maximal fluorescence excitation wavelength of equal to or greater than about 660 nm or a substituted cyanine dye comprising a reactive group and one or more water soluble polymer groups, wherein the cyanine dye has an absorption maximal wavelength of equal to or greater than about 660 nm.

In another aspect, the invention provides an immunoglobulin labeled with a fluorescent compound comprising a polyalkylene oxide and a fluorophore that has an absorption maximal wavelength at or greater than 750 nm. In some embodiments, the immunoglobulin retains binding specificity to a target upon conjugation to the fluorescent compound. In some embodiments, the immunoglobin is an antibody that binds specifically to an antigen on a cancer cell. In some embodiments, the antibody binds to erb2. In some embodiments, the fluorescent compound is a compound having a structure of Formula I, II, III, V, a substituted cyanine dye comprising a reactive group and one or more water soluble polymer groups, wherein the cyanine dye has a maximal fluorescence excitation wavelength of equal to or greater than about 660 nm or a substituted cyanine dye comprising a reactive group and one or more water soluble polymer groups, wherein the cyanine dye has an absorption maximal wavelength of equal to or greater than about 660 nm.

In yet a further aspect, the invention provides a polypeptide labeled with a fluorescent compound, the polypeptide exhibiting a serum half-life no shorter than that of a corresponding polypeptide that lacks the fluorescent compound, wherein the fluorescent compound is a compound having a structure of Formula I, II, III, V, a substituted cyanine dye comprising a reactive group and one or more water soluble polymer groups, wherein the cyanine dye has a maximal fluorescence excitation wavelength of equal to or greater than about 660 nm or a substituted cyanine dye comprising a reactive group and one or more water soluble polymer groups, wherein the cyanine dye has an absorption maximal wavelength of equal to or greater than about 660 nm.

In another aspect, the invention provides a method of labeling a polypeptide comprising: forming a complex that comprises the polypeptide and a binding agent, wherein the binding agent comprises a fluorescent label having a structure of Formula I, II, III, V, a substituted cyanine dye comprising a reactive group and one or more water soluble polymer groups, wherein the cyanine dye has a maximal fluorescence excitation wavelength of equal to or greater than about 660 nm or a substituted cyanine dye comprising a reactive group and one or more water soluble polymer groups, wherein the cyanine dye has an absorption maximal wavelength of equal to or greater than about 660 nm, wherein the at least one reactive moiety of the Formula has undergone a reaction which attaches the label to the binding agent. In some embodiments, the binding agent is an antibody. In some embodiments, the complex comprises (a) a primary antibody that binds to the polypeptide, and (b) the binding agent which functions as a secondary antibody exhibiting binding capability to the primary antibody. In some embodiments, the labeling occurs on a solid substrate. In some embodiments, that labels a polypeptide intracellularly. In some embodiments, the complex yields a signal to noise ratio greater than about 100, wherein the signal to noise ratio is calculated by the formula: (fluorescent signal from a complex comprising the polypeptide bound by a primary antibody which in turn is bound to the binding agent)/(fluorescent signal from a mixture of the polypeptide, an isotype control primary antibody and the binding agent). In other embodiments, the complex yields a signal to noise ratio greater than about 250, wherein the signal to noise ratio is calculated by the formula: (fluorescent signal from a complex comprising the polypeptide bound by a primary antibody which in turn is bound to the binding agent)/(fluorescent signal from a mixture of the polypeptide, an isotype control primary antibody and the binding agent). In yet other embodiments, the complex yields a signal to noise ratio greater than about 270, wherein the signal to noise ratio is calculated by the formula: (fluorescent signal from a complex comprising the polypeptide bound by a primary antibody which in turn is bound to the binding agent)/(fluorescent signal from a mixture of the polypeptide, an isotype control primary antibody and the binding agent).

In some embodiments, the complex yields a total fluorescence signal at least 5% greater than that generated by a complex formed with the same primary antibody and with the same secondary antibody that has a comparable degree of labeling with a DyLight 680™ dye. In other embodiments, the complex yields a total fluorescence signal at least 5% greater than that generated by a complex formed with the same primary antibody and with the same secondary antibody that has a comparable degree of labeling with a Cy5.5® dye. In yet other embodiments, the complex yields a total fluorescence signal at least 5% greater than that generated by a complex formed with the same primary antibody and with the same secondary antibody that has a comparable degree of labeling with an Alexa Fluor 680® dye. In some embodiments, the label having a structure of a Formula of Formula II is the compound having the structure:

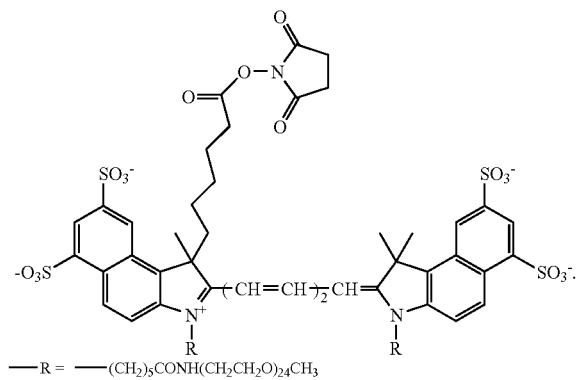

In some embodiments, each complex is excited at 635 nm or 633 nm. In some embodiments, each complex is present at identical protein concentrations.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

41 (Example 41) and Cy5® dye at identical protein concentrations in an aqueous buffer, when excited at 630 nm. The data shows that the fluorescent group of the invention has less fluorescence quenching than Cy5® dye when the antibody is at higher degrees of labeling. (See Example 97.)

Figure 4:
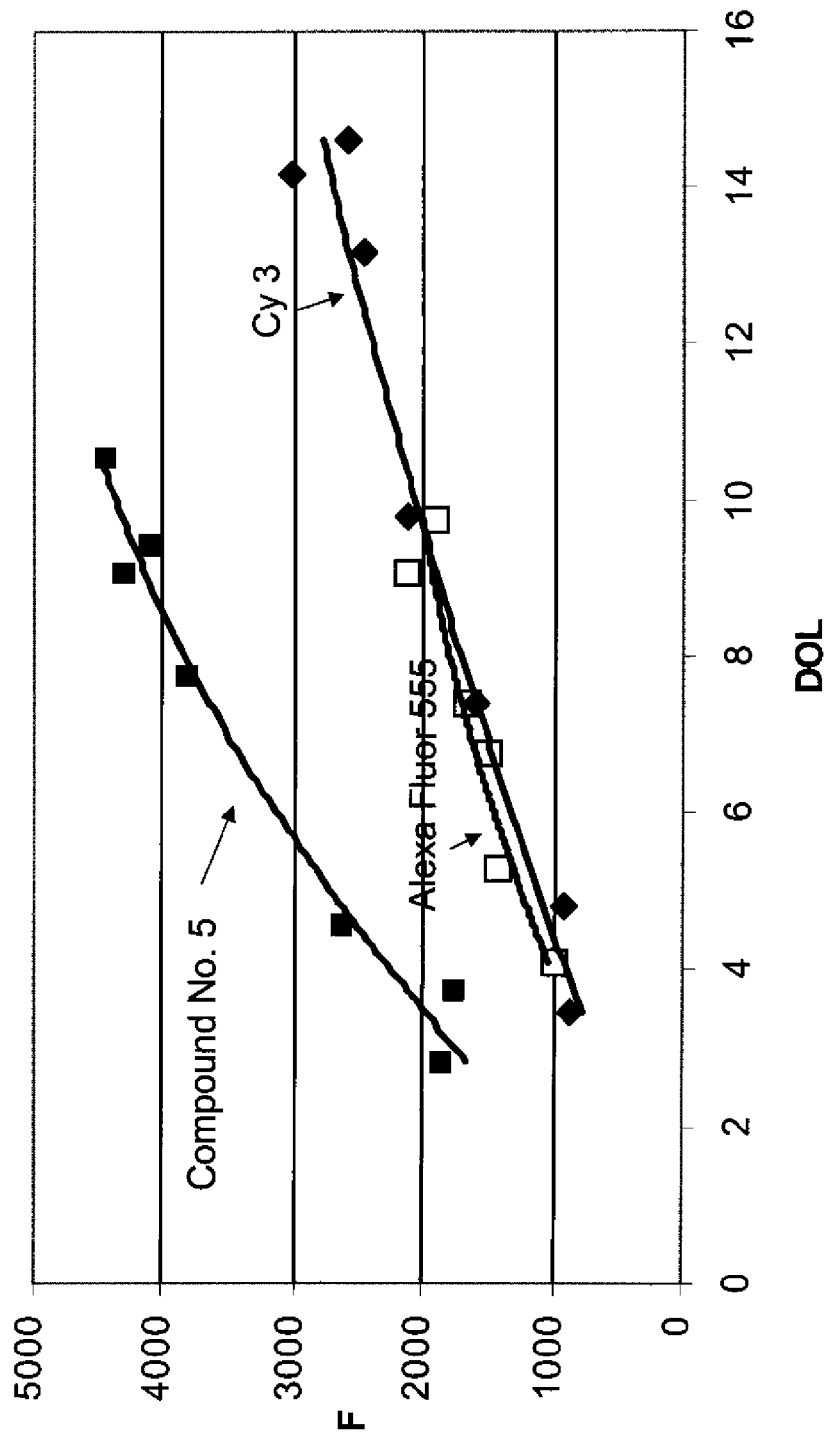

FIG. 4 is a plot of total fluorescence vs. degree of labeling (DOL) for streptavidin conjugates of Compound No. 5 (Example 5), Cy3® dye and Alexa Fluor 555® dye at identical protein concentrations in an aqueous buffer, when excited at 530 nm. The higher slope given by the fluorescent group of the invention demonstrates that the fluorescent group of the invention is intrinsically more fluorescent than either Cy3® dye or Alexa Fluor 555® dye. (See Example 97.)

Figure 5:
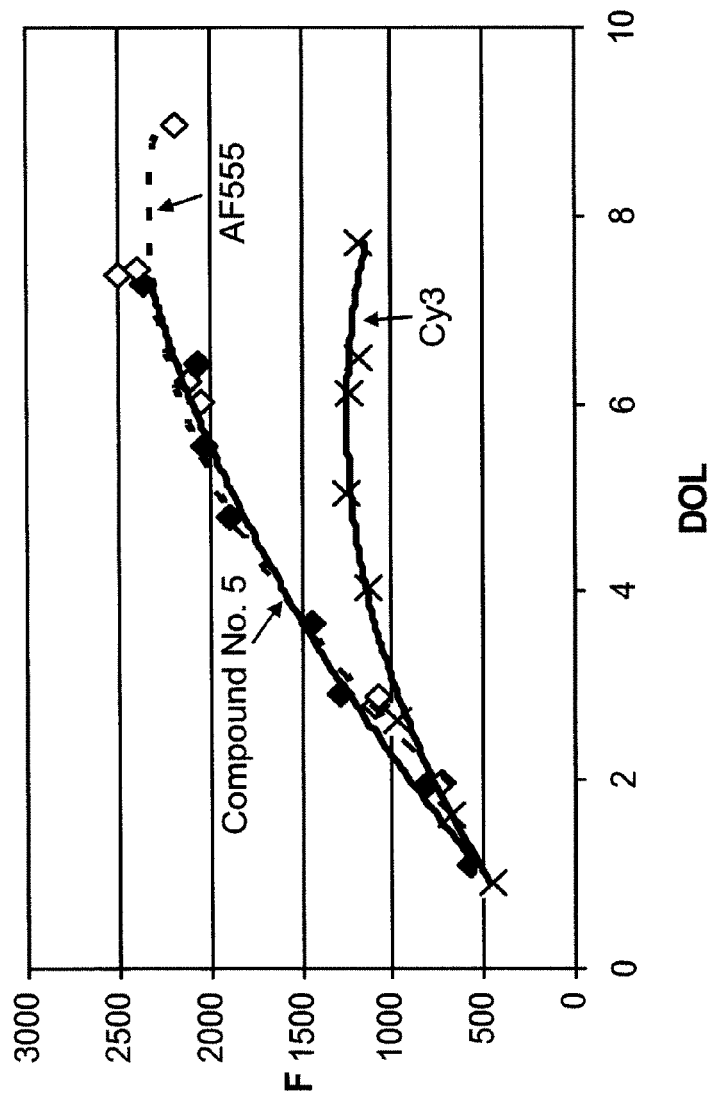

FIG. 5 is a plot of total fluorescence vs. degree of labeling (DOL) for goat anti-mouse conjugates of Compound No. 5 (Example 5), Cy3® dye and Alexa Fluor 555® dye at identical protein concentrations in an aqueous buffer, when excited at 530 nm. All three fluorescent groups have similar absorption and emission maxima, but Cy3® dye and Alexa Fluor 555® dye do not have a water soluble polymer group. The data shows that the fluorescent group of the invention is as bright as Alexa Fluor 555® dye over a wide range of degree of labeling. However, the fluorescence of Cy3® dye is substantially quenched at higher degrees of labeling. (See Example 97.)

Figure 6:
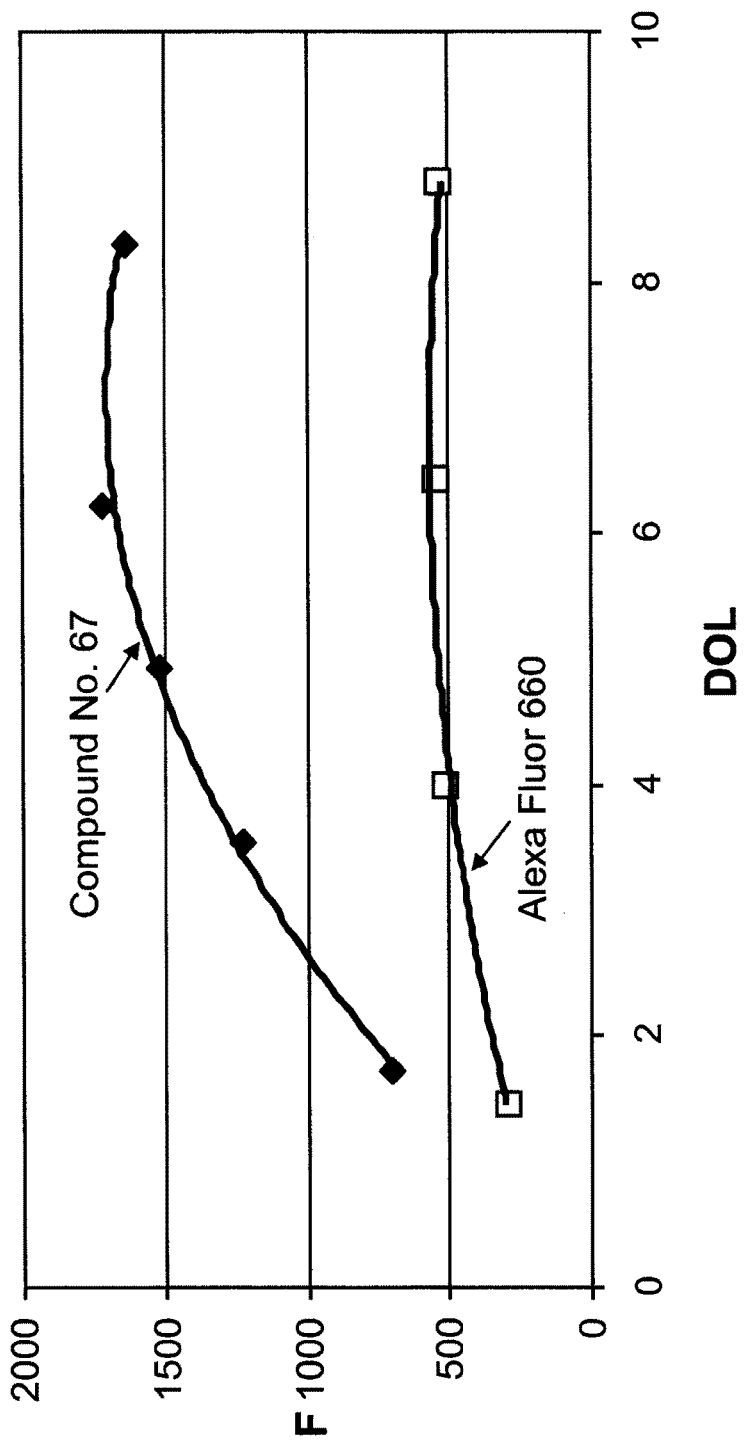

FIG. 6 is a plot of total fluorescence vs. degree of labeling (DOL) for goat anti-mouse IgG conjugates of Compound No. 67 (Example 67) and a spectrally similar fluorescent group without a water soluble polymer group, Alexa Fluor 660® dye, at identical protein concentrations in an aqueous buffer, when excited at 640 nm. The data shows that, compared to Alexa Fluor 660® dye, the fluorescent group of the invention has higher fluorescence quantum yield over a wide of degree of labeling and has less fluorescence quenching when the antibody is at higher degrees of labeling. (See Example 97.)

Figure 7:
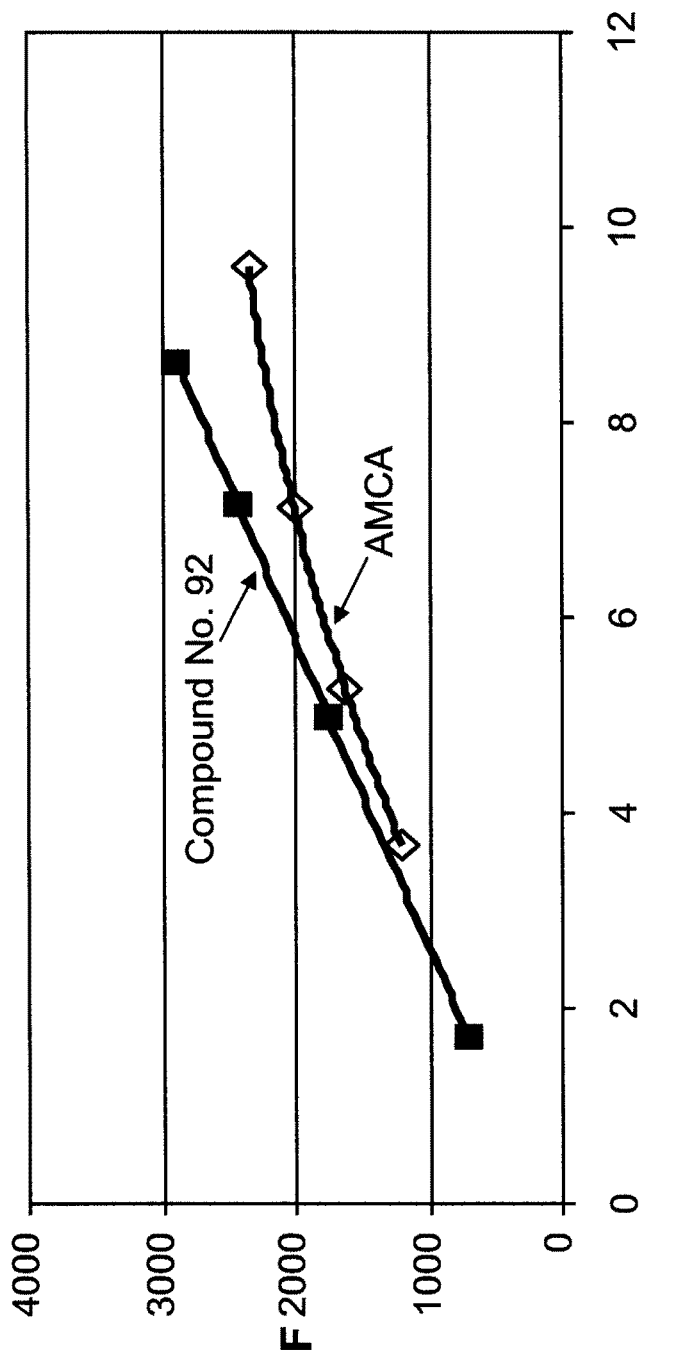

FIG. 7 is a plot of total fluorescence vs. degree of labeling (DOL) for goat anti-mouse IgG conjugates of Compound No. 92 (Example 92) and a similar fluorescent group without a water soluble polymer group, AMCA, at identical protein concentrations in an aqueous buffer, when excited at 350 nm. The data shows that, compared to AMCA, the fluorescent group of the invention has higher fluorescence quantum yield over a wide of degree of labeling and has less fluorescence quenching when the antibody is at higher degrees of labeling. (See Example 97.)

Figure 8:
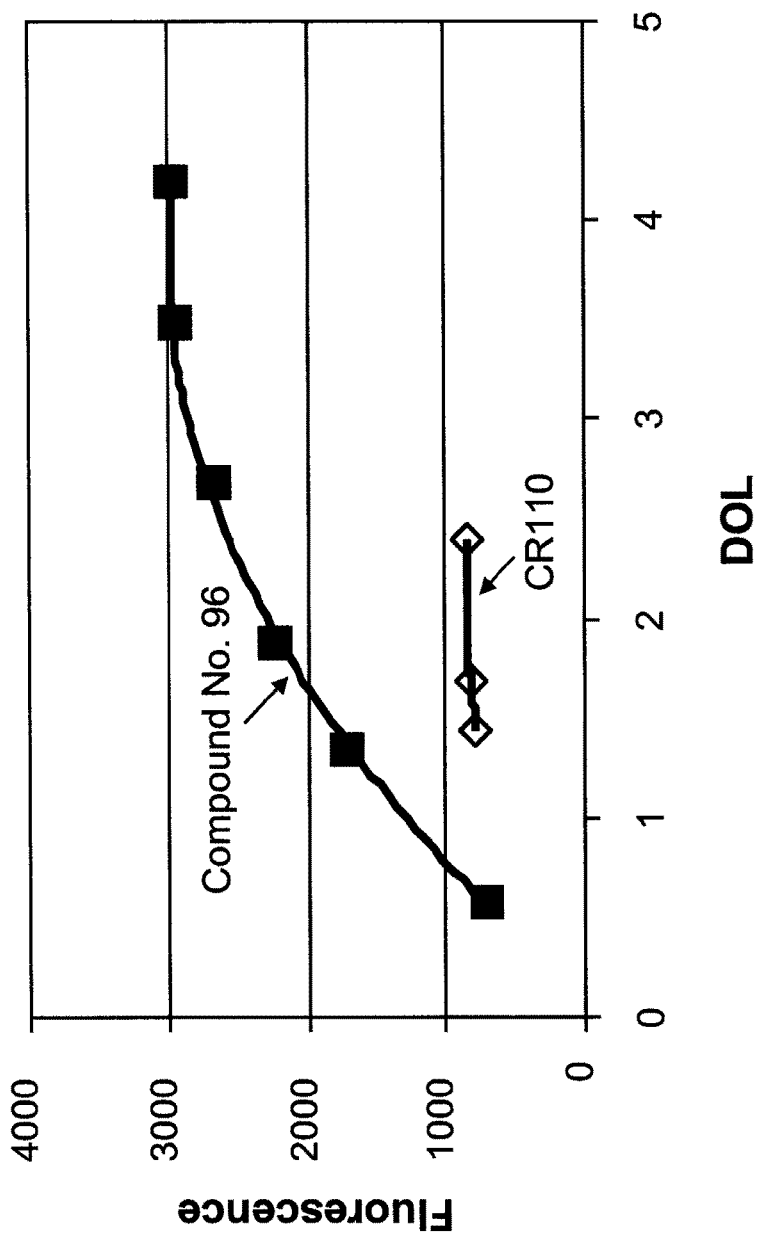

FIG. 8 is a plot of total fluorescence vs. degree of labeling (DOL) for goat anti-mouse IgG conjugates of Compound No. 96 (Example 96) and a similar fluorescent group without a water soluble polymer group, 5(6)-carboxyrhodamine 110 (CR110), at identical protein concentrations in an aqueous buffer, when excited at 488 nm. The data shows that, compared to CR110, the fluorescent group of the invention has higher fluorescence quantum yield over a wide degree of labeling and has less fluorescence quenching when the antibody is at higher degrees of labeling. (See Example 97.)

Figure 9:
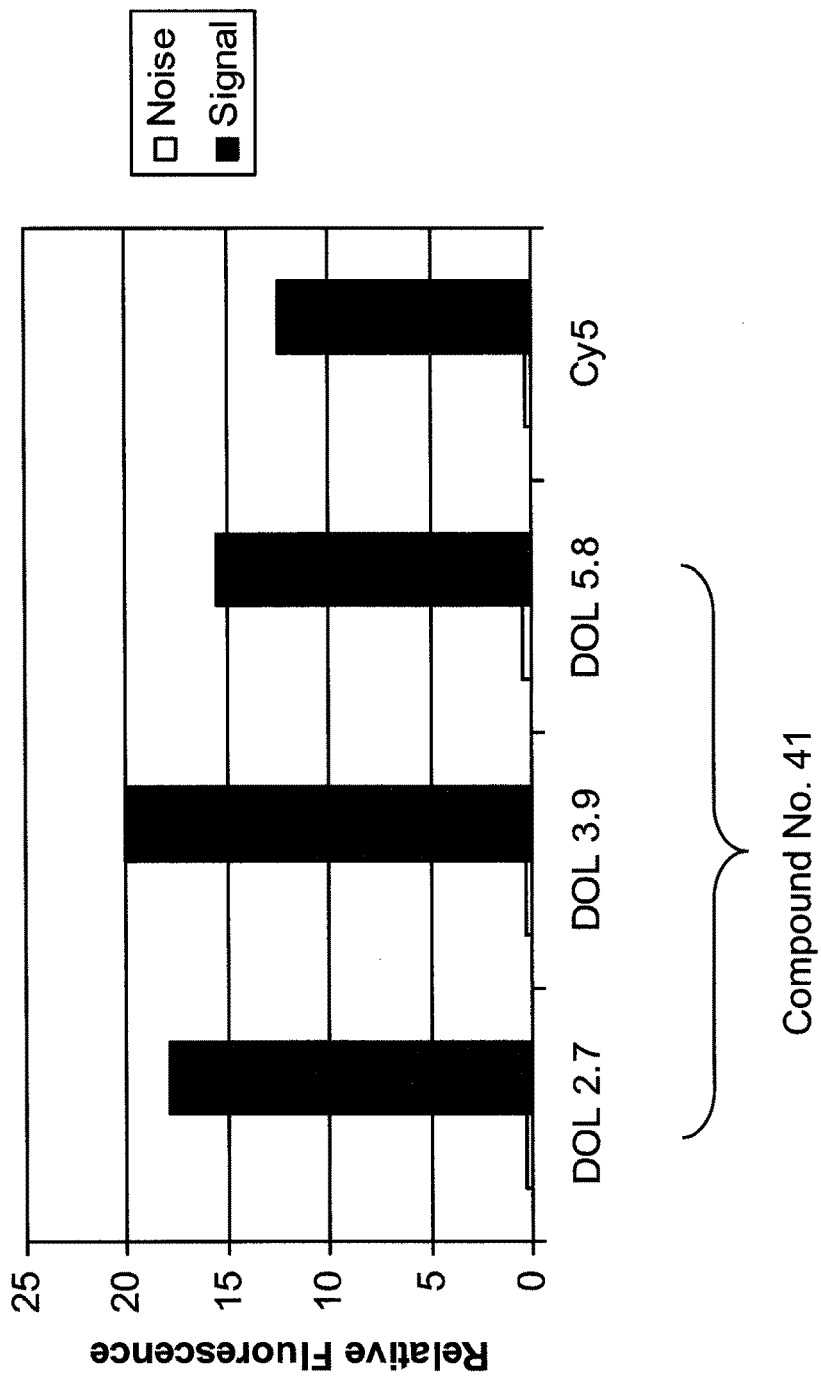

FIG. 9 is a graphical representation showing the relative fluorescence levels of Jurkat cells stained with various fluorescently labeled antibodies as measured by flow cytometry. The cells were first labeled with mouse anti-human CD3 antibody and then stained with goat anti-mouse IgG labeled with Compound No. 41 at a degree of labeling of 2.7, 3.9 and 5.8, respectively, or with a commercially available goat anti-mouse IgG labeled with Cy5® dye ~(dark columns). To measure the background fluorescence from each labeled secondary antibody, the cells were also stained directly with each of the fluorescent secondary antibody without the primary antibody (blank columns). The results show that cells stained with antibody conjugates of this invention are 25-60% brighter than cells stained with the commercial antibody conjugate, with excellent signal to noise ratio. (See Example 104.)

Figure 10:
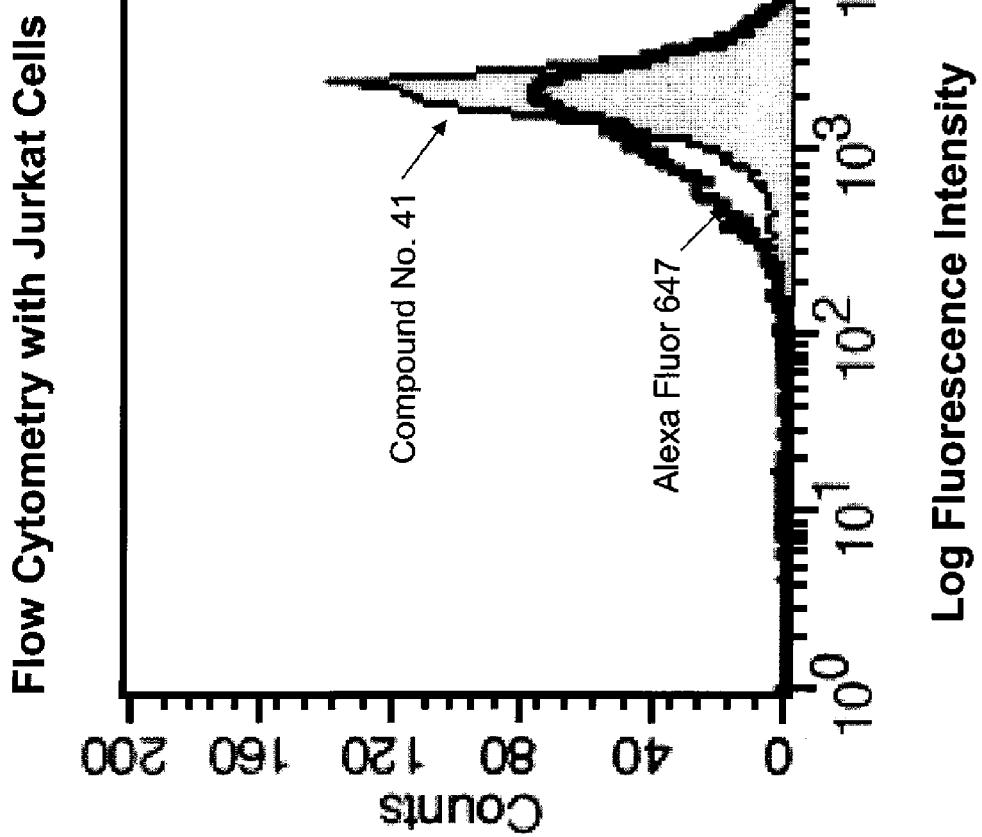

FIG. 10 is a flow cytometry histogram showing the distribution of immunofluorescently stained cells as a function of fluorescence intensity. Jurkat cells were fixed, permeabilized, and incubated with mouse anti-human CD3 antibody. The CD3 antibody was followed by incubation with goat anti-mouse IgG labeled with AlexaFluor647® dye (DOL 3.1) (gray-lined peak) or with compound No. 41 (DOL 3.9) (dark-lined peak). The figure shows that AlexaFluor647® dye-labeled antibody gave more weakly stained cells and more scattered fluorescence staining than the antibody labeled with the fluorescent group of the invention. (See Example 105.)

Figure 11:
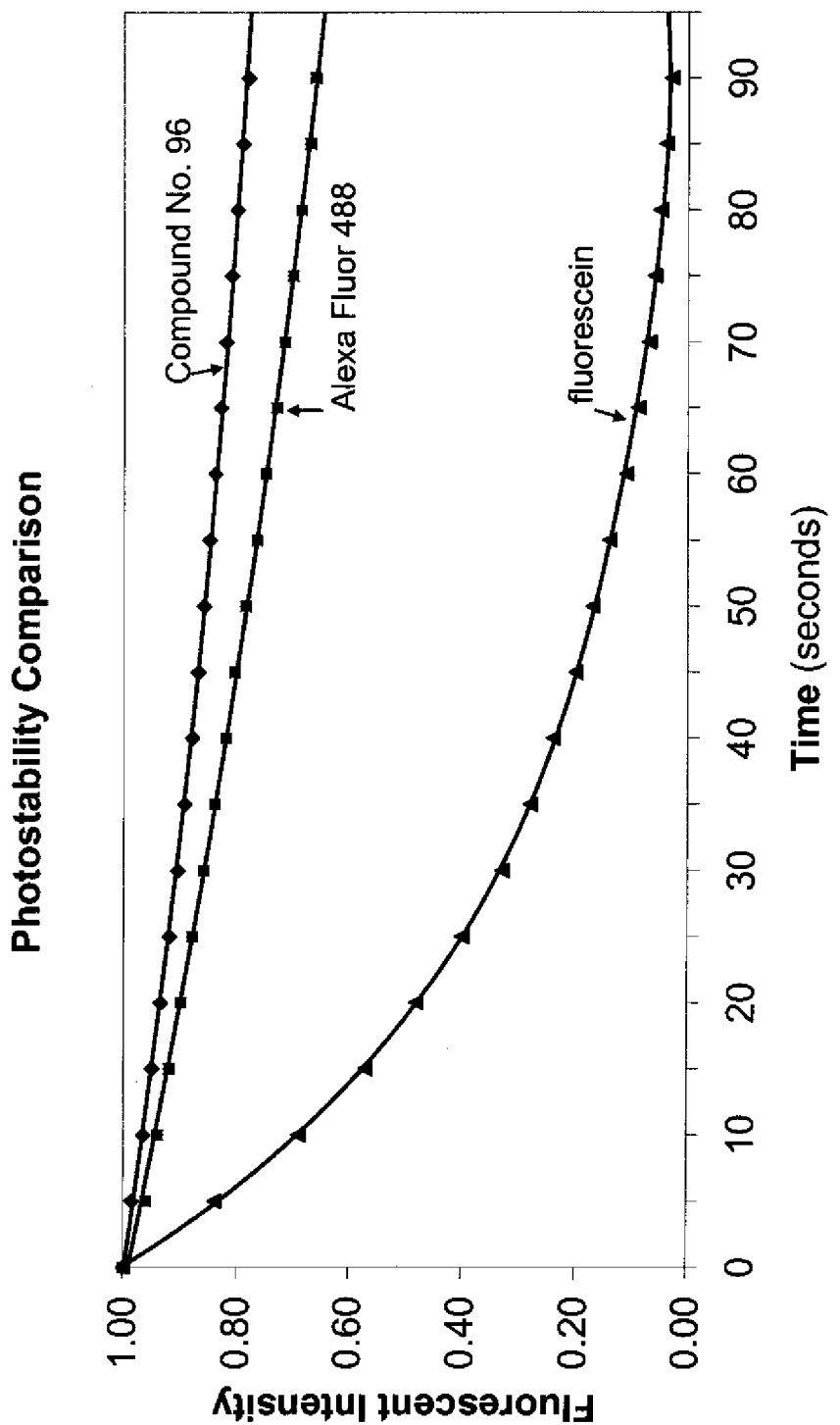

FIG. 11 shows a comparison of the photostability of a fluorescent group of the invention over time compared to the fluorescein and Alexa Fluor 488® dye. Actin filaments were stained with phalloidin labeled with compound No. 96, Alexa Fluor 488® dye or fluorescein and the relative fluorescence of each sample was plotted vs. time. FIG. 11 shows that the photostability of a biomolecule labeled using compound 96 is superior to fluorescein as well as Alexa Fluor 488® dye. (See Example 107.)

Figure 12A:
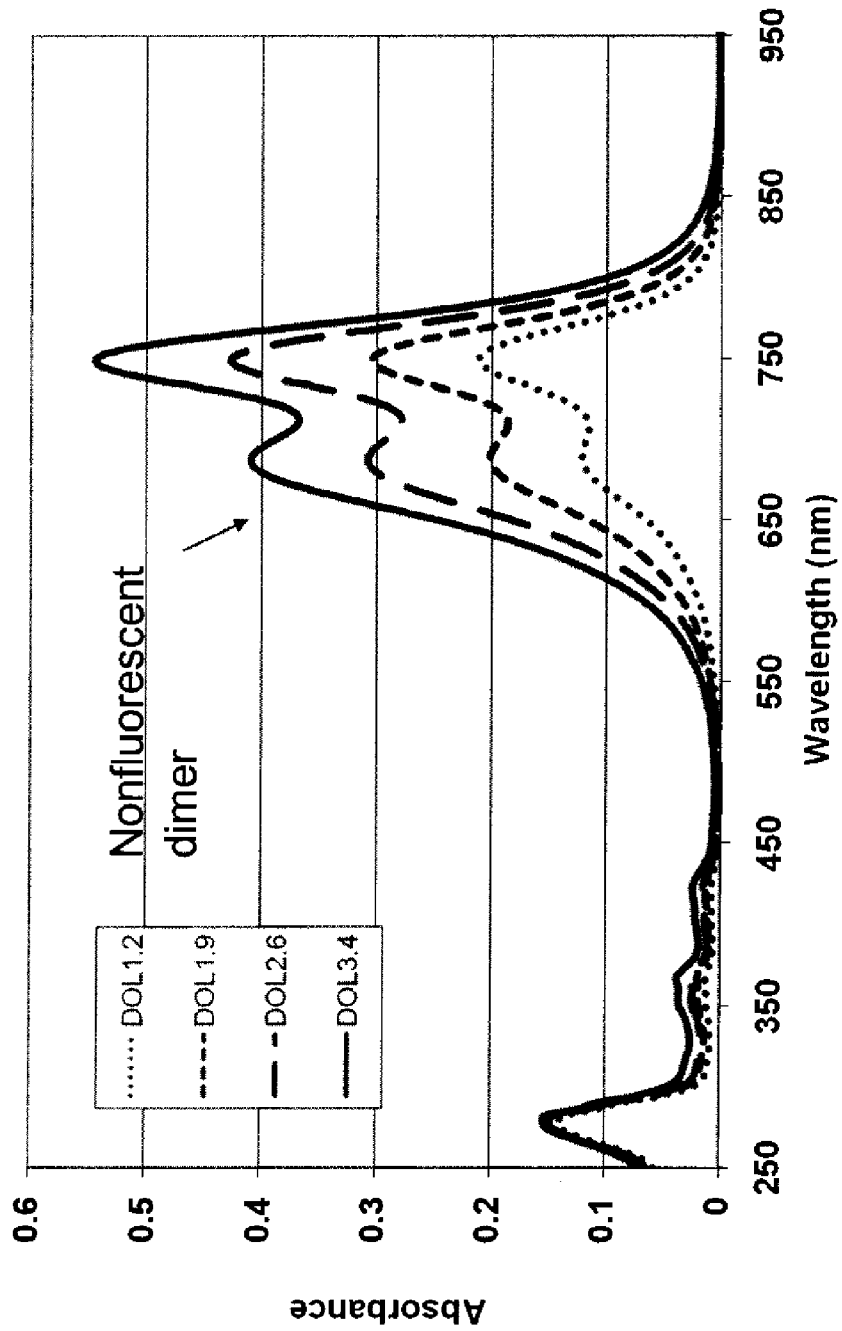
Figure 12B:
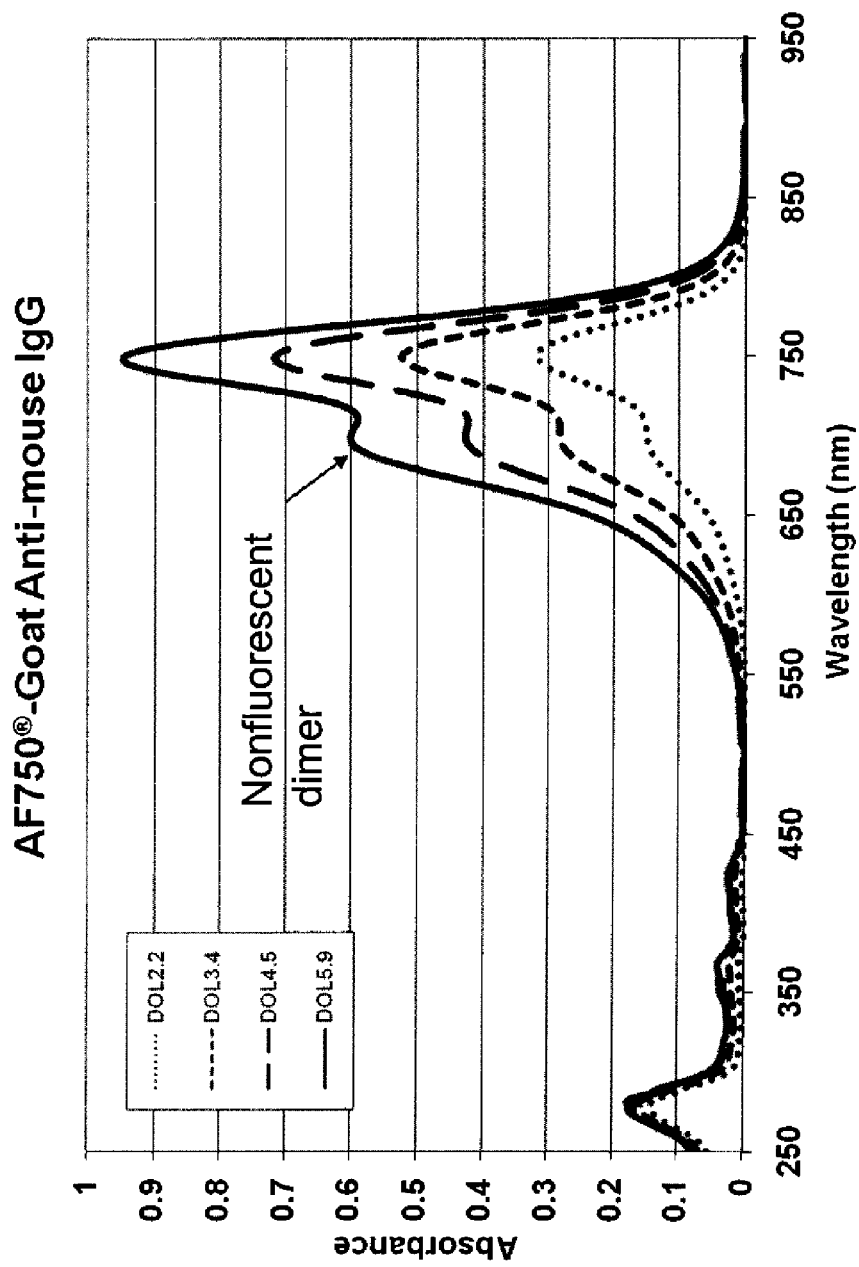
Figure 12C:
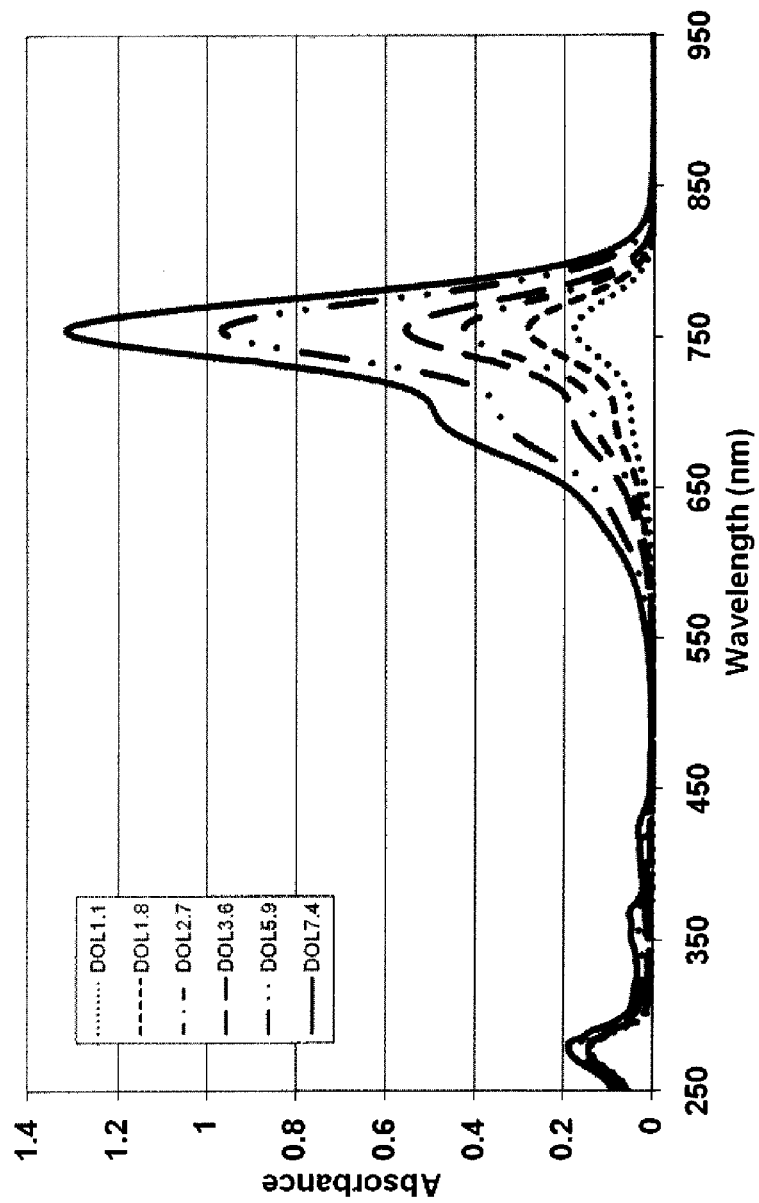

FIGS. 12A, B, and C are graphical representations showing the absorption spectra of goat anti-mouse IgG conjugates prepared at different degree of labeling (DOL) with three near-IR dyes: FIG. 12A represents the absorption spectra of the conjugate formed from labeling goat anti-mouse IgG with Cy7® dye at 4 different DOL (1.2 to 3.4 dye molecules per antibody). FIG. 12B represents the absoprtion specta of the conjugate formed from labeling goat anti-mouse IgG with Alexa Fluor 750® (AF750®) dye at four different DOL (2.2 to 5.9 dye molecules per antibody). FIG. 12C represents the absorption spectra of the conjugate formed from labeling goat anti-mouse IgG with Dye No. 29 (Table 3), at six different DOL (1.1 to 7.4 dye molecules per antibody). All spectra were taken at room temperature in PBS 7.4 buffer. The spectra of both Cy7® dye- and AF750® dye-labeled conjugates (A and B) display a double peak characteristic of dye aggregation while the spectra of Compound No. 29-labeled conjugates (C) show mainly a single peak, indicating a substantial lack of dye aggregation.

Figure 13:
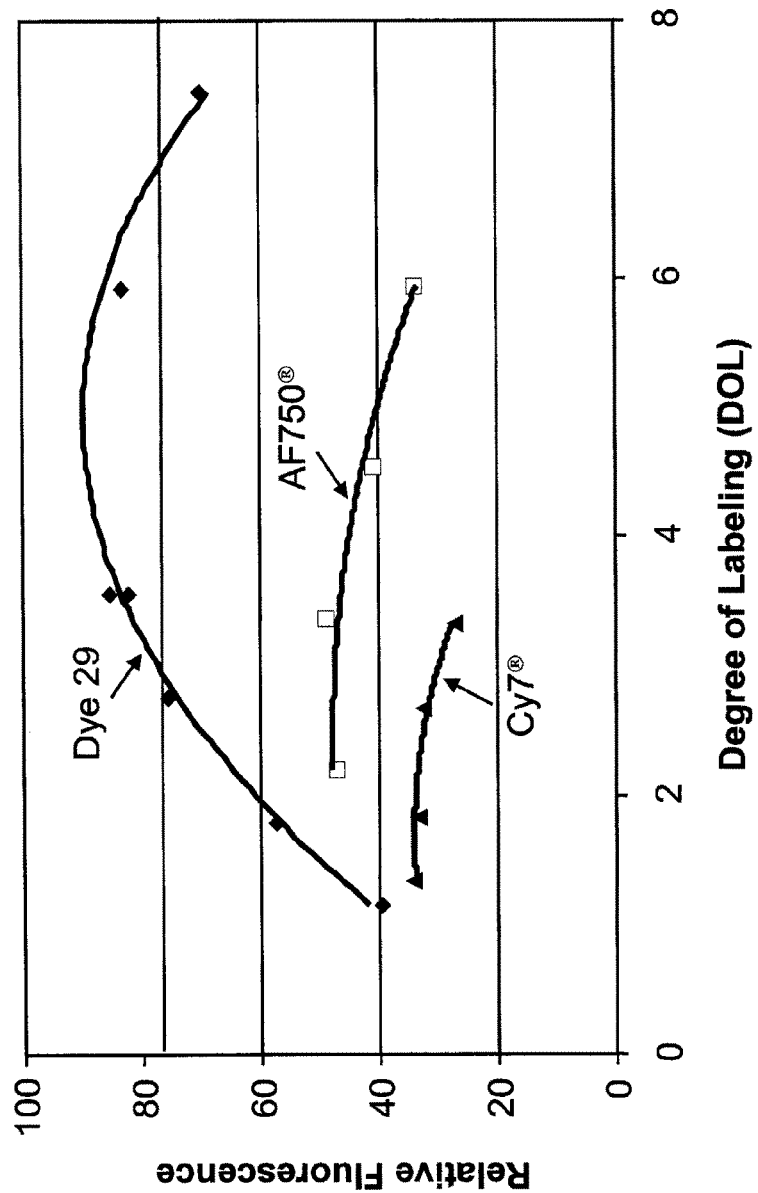

FIG. 13 is a graphical representation of total fluorescence vs. degree of labeling (DOL) for goat anti-mouse IgG conjugates labeled with a near-IR dye of the invention, Dye No. 29 (Table 3), and goat anti-mouse IgG conjugates labeled each labeled with one of two other spectrally similar near-IR fluorescent groups without a water soluble polymer group, Alexa Fluor 750® (AF750®) dye and Cy7® dye, at identical protein concentrations in pH 7.4 PBS buffer, when excited at 735 nm. The data shows that, compared to AF750® dye and Cy7® dye, the fluorescent group of Dye 29 has higher fluorescence quantum yield over a wide degree of labeling and has less fluorescence quenching when the antibody is at higher degrees of labeling.

Figure 14:
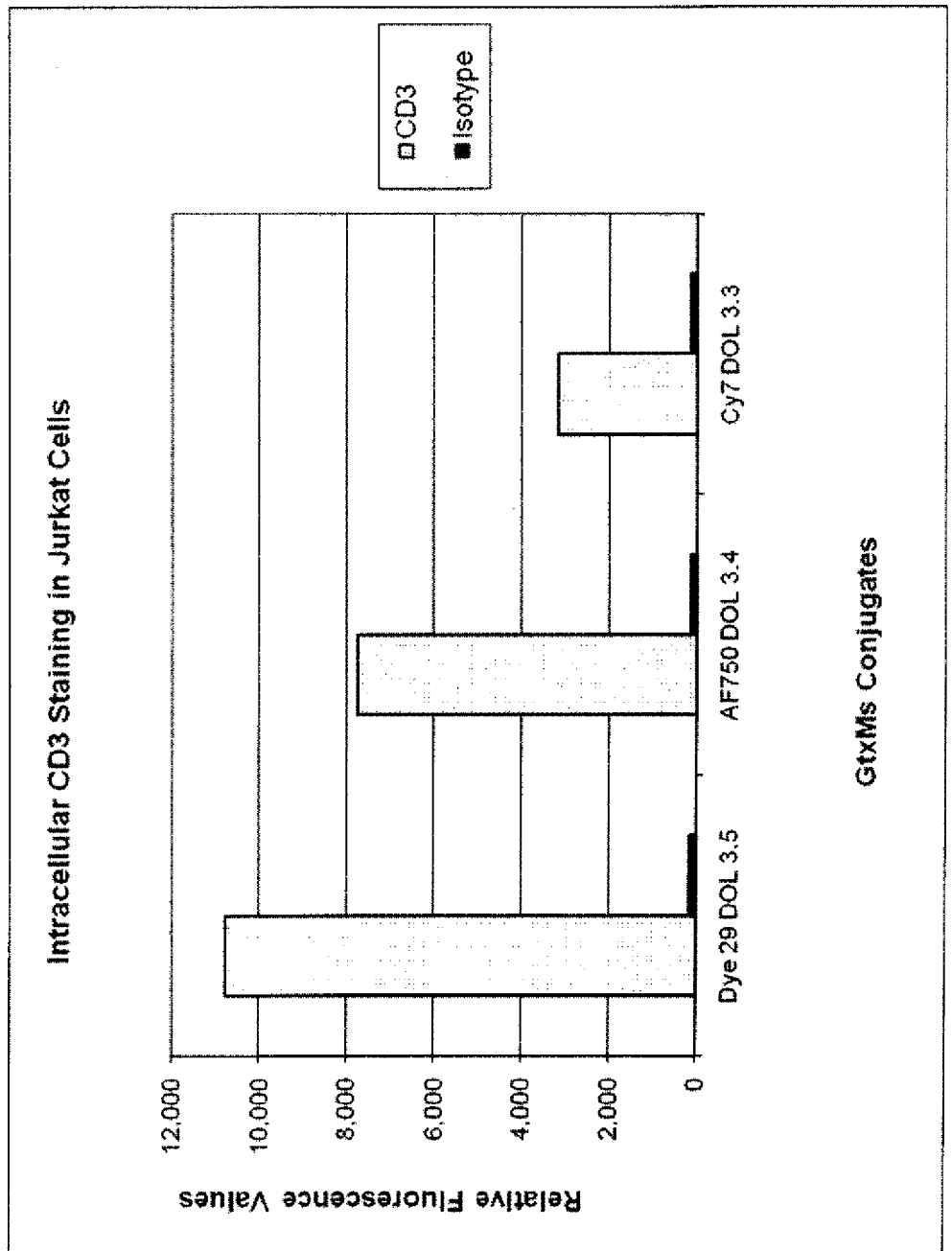

FIG. 14 is a graphical representation showing the relative fluorescence levels of Jurkat cells stained with goat anti-mouse IgG labeled with a near-IR dye of the invention, Dye No. 29 (Table 3), Alexa Fluor 750® dye and Cy7® dye, respectively, as measured by flow cytometry. The cells were first labeled with mouse anti-human CD3 antibody and then stained with one of the three labeled secondary antibodies, which all have a similar degree of labeling. To measure the background fluorescence from each labeled secondary antibody, the cells were also stained with an isotype control primary antibody and each of the fluorescent secondary antibody (dark columns). The results show that cells stained with antibody conjugate of this invention are significantly brighter and have excellent signal-to-noise ratio.

Figure 15:
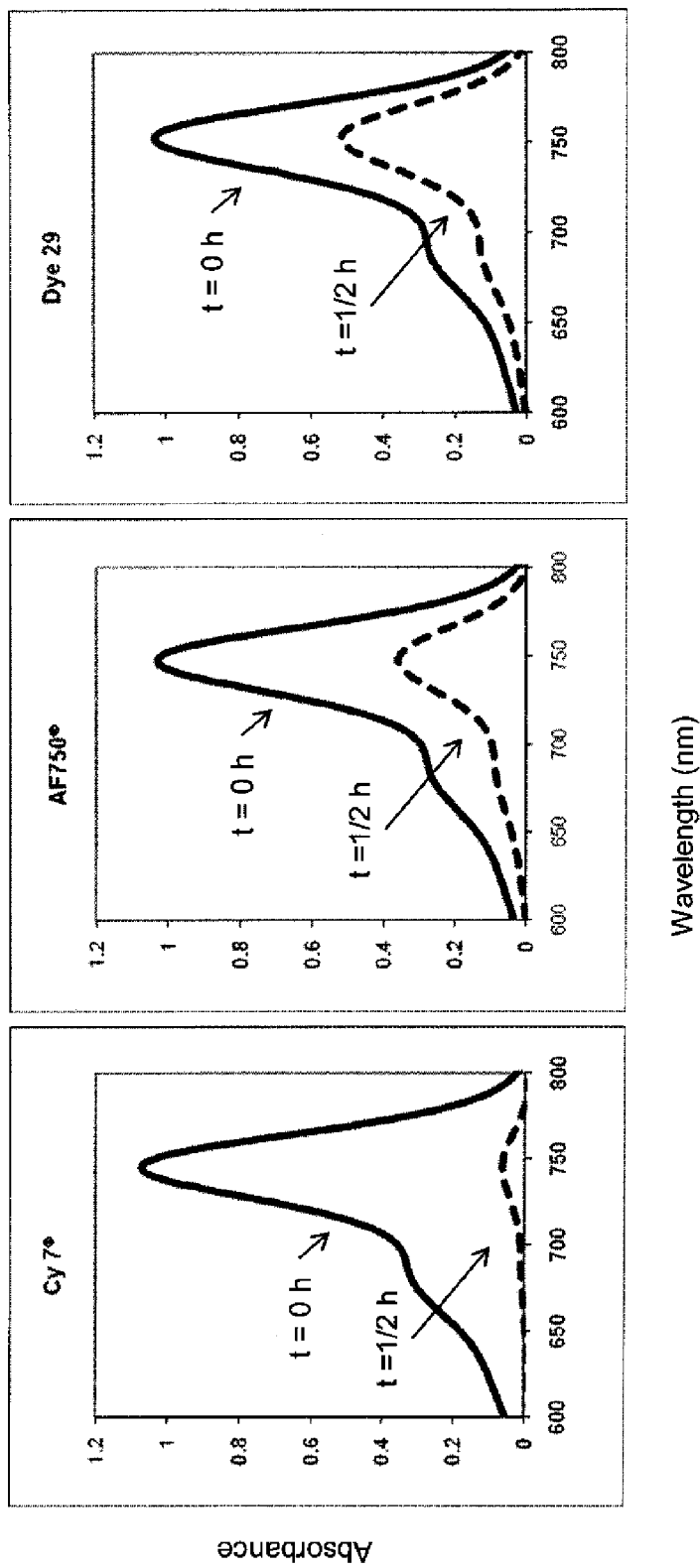

FIG. 15 compares the photostability of three near-IR dyes: Compound No. 29 of Table 3, Alexa Fluor 750® (AF750®) dye and Cy7® dye. Solutions of the three dyes at 5 μM dye concentration were exposed to sun light for ½ hour. Absorption spectra of the solutions were recorded before and after the photolysis. The results show the near-IR dye of the invention is significantly more stable than both AF750® dye and Cy7® dye.

Figure 16A:
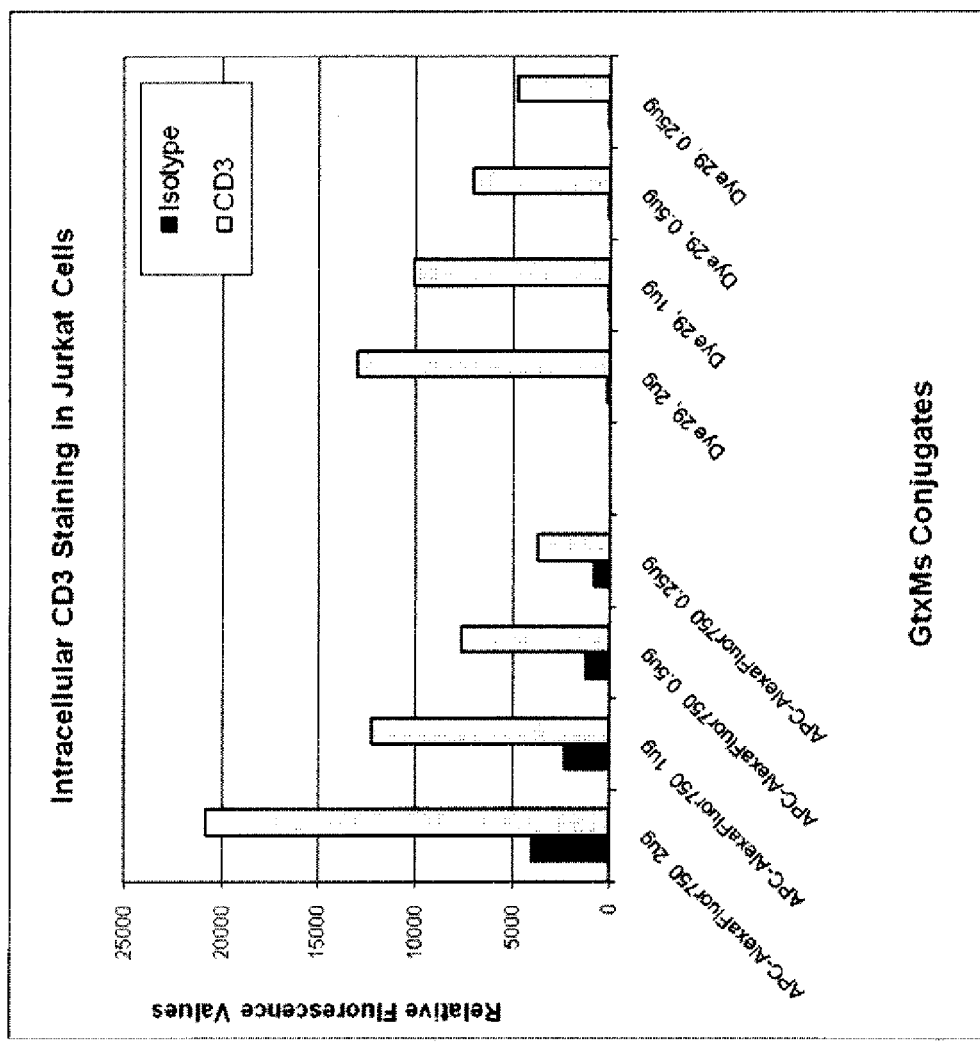
Figure 16B:
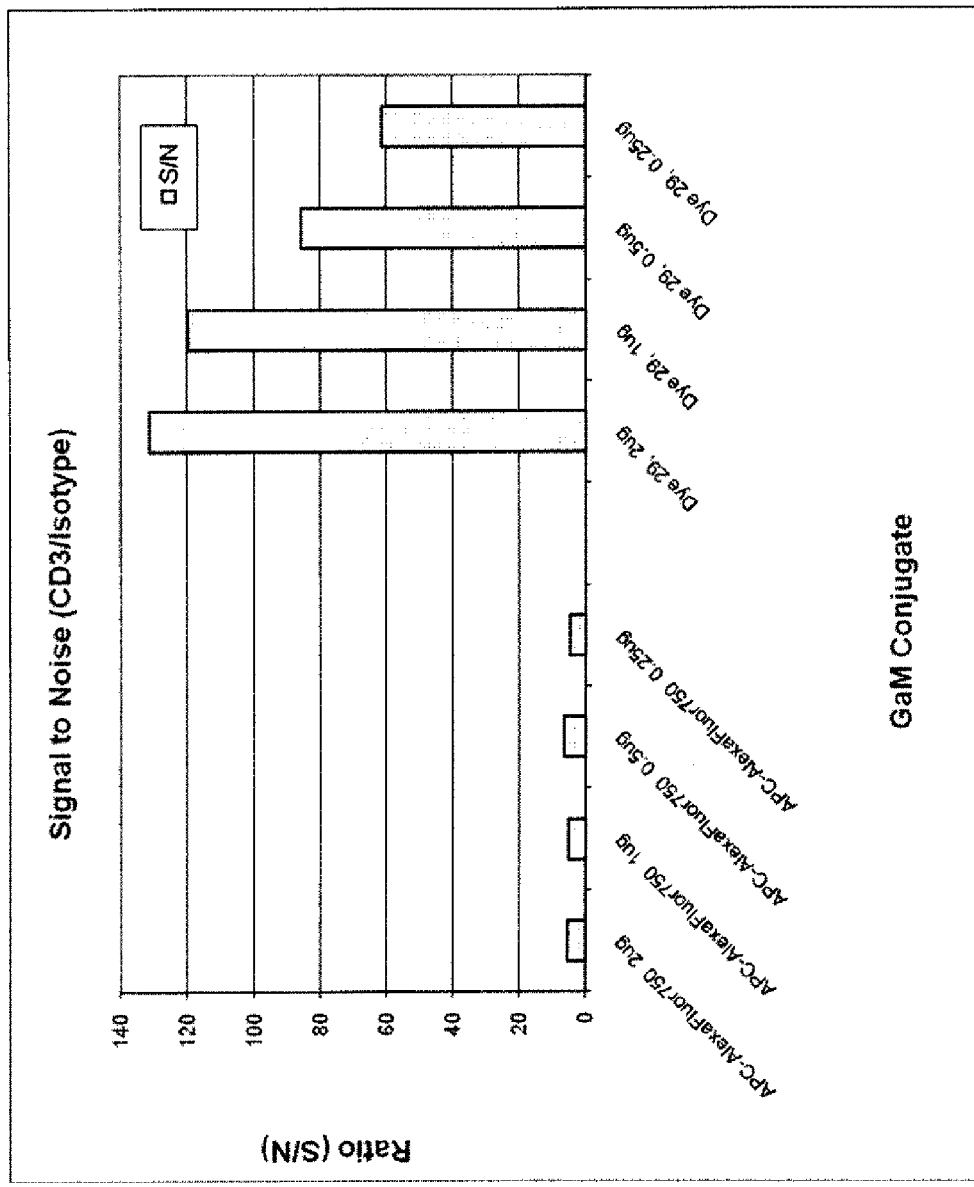

FIGS. 16A and B are graphical representations for relative fluorescence levels of Jurkat cells stained intracellularly with an antibody labeled with Alexa Fluor 750® (AF750®) dye or Dye 29 (Table 3). FIG. 16A is a graphical representation showing the relative fluorescence levels of Jurkat cells stained with indicated amount of either goat anti-mouse IgG labeled with compound No. 29 (DOL=3.5) or a commercially available goat anti-mouse IgG labeled with an APC-AF750® tandem dye (Invitrogen), as measured by flow cytometry. The cells were first labeled with mouse anti-human CD3 antibody and then stained with one of the two labeled secondary antibodies. To measure the background fluorescence from each labeled secondary antibody, the cells were also stained with an isotype control primary antibody and each of the fluorescent secondary antibody (darkened columns). FIG. 16B is a graphical representation showing the signal-to-noise ratios of the stainings from FIG. 16A. Flow cytometry experiments were performed on a BD LSR II equipped with a 633 nm laser and 780/60 nm PMT detector. The results show that Dye No. 29 gives high fluorescent signal with very little background while the APC-AF750® tandem dye showed significant non-specific staining. The results show that Dye No. 29 has very little absorption at 633 nm whereas the tandem dye has nearly maximal absorption at the laser wavelength due to the donor dye APC. Dye No. 29, near-IR dyes the like disclosed herein are particularly advantageous for flow cytometry analysis using a 633 nm or longer wavelength excitation source.

Figure 17:
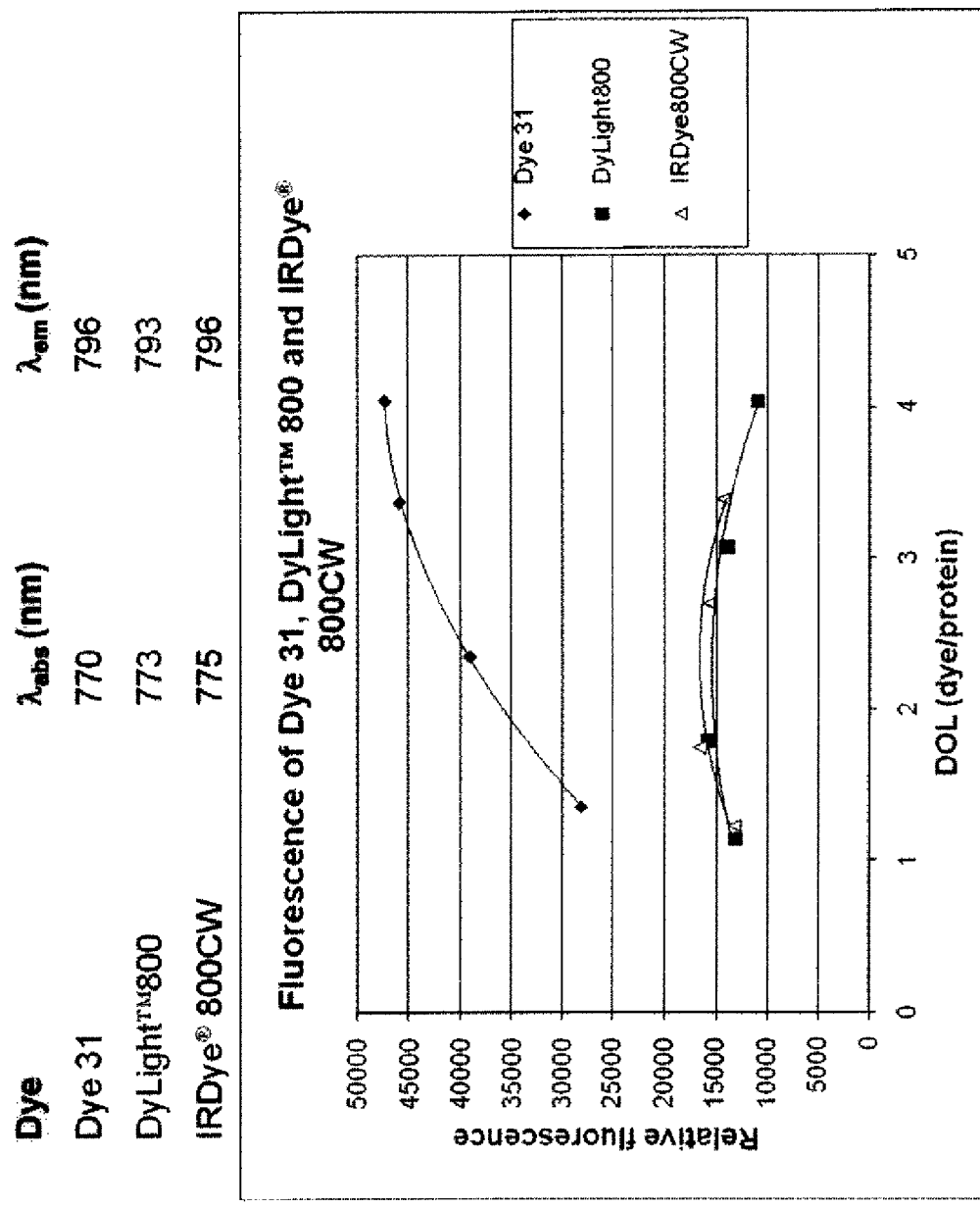

FIG. 17 is a graphical representation of total fluorescence vs. degree of labeling (DOL) for goat anti-mouse IgG conjugates of three near-IR dyes with similar wavelengths: Dye No. 31 (Table 3), Dylight™ 800 Dyefrom Thermo Fisher and IRDye 800® CW dye from Li-Cor Biosciences. The data show that Dye No. 31 is significantly brighter than the other two dyes over a wide range of DOL.

Figure 18:
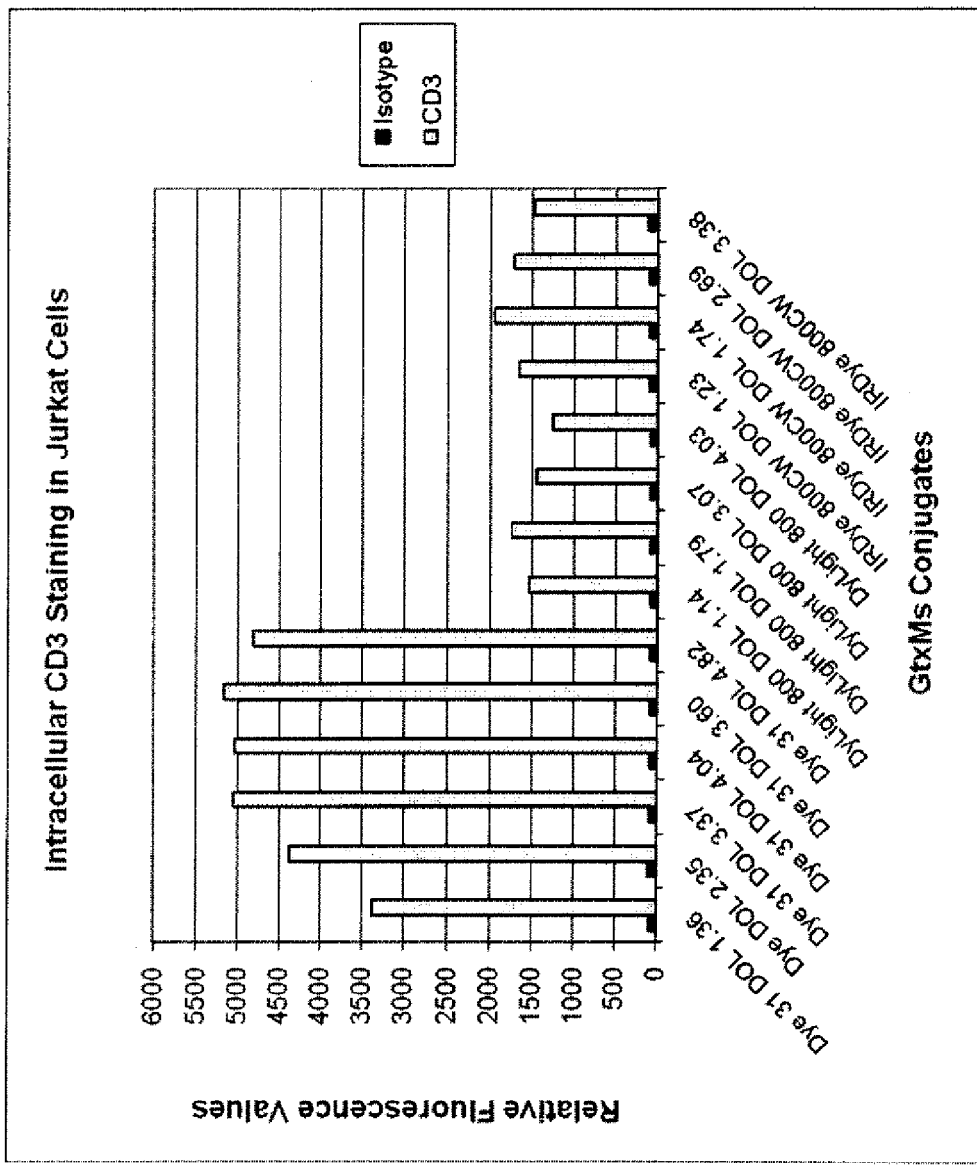

FIG. 18 is a graphical representation of the relative fluorescence levels of Jurkat cells stained with goat anti-mouse IgG antibodies labeled with Dye No. 31 (Table 3), Dylight™ 800 from Thermo Fisher and IRDye 800®CW dye from Li-Cor Biosciences, respectively, as measured by flow cytometry. To assess the fluorescence quenching of the three near-IR dyes, the antibody was labeled with each dye at different degree of labeling (DOL) as indicated. The cells were first labeled with mouse anti-human CD3 antibody and then stained with one of the labeled secondary antibodies. To measure the background fluorescence from each labeled secondary antibody, the cells were also stained with an isotype control primary antibody and each of the fluorescent secondary antibodies (isotype, dark columns). The results show that Dye No. 31 is significantly brighter than both Dylight™ 800 dye and IRDye 800® CW dye over a wide range of DOL. Also importantly, Dye No. 31 produced much better signal-to-noise ratio than the other two dyes.

Figure 19:
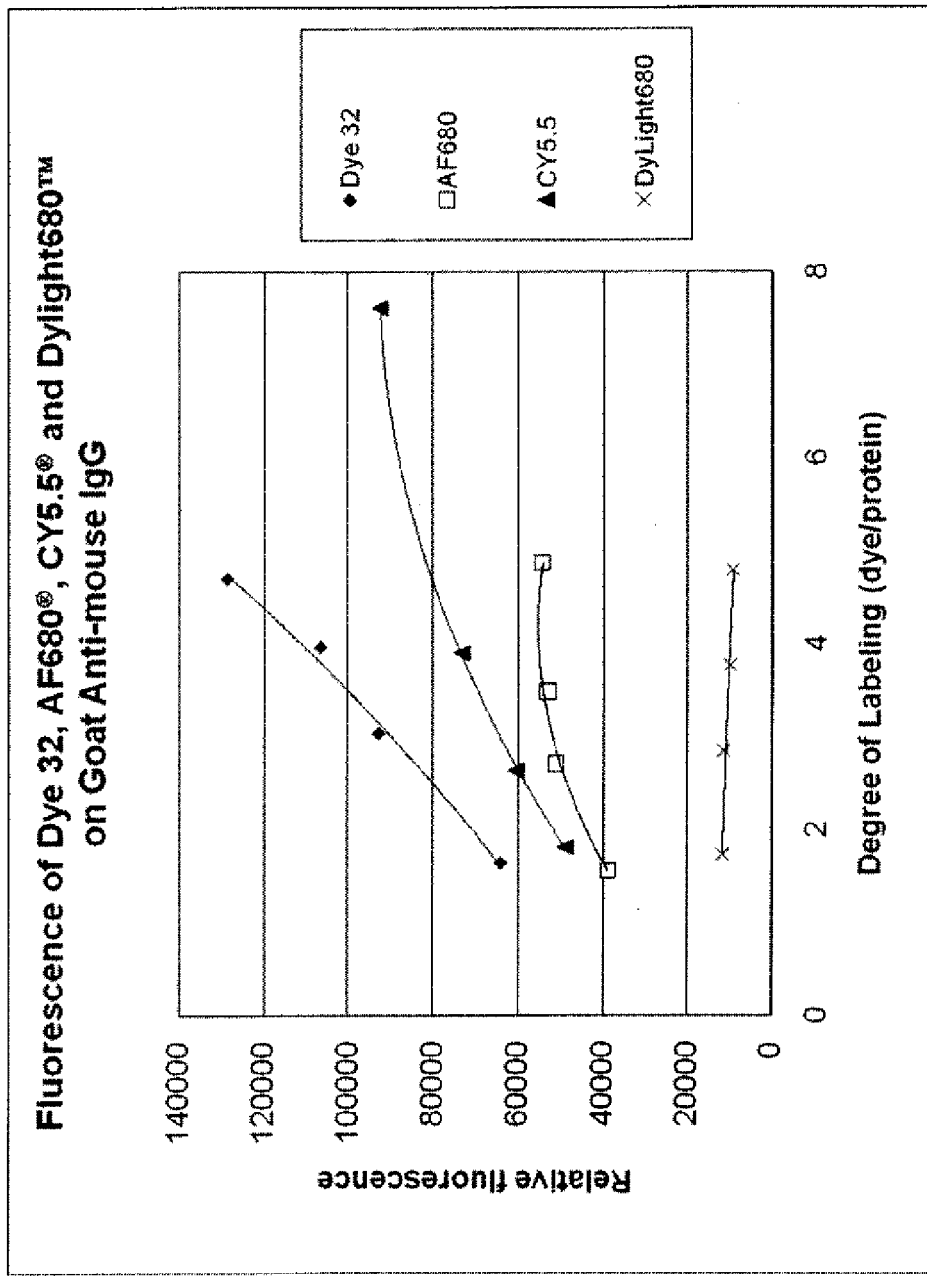

FIG. 19 is a plot of total fluorescence vs. degree of labeling (DOL) for goat anti-mouse IgG conjugates of a near-IR dye of the invention, Dye No. 32 (Table 3), and three spectrally similar near-IR fluorescent groups, Cy5.5® dye from GE Healthcare, Alexa Fluor 680® (AF680) dye from Invitrogen and Dylight™ 680 from Thermo Fisher, respectively. Fluorescence measurements were made in pH 7.4 PBS buffer using 660 nm excitation. The data shows that, compared to Cy5.5®, Alexa Fluor 680® and Dylight™ 680, the fluorescent group of the invention has higher fluorescence quantum yield over a wide degree of labeling.

Figure 20A:
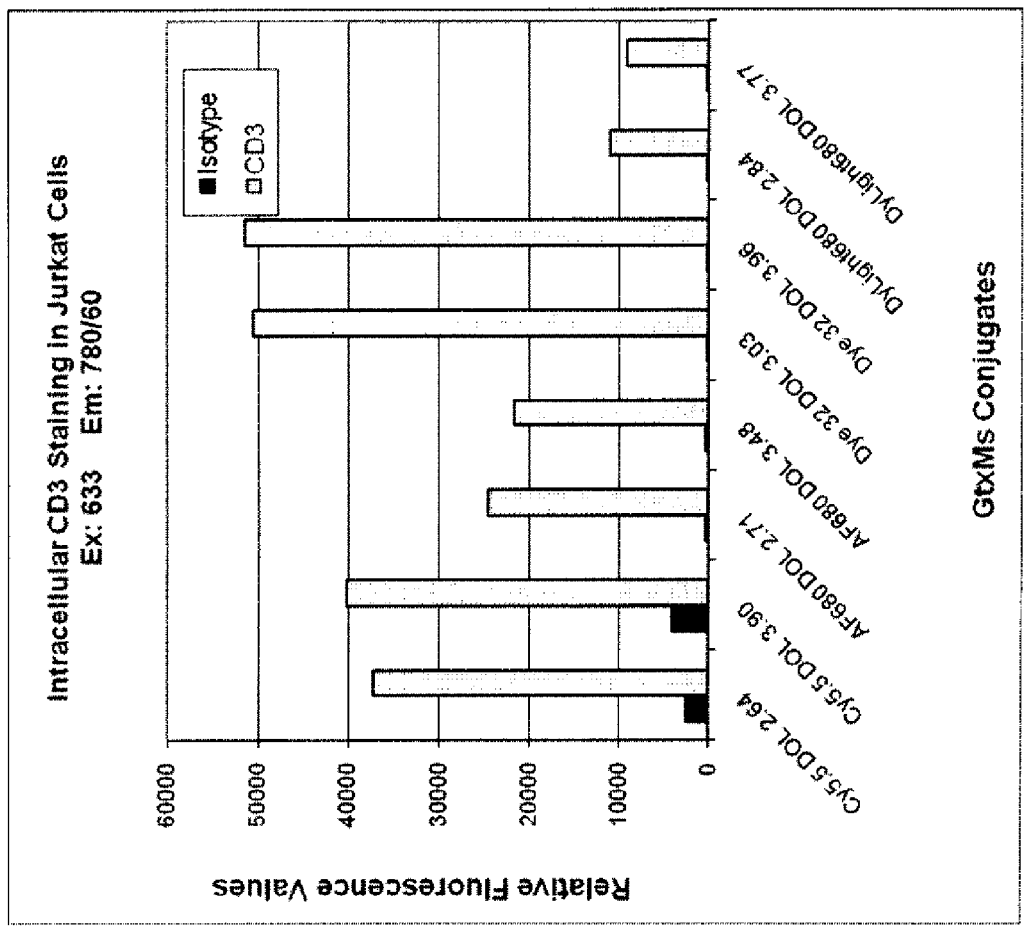
Figure 20B:
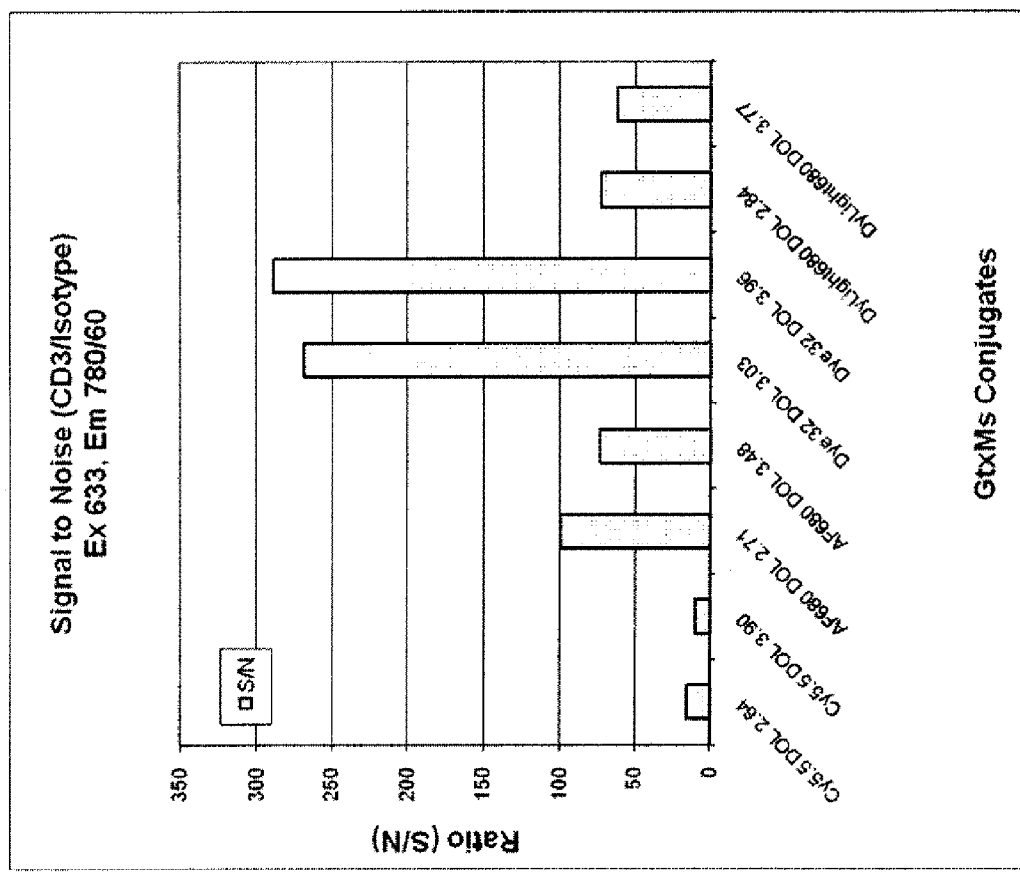

FIGS. 20A and B are graphical representations of data related to the relative fluorescence level of Jurkat cells stained with goat anti-mouse IgG antibodies labeled individually with four different near IR dyes. FIG. 20A is a graphical representation showing the relative fluorescence levels of Jurkat cells stained with goat anti-mouse IgG antibodies labeled with Dye No. 32 (Table 3), Cy5.5® dye from GE Healthcare, Dylight™ 680 dye from Thermo Fisher or Alexa Fluor 680® (AF680®) dye from Invitrogen, as measured by flow cytometry. To assess the fluorescence quenching of the three near-IR dyes, each portion of goat anti-mouse IgG antibody was labeled with one dye at one of two different degree of labeling (DOL) as indicated to form a set of eight antibodies. The cells were first labeled with mouse anti-human CD3 antibody and then stained with one of the labeled secondary antibodies. To measure the background fluorescence from each labeled secondary antibody, the cells were also stained with an isotype control primary antibody and each of the fluorescent secondary antibodies (isotype, dark columns). FIG. 20B is a plot of signal-to-noise ratio (S/N) for the staining results in FIG. 20A. The data show that conjugates labeled with Dye No. 32 are much brighter and more specific in staining than conjugates prepared from the other three commercial near-IR dyes.

DETAILED DESCRIPTION OF THE INVENTION

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

The present invention discloses fluorescent compounds comprising at least one reactive group and at least one water soluble polymer. Such compounds may have desirable properties such as restricted intramolecular mobility, increased fluorescence quantum yield, decreased aggregation, increased solubility, decreased quenching and increased in vivo and in vitro stability. The compounds may be used for labeling molecules and biomolecules such as polypeptides and polynucleotides and are suitable for use in a wide range of applications, including diagnostic and imaging systems.

Fluorescent compounds and labeled molecules of the invention may exhibit reduced aggregation. Dye aggregation is often seen as a major contributing factor to fluorescence quenching. Prevention of aggregation in the present invention may be achieved without the use of an excessive number of negatively charged sulfonate groups. This in turn may aid in the labeling of biomolecules such as proteins because the labeled protein may have an isoelectric point comparable to that of the substrate protein, and may thereby better maintain its biological specificity. The use of water soluble polymers of the invention may also aid in camouflaging or shielding the fluorophore to which it is linked. For example, such a water soluble polymer may be a relatively large group such as a polyethylene glycol moiety. This may be particularly desirable when the fluorophore is linked to a biomolecule such as a polypeptide. Consequently, compared to other fluorescently labeled proteins, proteins labeled with the compounds of the present invention may be more resistant to protease-catalyzed degradation. Accordingly, labeled proteins, such as labeled antibodies, of the invention may have a longer half-life in the circulation when applied to an animal's body, such as a mammal's body, and therefore may be suitable for in vivo imaging. Labeled biomolecules may also exhibit a longer half-life in in vitro systems, for example in assays employing serum or other biological extracts.

A water soluble polymer may restrict or reduce the intramolecular mobility, such as the vibration and rotation, of the fluorophore to which it is attached. This may increase the fluorescence quantum yield of the fluorescent group. The fluorescence enhancement effect may be particularly effective for fluorescent groups that have a relatively flexible core structure. Additionally, labeled molecules of the invention may be less immunogenic and less antigenic in vivo than the corresponding substrate biomolecules. Furthermore, the compounds and labeled molecules of the invention may exhibit higher photostability and resistance to bleaching of the fluorescent group.

DEFINITIONS

The compounds of the present invention may have asymmetric centers, chiral axes, and chiral planes (as described in: E. L. Eliel and S. H. Wilen, Stereo-chemistry of Carbon Compounds, John Wiley & Sons, New York, 1994, pages 1119 1190), and occur as racemates, racemic mixtures, and as individual diastereomers, with all possible isomers and mixtures thereof, including optical isomers, being included in the present invention. In addition, the compounds disclosed herein may exist as tautomers and both tautomeric forms are intended to be encompassed by the scope of the invention, even though only one tautomeric structure is depicted.

When any variable (e.g. R, L, $(R_1)_a$, $(L)_q$) occurs more than one time in any constituent, its definition on each occurrence is independent at every other occurrence. Combinations of substituents and variables are permissible only if such combinations result in stable compounds. Lines drawn into the ring systems from substituents indicate that the indicated bond may be attached to any of the substitutable ring carbon atoms. If the ring system is polycyclic, it is intended that the bond be attached to any of the suitable carbon atoms on the proximal ring only. Substitution of a ring by a substituent generally allows the substituent to be a cyclic structure fused to the ring.

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results. The phrase "optionally substituted with one or more substituents" should be taken to be equivalent to the phrase "optionally substituted with at least one substituent" and in such cases the preferred embodiment will have from zero to three substituents.

As used herein, "alkyl" is intended to include both branched, straight-chain, and cyclic saturated aliphatic hydrocarbon groups. Alkyl groups specifically include methyl, ethyl, propyl, butyl, pentyl, hexyl, heptyl, octyl, nonyl, decyl, and so on, as well as cycloalkyls such as cyclopropyl, cyclobutyl, cyclopentyl, cyclohexyl, tetrahydronaphthalene, methylenecylohexyl, and so on. "Alkoxy" represents an alkyl group attached through an oxygen bridge.

The term "alkenyl" refers to a non-aromatic hydrocarbon group, straight, branched or cyclic, containing at least one carbon to carbon double bond. Alkenyl groups include, but are not limited to, ethenyl, propenyl, butenyl and cyclohexenyl. The straight, branched or cyclic portion of the alkenyl group may contain double bonds and may be substituted if a substituted alkenyl group is indicated.

The term "alkynyl" refers to a hydrocarbon group, straight, branched or cyclic, containing at least one carbon to carbon triple bond. Alkynyl groups include, but are not limited to, ethynyl, propynyl and butynyl. The straight, branched or cyclic portion of the alkynyl group may contain triple bonds and may be substituted if a substituted alkynyl group is indicated.

As used herein, "aryl" is intended to mean any stable monocyclic or polycyclic carbon ring of up to 7 atoms in each ring, wherein at least one ring is aromatic. Examples of such aryl elements include phenyl, naphthyl, tetrahydronaphthyl, indanyl, biphenyl, phenanthryl, anthryl or acenaphthyl. In cases where the aryl substituent is bicyclic and one ring is non-aromatic, it is understood that attachment is via the aromatic ring.

The term "heteroaryl", as used herein, represents a stable monocyclic or bicyclic ring of up to 7 atoms in each ring, wherein at least one ring is aromatic and contains from 1 to 4 heteroatoms selected from the group consisting of O, N and S. Heteroaryl groups within the scope of this definition include but are not limited to acridinyl, carbazolyl, cinnolinyl, quinoxalinyl, pyrrazolyl, indolyl, benzotriazolyl, furanyl, thienyl, benzothienyl, benzofuranyl, quinolinyl, isoquinolinyl, oxazolyl, isoxazolyl, pyrazinyl, pyridazinyl, pyridinyl, pyrimidinyl, pyrrolyl, tetrahydroquinoline, xanthenyl, and coumarinyl. In cases where the heteroaryl substituent is bicyclic and one ring is non-aromatic or contains no heteroatoms, it is understood that attachment is via the aromatic ring or via the heteroatom containing ring, respectively.

The term "heterocycle" or "heterocyclyl" as used herein is intended to mean a 5- to 10-membered aromatic or nonaromatic heterocycle containing at least one heteroatom which is O, N or S. This definition includes bicyclic groups. "Heterocyclyl" therefore includes the above mentioned heteroaryls, as well as dihydro and tetrahydro analogs thereof. Further examples of "heterocyclyl" include, but are not limited to the following: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrazolyl, tetrazolopyridyl, thiadiazolyl, thiazolyl, thienyl, triazolyl, azetidinyl, aziridinyl, 1,4-dioxanyl, hexahydroazepinyl, piperazinyl, piperidinyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl.

The alkyl, alkenyl, alkynyl, cycloalkyl, aryl, heteroaryl and heterocyclyl substituents may be unsubstituted or unsubstituted, unless specifically defined otherwise. For example, an alkyl group may be substituted with one or more substituents selected from OH, oxo, halo, alkoxy, dialkylamino, or heterocyclyl, such as morpholinyl or piperidinyl.

The terms "halo" or "halogen" are intended to include chloro, fluoro, bromo and iodo groups.

The term "aromatic" is used in its usual sense, including unsaturation that is essentially delocalized across multiple bonds, such as around a ring.

The term "substituent" refers to an atom, radical or chemical group which replaces a hydrogen in a substituted chemical group, radical, molecule, moiety or compound.

"Spiro" as used herein, refers to a cyclic moiety which is attached to another group such that one of the ring atoms of the cyclic moiety is also an atom of said other group. A non-spiro substituent is a moiety cyclic or noncyclic which is directly attached to said other group via bond connection between atoms of the non-spiro moiety and said other group. An example of a spiro moiety is, for instance, a substitutent Ring B on cyclohexanone Ring A.

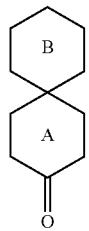

Unless otherwise stated, the term "radical", as applied to any molecule or compound, is used to refer to a part, fragment or group of the molecule or compound rather than to a "free radical". A radical may be linked to another moiety through a covalent bond.

The terms "polynucleotides", "nucleic acids", "nucleotides", "probes" and "oligonucleotides" are used interchangeably. They refer to a polymeric form of nucleotides of any length, either deoxyribonucleotides or ribonucleotides, or analogs thereof. Polynucleotides may have any three-dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component. "Polynucleotide" may also be used to refer to peptide nucleic acids (PNA), locked nucleic acids (LNA), threofuranosyl nucleic acids (TNA) and other unnatural nucleic acids or nucleic acid mimics. Other base and backbone modifications known in the art are encompassed in this definition. See, e.g. De Mesmaeker et al (1997) Pure & Appl. Chem., 69, 3, pp 437-440.

The terms "polypeptide", "peptide" and "protein" are used interchangeably herein to refer to polymers of amino acids of any length. The polymer may be linear, cyclic, or branched, it may comprise modified amino acids, and it may be interrupted by non-amino acids. The terms also encompass amino acid polymers that have been modified, for example, via sulfonation, glycosylation, lipidation, acetylation, phosphorylation, iodination, methylation, oxidation, proteolytic processing, phosphorylation, prenylation, racemization, selenoylation, transfer-RNA mediated addition of amino acids to proteins such as arginylation, ubiquitination, or any other manipulation, such as conjugation with a labeling component. As used herein the term "amino acid" refers to either natural and/or unnatural or synthetic amino acids, including glycine and both the D or L optical isomers, and amino acid analogs and peptidomimetics.

The term "antibody" as used herein refers to immunoglobulin molecules and immunologically active portions of immunoglobulin molecules, i.e., molecules that contain an antigen-binding site which specifically binds ("immunoreacts with") an antigen. Structurally, the simplest naturally occurring antibody (e.g., IgG) comprises four polypeptide chains, two heavy (H) chains and two light (L) chains interconnected by disulfide bonds. The immunoglobulins represent a large family of molecules that include several types of molecules, such as IgD, IgG, IgA, IgM and IgE. The term "immunoglobulin molecule" includes, for example, hybrid antibodies, or altered antibodies, and fragments thereof. It has been shown that the antigen binding function of an antibody can be performed by fragments of a naturally-occurring antibody. These fragments are collectively termed "antigen-binding units". Antigen binding units can be broadly divided into "single-chain" ("Sc") and "non-single-chain" ("Nsc") types based on their molecular structures.

Also encompassed within the terms "antibodies" are immunoglobulin molecules of a variety of species origins including invertebrates and vertebrates. The term "human" as applies to an antibody or an antigen binding unit refers to an immunoglobulin molecule expressed by a human gene or fragment thereof. The term "humanized" as applies to a non-human (e.g. rodent or primate) antibodies are hybrid immunoglobulins, immunoglobulin chains or fragments thereof which contain minimal sequence derived from non-human immunoglobulin. For the most part, humanized antibodies are human immunoglobulins (recipient antibody) in which residues from a complementary determining region (CDR) of the recipient are replaced by residues from a CDR of a non-human species (donor antibody) such as mouse, rat, rabbit or primate having the desired specificity, affinity and capacity. In some instances, Fv framework region (FR) residues of the human immunoglobulin are replaced by corresponding non-human residues. Furthermore, the humanized antibody may comprise residues which are found neither in the recipient antibody nor in the imported CDR or framework sequences. These modifications are made to further refine and optimize antibody performance and minimize immunogenicity when introduced into a human body. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin sequence. The humanized antibody may also comprise at least a portion of an immunoglobulin constant region (Fc), typically that of a human immunoglobulin.

The term "stable" refers to compositions and compounds which have sufficient chemical stability to survive isolation from a reaction mixture to a useful degree of purity for use in a desired application.

The terms "fluorescent group", "fluorophore", "dye" or "fluorescent group" refer interchangeably to molecules, groups or radicals which are fluorescent. The term "fluorescent" as applied to a molecule of compound is used to refer to the property of the compound of absorbing energy (such as UV, visible or IR radiation) and re-emitting at least a fraction of that energy as light over time. Fluorescent groups, compounds or fluorophores include, but are not limited to discrete compounds, molecules, proteins and macromolecular complexes. Fluorophores also include compounds that exhibit long-lived fluorescence decay such as lanthanide ions and lanthanide complexes with organic ligand sensitizers.

A "subject" as used herein refers to a biological entity containing expressed genetic materials. The biological entity is in various embodiments, a vertebrate. In some embodiment, the biological entity is a mammal. In other embodiments, the subject is a biological entity which comprises a human.

A "control" is an alternative subject or sample used in an experiment for comparison purposes. A control can be "positive" or "negative". For example, where the purpose of the experiment is to detect a differentially expressed transcript or polypeptide in cell or tissue affected by a disease of concern, it is generally preferable to use a positive control (a subject or a sample from a subject, exhibiting such differential expression and syndromes characteristic of that disease), and a negative control (a subject or a sample from a subject lacking the differential expression and clinical syndrome of that disease.

The term "FRET" refers to Foerster resonance energy transfer. In the present invention, FRET refers to energy transfer processes occurring between at least two fluorescent compounds, between a fluorescent compound and a non-fluorescent component or between a fluorescent component and a non-fluorescent component.

A "binding agent" is a molecule that exhibits binding selectivity towards a binding partner or a target molecule to which it binds. A binding agent may be a biomolecule such as a polypeptide such as an antibody or protein, polypeptide-based toxin, amino acid, nucleotide, polynucleotides including DNA and RNA, lipids, and carbohydrates, or a combination thereof. A binding agent may also be a hapten, drug, ion-complexing agent such as metal chelators, microparticles, synthetic or natural polymers, cells, viruses, or other fluorescent molecules including the dye molecule according to the invention.

A "targeting moiety" is the portion of the binding agent that binds to a binding partner. A targeting moiety may be, without limitation, a nucleotide sequence within a polynucleotide that selectively binds to another polynucleotide or polypeptide. Another nonlimiting example of a targeting moiety may be a polypeptide sequence within a larger polypeptide sequence which binds specifically to a polynucleotide sequence or a second polypeptide sequence. A targeting moiety may be a small molecule or structural motif which will bind to a protein receptor, another small molecule motif, or complexing agent, without limitation. The selective binding may be a specific binding event.

A "binding partner" is a molecule or particle which is bound by the targeting moiety. It can be a cell, virus, fragment of a cell, antibody, fragment of an antibody, peptide, protein, polynucleotide, antigen, small molecule, or a combination thereof. It may be bound selectively or specifically by the binding agent.

The term "signal to noise ratio" of fluorescence as referred to herein in the context of a polypeptide-antibody complex, is the ratio of (fluorescent signal from a complex comprising a polypeptide bound by a primary antibody which in turn is bound to a binding agent labeled with a compound of the invention)/(fluorescent signal from a mixture of the polypeptide, an isotype control primary antibody, and the labeled binding agent).

"Degree of labeling" or "DOL" as used herein refers to the number of dye molecules which are attached per target molecule (including but not limited to polypeptide and polynucleotide). For example, a single dye molecule per a polypeptide such as an antibody represents a 1.0 degree of labeling (DOL). If more than one dye molecule, on average, reacts with and is crosslinked to a polypeptide such as an antibody, the degree of labeling is greater than 1 and may further be a number other than a whole integer. The higher the number of DOL, the greater extent of labeling.

"Intracellular" as used herein refers to the presence of a given molecule in a cell. An intracellular molecule can be present within the cytoplasm, attached to the cell membrane, on the surface of an organelle, or within an organelle of a cell.

"Substrate" or "solid substrate" when used in the context of a reaction surface refers to the material that certain interaction is assayed. For example, a substrate in this context can be a surface of an array or a surface of microwell. It may also be a solid such as a polymer which does not form a specific shape but has attachment points on its surface.

The terms "wavelength of maximum excitation" and "maximal fluorescence excitation wavelength" are used herein interchangeably. These terms refer to the maximum wavelength at which a fluorescent compound absorbs light energy which excites the dye to emit maximal fluorescence. The term "absorption maximal wavelength" as applied to a dye refers the wavelength of light energy at which the dye most effectively absorbs excitation energy to fluoresce. A fluorescent dye has a "maximal fluorescence emission wavelength" which is the wavelength at which the dye most intensely fluoresces. When a single wavelength is referred to for any dye, it refers to the maximal wavelength of excitation, absorption, or emission, according to the context of the term, for example, an absorption wavelength refers to the wavelength at which the compound has maximal absorption, and an emission wavelength refers to the wavelength at which the dye most intensely fluoresces.

Compounds of the Invention:

The present invention provides compounds of Formula I:

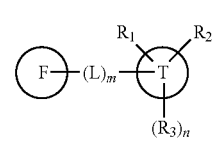

(Formula I)

Herein, F represents a fluorophore or fluorescent group. In general, fluorophores suitable for the compounds of the invention ("F" in formula I) are derived from fluorescent compounds which have substitution sites that allow the attachment to the -(L)$_m$- or T groups. The core structures of a number of fluorescent groups including those of their subcategories may be suitable as fluorophores. A fluorophore generally may comprise a structure comprising a minimal number of atoms necessary to form a fluorescent group belonging to a class of fluorescent groups. As an example, a coumarin fluorescent group comprises the core structure of formula A as set forth below:

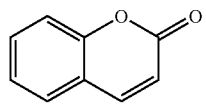

Formula A

As another example, a fluorescein fluorescent group comprises the core structure of formula B as set forth below:

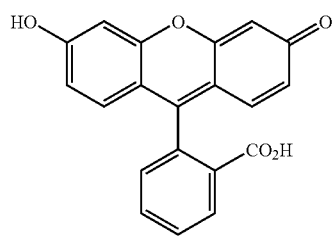

Formula B

As still another example, rhodamine fluorescent groups have the core structure of formula C as set forth below:

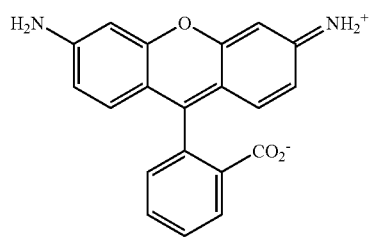

Formula C

As yet another example, indocarbocyanine fluorescent groups may have the core structure of formula D as set forth below:

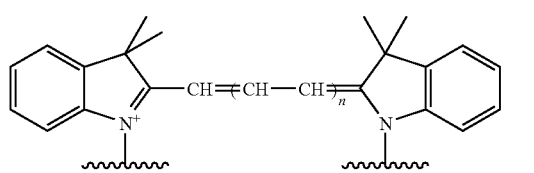

Formula D

Core structures for other classes of fluorescent groups can be readily determined by one of ordinary skill in the art using the above principle. One of skill can appreciate that the determination of a fluorescent group core structure can be somewhat arbitrary because the classification of fluorescent groups may be arbitrary by itself. A class of fluorescent groups, for example, may be sub-classified into different subclasses, wherein each subclass of fluorescent groups comprises one or more substituents unique to the particular subclass of fluorescent groups. Thus, there may be a core structure for each subclass of fluorescent groups. For example, 7-aminocoumarin, shown below as formula E, is the core structure for all 7-aminocoumarin derivatives, which are themselves a subclass of fluorescent groups belonging to the more general coumarin fluorescent groups that have the core structure of formula A.

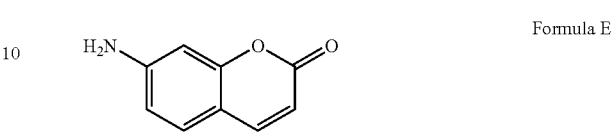

Formula E

The following table shows typical excitation and emission wavelengths for a number of common classes of fluorophores and core structures:

| Fluorescent Group | Typical Excitation Wavelengths | Typical Emission Wavelengths |
| --- | --- | --- |
| Coumarin | 300-500 nm | 350-550 nm |
| Fluorescein | 470-520 nm | 500-540 nm |
| Rhodamine | 480-640 nm | 510-660 nm |
| Cyanine | 350-1200 nm | 360-1250 nm |
| Pyrene | 350-490 nm | 400-510 nm |

In some embodiments, F may be a derived from cyanine fluorescent group, Cy fluorescent group, xanthene fluorescent group, Alexa Fluor fluorescent group, coumarin fluorescent group, pyrene fluorescent group, Bodipy fluorescent group, ATTO fluorescent group or DY fluorescent group. As commonly known in the field, cyanine fluorescent groups may comprise various sub-categories of cyanine fluorescent groups including, but not limited to, indocarbocyanine fluorescent groups, oxacarbocyanine fluorescent groups, thiacarbocyanine fluorescent groups, azacarbocyanine fluorescent groups (azacyanine fluorescent groups), styrylcyanine group and merocyanine fluorescent groups, merely by way of example. Similarly, xanthene fluorescent groups may include, but are not limited to, fluorescein and its derivatives and various rhodamine fluorescent groups, for example.

Other nonlimiting examples of fluorescent compounds for use as fluorophores in the invention include Acridine orange, Acridine yellow, Alexa Fluor fluorescent groups, ATTO fluorescent groups, Bodipy fluorescent groups, Auramine O, Benzanthrone, 9,10-Bis(phenylethynyl)anthracene, 5,12-Bis (phenylethynyl)naphthacene, Carboxyfluorescein diacetate, Calcein, Carboxyfluorescein, 1-Chloro-9,10-bis(phenylethynyl)anthracene, 2-Chloro-9,10-bis(phenylethynyl)anthracene, Coumarin, Cyanine, Cy2, Cy3, Cy3.5, Cy5, Cy5.5, Cy7, DyLight Fluor fluorescent groups, Fluorescein, 2',7'-dichlorodihydrofluorescein, Hilyte Fluor fluorescent groups, LDS 751, Oregon Green, Perylene, Phycobilin, Phycoerythrin, Phycoerythrobilin, Pyrene, Rhodamine and Ruthenium (II) tris(bathophenanthroline disulfonate). These compounds and derivatives or radicals of these compounds may be used as fluorophores of the invention.

Other examples of fluorescent groups which may be used in the present invention include but are not limited to 4-acetamido-4'-isothiocyanatostilbene-2,2'disulfonic acid, acridine and derivatives such as acridine and acridine isothiocyanate, 5-(2'-aminoethyl)aminonaphthalene-1-sulfonic acid (EDANS), 4-amino-N-[3-vinylsulfonyl)phenyl]naphthalimide-3,5 disulfonate (Lucifer Yellow VS), N-(4-anilino-1-naphthyl)maleimide, anthranilamide, BODIPY™ and its derivatives and analogs, Brilliant Yellow, cyanine fluorescent groups such as Cy3 and Cy5 and other derivatives, coumarin and derivatives such as coumarin, 7-amino-4-methylcoumarin (AMC, Coumaran 120), 7-amino-4-trifluoromethylcouluarin (Coumaran 151), 7-diethylamino-3-(4'-isothiocyanatophenyl)-4-methylcoumarin, 5-[dimethylamino] naphthalene-1-sulfonyl chloride (DNS, dansyl chloride), fluorescein and derivatives such as 5-carboxyfluorescein (FAM), 5-(4,6-dichlorotriazin-2-yl)aminofluorescein (DTAF), 2'7'-dimethoxy-4'5'-dichloro-6-carboxyfluorescein (JOE), fluorescein, fluorescein isothiocyanate (FITC), and QFITC (XRITC); fluorescamine; 4-methylumbelliferone, oxazine fluorescent groups such as Nile Blue and other analogs; pyrene and derivatives such as pyrene, pyrene butyrate and succinimidyl 1-pyrene butyrate; rosamine fluorescent groups, tetramethyl rosamine, and other analogs, rhodamine and derivatives such as 6-carboxy-X-rhodamine (ROX), 6-carboxyrhodamine (R6G), lissamine rhodamine B sulfonyl chloride, rhodamine (Rhod), rhodamine B, rhodamine 123, rhodamine X isothiocyanate, sulforhodamine B, sulforhodamine 101 and sulfonyl chloride derivative of sulforhodamine 101 (Texas Red); N,N,N',N'-tetramethyl-6-carboxyrhodamine (TAMRA), tetramethyl rhodamine; tetramethyl rhodamine isothiocyanate (TRITC) and thiazine fluorescent groups such as methylene blue and analogs. Additional fluorophores applicable for use in the present are disclosed in US patent application Nos. 2003/0165942, 2003/0045717, and 2004/0260093 and U.S. Pat. No. 5,866,366 and WO 01/16375, both of which are incorporated herein by reference. Additional examples are described in U.S. Pat. No. 6,399,335, published U.S. patent application No. 2003/0124576, and The Handbook-'A Guide to Fluorescent Probes and Labeling Technologies, Tenth Edition' (2005) (available from Invitrogen, Inc./Molecular Probes), all of which are incorporated herein by reference.

Fluorescent groups of the invention may also include fluorescent proteins. Such fluorescent proteins known in the art include GFP and its various derivatives, described e.g. in U.S. Pat. Nos. 5,625,048; 5,777,079; 6,066,475; 6,319,669; 6,046,925; 6,124,128 and 6,077,707. Additional fluorescent proteins are Y66F, Y66H, EBFP, GFPuv, ECFP, AmCyan1, Y66W, S65A, S65C, S65L, S65T, EGFP, ZsGreen1, EYFP, ZsYellow1, DsRed, DsRed2, AsRed2, mRFP1 and HcRed1.

Many such fluorescent groups are commercially available and may be used in the synthesis of compounds of the present invention. Commercial sources of reactive fluorescent groups include Invitrogen (Molecular Probes), AnaSpec, Amersham (AP Biotech), Atto-Tec, Dyomics, Clontech and Sigma-Aldrich.

The fluorophore may be attached through a linking moiety -(L)$_m$- to a joining moiety T. In general, linking moieties (generally represented by "L") may be any group connecting two moieties, such as fluorophores, water soluble polymers and reactive groups to each other or to any other group included in the compound of the invention. Synthetic accessibility and convenience may generally dictate the nature of each linking moiety. In some embodiments, a linking moiety is a group containing about 1-100 atoms and formed of one or more chemical bonds selected such that the group is a stable moiety. In other embodiments, a linking moiety is formed of one or more carbon-hydrogen, carbon-nitrogen, carbon-oxygen, carbon-sulfur, carbon-phosphorus, nitrogen-hydrogen, sulfur-hydrogen, phosphorus-hydrogen, sulfur-oxygen, sulfur-nitrogen, sulfur-phosphorus, phosphorus-oxygen, phosphorus-nitrogen and oxygen-nitrogen bonds, wherein such bonds may be single, double, triple, aromatic and heteroaromatic bonds selected such that the linking moiety is stable. A linking moiety can be, for example, a divalent alkyl radical.

Alternatively, a linking moiety may be an alkyl group comprising additional ether, amine, amide, ester, sulfonyl, thioether, carboxamide, sulfonamide, hydrazide or morpholino, aryl and heteroaryl groups.

Linking moieties are generally formed of about 1-100 atoms. In some embodiments, linking moieties are formed of 1-50 non-hydrogen atoms as well as additional hydrogen atoms. Such atoms may be, for example, C, N, O, P or S. In other embodiments, a linker moiety connecting two groups comprises 1 to 50 consecutive bonds between the groups. Some linker moieties may have 1 to 40, 1 to 30, 1 to 20, 1 to 10, 1 to 5, 5 to 25, or 5 to 20 such consecutive bonds.

Non-limiting exemplary linking moieties are illustrated below:

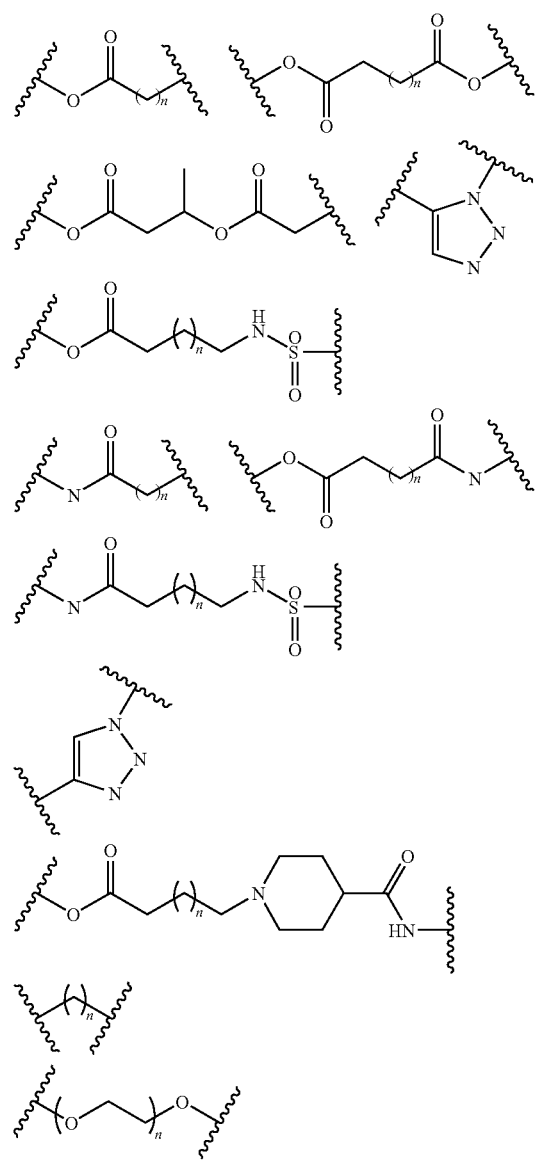

In the above image, n represents a number of repeating methylene units which can be varied such as to provide a desired length of the linker. Typically, n ranges from 1 to about 50. Some linkers will have an n of 1 to 40, 1 to 30, 1 to 20, 1 to 10, 1 to 5, 5 to 30, 5 to 20, or 5 to 15.

Similarly, joining moieties (generally represented by "T") may be any group connecting three or more distinct moieties such as fluorophores, water soluble polymers and reactive groups to each other or to any other group, such as a linker moiety, included in the compound of the invention. In some embodiments, a joining moiety is a group containing about 1-100 atoms and formed of one or more chemical bonds. The bonds may be selected such that the group is a stable moiety. In other embodiments, a joining moiety is formed of one or more carbon-hydrogen, carbon-nitrogen, carbon-oxygen, carbon-sulfur, carbon-phosphorus, nitrogen-hydrogen, sulfur-hydrogen, oxygen-hydrogen, phosphorus-hydrogen, sulfur-oxygen, sulfur-nitrogen, sulfur-phosphorus, phosphorus-oxygen, phosphorus-nitrogen and oxygen-nitrogen bonds, wherein such bonds may be single, double, triple, aromatic and heteroaromatic bonds selected such that the group is a stable moiety. In some embodiments, T contains between 1 and 50 atoms, or alternatively between 1 and 40, 1 and 30, 1 and 20, or 1 and 10 atoms. T may be a single atom such as N or C. T may also be a small cyclic group such as a carbocycle, a heterocycle, or an aromatic group. Nonlimiting examples include substituted phenyl, naphthyl, tetrahydronaphthyl, indanyl, biphenyl, phenanthryl, anthryl, acenaphthyl, benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrazolyl, tetrazolopyridyl, thiadiazolyl, thiazolyl, thienyl, triazolyl, azetidinyl, aziridinyl, 1,4-dioxanyl, hexahydroazepinyl, piperazinyl, piperidinyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl. Joining moieties may be, for example, trivalent, tetravalent, pentavalent or hexavalent. Examples of joining moieties are depicted below:

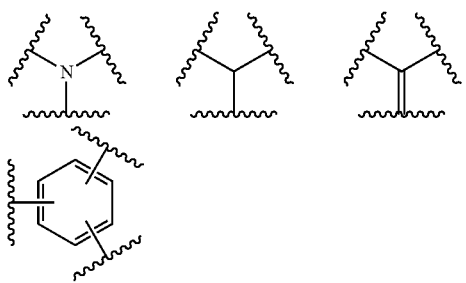

The subscripts m and n of Formula I indicate the number of linker moieties present and are independently integers ranging from 0 to 20. When m is 0, the linker moiety is understood to be absent and any two moieties shown as attached to such a linker moiety are understood to be connected through a bond. When n is 0, any substituent qualified by "n" will be understood to be absent.

Groups denoted as $R_1$, $R_2$, and $R_3$ of Formula I are groups of the formula $(R)_p$-$(L)_q$-. When multiple $(R)_p$ $(L)_q$- groups are present in a compound, each R, L, p or q is independent of any other R, L, p or q group present in the same compound. Each p is generally an integer ranging from 1 to 20. In some embodiments, p is 1. In other embodiments, p may range from 1 to 2, 3, 4, 5, 10 or 15. Each q is generally an integer ranging from 0 to 20. In embodiments where p is 0, L is understood to be absent and any R group shown as attached to L is understood to be connected directly through a bond. Alternatively, p may be 1. In other cases, q may range from 1 to 2, 3, 4, 5, 10 or 15.

"R" may be any group that confers a desirable functional property to the compound of the invention. More specific embodiments of R groups will be discussed below.

Compounds of the invention comprise at least one R which is a reactive group. A reactive group is a chemical moiety capable of reacting with a reaction partner on a substrate or substrate molecule to form a covalent bond. A compound of the invention can be used to label a wide variety of molecules or substrates that contain a suitable reaction partner or are derivatized to contain a suitable reaction partner. "Reactive group" and "reaction partner" may refer to groups on a compound of the present invention, or to groups on a molecule to be labeled. Here, by way of convenience, but not limitation, a bond-forming group on a compound will generally be referred to as a reactive group and a bond-forming group on the substrate molecule will generally be referred to as a reaction partner. "Reaction substrate", "substrate" and "reaction partner" are used interchangeably throughout this document.

The reactive group and its reaction partner may be an electrophile and a nucleophile, respectively, that can form a covalent bond with or without a coupling agent or catalyst. According to one embodiment, the reactive group is a photoactivatable group capable of reacting with a hydrocarbon molecule upon ultraviolet photoactivation or photolysis. According to another embodiment, the reactive group is a dienophile capable of reacting with a conjugated diene via a Diels-Alder reaction. According to yet another embodiment, the reactive group is a 1,3-diene capable of reacting with a dienophile. According to still another embodiment, the reactive group is an alkyne capable of reacting with an azido functional group to form a 1,2,3-triazole linkage. According to still another embodiment, the reactive group is a 2-(diphenylphosphino)benzoic acid methyl ester capable of reacting with an azido functional group to form an amide linkage via so-called Staudinger reaction. Merely by way of example, examples of useful reactive groups, functional groups, and corresponding linkages according to the present invention are listed below in Table 1.

TABLE 1

Examples of Reactive Groups, Functional Groups, and Covalent Linkages

| Reactive Group | Reaction Partner/ Substrate | Resulting Covalent Linkage |
|---|---|---|
| activated esters* | amines/anilines | Carboxamides |
| acrylamides | Thiols | Thioethers |
| acyl azides** | amines/anilines | Carboxamides |
| acyl halides | amines/anilines | Carboxamides |
| acyl halides | Alcohols/phenols | Esters |
| acyl nitriles | Alcohols/phenols | Esters |
| acyl nitriles | amines/anilines | Carboxamides |
| aldehydes | amines/anilines | Imines |
| aldehydes or ketones | Hydrazines | Hydrazones |

TABLE 1-continued

Examples of Reactive Groups, Functional Groups, and Covalent Linkages

| Reactive Group | Reaction Partner/ Substrate | Resulting Covalent Linkage |
|---|---|---|
| aldehydes or ketones | Hydroxylamines | Oximes |
| alkyl halides | amines/anilines | alkyl amines |
| alkyl halides | Thiols | Thioethers |
| alkyl halides | alcohols/phenols | Esters |
| alkyl sulfonates | Thiols | Thioethers |
| alkyl sulfonates | carboxylic acids | Esters |
| alkyl sulfonates | alcohols/phenols | Esters |
| anhydrides | alcohols/phenols | Esters |
| anhydrides | amines/anilines | Carboxamides |
| aryl halides | Thiols | Thiophenols |
| aryl halides | Amines | aryl amines |
| aziridines | Thiols | Thioethers |
| boronates | Glycols | boronate esters |
| epoxides | Thiols | Thioethers |
| haloacetamides | Thiols | Thioethers |
| halotriazines | amines/anilines | Aminotriazines |
| halotriazines | alcohols/phenols | triazinyl ethers |
| imido esters | amines/anilines | Amidines |
| isocyanates | amines/anilines | Ureas |
| isocyanates | alcohols/phenols | Urethanes |
| isothiocyanates | amines/anilines | Thioureas |
| maleimides | Thiols | Thioethers |
| phosphoramidites | Alcohols | phosphite esters |
| silyl halides | Alcohols | silyl ethers |
| sulfonate esters | amines/anilines | alkyl amines |
| sulfonate esters | Thiols | Thioethers |
| sulfonate esters | Alcohols | Ethers |
| sulfonyl halides | amines/anilines | Sulfonamides |
| sulfonyl halides | phenols/alcohols | sulfonate esters |
| azide | alkyne | 1,2,3-triazole |
| Cis-platinum | guanosine | Platinum-guanosine complex |

*Activated esters, as understood in the art, generally have the formula —COΩ, where Ω is a good leaving group, such as succinimidyloxy (—OC$_4$H$_4$O$_2$), sulfosuccinimidyloxy (—OC$_4$H$_3$O$_2$—SO$_3$H), or -1-oxybenzotriazolyl (—OC$_6$H$_4$N$_3$), for example; or an aryloxy group or aryloxy substituted one or more times by electron-withdrawing substituent(s), such as nitro, fluoro, chloro, cyano, trifluoromethyl, or combinations thereof, for example, used to form activated aryl esters; or a carboxylic acid activated by a carbodiimide to form an anhydride or mixed anhydride —OCOR$^a$ or —OCNR$^a$NHR$^b$, where R$^a$ and R$^b$, which may be the same or different, are independently C$_1$-C$_6$ alkyl, C$_1$-C$_6$ perfluoroalkyl, or C$_1$-C$_6$ alkoxy; or cyclohexyl, 3-dimethylaminopropyl, or N-morpholinoethyl.
**Acyl azides can also rearrange to isocyanates.

The reactive group may be one that will react with an amine, a thiol, a hydroxyl or an aldehyde. The reactive group may be an amine-reactive group, such as a succinimidyl ester (SE), for example, or a thiol-reactive group, such as a maleimide, a haloacetamide, or a methanethiosulfonate (MTS), for example, or an aldehyde-reactive group, such as an amine, an aminooxy, or a hydrazide, for example.

The compounds of the invention also comprise at least one R which is a water-soluble polymer group. According to the invention, water soluble polymer groups may significantly reduce the intramolecular mobility of the fluorescent group core structure and may thus improve the fluorescent group's fluorescence quantum yield. Such groups may also confer other properties to the compounds to which they are attached, such as improvements of the photostability of the fluorescent group, reduced fluorescent group aggregation for biomolecule labeling, increased staining specificity of fluorescently labeled biomolecules (such as antibodies); and reduced immunogenicity and antigenicity of labeled biomolecules (such as antibodies) in vivo.

Each water soluble polymer group is generally a substantially unreactive and water-soluble moiety sufficiently large to improve the fluorescence properties of a compound. The term "polymer" used in this context does not require the presence of strictly repeating units. A molecule of sufficient molecular size and solubility but without repeating units is considered a "water soluble polymer group" for the purposes of the invention.

Water soluble polymer groups include, but are not limited to, organic polymers and biomolecules such as polypeptides and carbohydrates. Water soluble polymers may comprise ether groups, hydroxyl groups, tertiary amine groups, quaternized amine groups, and/or guanidine groups. Each water soluble polymer may be linear, branched, cyclic or a combination thereof. Water soluble polymers of the invention may comprise a single chain or alternatively one, two, three, four or more chains. Water soluble polymers with one, two, three, four or more branches may be used. The compounds of the invention may comprise any number of water soluble polymer groups. Generally, compounds of the invention comprise at least 1 water soluble polymer groups up to about 8 water soluble polymer groups. In one embodiment, a compound comprises at least 2 water soluble polymer groups to about 8 water soluble polymer groups. In another embodiment, a compound comprises at least 3 water soluble polymer groups up to about 8 water soluble groups. Suitable molecular weights of each water soluble polymer group or, alternatively, of all water soluble polymer groups in one compound may be about 100, 200, 300, 400, 500, 600, 700, 800, 900, 1000, 1500, 2000, 2500, 3000, 3500, 4000, 4500, 5000, 10000, 15000, 20000 Da or greater. In one embodiment, the water soluble polymer group of the invention has a molecular weight between 450 and 5000 Da. In another embodiment, the water soluble polymer group of the invention has a molecular weight between about 800 and about 3000 Da. In yet another embodiment, the combined molecular weight of all water soluble polymer groups within a compound is from about 450 to about 5,000 Da. In still another embodiment, the combined molecular weight of all water soluble polymer groups within a compound is from about 1,000 to about 3,000 Da.

In one embodiment, the water soluble polymer of the invention is a polyalkylene oxide. Suitable polyalkylene oxides include polyethylene glycol (PEG), polypropylene glycol (PPG), polyethylene glycol-polypropylene glycol (PEG-PPG) copolymers, and N-substituted methacrylamide-containing polymers and copolymers. Various polyalkylene oxides suitable for the present invention, as well as methods of making and using them are described in the following references: U.S. Pat. Nos. 5,637,749; 5,650,388; 5,298,643; 5,605,976; 5,567,422; 5,681,567; 5,321,095; 5,349,001; 5,405,877; 5,234,903; 5,478,805; 5,324,844; 5,612,460; 5,756,593; 5,686,110; 5,880,131; 6,824,782; 5,808,096; 6,013,283; 6,251,382. Commercial sources of polyalkylene oxide reagents include Sigma-Aldrich, Nanocs, Creative Biochem, Pierce, Enzon, Nektar and Nippon Oils and Fats. Exemplary polyalkylene oxide groups are shown below:

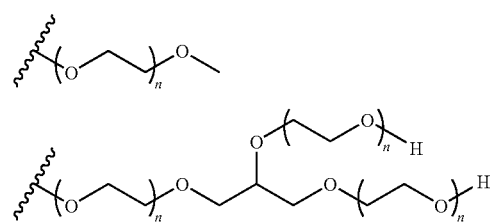

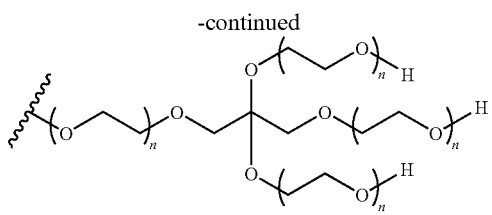

Polyalkylene oxides may be additionally substituted as necessary to confer other desired properties to the polymer. Such modifications may comprise, for example, chemical linkages that increase or decrease the chemical stability of the polymer, which would allow tuning of the chemical or biological stability of the half-life of the polymer. In some cases, polyalkylene oxide molecules are terminated or "capped" with various groups. Examples of such groups are hydroxy, alkyl ether (e.g. methyl, ethyl, propyl ethers), carboxymethyl ether, carboxyethyl ether, benzyl ether, dibenzylmethylene ether or dimethylamine. A polyalkylene oxide may have one of many possible terminals, including but not limited to hydroxyl, methyl ether, ethyl ether, carboxymethyl ether, and carboxyethyl ether. In one embodiment, a polyalkylene oxide is a polyethylene glycol polymer terminated with a methyl ether. Such a group may be referred to as an mPEG. An mPEG generally has the formula of —$(CH_2CH_2O)CH_3$, wherein n is the number of ethylene glycol units and is determined by the size of said mPEG.

Other suitable polymers include derivatives and conjugates of poly(2-hydroxyethyl methacrylate), polyhydroxypropyl methacrylamide, poly(styrene sulfonic acid), poly(vinyl alcohol), or poly(2-vinyl N-methylpyridinium iodide).

In another embodiment, the water soluble polymer of the invention is a carbohydrate. Such carbohydrates include monosaccharides or polysaccharides and may be, for example, soluble starch, glycogen, dextran, pectin, mannan, galactan, hydroxymethylcellulose, hydroxyethylcellulose and other derivatized celluloses. When the water soluble polymer is a carbohydrate, at least 30% of the hydroxyl groups present in the carbohydrate may be masked as methyl ethers, sulfonatoalkyl ethers, and/or acetate esters.

In yet another embodiment, the water soluble polymer of the invention is a polypeptide. Suitable polypeptides may comprise, for example, serine, arginine, polylysine with modified epsilon amino groups, or cysteinic acid. Other examples of such polypeptides are disclosed, for example, in WO 2006/081249. It is contemplated that such polypeptides may be used as the water soluble polymer of the invention.

Water soluble polymers of the invention also comprise combinations of the different classes described above. For example, such a water soluble polymer would be a polypeptide linked to a polyalkylene oxide moiety.

Water soluble polymers do not generally comprise any group or groups that are incompatible with the chemistry of the reactive group or groups included in the compound of the invention. For example, a water soluble polymer should not comprise strong nucleophiles if a reactive group is an electrophile. In a more specific example, a water soluble polymer should not comprise primary or secondary amines if a reactive group is an N-hydroxysuccinimidyl ester. As another specific example, a water soluble polymer should not comprise a thiol when a reactive group is a maleimide. Likewise, a water soluble polymer should generally not comprise a strong electrophile if a reactive group is a nucleophile. However, a water soluble may comprise a minimal number of weak nucleophiles or a minimal number of weak electrophiles such that the chemistry of the reactive group is not significantly affected, or the stability of the compound of the invention is not affected during storage and handling. Examples of weak nucleophiles are hydroxyl groups, which are commonly present in carbohydrate molecules. Thus, in some embodiments, when a water soluble polymer is a carbohydrate molecule, at least 30% of the hydroxyl groups are preferably masked as ethers, such as methyl ether, and/or esters, such as acetate esters. In other embodiments, all of the hydroxyl groups may be masked as ethers and/or esters.

In general, additional substituents ("R") of the compounds of the invention may in some cases be groups such as sulfonate (—$SO_3^-$), phosphonate (—$PO_3^{2-}$), and ammonium groups. Herein, the term ammonium means $NH_4^+$, a trialkylammonium, or a tetraalkylammonium. One of skills can appreciate that an ionic group requires a counter ion to balance its charge. For example, each negatively charged —$SO_3^-$ or —$PO_3^{2-}$ may necessitate one or two cations to balance the negative charge. Likewise, a positively charged ammonium may require an anion to maintain neutrality. In general, the nature of the counter ion is not critical as long as the counter ion does not lower the solubility of said fluorescent group. In some embodiments, when a substituent is —$SO_3^-$ or —$PO_3^{2-}$, the counter ion is $H^+$, $Na^+$, $K^+$ or an ammonium. In other embodiments, when the substituent is ammonium, the counter ion is preferably chloride, fluoride, bromide, sulfate, phosphate, acetate or the like. Some fluorescent groups may intrinsically possess a positive charge or negative charge. In such a case, the intrinsic charge may act as a counter ion. Alternatively, the intrinsic charge may require a counter ion for maintaining neutrality. The rule for selecting a counter ion for any intrinsic charge is as previously described. In some embodiments of the invention, at least one sulfonate group is present (—$SO_3^-$) and any necessary counter ion is selected from $H^+$, $Na^+$, $K^+$ and an ammonium. For reason of simplicity, any dissociable counter ion or counter ions for most of the fluorescent group structures depicted herein may not be shown.

Such substituents may increase a compound's water solubility and/or its fluorescent quantum yield. However, a relatively high number of charged groups is generally not desirable because it would result in a highly charged fluorophore, which on conjugation to a protein, for example, may significantly change the isoelectric point of the protein, thus possibly affecting the biological properties of the labeled protein. For example, an antibody labeled with a highly charged fluorescent molecule may show high background in staining. In some embodiments, the number of such charged water-soluble R groups is 0-4, or 0-3. Because the fluorescent group of the invention has at least one water soluble polymer group, which is also capable of increasing the water solubility and/or the quantum yield of the fluorescent group, the number of charged R groups, such as sulfonate groups, can be kept to a minimum, thereby minimizing the loss of biological specificity of labeled proteins.

Each substituent R may be the same or different and may be selected from halogens, —OH, —$NH_2$, —$SO_2NH_2$, and any carbon-containing substituents comprising 1 to about 15 carbon atoms and optionally at least one hetero atom. When present, the at least one hetero atom is preferably selected from the group consisting of halogens, N, O, S, P and Si. In some cases, R may be a dialkylamine substituent such as, for example, diethylamine or dimethylamine. When R is a carbon-containing substituent, it may assume any structure or conformation, including, for instance, alkyl, cycloalkyl, alkenyl or alkynyl.

Compounds of the invention may adopt a variety of configurations. Exemplary configurations of specific configurations are shown in Table 2 below:

TABLE 2

Exemplary configurations of compounds of formula I

| F | (L)$_m$ | (R)$_p$ WSP | (L)$_q$ | (R)$_p$ RG | (L)$_q$ | (R)$_p$ | (L)$_q$ | n | T |
|---|---|---|---|---|---|---|---|---|---|
| | | | | R$_1$ | | | R$_2$ | R3 | |
| Coumarin, unsubstituted | alkylene, m = 0 or 1 | PEG, MW 300-800 | alkylene, q = 0 or 1 | Amine-reactive | alkylene, q = 0 or 1 | | | 0 | trivalent atom or group such as N or CH |
| | | | | Thiol-reactive | | | | | |
| | | | | Alcohol-reactive | | | | | |
| | | PEG, MW 800-2000 | | Amine-reactive | | | | | |
| | | | | Thiol-reactive | | | | | |
| | | | | Alcohol-reactive | | | | | |
| | | PEG, MW 2000-5000 | | Amine-reactive | | | | | |
| | | | | Thiol-reactive | | | | | |
| | | | | Alcohol-reactive | | | | | |
| Coumarin, 1 additional substitution (alkyl, halo, amino, hydroxyl or sulfonyl) | alkylene, m = 0 or 1 | PEG, MW 300-800 | alkylene, q = 0 or 1 | Amine-reactive | alkylene, q = 0 or 1 | | | 0 | trivalent atom or group such as N or CH |
| | | | | Thiol-reactive | | | | | |
| | | | | Alcohol-reactive | | | | | |
| | | PEG, MW 800-2000 | | Amine-reactive | | | | | |
| | | | | Thiol-reactive | | | | | |
| | | | | Alcohol-reactive | | | | | |
| | | PEG, MW 2000-5000 | | Amine-reactive | | | | | |
| | | | | Thiol-reactive | | | | | |
| | | | | Alcohol-reactive | | | | | |
| Coumarin, 2 additional substitutions (alkyl, halo, amino, hydroxyl or sulfonyl) | alkylene, m = 0 or 1 | PEG, MW 300-800 | alkylene, q = 0 or 1 | Amine-reactive | alkylene, q = 0 or 1 | | | 0 | trivalent atom or group such as N or CH |
| | | | | Thiol-reactive | | | | | |
| | | | | Alcohol-reactive | | | | | |
| | | PEG, MW 800-2000 | | Amine-reactive | | | | | |
| | | | | Thiol-reactive | | | | | |
| | | | | Alcohol-reactive | | | | | |
| | | PEG, MW 2000-5000 | | Amine-reactive | | | | | |
| | | | | Thiol-reactive | | | | | |
| | | | | Alcohol-reactive | | | | | |
| Coumarin, 3 additional substitutions (alkyl, halo, | alkylene, m = 0 or 1 | PEG, MW 300-800 | alkylene, q = 0 or 1 | Amine-reactive | alkylene, q = 0 or 1 | | | 0 | trivalent atom or group such as |

TABLE 2-continued

Exemplary configurations of compounds of formula I

| F | (L)$_m$ | R$_1$ (R)$_p$ WSP | (L)$_q$ | R$_2$ (R)$_p$ RG | (L)$_q$ | R3 (R)$_p$ | (L)$_q$ | n | T |
|---|---|---|---|---|---|---|---|---|---|
| amino, hydroxyl or sulfonyl) | | | | | | | | | N or CH |
| | | PEG, MW 800-2000 | | Thiol-reactive Alcohol-reactive Amine-reactive | | | | | |
| | | PEG, MW 2000-5000 | | Thiol-reactive Alcohol-reactive Amine-reactive | | | | | |
| | | | | Thiol-reactive Alcohol-reactive | | | | | |
| Coumarin, substituted with fused ring (optionally substituted with another | alkylene, m = 0 or 1 | PEG, MW 300-800 | alkylene, q = 0 or 1 | Amine-reactive | alkylene, q = 0 or 1 | | | 0 | trivalent atom or group such as N or CH |
| | | PEG, MW 800-2000 | | Thiol-reactive Alcohol-reactive Amine-reactive | | | | | |
| | | PEG, MW 2000-5000 | | Thiol-reactive Alcohol-reactive Amine-reactive | | | | | |
| | | | | Thiol-reactive Alcohol-reactive | | | | | |
| Indocarbocyanine fluorescent group, unsubstituted | alkylene, m = 0 or 1 | PEG, MW 300-800 | alkylene, q = 0 or 1 | Amine-reactive | alkylene, q = 0 or 1 | | | 0 | trivalent atom or group such as N or CH |
| | | PEG, MW 800-2000 | | Thiol-reactive Alcohol-reactive Amine-reactive | | | | | |
| | | PEG, MW 2000-5000 | | Thiol-reactive Alcohol-reactive Amine-reactive | | | | | |
| | | | | Thiol-reactive Alcohol-reactive | | | | | |
| Indocarbocyanine fluorescent group, With additional substitution (alkyl, halo, amino, hydroxyl or sulfonyl) | alkylene, m = 0 or 1 | PEG, MW 300-800 | alkylene, q = 0 or 1 | Amine-reactive | alkylene, q = 0 or 1 | | | 0 | trivalent atom or group such as N or CH |
| | | PEG, MW | | Thiol-reactive Alcohol-reactive Amine- | | | | | |

TABLE 2-continued

Exemplary configurations of compounds of formula I

| F | (L)$_m$ | R$_1$ | | | R$_2$ | | R$_3$ | | n | T |
| | | (R)$_p$ WSP | (L)$_q$ | (R)$_p$ RG | (L)$_q$ | (R)$_p$ | (L)$_q$ | | |
|---|---|---|---|---|---|---|---|---|---|
| | | 800-2000 | | reactive Thiol-reactive Alcohol-reactive | | | | | |
| | | PEG, MW 2000-5000 | | Amine-reactive Thiol-reactive Alcohol-reactive | | | | | |
| Rhodamine fluorescent group | alkylene, m = 0 or 1 | PEG, MW 300-800 | alkyl, q = 0 or 1 | Amine-reactive | alkylene, q = 0 or 1 | | | 0 | trivalent atom or group such as N or CH |
| | | PEG, MW 800-2000 | | Thiol-reactive Alcohol-reactive Amine-reactive Thiol-reactive Alcohol-reactive | | | | | |
| | | PEG, MW 2000-5000 | | Amine-reactive Thiol-reactive Alcohol-reactive | | | | | |
| Rhodamine fluorescent group, additional substitutions (alkyl, halo, amino, hydroxyl or sulfonyl) | alkylene, m = 0 or 1 | PEG, MW 300-800 | alkylene, q = 0 or 1 | Amine-reactive | alkylene, q = 0 or 1 | | | 0 | trivalent atom or group such as N or CH |
| | | PEG, MW 800-2000 | | Thiol-reactive Alcohol-reactive Amine-reactive Thiol-reactive Alcohol-reactive | | | | | |
| | | PEG, MW 2000-5000 | | Amine-reactive Thiol-reactive Alcohol-reactive | | | | | |
| Fluorescein fluorescent group | alkylene, m = 0 or 1 | PEG, MW 300-800 | alkylene, q = 0 or 1 | Amine-reactive | alkylene, q = 0 or 1 | | | 0 | trivalent atom or group such as N or CH |
| | | PEG, MW 800-2000 | | Thiol-reactive Alcohol-reactive Amine-reactive Thiol-reactive Alcohol-reactive | | | | | |
| | | PEG, MW 2000-5000 | | Amine-reactive Thiol- | | | | | |

TABLE 2-continued

Exemplary configurations of compounds of formula I

| F | $R_1$ | | | $R_2$ | | $R_3$ | | n | T |
|---|---|---|---|---|---|---|---|---|---|
| | $(L)_m$ | $(R)_p$ WSP | $(L)_q$ | $(R)_p$ RG | $(L)_q$ | $(R)_p$ | $(L)_q$ | | |
| Fluorescein fluorescent group, additional substitutions (alkyl, halo, amino, hydroxyl or sulfonyl) | alkylene, m = 0 or 1 | PEG, MW 300-800 | alkylene, q = 0 or 1 | reactive Alcohol-reactive Amine-reactive | alkylene, q = 0 or 1 | | | 0 | trivalent atom or group such as N or CH |
| | | PEG, MW 800-2000 | | Thiol-reactive Alcohol-reactive Amine-reactive Thiol-reactive Alcohol-reactive | | | | | |
| | | PEG, MW 2000-5000 | | Amine-reactive Thiol-reactive Alcohol-reactive | | | | | |
| Pyrene | alkylene, m = 0 or 1 | PEG, MW 300-800 | alkylene, q = 0 or 1 | Amine-reactive | alkylene, q = 0 or 1 | | | 0 | trivalent atom or group such as N or CH |
| | | PEG, MW 800-2000 | | Thiol-reactive Alcohol-reactive Amine-reactive Thiol-reactive Alcohol-reactive | | | | | |
| | | PEG, MW 2000-5000 | | Amine-reactive Thiol-reactive Alcohol-reactive | | | | | |
| Pyrene, additional substitutions (alkyl, halo, amino, hydroxyl or sulfonyl) | alkylene, m = 0 or 1 | PEG, MW 300-800 | alkylene, q = 0 or 1 | Amine-reactive | alkylene, q = 0 or 1 | | | 0 | trivalent atom or group such as N or CH |
| | | PEG, MW 800-2000 | | Thiol-reactive Alcohol-reactive Amine-reactive Thiol-reactive Alcohol-reactive | | | | | |
| | | PEG, MW 2000-5000 | | Amine-reactive Thiol-reactive Alcohol-reactive | | | | | |

In the above Table, "WSP" signifies a water soluble polymer group, while "RG" represents a reactive group.

In one embodiment, the compound of formula I comprises a fluorophore which is a xanthene fluorescent group, a coumarin fluorescent group, a pyrene fluorescent group or a cyanine fluorescent group. In some embodiments, the fluorophore is a coumarin fluorescent group. Such a fluorophore may have the formula

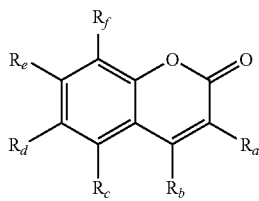

where one moiety of $R_a$, $R_b$, $R_c$, $R_d$, $R_e$ and $R_f$ is a bond connecting the fluorophore to a moiety $-(L)_m$- or a moiety

as indicated in Formula I. The remaining moieties $R_a$, $R_b$, $R_c$, $R_d$, $R_e$ and $R_f$ have the formula $(R)_p$-$(L)_q$-, where R, L, p and q are as previously defined. For example, any adjacent pair of $R_a$, $R_b$, $R_c$, $R_d$, $R_e$ and $R_f$ may join to form a 5- or 6-membered, saturated or unsaturated ring that may optionally comprise additional heteroatoms in the ring as well as additional R substituents. In some embodiments, such R substituents are $SO_3^-$, sulfonamido, halo, hydroxy, amino or alkyl groups.

In another embodiment, the fluorophore is a compound of the formula:

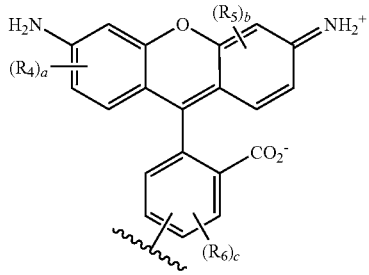

wherein

connects said fluorophore to said moiety $-(L)_m$- or said moiety

$R_4$, $R_5$, and $R_6$ are each independently $(R)_p$-$(L)_q$-; each R of $R_4$, $R_5$, $R_6$ is independently i) a reactive group capable of forming a covalent bond upon reacting with a reaction partner; ii) a water soluble polymer group; iii) an alkyl group, a trifluoroalkyl group, a halogen group, a sulfonate group or a sulfonamido group; or iv) —H; each L of $R_4$, $R_5$ and $R_6$ is independently a linking moiety formed of one or more chemical bonds and containing about 1-100 atoms; each p of $R_4$, $R_5$, and $R_6$ is independently an integer ranging from 1 to 20; each q of $R_4$, $R_5$, and $R_6$ is independently an integer ranging from 0 to 20; and a, b, and c are independently 0, 1, 2, or 3.

In one embodiment, T is a trivalent moiety comprising one carbon atom such as

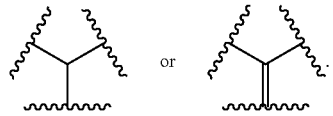

Alternatively, T may be a trivalent nitrogen atom. For example,

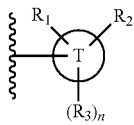

in Formula I may have the formula

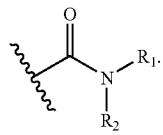

When $R_1$ is a water soluble polymer, said water-soluble polymer may have a molecular weight of greater than about 300 Da. Alternatively, the molecular weight may be greater than 800 Da, or it may range from about 800 Da to about 3000 Da. $R_1$, may, for example, comprise a water soluble group such as a polyethylene glycol group. In some embodiments, the molecular weight of the polyethylene glycol group is between 450 and 5000 Da.

When $R_2$ is a reactive group, the reactive group may form a covalent bond, for example, with amino, sulfhydryl or hydroxy nucleophiles. In some embodiments, the reactive group is an isothiocyanate, an isocyanate, a monochlorotriazine, a dichlorotriazine, a halogen-substituted pyridine, a halogen-substituted diazine, a phosphoramidite, a maleimide, an aziridine, a sulfonyl halide, an acid halide, a hydroxysuccinimide ester, a hydroxysulfosuccinimide ester, an imido ester, a hydrazine, an azidonitrophenyl, an azide, an alkyne, a 3-(2-pyridyl dithio)-propionamide, a glyoxal or an aldehyde. In some embodiments, the reactive group is an N-hydroxysuccinimide ester.

In another aspect of the invention, a compound is provided having a maximal fluorescence excitation wavelength wherein the compound has a structure of Formula II:

$$F-Y=\Psi \qquad \text{Formula II}$$

wherein:

F is a moiety having the structure:

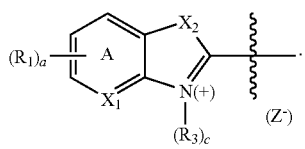

Z⁻ is a counterion.

Y is a bridge unit permitting electron delocalization between F and ☐. Suitable moieties are well known in the art in the context of cyanine fluorescent groups. Generally, a Y group will allow electron delocalization between said two structures. For example, Y may be a methine unit or may alternatively be a polymethine unit (tri-, penta- or heptamethine) optionally incorporating one or more 4, 5, or 6-membered rings. Additional substitutions with R groups of the invention are also contemplated. For example, Y may comprise an R group which is a water soluble polymer, a reactive group or an additional substituent as defined above. For example, alkyl, $SO_3^-$ and halogen are all possible substituents present as part of the Y group.

In some embodiments, Ψ is a moiety having one of the following structures:

Formula 1

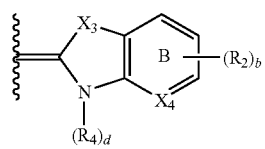

Formula 2

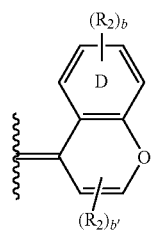

Formula 3

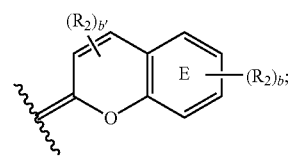

Formula 4

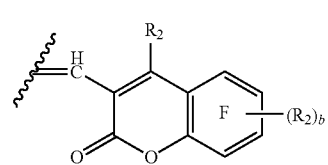

Formula 5

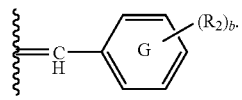

$X_1$ and $X_4$ are independently

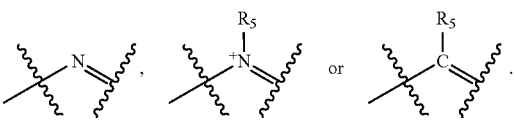

$X_1$ and $X_4$ may or may not be additionally substituted.

$X_2$ and $X_3$ are independently

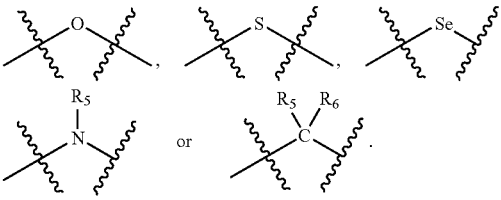

The elements a and b are independently 0, 1, 2, or 3.

The element b' is 0, 1 or 2.

In some embodiments, when Ψ is Formula 1, and the maximal fluorescence excitation wavelength of the compound is less than 660 nm, then $R_5$ and $R_6$ are independently $(R)_p\,(L)_q$-, wherein $R_5$ and $R_6$ are not combinable to form a substituted ring; In other embodiments of the invention, when Ψ is Formula 1, and the maximal fluorescence excitation wavelength of the compound is equal to or greater than 660 nm, or Ψ is other than Formula 1, then $R_5$ and $R_6$ are independently $(R)_p$-$(L)_q$-, or $R_5$ and $R_6$ are combinable to form a cyclic moiety which is unsubstituted or substituted by one or more $(R)_p$-$(L)_q$-. The cyclic moiety so formed is a 5, 6, or 7 membered ring with is carbocyclic or heterocyclic, and in some embodiments, substituted by one or more reactive groups and/or one or more water soluble polymers.

In yet other embodiments, when Ψ is Formula 1, and the maximal fluorescence excitation wavelength of the compound is less than 655 nm, then $R_5$ and $R_6$ are independently $(R)_p\,(L)_q$-, wherein $R_5$ and $R_6$ are not combinable to form a substituted ring; In other embodiments of the invention, when Ψ is Formula 1, and the maximal fluorescence excitation wavelength of the compound is equal to or greater than 655 nm, or Ψ is other than Formula 1, then $R_5$ and $R_6$ are independently $(R)_p$-$(L)_q$, or $R_5$ and $R_6$ are combinable to form a cyclic moiety which is unsubstituted or substituted by one or more $(R)_p\,(L)_q$-.

In various embodiments, Y is:

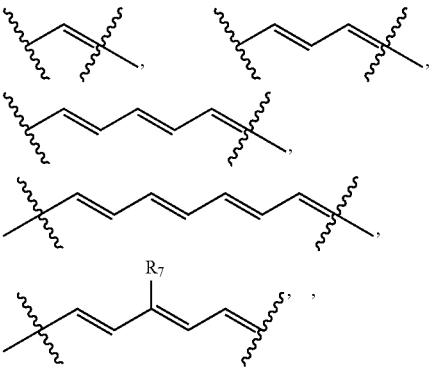

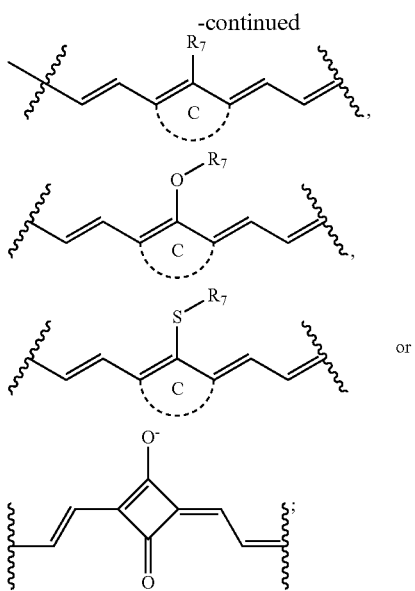

wherein when C is present, it is a five- or six-membered cyclic group.

$R_1$, $R_2$, $R_3$, $R_4$, $R_5$, $R_6$ and $R_7$ are each independently $(R)_p\text{-}(L)_q\text{-}$.

Each R of each $(R)_p\text{-}(L)_q\text{-}$ of the compound is independently i) a reactive group capable of forming a covalent bond upon reacting with a reaction substrate; ii) a water soluble polymer group; iii) an alkyl group, an aryl group, an alkylamino group, a dialkylamino group, an alkoxy group, a trifluoroalkyl group, a halogen group, a sulfonyl group, a sulfonate group or a sulfonamido group; or iv) —H.

Each L of each $(R)_p\text{-}(L)_q\text{-}$ of the compound is independently a linking moiety formed of one or more chemical bonds and containing about 1-100 atoms.

Each p of each $(R)_p\text{-}(L)_q\text{-}$ is independently an integer of about 1 to about 20.

Each q of each $(R)_p\text{-}(L)_q\text{-}$ of $R_1$ or $R_2$ is independently an integer of 0 to about 20.

Each q of each $(R)_p\text{-}(L)_q\text{-}$ of $R_3$, $R_4$, $R_5$, $R_6$, or $R_7$, is independently an integer of 1 to about 20.

The element c is 0 or 1.

The element d is 0 or 1.

At least one R of the $(R)_p$ $(L)_q$- of the compound is a reactive moiety; and at least one R of the $(R)_p\text{-}(L)_q\text{-}$ of the compound is a water-soluble polymer.

In some embodiments, when at least two adjacent $R_1$, and/or two adjacent $R_2$ are present, the two adjacent $R_1$, and/or the two adjacent $R_2$ are combinable to form a 6-membered ring which is unsubstituted or substituted by one or more $(R)_p\text{-}(L)_q\text{-}$. In some other embodiments, when the two adjacent $R_1$, and/or the two adjacent $R_2$ are combinable to form a 6-membered ring, the ring so formed is aromatic. In some embodiments, two adjacent $(R_2)_b$ and the atoms in ring B to which it is attached are combined to form a carbocyclic ring, optionally additionally substituted with groups that may further increase the solubility of the fluorescent group. In some embodiments, two adjacent $(R_2)_b$ and the atoms in ring B to which it is attached are combined to form a carbocyclic ring which is aromatic and optionally additionally substituted with groups that may further increase the solubility of the fluorescent group. In some embodiments, two adjacent $(R_1)_b$ and the atoms in ring A to which it is attached are combined to form a carbocyclic ring, and optionally additionally substituted with groups that may further increase the solubility of the fluorescent group. In some embodiments, two adjacent $(R_1)_b$ and the atoms in ring A to which it is attached are combined to form a carbocyclic ring which is aromatic, which is optionally additionally substituted with groups that may further increase the solubility of the fluorescent group.

The element c may be 0 or 1. When c is 1, the nitrogen atom to which $R_3$ is attached is positively charged. Similarly, d may be 0 or 1.

In various embodiments, at least one R of $R_1$ and $R_2$ is a charged moiety. In some embodiments, at least one R of $R_1$ and $R_2$ comprises a sulfonate group or a phosphonate group. In yet other embodiments, each R of $R_1$ and $R_2$ comprises a sulfonate group or a phosphonate group.

In various embodiments of the invention, $X_2$ and $X_3$ are independently

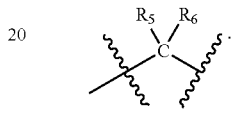

In related embodiments, $X_2$ and $X_3$ are alkyl groups such as methyl or ethyl. In some embodiments, $X_2$ and $X_3$ are

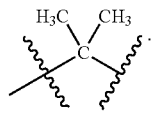

In some embodiments, $X_2$ and $X_3$ are:

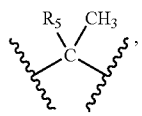

wherein $R_5$ comprises a reactive group or a water-soluble polymer.

The compound of formula II contains at least one reactive group and a water-soluble polymer. These groups may be attached at any position shown in formula II. For example, a reactive group or a water-soluble polymer may be attached to ring A or ring B. Alternatively, the reactive group or the water-soluble polymer may substitute the nitrogen atoms indicated in formula II, e.g. $R_3$ could be a reactive group and $R_4$ could be a water-soluble polymer, optionally attached through L linker moieties. Furthermore, reactive groups and/or water-soluble polymers may also be attached to the $X_2$ and/or $X_3$ positions in formula II, or may be part of the linker structure Y.

In some cases, it may be desirable to include at least one R substituent which is a charged moiety on ring A or one ring of B, D, E, F, and G or both ring A and one ring of B, D, E, F and G such as to increase the solubility of the compound of formula II. Such a moiety may be a sulfonate group or any other group as previously described. Similar substitution can be made as part of the groups $R_3$, $R_4$, $X_2$ and $X_3$, for example by attaching a linker moiety which is substituted with a sulfonate, phosphonate or other charged group.

In various embodiments of the invention, the water-soluble polymer is a polyalkylene oxide. In other embodiments, the water-soluble polymer is a polyethylene oxide. In yet other embodiments, the water-soluble polymer is a carbohydrate. In some other embodiments, the water-soluble polymer is a polypeptide. In various embodiments, the water-soluble polymer has a molecular weight ranging from about 800 to about 3000. In some embodiments, the water-soluble polymer has a molecular weight of greater than 300. In other embodiments, the water-soluble polymer has a molecular weight of greater than 800.

In some embodiments the compound of Formula II comprises at least one reactive group and at least two water-soluble polymers.

In some embodiments of the compound of Formula II, the compound has the formula:

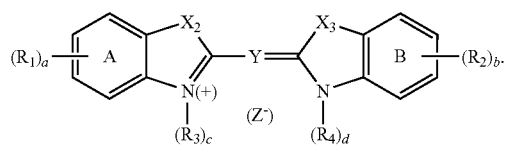

In various embodiments, the compound of Formula II has the formula:

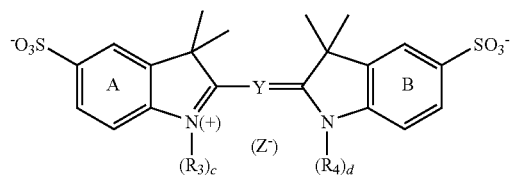

wherein c is 1; d is 1; at least one R of $R_3$ and $R_4$ is a reactive group capable of forming a covalent bond upon reacting with a reaction substrate; and at least one R of $R_3$ and $R_4$ is a water soluble polymer group.

In other embodiments, the compound has the formula:

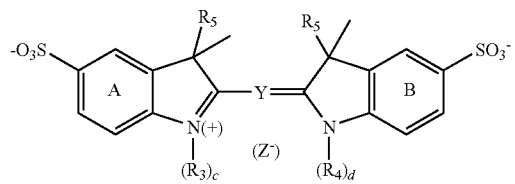

wherein c is 1; and d is 1; at least one R of $R_3$, $R_4$ and $R_5$ is a reactive group capable of forming a covalent bond upon reacting with a reaction substrate; and at least one R of $R_3$, $R_4$ and $R_5$ is a radical of a water-soluble polymer. In another embodiment, c is 1; d is 1; one R of $R_3$, $R_4$ and $R_5$ is a reactive group; and at least two R of $R_3$, $R_4$ and $R_5$ are a radical of a water-soluble polymer. In one embodiment, Y is selected such that the absorption maximal wavelength is about 550 nm, about 650 nm, or about 750 nm.

In yet other embodiments, the compound has the formula:

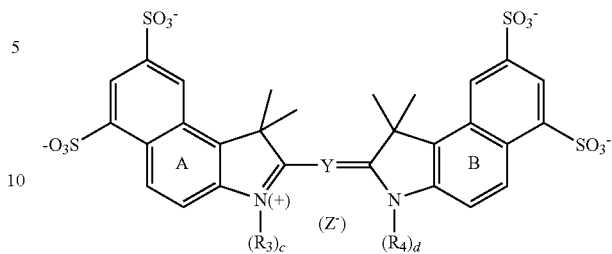

wherein c is 1; d is 1;

one R of $R_3$ and $R_4$ is a reactive group capable of forming a covalent bond upon reacting with a reaction substrate; and one R of $R_3$ and $R_4$ is a water soluble polymer group.

In some other embodiments, the compound has the formula:

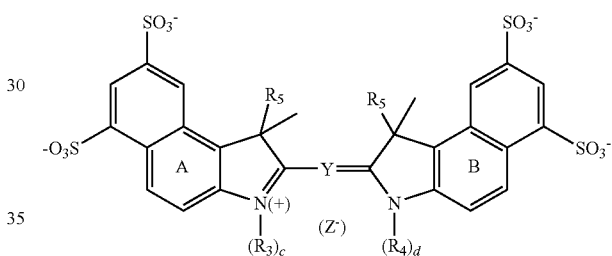

wherein c is 1; d is 1;

at least one R of $R_3$, $R_4$ and $R_5$ is a reactive group capable of forming a covalent bond upon reacting with a reaction substrate; and at least one R of $R_3$, $R_4$ and $R_5$ is a radical of a water-soluble polymer.

In other embodiments, the compound has the formula:

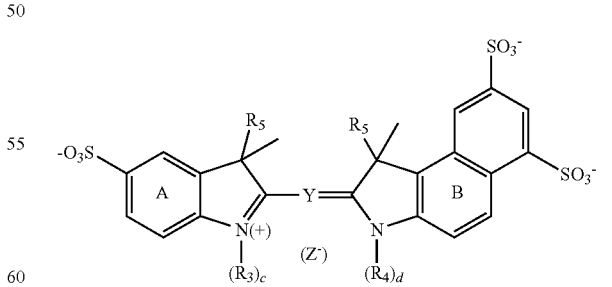

wherein c is 1; d is 1;

at least one R of $R_3$, $R_4$ and $R_5$ is a reactive group capable of forming a covalent bond upon reacting with a reaction substrate; and at least one R of $R_3$, $R_4$ and $R_5$ is a radical of a water-soluble polymer. In another embodiment, In another embodiment, the compound has the structure:

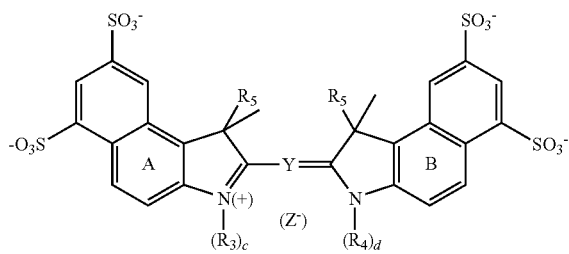

wherein, c is 1; d is 1; one R of $R_3$, $R_4$ and $R_5$ is a reactive group; and at least two R of $R_3$, $R_4$ and $R_5$ each comprise a radical of a water-soluble polymer. In one embodiment, Y is selected such that the absorption maximal wavelength is about 580 nm, about 680 nm, or about 790 nm.

In yet another embodiment, the compound has the structure:

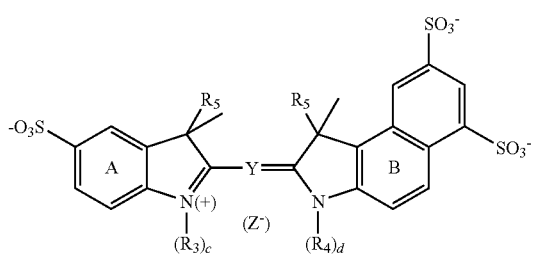

wherein, c is 1; d is 1; one R of $R_3$, $R_4$ and $R_5$ is a reactive group; and at least two R of $R_3$, $R_4$ and $R_5$ are each a radical of water-soluble polymers. In one embodiment, Y is selected such that the absorption maximal wavelength is around 560 nm, around 660 nm, or around 770 nm.

For compounds of Formula II, it is well known to a person of skill in the art to select the bridging unit Y, in combination with a specific embodiment of a moiety of Formula F, in combination with a specific embodiment of moiety Y, and in combination with specific substituents such that the maximal fluorescence excitation wavelength of the compound ranges from about 350 to about 1200 nm. Standard analysis well known in the art is used to obtain the absorption and emission spectra of the dyes in order to ascertain the absorption maximal wavelength and the maximal fluorescence emission wavelength. Any combinations of the above described groups may be used to form a compound of the invention with a maximal fluorescence excitation wavelength of about 550 nm, about 560 nm, about 570 nm, about 580 nm, about 590 nm, about 600 nm, about 610 nm, about 620 nm, about 615 nm, about 620 nm, about 625 nm, about 630 nm, about 635 nm, about 640 nm, about 650 nm, about 655 nm, about 660 nm, about 665 nm, about 670 nm, about 675 nm, about 680 nm, about 685 nm, about 690 nm, about 695 nm, about 700 nm, about 705 nm, about 710 nm, about 715 nm, about 720 nm, about 725 nm, about 730 nm, about 735 nm, about 740 nm, about 745 nm, about 750 nm, about 755 nm, about 760 nm, about 765 nm, about 770 nm, about 775 nm, about 780 nm, about 790 nm, about 800 nm, about 810 nm, about 820 nm, about 830 nm, about 840 nm, about 850 nm, about 860 nm, about 870 nm, about 880 nm, about 890 nm, about 900 nm, about 910 nm, about 920 nm, about 930 nm, about 940 nm, about 950 nm, about 960 nm, about 970 nm, about 980 nm, about 990 nm, about 1000 nm, about 1020 nm, about 1040 nm, about 1060 nm, about 1080 nm, about 1100 nm, about 1120 nm, about 1140 nm, about 1160 nm, about 1180 nm, or about 1200 nm. The moieties described above may be used in any combination. The maximal fluorescence excitation wavelength of the dye is typically the wavelength at which the dye has a maximal absorption or maximal optical density, which excites the dye to fluoresce. In some embodiments, the compound of Formula II has an absorption maximal wavelength at >670 nm. In one embodiment, the absorption maximal wavelength is at >700 nm. According to another embodiment, the absorption maximal wavelength is at >800 nm.

A person of skill can also combine select the bridging unit Y, in combination with a specific embodiment of a moiety of Formula F, in combination with a specific embodiment of moiety Y, and in combination with specific substituents such that one obtains a compound of Formula II having a maximal fluorescence emission wavelength of about 550 nm, about 560 nm, about 570 nm, about 580 nm, about 590 nm, about 600 nm, about 610 nm, about 620 nm, about 615 nm, about 620 nm, about 625 nm, about 630 nm, about 635 nm, about 640 nm, about 650 nm, about 655 nm, about 660 nm, about 665 nm, about 670 nm, about 675 nm, about 680 nm, about 685 nm, about 690 nm, about 695 nm, about 700 nm, about 705 nm, about 710 nm, about 715 nm, about 720 nm, about 725 nm, about 730 nm, about 735 nm, about 740 nm, about 745 nm, about 750 nm, about 755 nm, about 760 nm, about 765 nm, about 770 nm, about 775 nm, about 780 nm, about 790 nm, about 800 nm, about 810 nm, about 820 nm, about 830 nm, about 840 nm, about 850 nm, about 860 nm, about 870 nm, about 880 nm, about 890 nm, about 900 nm, about 910 nm, about 920 nm, about 930 nm, about 940 nm, about 950 nm, about 960 nm, about 970 nm, about 980 nm, about 990 nm, about 1000 nm, about 1020 nm, about 1040 nm, about 1060 nm, about 1080 nm, about 1100 nm, about 1120 nm, about 1140 nm, about 1160 nm, about 1180 nm, about 1200 nm, about 1220 nm, about 1240 nm, or about 1250 nm. The moieties described above may be used in any combination.

According to one embodiment, the wavelength of the absorption maximum of a compound of formula II is at least greater than 655 nm.

According to one embodiment, the wavelength of the absorption maximum of a compound of formula II is at least greater than 670 nm. In still another embodiment, the wavelength of the absorption maximum of a compound of formula II is at least greater than 670 nm. In yet another embodiment, the wavelength of the absorption maximum of a compound of formula II is at least greater than 700 nm.

In another aspect of the invention, a substituted cyanine dye is provided which comprises one or more water soluble polymer groups, wherein the cyanine dye has a maximal fluorescence excitation wavelength of equal to or greater than about 660 nm. In some embodiments, the substituted cyanine dye comprises at least one reactive group. In some embodiments, the substituted cyanine dye is substituted by a non-spiro moiety.

In a further aspect of the invention, a substituted cyanine dye is provided which comprises one or more water soluble polymer groups, wherein the cyanine dye has an absorption maximal wavelength of equal to or greater than about 660 nm. In some embodiments, the substituted cyanine dye comprises at least one reactive group. In some embodiments, the substituted cyanine dye is substituted by a non-spiro moiety.

Exemplary Structures of Compounds of the Formula II are Shown Below in Table 3

TABLE 3
Exemplary structures of compounds of the formula II
| Dye No. | Structure | $\lambda_{abs}/\lambda_{em}$ (nm) (H$_2$O) |
|---|---|---|
| 1 | 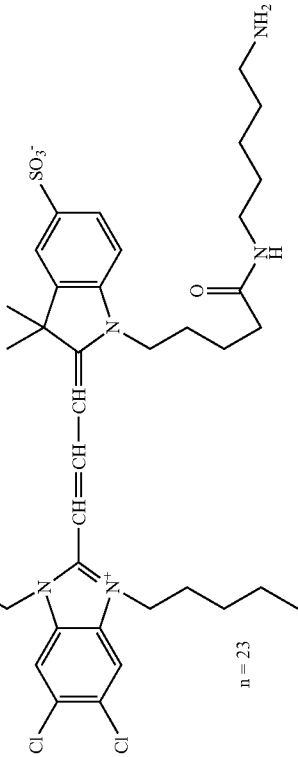 | 457/ |

TABLE 3-continued
Exemplary structures of compounds of the formula II
| Dye No. | Structure | $\lambda_{abs}/\lambda_{em}$ (nm) (H$_2$O) |
|---|---|---|
| 2 | 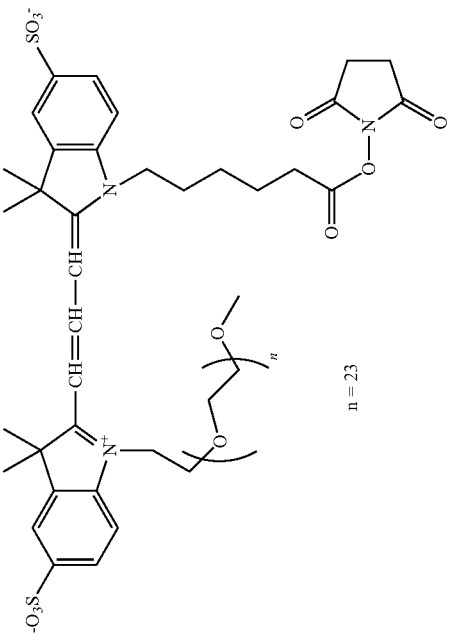 | 550/570 |
| 3 | 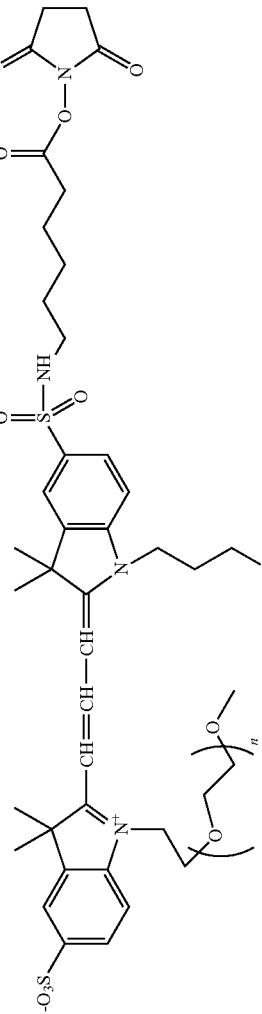 | 550/570 |

TABLE 3-continued
Exemplary structures of compounds of the formula II
| Dye No. | Structure | $\lambda_{abs}/\lambda_{em}$ (nm) ($H_2O$) |
|---|---|---|
| 4 | 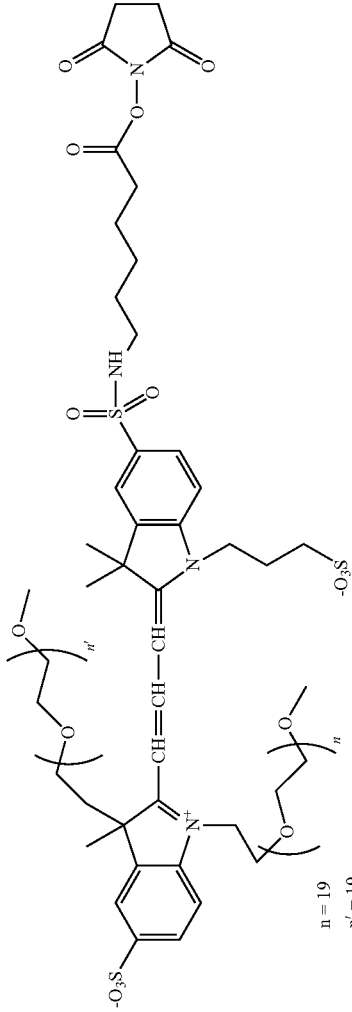 n = 19, n' = 19 | 550/570 |
| 5 | 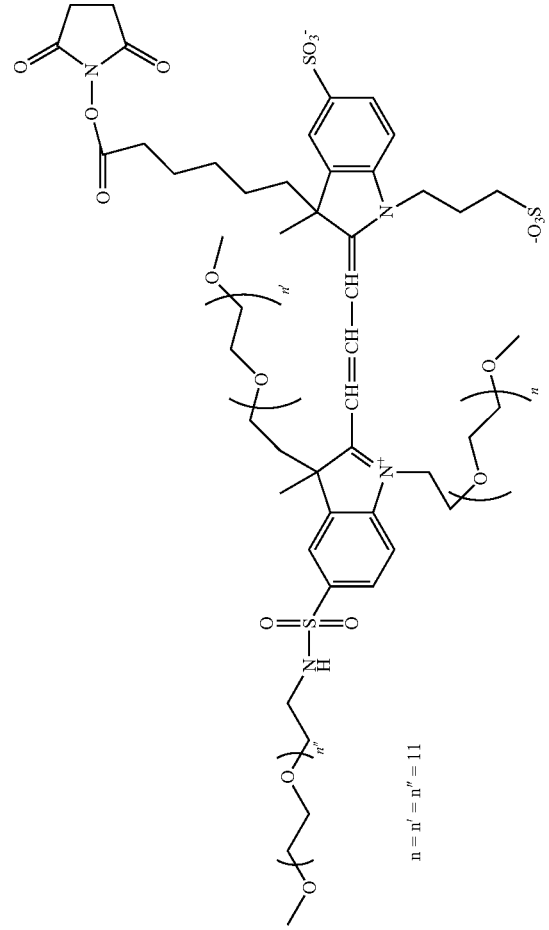 n = n' = n'' = 11 | 550/570 |

TABLE 3-continued
Exemplary structures of compounds of the formula II
| Dye No. | Structure | $\lambda_{abs}/\lambda_{em}$ (nm) (H$_2$O) |
|---|---|---|
| 6 | 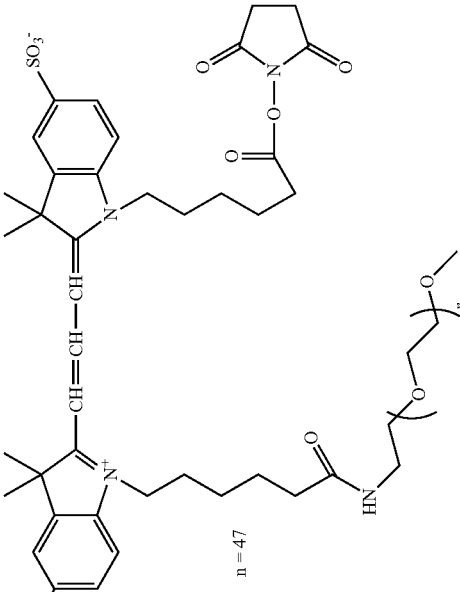 n = 47 | 550/570 |
| 7 | 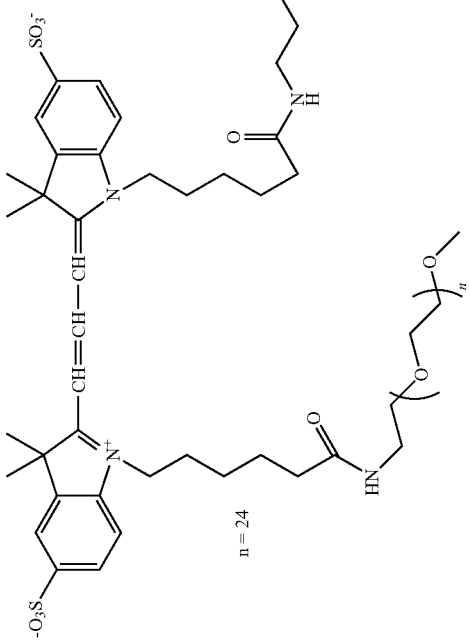 n = 24 | 550/570 |

TABLE 3-continued

Exemplary structures of compounds of the formula II

| Dye No. | Structure | $\lambda_{abs}/\lambda_{em}$ (nm) (H$_2$O) |
|---|---|---|
| 8 | 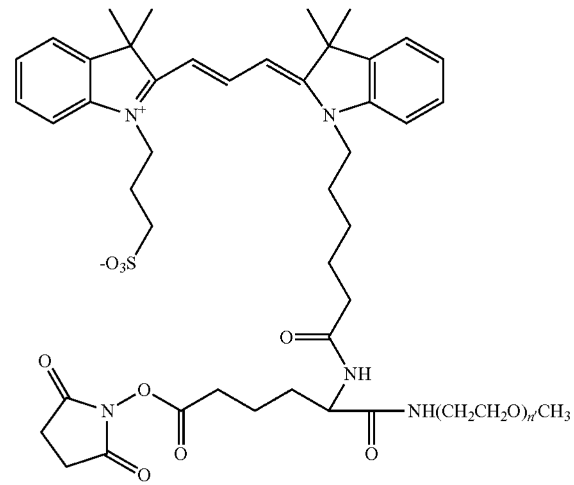 | 550/570 |
| 9 | 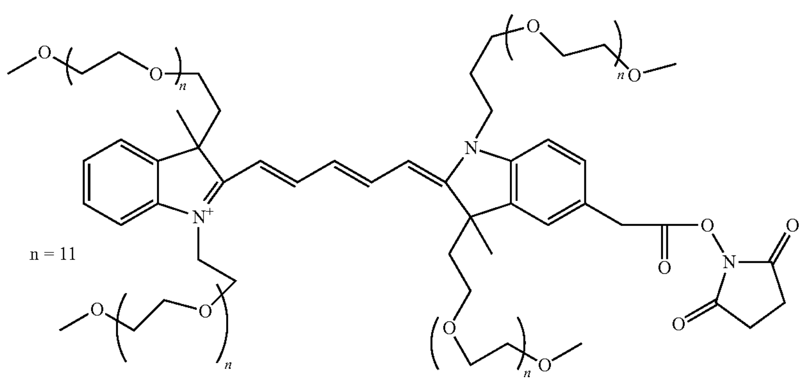 | 650/665 |

TABLE 3-continued
Exemplary structures of compounds of the formula II
| Dye No. | Structure | $\lambda_{abs}/\lambda_{em}$ (nm) (H$_2$O) |
|---|---|---|
| 10 | 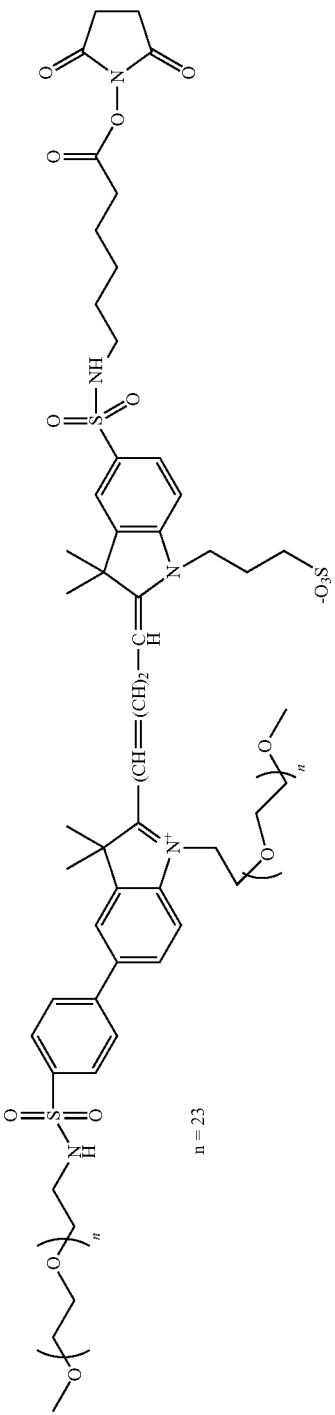 | 650/665 |
| 11 | 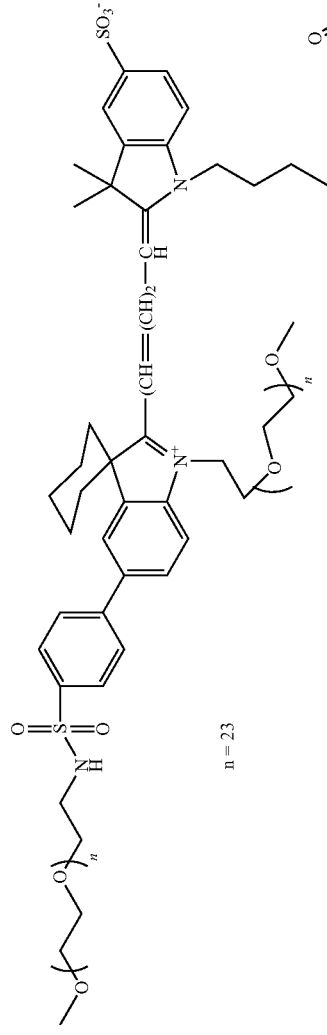 | 650/665 |

TABLE 3-continued
Exemplary structures of compounds of the formula II
| Dye No. | Structure | $\lambda_{abs}/\lambda_{em}$ (nm) (H$_2$O) |
|---|---|---|
| 12 | 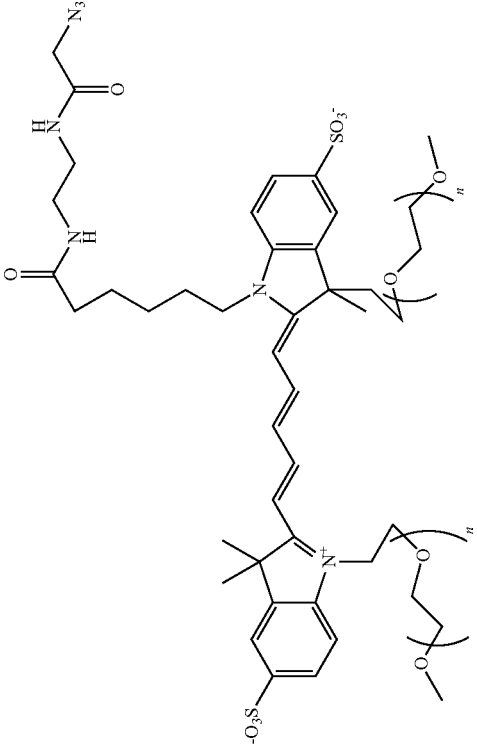 n = 23 | 650/665 |
| 13 | 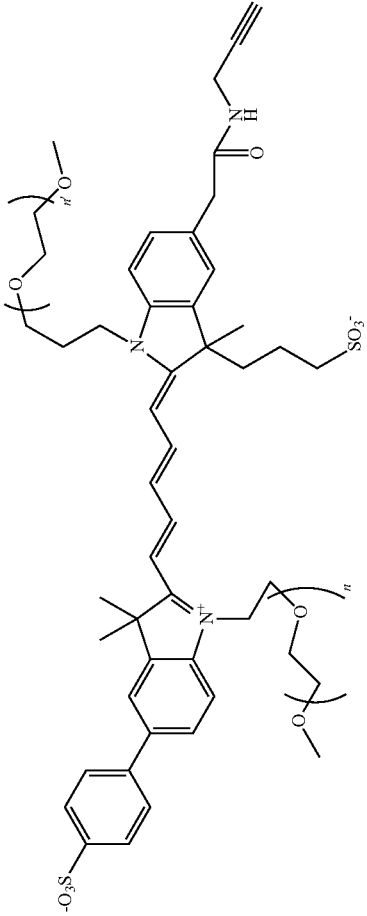 n = 23, n' = 11 | 650/665 |

TABLE 3-continued
Exemplary structures of compounds of the formula II
| Dye No. | Structure | $\lambda_{abs}/\lambda_{em}$ (nm) ($H_2O$) |
|---|---|---|
| 14 | 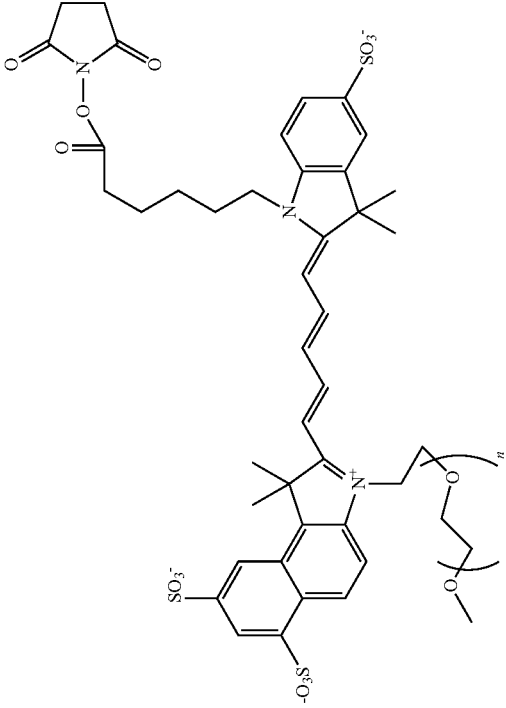 n = ~100 | 660/680 |

TABLE 3-continued
Exemplary structures of compounds of the formula II
| Dye No. | Structure | $\lambda_{abs}/\lambda_{em}$ (nm) (H$_2$O) |
|---|---|---|
| 15 | 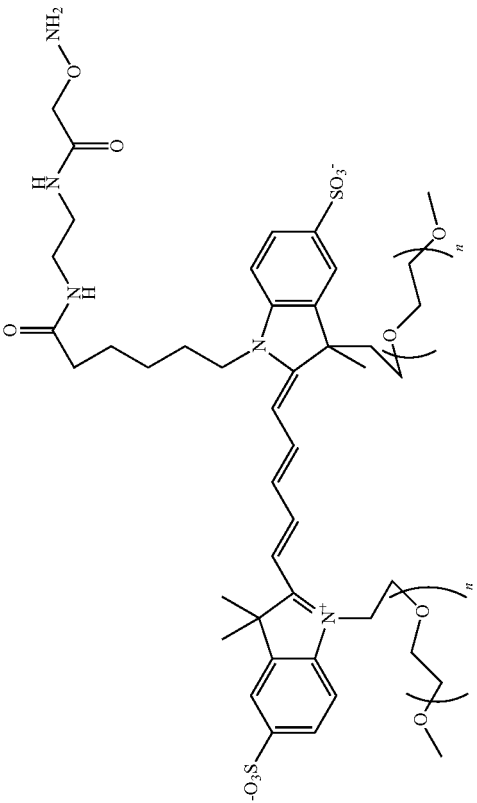 n = 23 | 650/665 |

TABLE 3-continued
Exemplary structures of compounds of the formula II
| Dye No. | Structure | $\lambda_{abs}/\lambda_{em}$ (nm) ($H_2O$) |
|---|---|---|
| 16 | 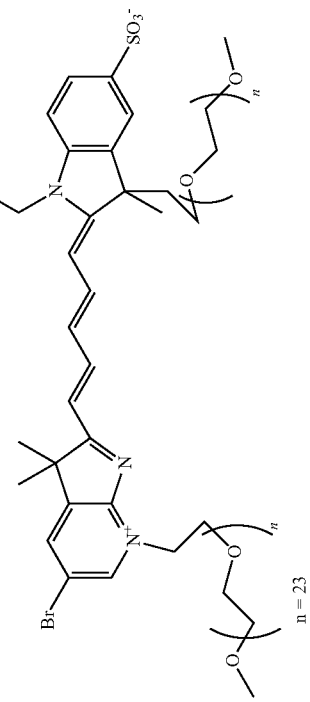 | 663/690 |

TABLE 3-continued

Exemplary structures of compounds of the formula II

| Dye No. | Structure | $\lambda_{abs}/\lambda_{em}$ (nm) (H$_2$O) |
|---|---|---|
| 17 | (structure shown; n = 23, n' = 11) | 752/778 |

TABLE 3-continued
Exemplary structures of compounds of the formula II
| Dye No. | Structure | $\lambda_{abs}/\lambda_{em}$ (nm) ($H_2O$) |
|---|---|---|
| 18 | 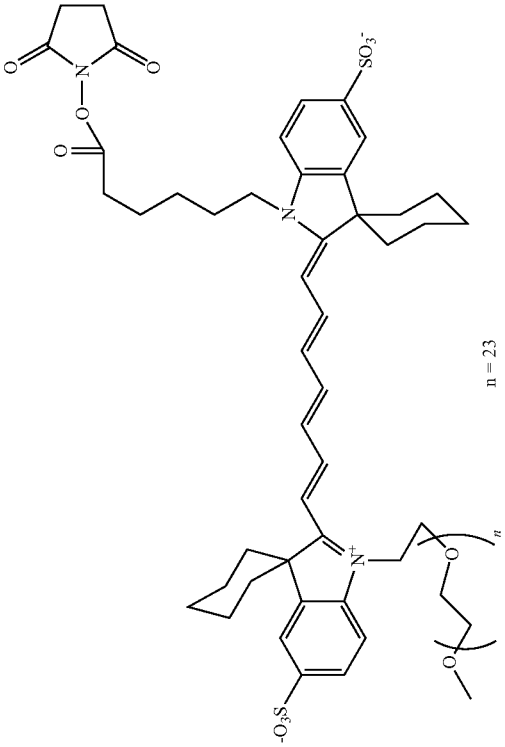 n = 23 | 750/775 |

TABLE 3-continued
Exemplary structures of compounds of the formula II
| Dye No. | Structure | $\lambda_{abs}/\lambda_{em}$ (nm) (H$_2$O) |
|---|---|---|
| 19 | 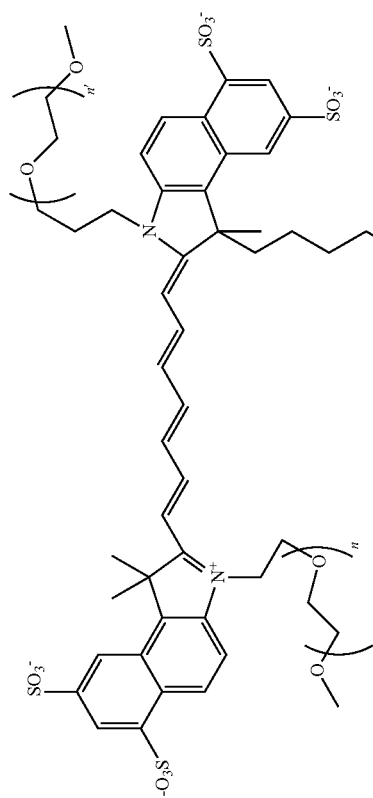 n = 23 n' = 11 | 675/694 |

TABLE 3-continued
Exemplary structures of compounds of the formula II
| Dye No. | Structure | $\lambda_{abs}/\lambda_{em}$ (nm) (H$_2$O) |
|---|---|---|
| 20 | 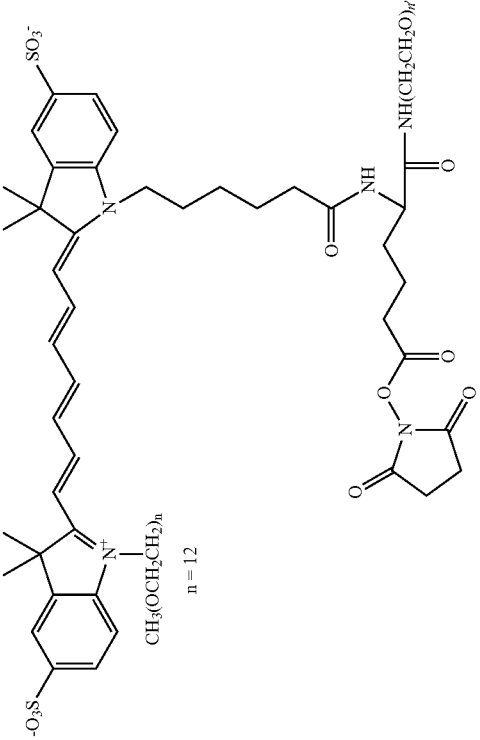 | 750/775 |
| 21 | 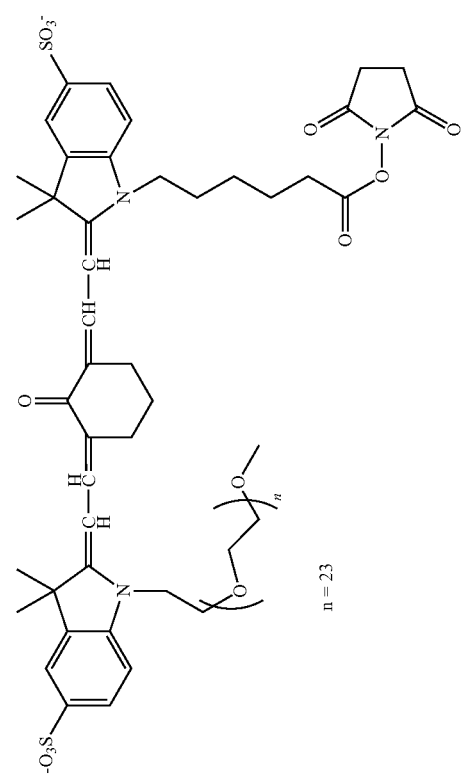 | |

TABLE 3-continued

Exemplary structures of compounds of the formula II

| Dye No. | Structure | $\lambda_{abs}/\lambda_{em}$ (nm) (H$_2$O) |
|---|---|---|
| 22 | 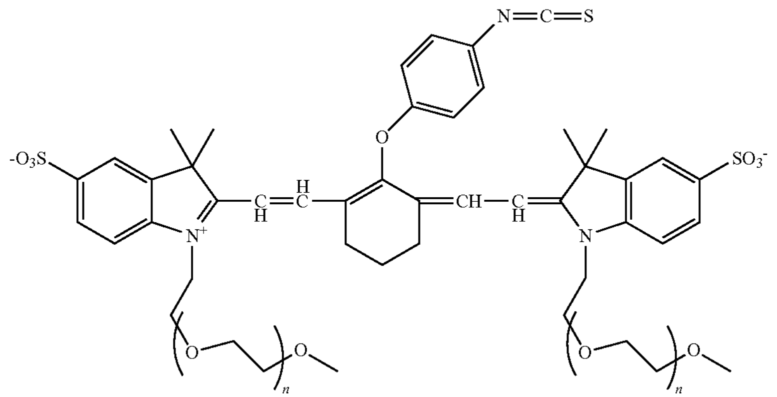 | 768/788 |
| 23 | 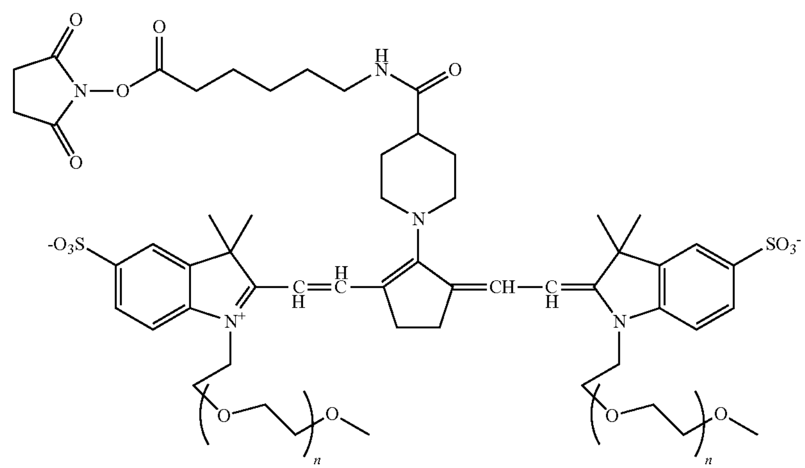 | |

TABLE 3-continued
Exemplary structures of compounds of the formula II
| Dye No. | Structure | $\lambda_{abs}/\lambda_{em}$ (nm) (H$_2$O) |
|---|---|---|
| 24 | 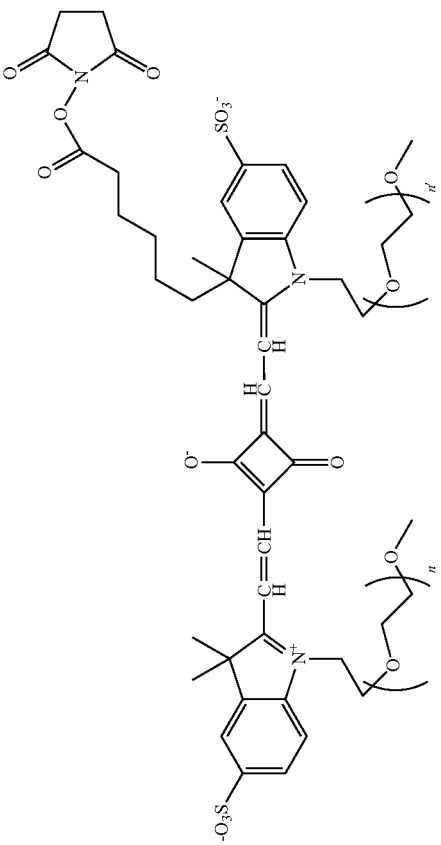 | 635/642 |
| 25 | 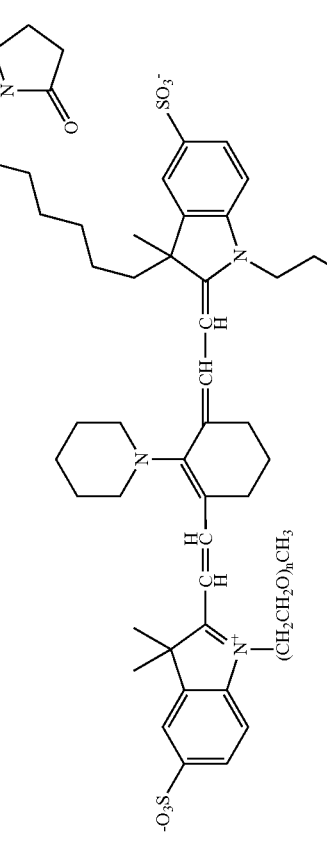 | |

TABLE 3-continued
Exemplary structures of compounds of the formula II
| Dye No. | Structure | $\lambda_{abs}/\lambda_{em}$ (nm) (H$_2$O) |
|---|---|---|
| 26 | 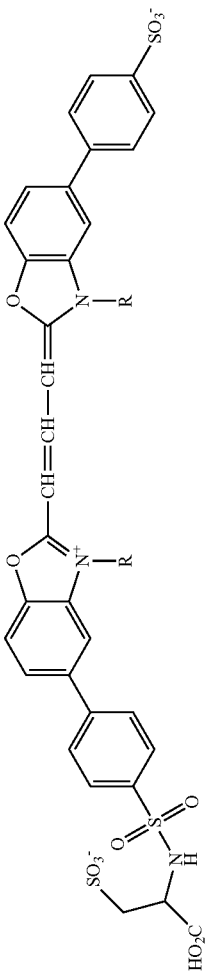 R = —(CH$_2$)$_5$CONH(CH$_2$CH$_2$O)$_{24}$CH$_3$ | 497/513 |
| 27 | 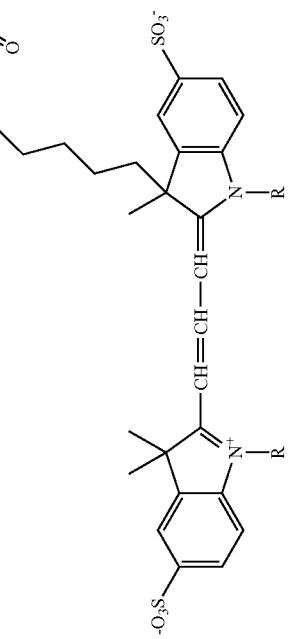 R = —(CH$_2$)$_5$CONH(CH$_2$CH$_2$O)$_{24}$CH$_3$ | 555/565 |

TABLE 3-continued
Exemplary structures of compounds of the formula II
| Dye No. | Structure | $\lambda_{abs}/\lambda_{em}$ (nm) (H$_2$O) |
|---|---|---|
| 28 | 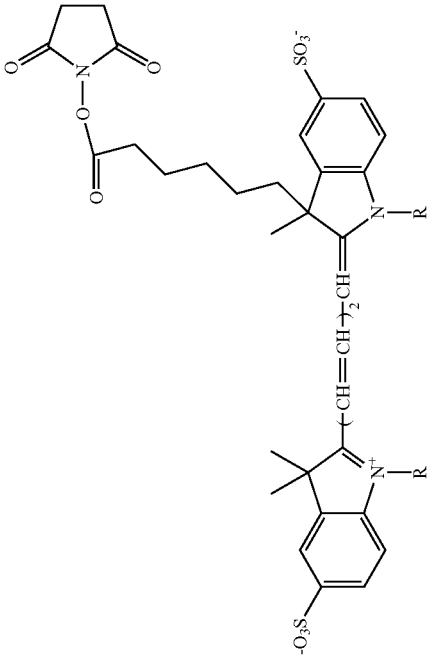 R = —(CH$_2$)$_5$CONH(CH$_2$CH$_2$O)$_{24}$CH$_3$ | 650/665 |
| 29 | 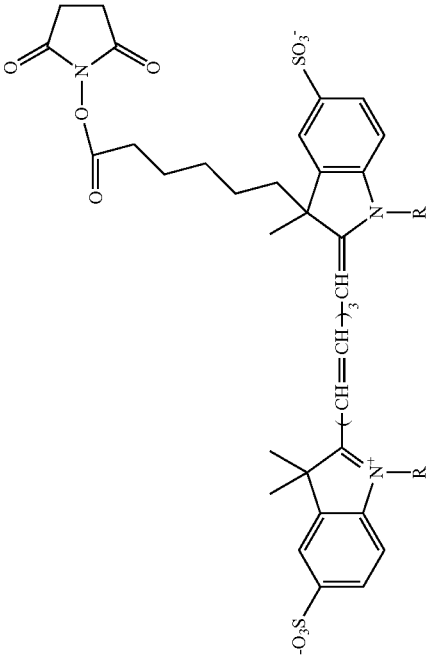 R = —(CH$_2$)$_5$CONH(CH$_2$CH$_2$O)$_{24}$CH$_3$ | 750/770 |

TABLE 3-continued

Exemplary structures of compounds of the formula II

| Dye No. | Structure | $\lambda_{abs}/\lambda_{em}$ (nm) (H$_2$O) |
|---|---|---|
| 30 | R = —(CH$_2$)$_5$CONH(CH$_2$CH$_2$O)$_{24}$CH$_3$ | 660/675 |
| 31 | R = —(CH$_2$)$_5$CONH(CH$_2$CH$_2$O)$_{24}$CH$_3$ | 770/790 |

TABLE 3-continued

Exemplary structures of compounds of the formula II

| Dye No. | Structure | $\lambda_{abs}/\lambda_{em}$ (nm) (H$_2$O) |
|---|---|---|
| 32 | [structure with n=2; R = —(CH$_2$)$_5$CONH(CH$_2$CH$_2$O)$_{24}$CH$_3$] | 680/700 |
| 33 | [structure with n=3; R = —(CH$_2$)$_5$CONH(CH$_2$CH$_2$O)$_{24}$CH$_3$] | 790/810 |

*For simplicity, counter ions are not shown.

Dye compounds of formula II have excellent solubility and superior fluorescence brightness and photostability. In particular, compounds of formula II having an absorption maximal wavelength greater than about 655 nm, typically referred to as near-IR dyes, showed major advantages over prior art dyes of similar wavelengths. The water-soluble polymer substituents drastically improved the performance of the near-IR dyes of the invention, resulting in unprecedented fluorescence brightness (See Figures). The water-soluble polymer substituents dramatically improved the stability of the near-IR dyes (See Figures). The stability of near-IR dyes has been a problem, which demands extreme care in storage and handling and therefore limits the use of the dyes.

The invention also provides a compound of the formula III:

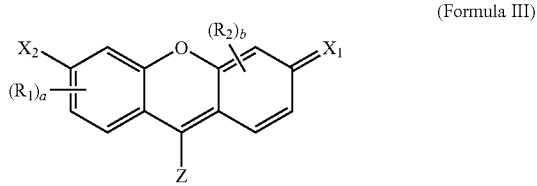

(Formula III)

Z may be —H, alkyl or a substituent such as —$CF_3$, or —CN. Alternatively, Z is:

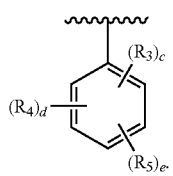

Compounds of formula III generally belong to the class of xanthene fluorescent groups. The choice of $X_1$, $X_2$ and Z further determines whether the compound belongs to the class of fluorescein fluorescent groups ($X_1$ is =O, $X_2$ is —OH, Z is substituted phenyl), or rhodamine fluorescent groups ($X_1$ is =$NH_2^+$ or =$NR_6R_7^+$, $X_2$ is —$NH_2$ or —$N_8R_9$, Z is substituted phenyl), or rhodol groups ($X_1$ is =O, $X_2$ is —$NH_2$ or —$NR_8R_9$). $R_1$, $R_2$, $R_3$, $R_4$, $R_5$, $R_6$, $R_7$, $R_8$ and $R_9$ are each independently $(R)_p (L)_q$-, where L, p and q are as generally defined elsewhere in this document. R is as previously defined, with the addition that R also includes moieties which have both a water-soluble polymer and a reactive group, for example joined by a joining moiety. The variables c, d and e indicate the numbers of $R_3$, $R_4$ and $R_5$ substituents on the phenyl ring in group Z and may be 0, 1, 2 or 3, such that the sum of c, d and e is less or equal to 5.

Each compound of formula III comprises a reactive moiety as well as a water-soluble polymer. Therefore, at least one R of $R_1$, $R_2$, $R_3$, $R_4$, $R_5$, $R_6$ and $R_7$ is a reactive moiety while at least one R of $R_1$, $R_2$, $R_3$, $R_4$, $R_5$, $R_6$ and $R_7$ is a water-soluble polymer group.

In some embodiments, the compound of formula III belongs to the class of fluorescein fluorescent groups and $X_1$ and $X_2$ are =O and —OH, respectively, while Z is a phenyl group substituted with at least one moiety of the formula $(R)_p (L)_q$-. In a related embodiment, Z comprises at least one R which is a water soluble polymer and at least one R which is a reactive group.

In other embodiments, the compound of formula III belongs to the class of rhodamine fluorescent groups, wherein $X_1$ is =$NH_2^+$ or =$NR_6R_7^+$, $X_2$ is —$NH_2$ or —$NR_8R_9$, and Z is a phenyl moiety substituted with at least one $(R)_p$-$(L)_q$- moiety (at least one of c, d or e is not 0). By way of example, $X_2$ may be an amino group which is optionally substituted with one or two groups such as alkyl. In such cases, $X_2$ may be, for instance, a dimethylamino, diethylamino, methylamino or ethylamino substituent. If neither $R_1$ or $X_2$ comprises a water-soluble polymer group or reactive group, group Z may be substituted with at least one reactive group and at least one water soluble polymer.

In other cases, $R_1$ and $X_2$ taken together form a carbocyclic or heterocyclic ring fused to ring A in formula III. In related embodiments, $R_2$ and $X_1$ taken together form a carbocyclic or heterocyclic ring fused to ring B in formula III. Such fused rings may additionally be substituted with additional R groups, for example $SO_3^-$, alkyl, or even water soluble polymer groups or reactive groups. The rings so formed by combining one of $R_6$, $R_7$, $R_8$ and $R_9$ with a neighboring $R_1$, and/or R2 are unsaturated or saturated and may be unsubstituted or substituted by one or more $(R)_p$-$(L)_q$-.

When group Z is —H, —CN, or —$CF_3$, one R of $R_1$, $X_1$, $R_2$ or $X_2$ comprises a water soluble polymer group while another R of $R_1$, $X_1$, $R_2$ or $X_2$ comprises a reactive group.

In some embodiments, water soluble groups comprise a polyalkylene oxide attached to the core structure of formula III via a linker moiety or joining moiety. It is possible for either $R_3$, $R_4$ or $R_5$ to be a joining moiety to which both a water soluble polymer and a reactive group are connected via independent linker moieties.

Exemplary compounds of formula III are illustrated in Table 4.

TABLE 4

Exemplary Xanthene Compounds*

| Dye No. | Structure | $\lambda_{abs}/\lambda_{em}$ (nm) (H$_2$O) |
|---|---|---|
| 34 | [Structure: fluorescein with carboxamide linker to CH$_3$(OCH$_2$CH$_2$)$_n$ and hexanoate-NHS ester; n = 24; Formula I] | 494/520 |
| 35 | [Structure: rhodamine 110 derivative with sulfonamide-PEG (CH$_3$(OCH$_2$CH$_2$)$_n$NH) and piperidine-4-carboxylate NHS ester; n = 24; Formula III] | |
| 36 | [Structure: rhodamine 110 with carboxamide linker to CH$_3$(OCH$_2$CH$_2$)$_n$ and hexanoate-NHS ester; n = 24; Formula I] | 501/524 |

TABLE 4-continued
Exemplary Xanthene Compounds*
| Dye No. | Structure | $\lambda_{abs}/\lambda_{em}$ (nm) (H$_2$O) |
|---|---|---|
| 37 | 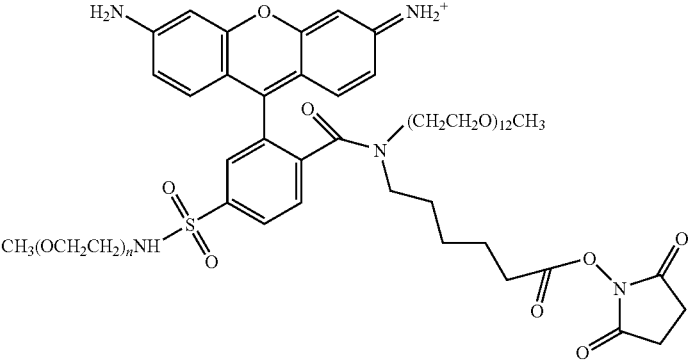<br>n = 24<br>Formula III | |
| 38 | 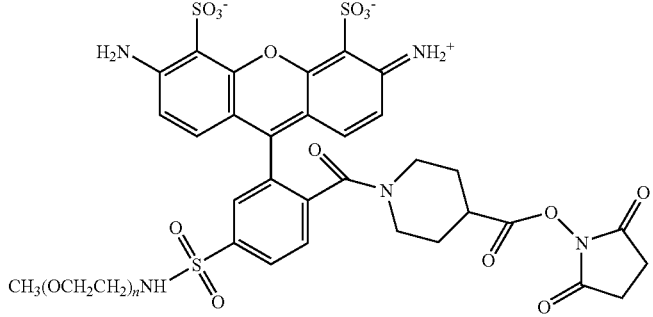<br>Formula III | |
| 39 | 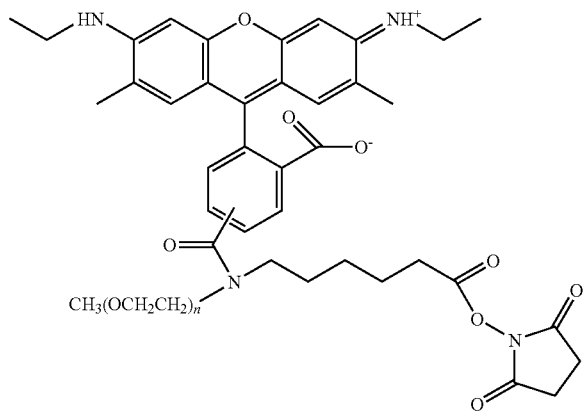<br>n = 20<br>Formula I | 520/546 |

TABLE 4-continued
Exemplary Xanthene Compounds*
| Dye No. | Structure | $\lambda_{abs}/\lambda_{em}$ (nm) (H$_2$O) |
|---|---|---|
| 40 | 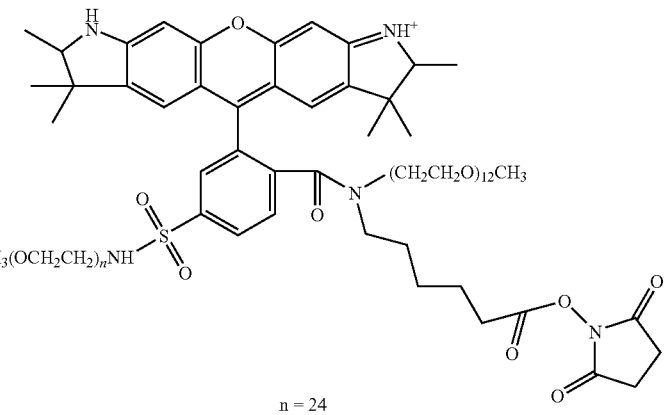<br>n = 24<br>Formula III | |
| 41 | 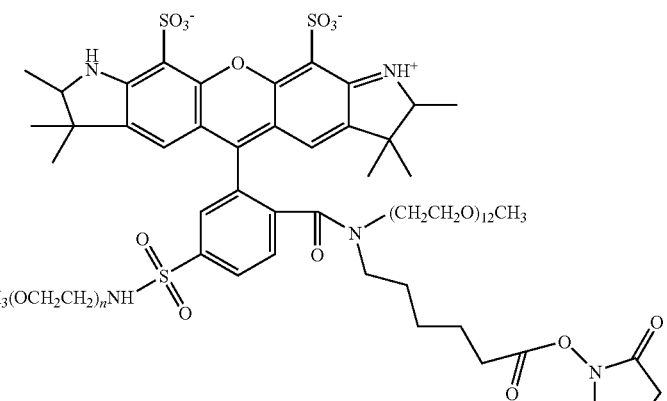<br>n = 24<br>Formula III | |
| 42 | 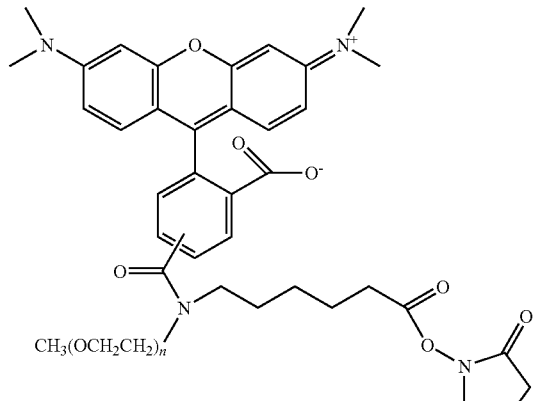<br>n = 30<br>Formula I | 540/565 |

TABLE 4-continued
Exemplary Xanthene Compounds*
| Dye No. | Structure | $\lambda_{abs}/\lambda_{em}$ (nm) (H$_2$O) |
|---|---|---|
| 43 | 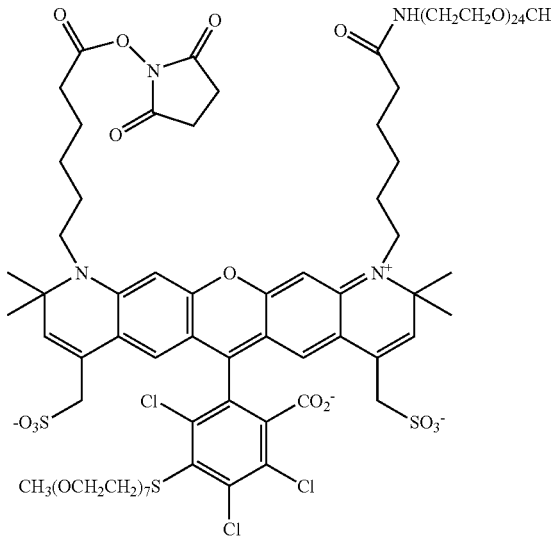  Formula III | |
| 44 | 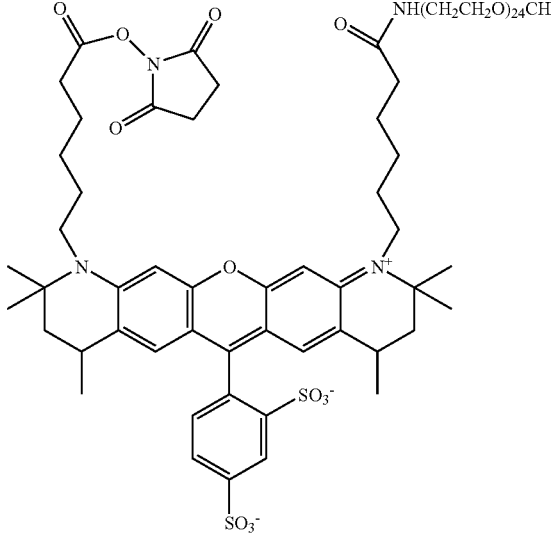  Formula III | |

111
TABLE 4-continued
Exemplary Xanthene Compounds*
| Dye No. | Structure | $\lambda_{abs}/\lambda_{em}$ (nm) (H$_2$O) |
|---|---|---|
| 45 | 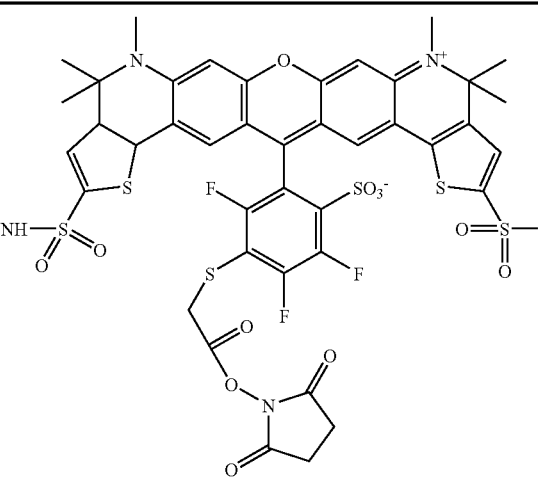<br>Formula III | |
| 46 | 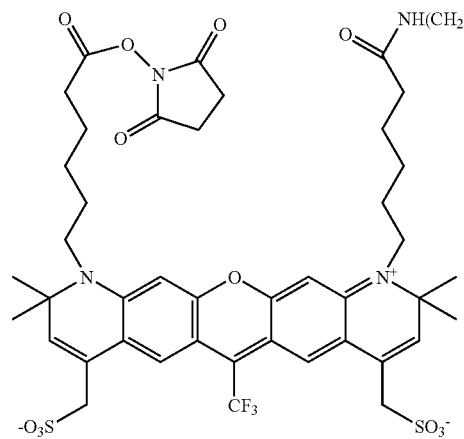<br>Formula III | |
| 47 | 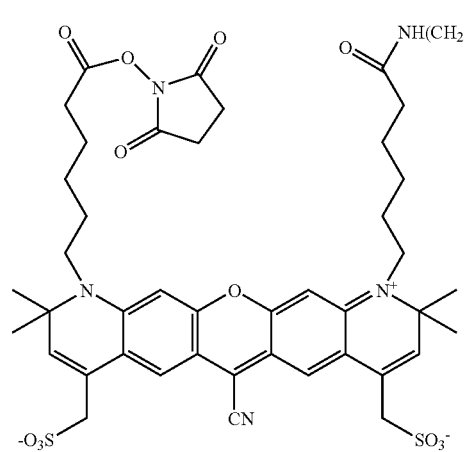<br>Formula III | |

TABLE 4-continued

Exemplary Xanthene Compounds*

| Dye No. | Structure | $\lambda_{abs}/\lambda_{em}$ (nm) (H$_2$O) |
|---|---|---|
| 48 | [structure shown]<br>—R = —(CH$_2$CH$_2$O)$_{24}$CH$_3$<br>Formula III | 488/515 |
| 49 | [structure shown]<br>—R = —(CH$_2$CH$_2$O)$_{24}$CH$_3$<br>Formula III | 494/520 |

*For simplicity, counter ions are not shown.

In one embodiment of the invention, the compound is a coumarin fluorescent group having the formula IV shown below:

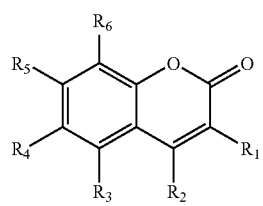

Formula IV wherein $R_1$, $R_2$, $R_3$, $R_4$, $R_5$ and $R_6$ are $(R)_p$-$(L)_q$- as defined previously, provided that at least one R of $R_1$, $R_2$, $R_3$, $R_4$, $R_5$ and $R_6$ comprises a water soluble polymer and at least one other R of $R_1$, $R_2$, $R_3$, $R_4$, $R_5$ and $R_6$ comprises a reactive group.

According to one embodiment, $R_5$ is —OH or —NR$_7$R$_8$ where $R_7$ and $R_8$ are independently H, an alkyl group optionally comprising at least one heteroatom, a reactive group, a water-soluble polymer group, or a sulfonate group. Alternatively, $R_7$ in combination with $R_8$ forms a substituted or unsubstituted 5- or 6-membered ring that optionally comprises at least one heteroatom. In another aspect of the invention, $R_7$ in combination with $R_4$, and/or $R_8$ in combination with $R_6$ form a saturated or unsaturated 5- or 6-membered ring that may be substituted or unsubstituted, and/or may fuse with another 5-membered heterocyclic ring, optionally substituted with additional R groups.

According to another embodiment, $R_3$ and $R_6$ are each H; $R_2$ and $R_1$, independently comprise R groups as previously defined; $R_1$, may additionally comprise an R group which is aryl, where the aryl optionally comprises at least one heteroatom selected from halogens, N, P, O, S and Si, and optionally comprises one or more additional R substituents.

Selected coumarin dyes according to the invention are listed in Table 5.

TABLE 5
List of selected coumarin-based fluorescent groups according to the invention*
| Dye No. | Structure | $\lambda_{abs}/\lambda_{em}$ (nm) (H$_2$O) |
|---|---|---|
| 50 | 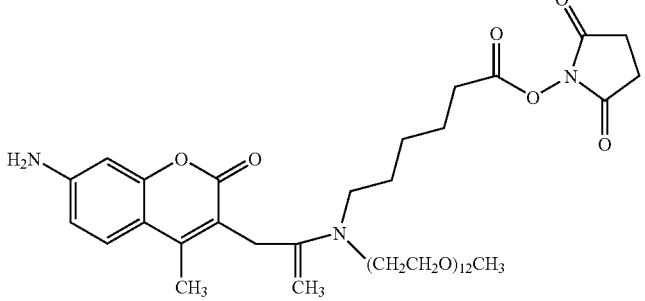 Formula I | 353/442 |
| 51 | 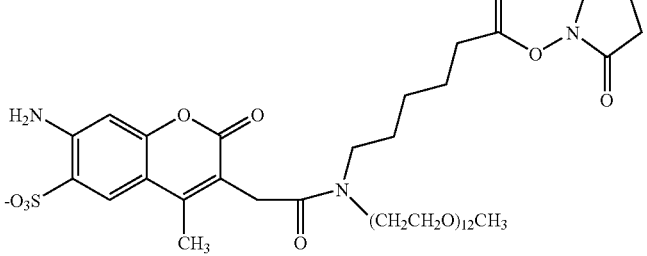 Formula I | 346/442 |
| 52 | 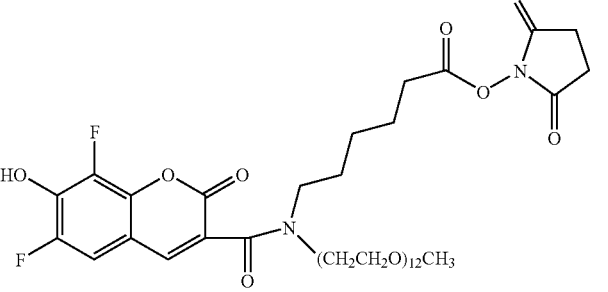 Formula I | 416/465 |

TABLE 5-continued

List of selected coumarin-based fluorescent groups according to the invention*

| Dye No. | Structure | $\lambda_{abs}/\lambda_{em}$ (nm) (H$_2$O) |
|---|---|---|
| 53 | 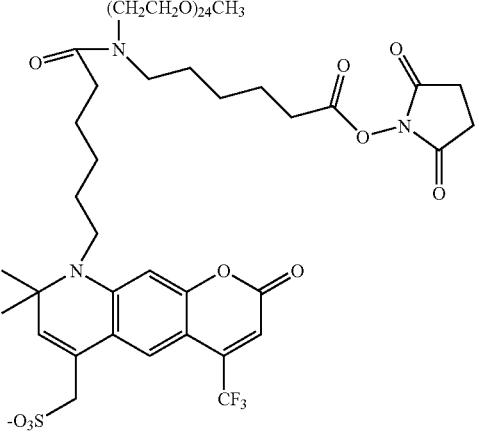Formula I | 430/545 |
| 54 | 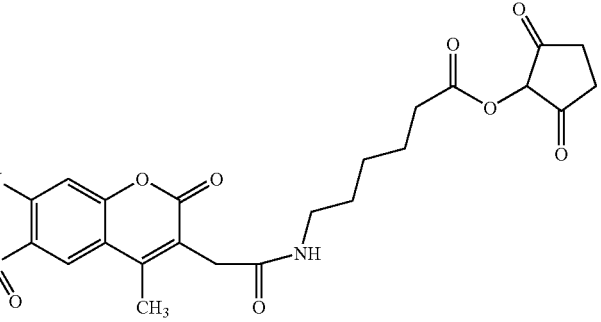Formula IV | 350/440 |

*For simplicity, any counter ions for the structures are not shown.

The invention also provides a compound of the formula V:

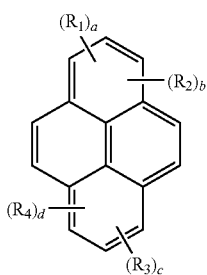

Formula V

In Formula V, $R_1$, $R_2$, $R_3$, and $R_4$ are each independently $(R)_p$-$(L)_q$-, provided that at least one R of $R_1$, $R_2$, $R_3$ and $R_4$ is a reactive moiety; and at least one R of $R_1$, $R_2$, $R_3$ and $R_4$ is a water-soluble polymer group. The variables a, b, c and d are independently 0, 1, 2 or 3. Generally, the sum of a, b, c and d is 2, 3 or 4. In one embodiment, the sum of a, b, c and d is 4. For example, $R_1$, $R_2$ and $R_3$ may each comprise water soluble polymer groups, such that each $(R)_p$-$(L)_q$- group may independently have the formula —SO$_2$NH(CH$_2$CH$_2$O)$_n$CH$_3$, where n is from about 3 to about 30, or from about 7 to about 24. In this embodiment, $R_4$ comprises an R which is a reactive group such as an activated ester of a carboxylic acid.

In other embodiments, L may comprise a C1-C8 N-alkyl sulfonamide or a C2-C10 N,N-dialkyl sulfonamide group linking either a reactive group or a water soluble polymer group to the pyrene moiety in formula V, such that each sulfonamide is covalently linked to the pyrene carbon via S—C bond and where each alkyl portion optionally comprises at least one O.

In another embodiment, $R_1$, $R_2$ and $R_3$ comprise substituents such as sulfonate groups and $R_4$ is a joining moiety to which both a water soluble polymer and a reactive group are connected via independent linker moieties.

Exemplary compounds of the Formula V are listed in Table 6.

TABLE 6

Exemplary Pyrene compounds*

| Dye No. | Structure | $\lambda_{abs}/\lambda_{em}$ (nm) (H$_2$O) |
|---|---|---|
| 44 | 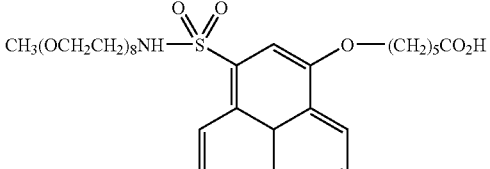<br>Formula V | |
| 45 | 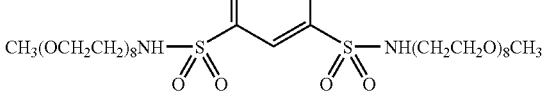<br>Formula V | |
| 46 | 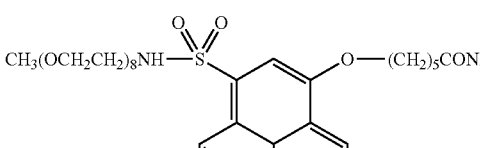<br>Formula I | 400/424 |

For simplicity, any counter ions for the structures are not shown.

The present invention provides a method of preparing a compound of the invention, the method comprising the steps of: 1) reacting a compound comprising a fluorophore linked to an amine-reactive group with an amino compound having the following structural formula:

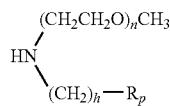

wherein n may be an integer selected from about 3 to about 30; h is an integer selected from 1 to 5; and $R_p$ is a latent or a protected reactive group; 2) converting the latent or protected reactive group $R_p$ in the resulting compound to a reactive group.

The above amino compound shown above can be readily prepared, for example, by reacting a suitable mPEG alkylating compound, such as a mPEG tosylate or mPEG chloride, with a suitable aminoalkyl compound comprising a suitable $R_p$ group. Suitable $R_p$ groups include a carboxylic acid group, a methyl ester of a carboxylic acid group, a t-butyl ester group of a carboxylic acid group, a t-BOC-protected amine group and a benzyloxycarbonyl-protected group, merely by way of example. If the $R_p$ group is a latent reactive group, such as a free carboxylic acid group, it may be directly converted to a reactive group using methods well known to one of skills. If $R_p$ is a protected group, it is deprotected and then converted to a reactive group using a known method.

(1) Uses of the Subject Compounds.

The subject compounds find use in a variety of different applications. One application of interest is the use of the subject compounds as labeling agents which are capable of imparting a fluorescent property to a particular composition of matter. The compounds of the present invention can be used to react with any of a broad range of molecules, including but not limited to, biomolecules such as polypeptides, polypeptide-based toxins, amino acids, nucleotides, polynucleotides including DNA and RNA, lipids, and carbohydrates, and any combinations thereof. Additionally, the compounds of the invention can be used to react with haptens, drugs, ion-complexing agents such as metal chelators, microparticles, synthetic or natural polymers, cells, viruses, other fluorescent molecules including the dye molecule according to the invention, or surfaces. The substrate molecules typically comprise one or more functional groups, which react with the reactive group of the subject compounds to form covalent or non-covalent linkage. In one aspect, the reactive group of a compound of the invention is an activated ester (such as a succinimidyl ester, or SE), a maleimide, a hydrazide or an aminooxy group. Accordingly, in some aspects, functional group from a substrate molecule (or reaction substrate) is an amine, a thiol, an aldehyde or ketone. The resulting fluorescently labeled substrate molecules may be referred to as conjugates or labeled substrate molecules. Any methods practiced in the art (e.g., Brinkley, Bioconjugate Chem. 3, 2 (1992), incorporated herein by reference) for preparing fluorescent group-substrate conjugates are applicable for practicing the subject invention.

Conjugates of biomolecules and compounds of the invention usually have high fluorescence yield while typically retaining the critical parameters of unlabeled biomolecules, such as solubility, selective binding to a receptor or nucleic acid, activation or inhibition of a particular enzyme or the ability to incorporate into a biological membrane. Nevertheless, conjugates with the highest degree of labeling may still precipitate or bind nonspecifically. As necessary, a less-than-maximal degree of labeling may be acceptable in order to preserve function or binding specificity. Preparing the conjugates of the invention may involve experimentation to optimize properties. Following conjugation, unconjugated labeling reagent may be removed by techniques known in the art such as by gel filtration, dialysis, conjugate precipitation and resolubilization, HPLC or a combination of these techniques. The presence of free dye, particularly if it remains chemically reactive, may complicate subsequent experiments with the bioconjugate.

Nucleic Acids

In another embodiment, the subject compounds can be used to conjugate with a nucleoside, a nucleotide, or a polynucleotide, wherein any of such molecules may be natural or synthetic, modified or unmodified. The compound of the invention used for labeling may comprise a reactive group which is a phosphoramidite, an activated ester (such as a succinimidyl ester), an alkylating group or a reactive platinum complex. Such molecules may contain or are derivatized to contain one or more reaction partners for the reactive groups on the compounds of the invention. A reactive group of a compound of the invention may react with a suitable reaction partner on said molecule to form a covalent linkage. For example, a phosphoramidite group may react with a hydroxyl group to form a phosphate linkage after deprotection; a succinimidyl ester or the like may react with an amine group to form an amide linkage; and a reactive platinum complex may react with a guanosine base to form a platinum complex linkage. In one embodiment, a reactive compound of the invention comprising an activated ester is reacted with a nucleotide triphosphate comprising a base comprising an aminoalkynyl group, an aminoallyl group or an aminoalkyl group to form a fluorescently labeled nucleotide triphosphate. Such a labeled nucleotide triphosphate is often used to prepare a fluorescently labeled nucleic acid polymer via enzymatic incorporation.

In some embodiments, the fluorescent compound of the invention is reacted with a group or linker attached to the C-5 position of a uridine or cytidine residue. This position is not involved in Watson-Crick base-pairing and interferes little with hybridization to complementary sequences. An aminoalkynyl linker may be introduced between a fluorescent moiety and the nucleotide in order to reduce fluorophore interaction with enzymes or target binding sites. In addition to this four-atom bridge, seven- to 10-atom spacers may be introduced that further separate the fluorophore from the base. The use of longer spacers may result in brighter conjugates and increased hapten accessibility for secondary detection reagents.

Alternatively, deoxycytidine triphosphates may be prepared which are modified at the N-4 position of cytosine using a 2-aminoethoxyethyl (OBEA) linker. Possible steric interference caused by the presence of the fluorescent fluorophore may be reduced by the use of additional spacers.

Fluorescently labeled DNA may be prepared from a fluorescently labeled nucleotide triphosphate by PCR reaction, terminal transferase-catalyzed addition or nick translation. Various polymerases may be used in such reactions. Such polymerases include Taq polymerase (useful e.g. in polymerase chain reaction (PCR) assays), DNA polymerase I (useful e.g. in nick-translation and primer-extension assays), Klenow polymerase (useful e.g. in random-primer labeling), Terminal deoxynucleotidyl transferase (TdT) (useful e.g. for 3'-end labeling), Reverse transcriptase (e.g. for synthesizing DNA from RNA templates) or other polymerases such as SP6 RNA polymerase, T3 RNA polymerase and T7 RNA polymerase for in vitro transcription.

Alternatively, a fluorescently labeled nucleic acid polymer may be prepared by first enzymatically incorporating an amine-labeled nucleotide into a nucleic acid polymer to result in an amine-labeled nucleic acid polymer, followed by the labeling of said amine-labeled polymer with a compound of the invention. More information on the preparation and use of fluorescently labeled nucleotide triphosphates can be found in U.S. Pat. Nos. 4,711,955 and 5,047,519. Still alternatively, a nucleic acid polymer, such as a DNA, may be directly labeled with a compound of the invention comprising a reactive platinum complex as the reactive group, wherein the platinum complex form a coordinative bond with a nitrogen atom of a guanosine base such as described in U.S. Pat. No. 5,714,327.

Aminoacids and Polypeptides

In another embodiment, the subject compounds can be used to conjugate with an amino acid, amino acid analog or a polypeptide. Labeled aminoacids, amino acid analogs and polypeptides may be labeled by reacting the compounds of the invention with amino acids, amino acid analogs and polypeptides comprising reaction partners for the reactive groups on said compounds. Such reaction partners may be natural or unnatural groups present in said polypeptides. By way of example, reaction partners may be the natural residues such as amino groups, which are part of natural lysine residues, or thiol groups, which are part of natural cysteine groups.

Figure 1:
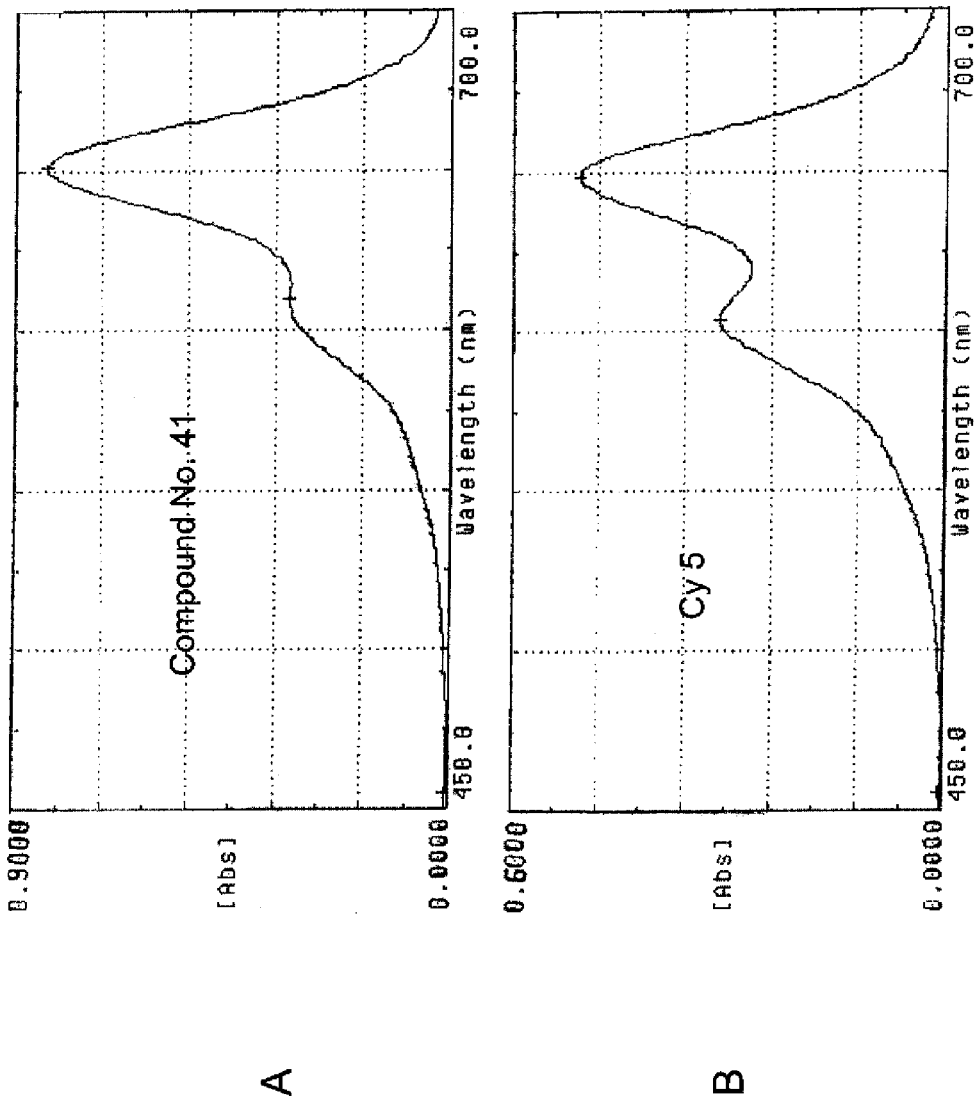
FIG. 1 is a graphical representation showing the absorption spectra of Cy5® dye and Compound No. 41 (Example 41), respectively, conjugated to goat anti-mouse IgG at similar degrees of labeling (i.e., ~4) in an aqueous buffer. The spectrum of Cy5® dye displays a double peak characteristic of dye aggregation while the spectrum of Compound No. 41 shows mainly a single peak, indicating a substantial lack of dye aggregation.
Figure 2:
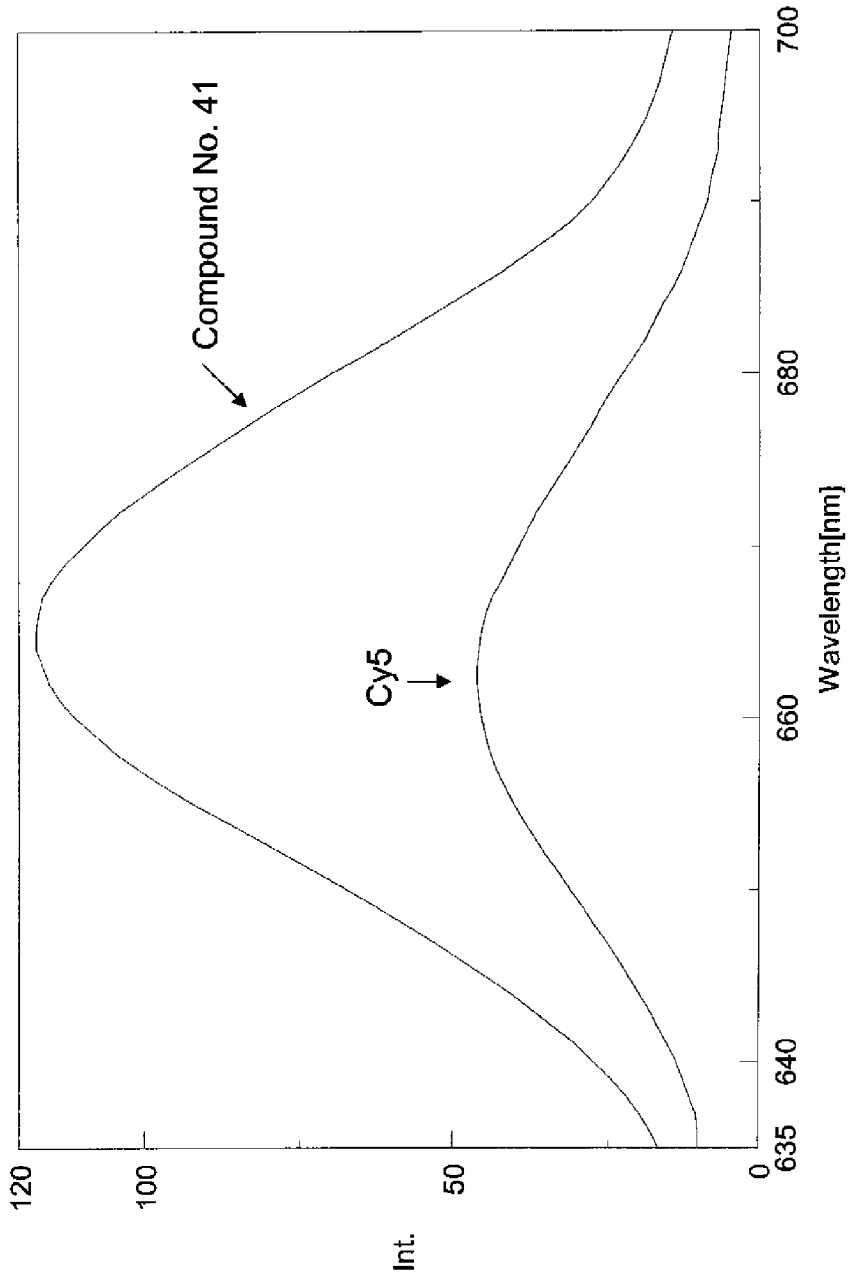
FIG. 2 is a graphical representation showing the fluorescence emission spectra of goat anti-rabbit IgG conjugates of Cy5® dye and Compound No. 41 (Example 41) at similar degrees of labeling (i.e., ~5) and equivalent protein concentrations, when excited at 630 nm. The data demonstrates that the fluorescent group of the invention is significantly more fluorescent than Cy5® dye.
Figure 3:
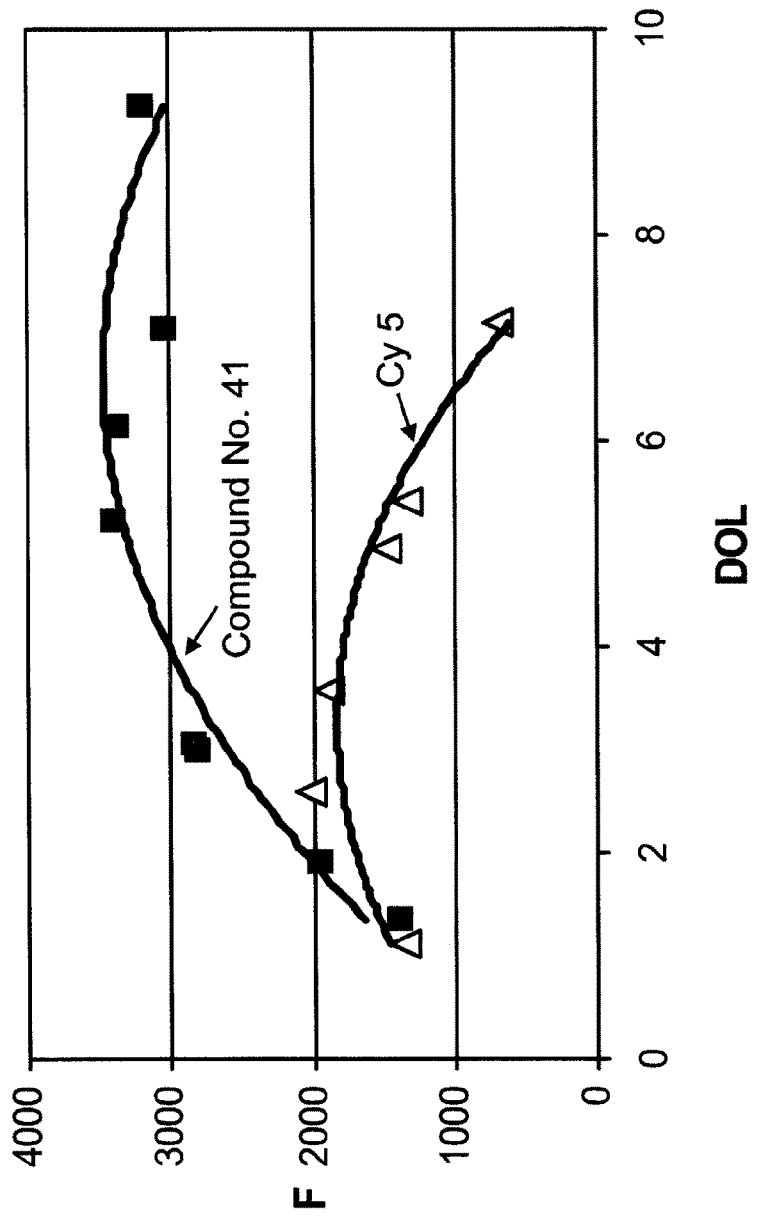
FIG. 3 is a plot of total fluorescence vs. degree of labeling (DOL) for goat anti-rabbit IgG conjugates of Compound No.

In order to achieve the maximal fluorescence possible, a protein may be labeled with as many molecules of the same fluorescent group as possible, to the degree that the biological activity of the protein is minimally affected by the labeling. In other cases it may be desirable to avoid fluorescence quenching resulting from multiple fluorescent group molecules on the protein interacting with each other. Dye-dye interactions may be physical, such as dye aggregation, or may be a spectral, such as FRET-based energy transfer, or a combination of both. Either type of interaction may lead to fluorescence quenching, which can be characterized by a slow rise and then a rapid drop of the total fluorescence of the labeled protein as the degree of labeling increases. FIGS. 1-9 show that a fluorescent group of the invention that is less likely or substantially less likely to quench its fluorescence on an antibody or streptavidin than a similar fluorescent group of prior art without a water soluble polymer group. A primary reason for fluorescence quenching of a labeling fluorescent group on protein is believed to be due to formation of dye aggregates such as dye dimer. When dye dimer formation occurs, the absorption spectrum of the fluorescent group-protein conjugate typically show a doublet peak. As shown in FIG. 1, a fluorescent group of the invention is much less likely to have dimer formation than a similar fluorescent group of prior art. Consequently, the fluorescent group of the invention is much brighter on proteins (FIG. 2). The relatively low tendency to aggregate on proteins for fluorescent groups of the invention permits a protein to be labeled multiple times (i.e., a higher degree of labeling (DOL)) for a greater fluorescence intensity (FIGS. 3-8). As a result, antibodies labeled with a fluorescent group of the invention are more sensitive in detecting their targets than antibodies labeled with a fluorescent group of prior art (FIG. 9). Another advantage for antibodies labeled with a fluorescent group of the invention is their improved staining specificity relative to fluorescently labeled antibodies (FIG. 10), e.g., antibodies labeled with a fluorescent group of the invention retain higher binding specificity with their antigen than the same antibody labeled with the same degree of labeling with a conventional fluorescent dye. A further advantage of the fluorescent groups of the invention is a consequence of decreased aggregation and increased binding specificity; a labeled biomolecule of the invention, upon binding with its binding partner, will provide a fluorescent signal with a higher signal-to-noise ratio than the complex formed with the same binding partner and the same biomolecule which has been labeled with a conventional fluorescent group that is not a compound of the invention.

In some embodiments, the complexes of the methods of the invention have a signal-to-noise ratio that is equal or greater than about 70, about 80, about 90, about 100, about 110, about 120, about 130, about 140, about 150, about 160, about 170, about 180, about 190, about 200, about 210, about 220, about 230, about 240, about 250, about 255, about 260, about 265, about 270, about 275, about 280, about 285, about 290, about 295, about 300, about 305, about 310, about 315, about 320, about 330, about 340, about 350, about 360, about 370, about 380, about 390, or about 400. In some embodiments of the complexes of the methods of the invention, the signal-to-noise ratio is no less than about 100, about 110, about 120, about 130, about 140, about 150, about 160, about 170, about 180, about 190, about 200, about 210, about 220, about 230, about 240, about 250, about 255, about 260, about 265, about 270, about 275, about 280, about 285, about 290, about 295, about 300, about 305, about 310, about 315, about 320, about 330, about 340, about 350, about 360, about 370, about 380, about 390, or about 400.

In some embodiments, a complex of a labeled biomolecule comprising a label of the invention, upon binding with its binding partner, will provide a fluorescent signal which is greater than that of a complex formed with the same binding partner and the same biomolecule which has been labeled to the same degree of labeling with a conventional fluorescent group by about 3%, about 4%, about 5%, about 6%, about 7%, about 8%, about 9%, about 10%, about 15%, about 20%, about 25%, about 30%, about 35%, about 40%, about 45%, about 50%, about 55%, about 60%, about 65%, about 70%, about 80%, about 90%, about 100%, about 125%, about 150%, about 175%, about 200%, about 300%, about 400%, about 500%, about 600%, about 700%, about 800%, about 900%, or about 1000%.

Still another advantage of the fluorescent group is their high photostability, which is of particular importance for fluorescence microscopy studies (FIG. 11). Additionally, a polypeptide labeled with a fluorescent compound of the invention may have a serum half life no shorter than than of the corresponding polypeptide that has no fluorescent label.

(2) Uses of the Labeled Biomolecules of the Invention

The subject compounds provide an effective tool for labeling biomolecules for a wide variety of applications. Labeling allows one to discern interactions involving biomolecules such as proteins, glycoproteins, nucleic acids, and lipids, as well as inorganic chemicals, or any combinations thereof. The interactions may be between nucleic acid molecules, between nucleic acid and protein, and between protein and small molecules. The interactions may be discerned in a cell-free biological system, in a cellular system (including intracellular and extracellular systems), or in vivo, which encompasses which encompasses activities within a cell that is within a tissue or organ or a subject Delineating the various interactions is often a significant step in scientific research and development, drug design, screening and optimization, phylogenetic classification, genotyping individuals, parental and forensic identification, environmental studies, diagnosis, prognosis, and/or treatment of disease conditions.

Biomolecules labeled according to the methods of the invention may be used as binding agents to detect their binding partners, the targets of their biological interaction, as described above. For example, a protein can be labeled with a dye of the invention and used to bind to a cell surface receptor. In some embodiments of the invention, a binding agent is labeled with a substituted cyanine dye having maximal fluorescence excitation wavelength of equal or greater than 660 nm, a water soluble polymer group, and a reactive group under conditions effective to crosslink the dye and the binding agent. In some embodiments, the substituted cyanine dye is substituted by a non-spiro substituent. A binding agent so labeled is contacted with its binding partner, and the fluorescent label is detected. In other embodiments, a binding agent is reacted with a compound of structure of Formula I, II, III, IV or V under conditions effective to crosslink the compound with the binding agent Labeled molecules of the invention may be used as part of FRET pairs in a variety of biological assays and methods, whether as donor or acceptor molecules. A person skilled in the art will know to select a suitable FRET partner based on the specific application. Such applications include, but are not limited to, assays involving molecular beacons, FRET protease assays, flow cytometry, nucleic acid hybridization and any other applications where the relative spatial localization of two or more moieties must be probed. FRET is generally useful on scales of 10 to 100 Å. In one embodiment, both the donor and the acceptor of a FRET pair are labeled molecules of the invention. In another embodiment, one member of a FRET pair is a labeled oligonucleotide of the invention which is capable of annealing to a complementary oligonucleotide labeled with a second member of the FRET pair, such that annealing leads to an increase in the efficiency of energy transfer. In this example, the second member of the FRET pair may be a fluorophore of the invention or may be a different fluorophore.

In some applications, it is desirable to quench the labeled molecules of the invention. A variety of quenchers known in the art may be used. Non-limiting examples include Black Hole Quencher™ moieties, DABCYL, Reactive Red 4 (Cibacron Brilliant Red 3B-A), Malachite Green, 4-Dimethylaminophenylazophenyl-4'-isothiocyanate (DABITC), and 4,4'-Diisothiocyanaitodihydro-stilbene-2,2'-disulfonic acid. By way of example, a molecular beacon may be labeled with a compound of the invention as well as with a suitable quencher. In the closed conformation of the beacon, the fluorophore is quenched. When the beacon opens as a result of a recognition or binding event, the fluorescence of the fluorophore increases significantly.

In still another embodiment, the invention provides an energy transfer fluorescent group comprising a first donor fluorescent group and second acceptor fluorescent group wherein: the donor fluorescent group and acceptor fluorescent group are covalently linked to form a FRET pair; at least one of the donor fluorescent group and acceptor fluorescent group is a fluorescent group of the invention; and the energy transfer fluorescent group optionally comprises a reactive group. Methods for preparing energy transfer fluorescent groups and uses thereof have been previously described. See U.S. Pat. No. 6,479,303 and WO 00/13026.

In one embodiment, a fluorescent group of the invention is used to label a fluorescent protein to form a so-called tandem dye, wherein the fluorescent group of the invention and the fluorophore of the fluorescent protein form an energy transfer pair (i.e., FRET pair). In such a FRET pair, the fluorescent group of the invention is either the donor fluorescent group or the acceptor fluorescent group and, likewise, the fluorophore of the protein is either the acceptor fluorescent group or the donor fluorescent group, such that the FRET pair can be excited at or near the absorption maxima of the donor fluorescent group and the fluorescence collected at the emission maxima of the acceptor fluorescent group, resulting in a large Stokes shift. Suitable fluorescent proteins for preparing tandem dyes include, but are not limited to, various phycobiliproteins such as Allophycocyanin B, Allophycocyanin (APC), C-Phycocyanin, R-Phycocyanin, Phycoerythrocyanin, C-Phycoerythrin, b-Phycoerythrin, B-Phycoerythrin, R-Phycoerythrin (R-PE), and the likes. Phycobiliproteins are proteins comprising bilin as prosthetic groups, which are also the fluorophores of the proteins. Preferably, the phycobiliproteins are R-PE or APC. To achieve suitable FRET efficiency, one may choose a fluorescent group of proper wavelengths so that the emission of the donor fluorescent group and the absorption of the acceptor fluorescent group have sufficient spectral overlap. Detailed methods for fluorescent group selection and for preparing tandem dyes are disclosed in U.S. Pat. Nos. 4,520,110 and 5,714,386. Because of their large Stokes shift, tandem dyes of the invention may be useful for multi-color detections where only a limited number of excitation light sources may be available. In particular, tandem dyes of the invention may be useful for fluorescence-activated cell sorting (FACS) or flow cytometry studies. Commercial flow cytometers are typically equipped with 1 to 3 excitation light sources, more commonly 1 to 2 excitation light sources. For example, some of the commercial flow cytometers are equipped with a 488 nm argon laser and a 633 nm He—Ne laser or a 635 nm red diode laser, and a significant number of flow cytometers have only the 488 nm argon laser. Thus, in order to detect multiple targets, each target may be stained with a different fluorescent group having a different emission and the different fluorescent groups all need to be efficiently excited by a common excitation source. Tandem dyes of the invention can fill this need as different tandem dyes having the same excitation maxima but different emission maxima can be readily prepared. For example, R-PE may be labeled with Dye No. 10 of Table 3 and compound No. 18 of Table 3, respectively, to result in two tandem dyes where the first tandem dye is excitable at 488 nm with emission at 665 nm and the second tandem dye is also excitable at 488 nm but with emission at 775 nm.

In one embodiment, a compound of the invention is applied to a biological sample comprising a plurality of polypeptides and optionally other biological molecules under a condition facilitating the covalent labeling of said polypeptides. In some embodiments, the reactive group of the compound is an activated ester, a maleimide, an iodoacetamide, a bromoacetamide, a hydrazide, an amine or an aminooxy group. The biological sample may be a cell lysate or a tissue lysate. The resulting labeled polypeptides or cellular components may be analyzed and/or purified by any of a variety of known tools or techniques, including, but not limited to, protein microarrays, chromatography and gel electrophoresis.

The present invention also provides kits comprising compounds of the invention and/or fluorescent group-substrate conjugates of the invention for various assays as selectively described above. A kit of the invention may comprise one or more compounds of the invention and instructions instructing the use of said compound. For example, a kit may comprise one or more compounds of the invention for labeling a substrate, one or more buffers for the labeling reaction and product purification, a chromatography column for purifying the resulting fluorescent group-substrate conjugate, a protocol for carrying out the procedure, optionally any additional reagents and optionally any reference standard. In another embodiment, a kit comprises one or more fluorescent group-substrate conjugates of the invention, one or more buffers, a protocol for the use of said conjugate(s), optionally any other reagents for an assay, and optionally any calibration standard(s). The kit may further contain other materials or devices of use in purifying the conjugation products.

The signals produced by the fluorescent groups of the invention may be detected in a variety of ways. Generally, a change of signal intensity can be detected by any methods known in the art and is generally dependent on the choice of fluorescent group used. It can be performed with the aid of an optical system. Such system typically comprises at least two elements, namely an excitation source and a photon detector. Numerous examples of these elements are available in the art. An exemplary excitation source is a laser, such as a polarized laser. The choice of laser light will depend on the fluorescent group attached to the probe. For most of the fluorescent groups, the required excitation light is within the range of about 300 nm to about 1200 nm, or more commonly from about 350 nm to about 900 nm. Alternatively, compounds of the invention may be excited using an excitation wavelength of about 300 to about 350 nm, 350 to 400 nm, 400 to 450 nm, 450 to 500 nm, 500 to 550 nm, 550 to 600 nm, 600 to 650 nm, 650 to 700 nm, 750 nm to 800 nm, or from 800 nm to 850 nm, merely by way of example. Those skilled in the art can readily ascertain the appropriate excitation wavelength to excite a given fluorophore by routine experimentation (see e.g., The Handbook—'A Guide to Fluorescent Probes and Labeling Technologies, Tenth Edition' (2005) (available from Invitrogen, Inc./Molecular Probes) previously incorporated herein by reference). Where desired, one can employ other optical systems. These optical systems may comprise elements such as optical reader, high-efficiency photon detection system, photo multiplier tube, gate sensitive FET's, nano-tube FET's, photodiode (e.g. avalanche photo diodes (APD)), camera, charge couple device (CCD), electron-multiplying charge-coupled device (EMCCD), intensified charge coupled device (ICCD), and confocal microscope. These optical systems may also comprise optical transmission elements such as optic fibers, optical switches, mirrors, lenses (including microlens and nanolens), collimators. Other examples include optical attenuators, polarization filters (e.g., dichroic filter), wavelength filters (low-pass, band-pass, or high-pass), wave-plates, and delay lines. In some embodiments, the optical transmission element can be planar waveguides in optical communication with the arrayed optical confinements. See, e.g., U.S. Pat. Nos. 7,292,742, 7,181,122, 7,013,054, 6,917, 726, 7,267,673, and 7,170,050. These and other optical components known in the art can be combined and assembled in a variety of ways to effect detection of distinguishable signals.

Fluorescently labeled polynucleotides of the invention find use in a variety of applications. Such applications can involve interactions between nucleic acids, e.g., interactions between DNA and DNA, DNA and RNA, and RNA and RNA, or any other non-naturally occurring nucleic acids PNA, LNA, and/or TNA. Various applications can also involve interactions between nucleic acids and proteins, lipids or combinations thereof. Non-limiting examples of specific nucleic acid assays include nucleic acid amplification, both quantitative or end-point amplification, hybridization in solution or on a substrate (e.g., array hybridization), gel shifts, and nucleic acid sequencing. The fluorescently labeled polynucleotides can be used in solution phase or immobilized on a substrate.

In one embodiment, the labeled polynucleotides are used as hybridization probes. One application of hybridization probes is fluorescent in situ hybridization (FISH). In this technique, a labeled polynucleotide complementary to a sequence of interest is annealed to fixed chromosomes preparations, and the presence of the sequence of interest as well as the chromosomal localization is detected by microscopy. FISH can be performed by immobilizing the nucleic acids of interest on a substrate including without limitation glass, silicon, or fiber. FISH may also be used quantitatively (Q-FISH) to detect the presence and length of repetitive sequences such as telomeres. This may be done by quantitating the intensity of emitted fluorescence as measured by microscopy. FISH assays utilizing the subject fluorescent compounds can be performed for detecting a specific segment of a DNA molecule or a chromosome. These features can be used in genetic counseling (e.g., prenatal-screens), medicine, and species identification.

In some embodiments, labeled polynucleotides can be used as primers in amplification reactions such as PCR. In yet another embodiment, a compound of the invention may be used to label a polynucleotide which is subsequently used as a probe may be a hybridization probe or a real-time PCR probe. Such a probe may be labeled with a second fluorescent group to form a FRET pair with the first fluorescent group of the invention. Methods for the preparation and use of PCR probes are well known to one skilled in the art.

In one embodiment of the invention, a method is provided for detecting or quantifying a target nucleic acid, the method comprising the steps of: a) providing a labeled polynucleotide ("probe") of the present invention; b) contacting said labeled polynucleotide with the nucleic acid target so as to allow for hybridization of the probe with the nucleic acid target; and c) detecting or quantifying said nucleic acid target by measuring a change in the fluorescence of the probe upon the hybridization of the nucleic acid probe with the nucleic acid target.

As used herein, hybridization occurs when the probe form a complex with the target nucleic acid. In general, the complex is stabilized, at least in part, via hydrogen bonding between the bases of the nucleotide residues. The hydrogen bonding may occur by Watson-Crick base pairing, Hoogstein binding, or in any other sequence-specific manner. Hybridization may constitute a step in a more extensive process, such as the initiation of a PCR reaction, or the enzymatic cleavage of a polynucleotide by a ribozyme.

After hybridization between the probe and the target has occurred, a change in the intensity of the fluorescence of the probe may be measured. Such change before and after hybridization can yield a positive gain or negative reduction in the detected signal intensity. Depending on the specific hybridization assay that is run, more than one event after hybridization may contribute to the generation of a change in signal intensity. For example, an increase in reporter signal may result by way of spatial extension or separation of the reporter fluorescent group from the quencher group while both are still attached to the probe. In addition, either the reporter or the quencher of the probe can be separated by way of cleavage via an enzyme (e.g., a polymerase having a 5' to 3' exonuclease), thereby generating a reporter signal that is detected. As noted above, both the reporter and the quencher are defined in functional terms, such that these groups can be identical though serving, relative to each other, a different function when used in a hybridization reaction. For example, a group attached to a probe is a quencher because it reduces the emission of an optical signal when the probe is not hybridized with the target nucleic acid (typically when the probe assumes a random state). The same group can become a reporter fluorescent group upon being cleaved by an enzyme after hybridization with the target nucleic acid as the signal of the fluorescent group is now detected during the assay.

The signal detection methods described previously can be applied to nucleic acid amplification in which the target nucleic acid is increased in copy number. Such increase may occur in a linear or in an exponential manner. Amplification may be carried out by natural or recombinant DNA polymerases such as Taq polymerase, Pfu polymerase, T7 DNA polymerase, Klenow fragment of *E. coli* DNA polymerase, Tma DNA polymerase, exo-Tli DNA polymerase, exo-KOD DNA polymerase, exo-JDF-3 DNA polymerase, exo-PGB-D DNA polymerase, U1Tma (N-truncated) *Thermatoga martima* DNA polymerase, Sequenase, and/or RNA polymerases such as reverse transcriptase.

A preferred amplification method is polymerase chain reaction (PCR). General procedures for PCR are taught in U.S. Pat. No. 4,683,195 (Mullis) and U.S. Pat. No. 4,683,202 (Mullis et al.). Briefly, amplification of nucleic acids by PCR involves repeated cycles of heat-denaturing the DNA, annealing two primers to sequences that flank the target nucleic acid segment to be amplified, and extending the annealed primers with a polymerase. The primers hybridize to opposite strands of the target nucleic acid and are oriented so that the synthesis by the polymerase proceeds across the segment between the primers, effectively doubling the amount of the target segment. Moreover, because the extension products are also complementary to and capable of binding primers, each successive cycle essentially doubles the amount of target nucleic acids synthesized in the previous cycle. This results in exponential accumulation of the specific target nucleic acids at approximately a rate of $2^n$, where n is the number of cycles.

A typical conventional PCR thermal cycling protocol comprises 30 cycles of (a) denaturation at a range of 90° C. to 95°

C. for 0.5 to 1 minute, (b) annealing at a temperature ranging from 50° C. to 65° C. for 1 to 2 minutes, and (c) extension at 68° C. to 75° C. for at least 1 minute. Other protocols including but not limited to universal protocol as well as fast cycling protocol can be performed the subject probes as well.

A variant of the conventional PCR is a reaction termed "Hot Start PCR". Hot Start PCR techniques focus on the inhibition of polymerase activity during reaction preparation. By limiting polymerase activity prior to PCR cycling, non-specific amplification is reduced and the target yield is increased. Common methods for Hot Start PCR include chemical modifications to the polymerase (see, e.g., U.S. Pat. No. 5,773,258), inhibition of the polymerase by a polymerase-specific antibody (see, e.g., U.S. Pat. No. 5,338,671), and introduction of physical barriers in the reaction site to sequester the polymerase before the thermal cycling takes place (e.g., wax-barrier methods). The reagents necessary for performing Hot Start PCR are conveniently packaged in kits that are commercially available (see, e.g., Sigma's JumpStart Kit).

Another variation of the conventional PCR that can be performed with the subject probes is "nested PCR" using nested primers. The method is preferred when the amount of target nucleic acid in a sample is extremely limited for example, where archival, forensic samples are used. In performing nested PCR, the nucleic acid is first amplified with an outer set of primers capable of hybridizing to the sequences flanking a larger segment of the target nucleic acid. This amplification reaction is followed by a second round of amplification cycles using an inner set of primers that hybridizes to target sequences within the large segment.

The subject probes can be employed in reverse transcription PCR reaction (RT-PCR), in which a reverse transcriptase first coverts RNA molecules to double stranded cDNA molecules, which are then employed as the template for subsequent amplification in the polymerase chain reaction. In carrying out RT-PCR, the reverse transcriptase is generally added to the reaction sample after the target nucleic acids are heat denatured. The reaction is then maintained at a suitable temperature (e.g., 30° C.-45° C.) for a sufficient amount of time (e.g., 5-60 minutes) to generate the cDNA template before the scheduled cycles of amplification take place. Such reaction is particularly useful for detecting the biological entity whose genetic information is stored in RNA molecules. Non-limiting examples of this category of biological entities include RNA viruses such as HIV and hepatitis-causing viruses. Another important application of RT-PCR embodied by the present invention is the simultaneous quantification of biological entities based on the mRNA level detected in the test sample.

The subject probes can also be employed to perform ligase chain polymerase chain reaction (LCR-PCR). The method involves ligating the target nucleic acids to a set of primer pairs, each having a target-specific portion and a short anchor sequence unrelated to the target sequences. A second set of primers containing the anchor sequence is then used to amplify the target sequences linked with the first set of primers. Procedures for conducting LCR-PCR are well known to artisans in the field, and hence are not detailed herein (see, e.g., U.S. Pat. No. 5,494,810).

The subject probes are particularly suited for use in a homogeneous assay. In such an assay, a target nucleic acid is detected and/or quantified without the requirement of post-assay processing to record the result of the assay. For example, a homogeneous PCR reaction can be carried out in a closed sample holder (e.g., a tube, a sample capillary or thermalchip), and no further addition or removal of reagents is necessary to record the result once the assay is started. Homogeneous assays allow recordation of the result of the assay in real time. Where desired, in practicing the subject methods, the result of the assay can be continuously recorded as the assay progresses in time or recorded intermittently at one or more point during the assay or upon completion of the assay.

Where desired, homogeneous assays can be multiplexed, i.e., more than one target nucleic acid can be detected in one assay. In a multiplex assay, two or more specific nucleic acid probes, which differ in the nature of their covalently attached fluorescent groups, are added to the mixture to be assayed. The fluorescent groups are chosen to produce distinguishable fluorescent signals from each specific nucleic acid probe. The signals of the different fluorescent group combinations of the nucleic acid probes can be recorded simultaneously to detect and/or quantify the corresponding target nucleic acids. Multiplexing greatly reduces the cost of analysis and can tremendously increase throughput in high volume settings.

The subject probes can be used to detect single mutations. Accordingly, methods are provided to use the probes of the invention to detect as few as a single mismatch between the probe sequence and a target sequence. Such high specificity in nucleic acid detection by PCR is highly valuable in clinical diagnosis and genetic research. For example, many diseases are associated with single mutations at different sites in the human genome. Although in theory this type of genetic variations, also called single nucleotide polymorphism or SNP, may be detected by sequencing, such sequencing method is not expected to be practical on a large scale due to high cost and low efficiency. Detection of SNP by an amplification reaction is feasible with the use of the subject probes.

The subject probes are also particularly suited for monitoring nucleic acid amplification reactions. In a related embodiment, the present invention provides a method of monitoring the increase in a target nucleic acid during amplification of said target. The method typically involves a) providing an amplification reaction mixture that comprises said target nucleic acid, at least one primer that hybridizes to the target nucleic acid, a labeled oligonucleotide probe of the present invention that provides a detectable signal, the intensity of which is proportional to the increase in the target nucleic acid in the amplification; (b) treating said mixture under conditions for amplifying said target nucleic acid; and (c) measuring the amount of said signal produced by said mixture during said treating step (c). Where desired, the amount of signal is determined continuously throughout the amplification reaction or determined intermittently during the amplification reaction. The amplification can be exponentially with the use of a primer pair or linearly with the use of one primer of the pair.

The increase in signal intensity during the amplification reaction may due to the step of hybridization of the probe to the target nucleic acid and also the step of cleavage via the action of the polymerase utilized in the amplification reaction.

In one aspect, the subject methods exploit the 5' to 3' nuclease activity of a polymerase when used in conjunction with PCR. When the subject probe is added concomitantly with the primer at the start of PCR, and the signal generated from hydrolysis of the labeled nucleotide(s) of the probe provides a means for detection of the target sequence during its amplification. Numerous polymerases are suited to catalyze primer and template-dependent nucleic acid synthesis and possess the 5' to 3' nuclease activity. Non-limiting examples include DNA polymerases such as *E. coli* DNA polymerase I, *Thermus thermophilus* (Tth) DNA polymerase, Bacillus stearothermophilus DNA polymerase, *Thermococcus littoralis* DNA polymerase, and *Thermus aquaticus* (Taq) DNA polymerase. Where desired, temperature stable polymerases can be employed in a nucleic acid amplification reaction. See, e.g., U.S. Pat. No. 4,889,818 that discloses a representative thermostable enzyme isolated from *Thermus aquaticus*. Additional representative temperature stable polymerases include without limitation, e.g., polymerases extracted from the thermostable bacteria *Thermus flavus, Thermus ruber, Thermus thermophilus, Bacillus stearothermophilus* (which has a somewhat lower temperature optimum than the others listed), *Thermus lacteus, Thermus rubens, Thermotoga maritima, Thermococcus littoralis*, and *Methanothermus fervidus*.

In another embodiment, nucleic acid amplification can be performed with polymerases that exhibit strand-displacement activity (also known as rolling circle polymerization). Strand displacement can result in the synthesis of tandem copies of a circular DNA template, and is particularly useful in isothermal PCR reaction. Non-limiting examples of rolling circle polymerases suitable for the present invention include but are not limited to T5 DNA polymerase (Chatterjee et al., Gene 97:13-19 (1991)), and T4 DNA polymerase holoenzyme (Kaboord and Benkovic, Curr. Biol. 5:149-157 (1995)), phage M2 DNA polymerase (Matsumoto et al., Gene 84:247 (1989)), phage PRD1 DNA polymerase (Jung et al., Proc. Natl. Aced. Sci. USA 84:8287 (1987), and Zhu and Ito, Biochim. Biophys. Acta. 1219:267-276 (1994)), Klenow fragment of DNA polymerase I (Jacobsen et al., Eur. J. Biochem. 45:623-627 (1974)).

A preferred class of rolling circle polymerases utilizes protein priming as a way of initiating replication. Exemplary polymerases of this class are modified and unmodified DNA polymerase, chosen or derived from the phages Φ29, PRD1, Cp-1, Cp-5, Cp-7, Φ15, Φ1, Φ21, Φ25, BS 32 L17, PZE, PZA, Nf, M2Y (or M2), PR4, PR5, PR722, B103, SF5, GA-1, and related members of the Podoviridae family. Specifically, the wildtype bacteriophage Φ29 genome consists of a linear double-stranded DNA (dsDNA) of 19,285 base pairs, having a terminal protein (TP) covalently linked to each 5' end. To initiate replication, a histone-like viral protein forms a nucleoprotein complex with the origins of replication that likely contributes to the unwinding of the double helix at both DNA ends (Serrano et al., The EMBO Journal 16(9): 2519-2527 (1997)). The DNA polymerase catalyses the addition of the first dAMP to the hydroxyl group provided by the TP. This protein-primed event occurs opposite to the second 3' nucleotide of the template, and the initiation product (TP-dAMP) slides back one position in the DNA to recover the terminal nucleotide After initiation, the same DNA polymerase replicates one of the DNA strands while displacing the other. The high processivity and strand displacement ability of Φ29 DNA polymerase makes it possible to complete replication of the Φ29 TP-containing genome (TP-DNA) in the absence of any helicase or accessory processivity factors (reviewed by Serrano et al, The EMBO Journal 16(9): 2519-2527 (1997)).

Strand displacement can be enhanced through the use of a variety of accessory proteins. They include but are not limited to helicases (Siegel et al., J. BioL Chem. 267:13629-13635 (1992)), herpes simplex viral protein ICP8 (Skaliter and Lehman, Proc. Natl, Acad. Sci. USA 91(22):10665-10669 (1994)), single-stranded DNA binding proteins (Rigler and Romano, J. Biol. Chem. 270:8910-8919 (1995)), adenovirus DNA-binding protein (Zijderveld and van der Vliet, J. Virology 68(2):1158-1164 (1994)), and BMRF1 polymerase accessory subunit (Tsurumi et al., J. Virology 67(12):7648-7653 (1993)).

The subject probes can be utilized in an isothermal amplification reaction. Such amplification reaction does not rely solely upon thermal cycling. The procedure can be applied at a wide range of ambient temperatures. In particular, denaturation of the double-stranded template sequence is not accomplished solely through an increase in temperature above the melting temperature of the double stranded sequence. Rather, the denaturation process involves physical or mechanical force that separates the strand to allow primer annealing and extension. Various mechanisms for conducting isothermal amplification reaction including isothermal PCR are described in US. Patent Publication No 20060019274 and U.S. Pat. Nos. 5,824,477 and 6,033,850, which are incorporated herein by reference.

Nucleic acid amplification is generally performed with the use of amplification reagents. Amplification reagents typically include enzymes, aqueous buffers, salts, primers, target nucleic acid, and nucleoside triphosphates. Depending upon the context, amplification reagents can be either a complete or incomplete amplification reaction mixture.

The choice of primers for use in nucleic acid amplification will depend on the target nucleic acid sequence. Primers used in the present invention are generally oligonucleotides, e.g., 10 to 100 or 10 to 25 bases in length, that can be extended in a template-specific manner via the action of a polymerase. In general, the following factors are considered in primer design: a) each individual primer of a pair preferably does not self-hybridize in an amplification reaction; b) the individual pairs preferably do not cross-hybridize in an amplification reaction; and c) the selected pair must have the appropriate length and sequence homology in order to anneal to two distinct regions flanking the nucleic acid segment to be amplified. However, not every nucleotide of the primer must anneal to the template for extension to occur. The primer sequence need not reflect the exact sequence of the target nucleic acid. For example, a non-complementary nucleotide fragment may be attached to the 5' end of the primer with the remainder of the primer sequence being complementary to the target. Alternatively, non-complementary bases can be interspersed into the primer, provided that the primer sequence has sufficient complementarily with the target for annealing to occur and allow synthesis of a complementary nucleic acid strand.

A nucleic acid amplification reaction typically comprises a target nucleic acid in a buffer compatible with the enzymes used to amplify the target. The buffer typically contains nucleotides or nucleotide analogs (ATP, TTP, CTP, GTP, or analogs thereof including without limitation pentaphosphates having the respective base unit) that are capable of being incorporated into a replica strand of the template sequence.

Where desired, amplification reaction is carried out as an automated process. Numerous thermocyclers are available in the art that are capable of holding 48, 96 or more samples. A suitable optical system moves the excitation light from the source to the reaction sites and measures the emission light from each sample. For example, multiple fiber optic leads simultaneously read all PCR tubes undergoing thermocycling. However, only a single fluorometer may be needed to read fluorescence from the reaction sites. An analogous detection scheme is suitable in a 96-well microtiter format. This type of format is frequently desirable in clinical laboratories for large scale sample screening, for example, for genetic analysis such as screening for AIDS virus in blood bank screening procedures.

Accordingly, the present invention also provides an apparatus for detecting the signal generated by the subject probe, which can be used to detect, measure, and quantify the signal before, during, and after amplification. The apparatus comprises a thermal unit (e.g., a thermocycler) capable of holding an amplification reaction mixture comprising the subject probes and effecting an amplification of the target sequence, and a detector that detects the signal generated from the subject probes.

In another embodiment of the present invention, the subject probes are employed in assays that are conducted on nucleic acid microarrays to detect or quantify nucleic acid targets. In such assays, a fluorescent signal is generated on a nucleic acid microarray upon the presence of a complementary target nucleic acid.

Nucleic acid microarrays including gene chips comprise ordered arrays of nucleic acids that are covalently attached to a solid surface, see e.g., U.S. Pat. Nos. 5,871,928, 6,040,193, 6,262,776, 6,403,320, and 6,576,424. The fluorescent signal that is generated in the assay can be monitored and quantified with optical detectors including but not limited to fluorescence imagers, e.g. commercial instruments supplied by Hitachi Corp., San Bruno, Calif. or confocal laser microscopes (confocal fluorescence scanners), e.g. commercial instruments from General Scanning, Inc., Watertown, Mass.

In assays that are conducted on nucleic acid microarrays, the target nucleic acids may be provided as a mixture of nucleic acid sequences derived from any suitable biological sources. They can be derived from body fluid, solid tissue samples, tissue cultures or cells derived therefrom and the progeny thereof, and sections or smears prepared from any of these sources, or any other samples that contain nucleic acids.

Where expression pattern is assayed, the mRNA sequences are first typically amplified by reverse transcription PCR with universal primers prior to their use as the target sequences in the assay. In one embodiment, all nucleic acid sequences present in the test sample are simultaneously applied to the microarray for analysis, thus allowing the interaction of all target nucleic acid sequences with all nucleic acids that are present on the array. In another embodiment, the target nucleic acids applied to the array are pre-selected to yield a subset for refined hybridization analysis utilizing a microarray. For example, a limited number of target sequences can contain more than one stretch of specific nucleotide sequence to be analyzed, e.g. more than one single nucleotide polymorphism. The nucleic acid sequences of this setting may be amplified by PCR with the aid of specific primers prior to their analysis on the microarray.

In assaying for expression of multiples genes of a subject, target polynucleotides are allowed to form stable complexes with probes on the aforementioned arrays in a hybridization reaction. It will be appreciated by one of skill in the art that where antisense RNA is used as the target nucleic acid, the sequence immobilized on the array are chosen to be complementary to sequences of the antisense nucleic acids. Conversely, where the target nucleic acid pool is a pool of sense nucleic acids, the sequence immobilized on the array are selected to be complementary to sequences of the sense nucleic acids. Finally, where the nucleic acid pool is double stranded, the probes may be of either sense and/or antisense as the target nucleic acids include both sense and antisense strands.

In one embodiment, labeled probes are utilized to perform a competitive hybridization on a microarray. In this assay format, a target nucleic acid from a test sample competes with a probe of the present invention for binding of a known sequence immobilized on the microarray. The amount of labeled probes that will bind to the immobilized known sequences is inversely proportional to the concentration of corresponding target nucleic acids in the test sample.

A variant hybridization assay involves the use of polymerases on a microarray to enhance the signals of the probes by performing cleavage of the reporters. For example, a mixture of target sequences are first allowed to hybridize with known sequences immobilized on the array. Unhybridized sequences are then washed away. Thereafter, probes corresponding to the target sequences are allowed to hybridize to different regions on the targets. Upon washing of the excessive unbound probes, the reporter fluorescent groups on the hybridized probes are cleaved via the action of polymerases, thereby generating a detectable signal that is indicative of the presence and/or quantity of a target sequence initially present in the test sample.

Suitable hybridization conditions for use of the labeled probes of the invention are such that the recognition interaction between the sequence on the array and target is both sufficiently specific and sufficiently stable. As noted above, hybridization reactions can be performed under conditions of different "stringency". Relevant conditions include temperature, ionic strength, time of incubation, the presence of additional solutes in the reaction mixture such as formamide, and the washing procedure. Higher stringency conditions are those conditions, such as higher temperature and lower sodium ion concentration, which require higher minimum complementarity between hybridizing elements for a stable hybridization complex to form. Conditions that increase the stringency of a hybridization reaction are widely known and published in the art. See, for example, (Sambrook, et al., (1989), supra).

In general, there is a tradeoff between hybridization specificity (stringency) and signal intensity. In a preferred embodiment, washing the hybridized array prior to detecting the target-probe complexes is performed to enhance the signal to noise ratio. Typically, the hybridized array is washed at successively higher stringency solutions and signals are read between each wash. Analysis of the data sets thus produced will reveal a wash stringency above which the hybridization pattern is not appreciably altered and which provides adequate signal for the particular polynucleotide probes of interest. Parameters governing the wash stringency are generally the same as those of hybridization stringency. Other measures such as inclusion of blocking reagents (e.g. sperm DNA, detergent or other organic or inorganic substances) during hybridization can also reduce non-specific binding.

Imaging specific hybridization event on a microarray is typically performed with the aid of an optical system. Non-limiting examples of suitable systems include camera, charge couple device (CCD), electron-multiplying charge-coupled device (EMCCD), intensified charge coupled device (ICCD), and confocal microscope.

The microarray provides a positional localization of the sequence where hybridization has taken place. The position of the hybridized region correlates to the specific sequence, and hence the identity of the target expressed in the test sample. The detection methods also yield quantitative measurement of the level of hybridization intensity at each hybridized region, and thus a direct measurement of the level of expression of a given gene transcript. A collection of the data indicating the regions of hybridization present on an array and their respective intensities constitutes a hybridization pattern that is representative of a multiplicity of expressed gene transcripts of a subject. Any discrepancies detected in the hybridization patterns generated by hybridizing target polynucleotides derived from different subjects are indicative of differential expression of a multiplicity of gene transcripts of these subjects.

In one aspect, the hybridization patterns to be compared can be generated on the same array. In such case, different patterns are distinguished by the distinct types of detectable labels. In a separate aspect, the hybridization patterns employed for the comparison are generated on different arrays, where discrepancies are indicative of a differential expression of a particular gene in the subjects being compared.

The test nucleic acids for a comparative hybridization analysis can be derived from (a) cells from different organisms of the same species (e.g. cells derived from different humans); (b) cells derived from the same organism but from different tissue types including normal or disease tissues, embryonic or adult tissues; (c) cells at different points in the cell-cycle; (d) cells treated with or without external or internal stimuli. Thus, the comparative hybridization analysis using the arrays of the present invention can be employed to monitor gene expression in a wide variety of contexts. Such analysis may be extended to detecting differential expression of genes between diseased and normal tissues, among different types of tissues and cells, amongst cells at different cell-cycle points or at different developmental stages, and amongst cells that are subjected to various environmental stimuli or lead drugs. Therefore, the expression detecting methods of this invention may be used in a wide variety of circumstances including detection of disease, identification and quantification of differential gene expression between at least two samples, linking the differentially expressed genes to a specific chromosomal location, and/or screening for compositions that upregulate or downregulate the expression or alter the pattern of expression of particular genes.

The subject amplification and any other hybridization assays described herein can be used to detect any target nucleic acids from any sources suspected to contain the target. It is not intended to be limited as regards to the source of the sample or the manner in which it is made. Generally, the test sample can be biological and/or environmental samples. Biological samples may be derived from human or other animals, body fluid, solid tissue samples, tissue cultures or cells derived therefrom and the progeny thereof, sections or smears prepared from any of these sources, or any other samples that contain nucleic acids. Preferred biological samples are body fluids including but not limited to urine, blood, cerebrospinal fluid, spinal fluid, sinovial fluid, semen, ammoniac fluid, cerebrospinal fluid (CSF), and saliva. Other types of biological sample may include food products and ingredients such as dairy items, vegetables, meat and meat by-products, and waste. Environmental samples are derived from environmental material including but not limited to soil, water, sewage, cosmetic, agricultural and industrial samples, as well as samples obtained from food and dairy processing instruments, apparatus, equipment, disposable, and non-disposable items.

Polynucleotides labeled according to the invention may also be used in gel shift assays. Such an assay, also known as electrophoretic mobility shift assay (EMSA), gel mobility shift assay, band shift assay, or gel retardation assay, is a common technique used to study protein-DNA or protein-RNA interactions. This procedure can determine if a protein or mixture of proteins is capable of binding to a given DNA or RNA sequence, and can sometimes indicate if more than one protein molecule is involved in the binding complex. Labeled oligonucleotides may be used in gel shift assays by performing electrophoresis and subsequently determining the extent of migration of the labeled oligonucleotides in the gel by visualizing the emission of the fluorescent label. Gel shift assays may be performed in vitro concurrently with DNase footprinting, primer extension, and promoter-probe experiments when studying transcription initiation, DNA replication, DNA repair or RNA processing and maturation. Methods of performing gel shift assays are known. See, e.g. Garner, M. M. and Revzin, A. (1981) "A gel electrophoresis method for quantifying the binding of proteins to specific DNA regions: application to components of the *Escherichia coli* lactose operon regulatory system." Nucleic Acids Res. 9:3047-3060 or Fried, M. and Crothers, D. M. (1981) "Equilibria and kinetics of lac repressor-operator interactions by polyacrylamide gel electrophoresis." Nucleic Acids Res., 9:6505-6525.

Fluorescently labeled polypeptides of the invention are useful in a wide variety of assays. Such assays can be performed to discern specific protein-protein interactions, protein-nucleic acid interaction, interactions between a protein of interest and candidate inhibitors or activators. Candidate inhibitors or activators include but are not limited to antisense oligonucleotides, double stranded RNAs, ribozymes, a ribozyme derivatives, antibodies, liposomes, small molecules, inorganic or organic compounds. The subject assays can also be performed to study enzymatic kinetics, for e.g., drug design, screen and/or optimization and can be performed using the fluorescently labeled polypeptides in solution or immobilized on a solid substrate.

Of particular interest is a specific interaction between a cell surface receptor and its corresponding ligand. Cell surface receptors are molecules anchored on or inserted into the cell plasma membrane. They constitute a large family of proteins, glycoproteins, polysaccharides and lipids, which serve not only as structural constituents of the plasma membrane, but also as regulatory elements governing a variety of biological functions. In another aspect, the specific protein-protein interaction involves a cell surface receptor and an immoliposome or an immunotoxin. In yet another aspect, the specific protein-protein interaction may involve a cytosolic protein, a nuclear protein, a chaperon protein, or proteins anchored on other intracellular membranous structures. In yet another aspect, the specific protein-protein interaction is between a target protein (e.g., an antigen) and an antibody specific for that antigen.

A specific interaction between a labeled polypeptide and an interacting entity is assayed by mixing the two entities under conditions such interaction is suspected to occur. Typically, the interaction is visualized with the aid of an optical device. Where desired, these entities can be placed within an optical confinement (see, e.g., U.S. Pat. Nos. 7,267,673, and 7,170,050). Where single molecule is to be detected, each optical confinement contains only one target that is being investigated. This can be achieved by diluting a minute amount of target in a large volume of solution, such that deposition over an array of confinements results in a primary distribution, or a majority of confinements will have a single target molecule disposed there. The labeled polypeptide and the interacting entity can be immobilized onto the inner surface of the optical confinement by any of the methods available in the art. Such methods encompass the uses of covalent and noncovalent attachments effected by a variety of binding moieties. The choice of the binding moieties will depend on the nature of the labeled polypeptide and/or the interacting entity. One way to immobilize the labeled polypeptide or the proteinaceous probe involves the use of the streptavidin or avidin/biotin binding pair.

In one embodiment, the polypeptide to be reacted with a compound of the invention comprises 3 to about 80 amino acids. Examples of such polypeptides include, but are not limited to, neuropeptides, cytokines, toxins and peptidase or protease substrates. Fluorescently labeled-neuropeptides, -cytokines and -toxins may be used to map or visualize the distribution of the receptors specific to the respective peptides. □s an example, when labeled with a compound of the invention, phalloidin, which is a toxin with a cyclic peptide structure, can be used to stain F-actin filaments in cells. As another example, when labeled with a fluorescent group of the invention, □-bungarotoxin, a peptide-based snake toxin, can be used to detect acetylcholine receptor. Peptidase or protease substrates labeled with a fluorescent group of the invention may be used to assay the activities of the peptidases or proteases, and used in screening drugs designed as inhibitors of the peptidases or proteases. For example, a peptide comprising a peptide sequence cleavable by a peptidase may be labeled at one end of the peptide sequence with a first fluorescent group, a fluorescence donor fluorescent group, selected from a fluorescent group of the invention and at the other end of the peptide sequence with a second fluorescent group, a fluorescence acceptor fluorescent group (such as another fluorescent group from the invention or a quencher), where the first dye and second dye form a fluorescence resonance energy transfer (FRET) pair. By detecting the fluorescence difference of either the donor fluorescent group or the acceptor fluorescent group of the FRET pair before and after the peptide is cleaved by said peptidase, the level of enzyme activity can be assessed.

Other polypeptide conjugates that can be prepared according to the invention include those of antibodies, lectins, enzymes, lipoproteins, albumins, avidin, streptavidin, annexins, protein A, protein G, transferrin, apotransferrin, phycobiliproteins and other fluorescent proteins, toxins, growth factors, tubulins, hormones, various receptors and ion channels.

In one embodiment, compounds of the invention may be reacted with antibodies. Such antibodies may be primary or secondary depending on the desired application. If the antigen to be detected is present in very small amounts, a secondary antibody may be used in order to provide signal amplification. Various secondary antibody isotypes may be labeled. Non-limiting examples of secondary antibody isotypes are Anti-mouse IgG, Anti-mouse IgM, Anti-rabbit IgG, Anti-rat IgG, Anti-rat IgM, Anti-guinea pig IgG, Anti-chicken IgG, Anti-hamster IgG, Anti-human IgG, Anti-human IgM, Anti-goat IgG, Anti-mouse IgG, Anti-rabbit IgG, Anti-rat IgG, Anti-sheep IgG, Anti-goat IgG, Anti-mouse IgG, Anti-human IgG, Anti-rat IgG, Anti-mouse IgG, Anti-human IgG, Anti-rat IgG, Anti-goat IgG, and Anti-rabbit IgG.

Alternatively, Fab fragments may be labeled with the compounds of the invention. Such fragments may be superior to whole antibody conjugates because they lack the Fc region, which would reduce nonspecific interactions with Fc receptor-bearing cell membranes and would allow better penetration into tissues.

Labeled secondary antibodies of the invention may be used in signal amplification kits such as those commercialized by Molecular Probes, Inc. Such kits could each provide two labeled antibodies specific to a primary antibodies, such as a mouse antibody. In one embodiment, a rabbit anti-mouse IgG antibody conjugate of the invention is first used to bind to the mouse-derived primary antibody. The fluorescence is then dramatically enhanced by the addition of a second conjugate of a goat anti-rabbit IgG antibody.

In yet another embodiment, the compounds of the invention may be used to label protein A and/or protein G. Protein A and protein G are bacterial proteins that bind with high affinity to the Fc portion of various classes and subclasses of immunoglobulins from a variety of species, such as Bovine, Cat, Chicken, Dog, Goat, Guinea pig, Horse, Human IgG1, IgG2, IgG3, IgG4, Human IgM, IgA, IgE, Human IgD, Mouse IgG1 or others, Pig, Rabbit, Rat or Sheep, which may be used in the detection of immunoglobulins. Alternatively, immunoglobins can be labeled with a compound of the invention having a structure of Formula I, II, III, IV, or V and retains binding specificity to its target after such labeling. These labeled immunoglobins can be used for in-vitro or in-vivo detection of the target antigen. In some embodiments, the labeled immunoglobins comprise a fluorophore that has an absorption maximal wavelength equal to or greater than 750 nm. In other embodiments labeled immunoglobins comprise a fluorophore that has an absorption maximal wavelength equal to or greater than 685 nm. In various embodiments of the invention, such labeled immunoglobins bind to an antigen on a cancer cell. In some embodiments, the labeled immunoglobin binds to erb2.

Labeled antibodies prepared according to the invention may be primary antibodies for various applications. While secondary detection methods can provide significant signal amplification, a directly labeled primary antibody often produces lower background fluorescence and less nonspecific binding. Using primary antibodies also allows multiple primary antibodies of the same isotype or derived from the same species to be used in the same experiment when they are directly labeled.

Examples of such primary antibodies include polyclonal antibodies specific for reporter gene products. These include Anti-Green-Fluorescent Protein Antibodies, Anti-Glutathione S-Transferase Antibody, Anti-beta-Glucuronidase Antibody, Anti-beta-Galactosidase Antibody, Monoclonal Antibodies Specific for Epitope Tags, Penta•His Antibody, Anti-HA Antibody and Anti-c-myc Antibody.

Organelle-specific labeled antibodies may also be prepared to label various subcellular organelles and components such as the endoplasmic reticulum, peroxisomes, mitochondria, or cytochrome c. Labeled antibodies may also be specific for proteins in the oxidative phosphorylation system, such as antibodies against cytochrome oxidase (Complex IV) or antibodies against Complexes I, II, III and V, or other mitochondrial proteins such as anti-mitochondrial porin antibodies or anti-pyruvate dehydrogenase antibodies.

In other embodiments, labeled antibodies specific for proliferation markers and cell-cycle control proteins may be prepared. Such antibodies include Anti-Bromodeoxyuridine Antibody (Anti-BrdU Antibody), which may for example be used in TUNEL assays, Anti-Human mRNA-Binding Protein HuR Antibody (Anti-HuR Antibody), Anti-Human Neuronal Protein HuC/HuD Antibody (Anti-Hu Antibody), Anti-cdc6 Peptide Antibody, Anti-CD Antibodies, Antibodies against D Cyclins/Cyclin-Dependent Kinase Inhibitors, and Anti-Phosphoinositide Antibodies.

Some labeled antibodies may be specific for structural cellular proteins. Examples of such antibodies are Anti-alpha-Tubulin Monoclonal Antibody, Anti-Glial Fibrillary Acidic Protein (GFAP) Antibody, Anti-Desmin Antibody, or Anti-Fibronectin Antibody. Additional antibodies suitable for use in the invention include antibodies specific for neuronal proteins such as Anti-Synapsin I Antibody or Anti-NMDA Receptor Antibodies. Other Polyclonal and Monoclonal Antibodies that may be labeled according to the invention include Anti-Human Golgin-97 Antibody, Anti-Human Transferrin Receptor Antibody, Antibodies against Matrix Metalloproteinases and Anti-Bovine Serum Albumin Antibody.

The specific interaction between an antigen and an antibody has been explored in the context of immunoassays utilizing the subject fluorescent compounds. The immunoassays can permit single-molecule detection or ensemble detection. The subject immunoassays can be performed to characterize biological entities, screen for antibody therapeutics, and determine the structural conformations of a target antigen. For instance, immunoassays involving antibodies that are specific for the biological entity or specific for a by-product produced by the biological entity have been routinely used to identify the entity by forming an antibody-entity complex. Immunoassays are also employed to screen for antibodies capable of activating or down-regulating the biological activity of a target antigen of therapeutic potential. Immunoassays are also useful for determining structural conformations by using anti-idiotypic antibodies capable of differentiating target proteins folded in different conformations.

According to one embodiment of the invention, biomolecules labeled with a fluorescent group of the invention such as proteins are suitable for in vivo imaging, including without limitation imaging a biomolecule present inside a cell, a cell, tissue, organ or a whole subject. Where desired, the labeled biomolecules can be used to perform "In Cell Western" in which given molecules (e.g., a specific cellular protein) present inside a cell are stained and imaged.

The fluorescent groups of the invention and/or the labeled biomolecules of the present invention can be administered to a subject in a variety of forms adapted to the chosen route of administration, i.e., orally, or parenterally. Parenteral administration in this respect includes, but is not limited to, administration by the following routes: intravenous, intramuscular, subcutaneous, parenteral, intraocular, intrasynovial, transepithelially including transdermal, opthalmic, sublingual, and buccal; topically including opthalmic, dermal, ocular, rectal and nasal inhalation via insufflation and aerosol and rectal systemic. In particular, proteins labeled with a fluorescent group of the invention comprising an mPEG as a water soluble polymer group may be advantageous. In vivo imaging may provide means for early detection, screening, diagnosis, image-guided surgical intervention, and treatment of various diseases. For example, Near IR fluorescent group-labeled toxin (Veiseh, et al. *Cancer Res.* 67(14), 6882 (2007)) and antibody (Kulbersh, et al. *Arch Otolaryngol Head Neck Surg.* 133(5), 511 (2007)) have been used to detect and guide the surgical removal of tumors. In in-vivo imaging, a fluorescent probe, such as an antibody labeled with a fluorescent group, is first administered to an animal (such as a mammal). The animal is then imaged by applying an excitation light with a wavelength appropriate for the absorption of the fluorescent group and collecting the fluorescence signal at another wavelength appropriate for the emission of the fluorescent group. Typically, for efficient tissue penetration of both the excitation and emission lights, the absorption and emission wavelengths of the fluorescent group may be greater than 470 nm, greater than 550 nm, greater than 600 nm, or greater than 640 nm. Absorption and emission wavelengths may be less than 1,200 nm. Fluorescent groups with wavelengths in the 640 nm-1,200 nm range may be referred to as near infrared dyes, or near IR dyes, which are preferred for tissue or in vivo imaging. An important challenge for in vivo imaging using antibodies has been the relatively short half-life of the fluorescently labeled antibodies. It has been reported that antibodies labeled with more than 3 fluorescent group molecules were rapidly cleared from the body by translocating into the liver, where they became metabolized (BioProbes 52, 10-11, March 2007, by Molecular Probes, Inc). In order to extend the half-life of the labeled antibodies so that enough of the antibodies were available over time for detecting the target, it was necessary to lower the number of fluorescent group molecules per antibody (i.e., degree of labeling or DOL) to about 2. However, the lowering of DOL was at the expense of fluorescence brightness of the individual labeled antibody molecules. Thus, it would be desirable to have antibodies that are labeled with 3 or more fluorescent group molecules and that have a relatively long half-life in vivo. PEG is a known biocompatible material often used in functionalizing the surface of implantable medical devices (Balakrishanan, et al. Biomaterials 26(17), 3495 (2005)) and in modifying drugs (Mehvar, et al. Pharm. Pharmaceut. Sci. 3, 125 (2000); Wang, et al. J. Biochem. Cell Biology 34, 396 (2002)). In practice of the subject invention, proteins, such as antibodies, may be labeled with single or multiple, such as more than 3, 4, 5, 6 or more fluorescent dye molecules of the invention and the antibodies labeled in such a manner can have a relatively long half-life in the body. In particular, the PEG group(s) in the fluorescent group can mask the fluorescent group such that an antibody labeled with multiple molecules of the fluorescent group is less immunogenic as compare to the same antibody labeled with a conventional fluorescent dye (such as Cy5.5, Cy7 or Alexa Fluor 750). In some aspects, PEG group(s) on the fluorescent group can mask or protect the antibody itself, making the antibody more resistant to hydrolysis by proteases.

In other embodiments of the invention, a method of in-vivo imaging of a subject is provided comprising the steps of administering to a subject in need thereof a biomolecule comprising a label having a structure of Formula I, II, III, IV or V wherein the at least one reactive moiety of label has undergone a reaction which attached the label to the biomolecule and wherein the biomolecule further comprises a targeting moiety that binds to a binding partner on a cell of the subject which is indicative of the cell; binding the binding partner on the cell with the targeting moiety of the biomolecule thereby differentially labeling the cell relative to neighboring cells; directing exciting wavelength to the cell; and detecting emitted fluorescence from the cell of the subject thereby detecting the differentially labeled cell of the subject. The biomolecule may be an antibody, fragment of an antibody, protein, peptide, lipid or carbohydrate.

The compounds of the invention may also be used to produce labeled biomolecules for use in immunohistochemistry and immunocytochemistry experiments. In immunohistochemistry (IHC), the presence and location of proteins is determined within a tissue section by exploiting the principle of an antibody binding specifically to an antigens present in a biological tissue. Such experiments may, for example, be used in the diagnosis and treatment of cancer. Specific molecular markers are characteristic of particular cancer types and are known to persons skilled in the art. IHC can also be used in basic research to determine the distribution and localization of biomarkers in different parts of a tissue. Visualization of antibody-antigen interactions can be accomplished by reacting an antibody with a reactive fluorescent compound of the invention and using the labeled antibody to stain tissue sections. In immunocytochemistry, the labeled antibody is used to stain populations of cultured cells. These techniques can be combined with confocal laser scanning microscopy, which is highly sensitive and can also be used to visualise interactions between multiple proteins. Subcellular localization of proteins may also be possible using confocal microscopy.

Of particular interest is the use of the labeled polypeptide for conducing immunocytochemistry. Fluorescence immunocytochemistry combined with fluorescence microscopy provides visualization of biomolecules such as proteins and nucleic acids within a cell. One method uses primary antibodies hybridized to the desired target. Then, secondary antibodies conjugated with the subject fluorescent dyes and targeted to the primary antibodies are used to tag the complex. The complex is visualized by exciting the dyes with a wavelength of light matched to the dye's excitation spectrum.

Immunocytochemistry can also be employed to discern subcellular localization of a given protein or nucleic acid. For instance, colocalization of biomolecules in a cell is performed using different sets of antibodies for each cellular target. For example, one cellular component can be targeted with a mouse monoclonal antibody and another component with a rabbit polyclonal antibody. These are designated as the primary antibody. Subsequently, secondary antibodies to the mouse antibody or the rabbit antibody, conjugated to different fluorescent dyes of the present invention having different emission wavelengths, are used to visualize the cellular target.

The compounds of the invention or the labeled biomolecules of the invention can also be used to label cells or particles for a variety of applications. Accordingly, the present invention provides a method of individually labeling a cell within a population of cells whereby the cell is differentially labeled relative to neighboring cells within the population. The method typically comprises contacting the cell with a labeled biomolecule of the present invention, wherein said biomolecule comprises a targeting moiety that binds to a binding partner that is indicative of said cell, and thereby differentially labeling the cell relative to neighboring cells within the population. The targeting moiety can be any biomolecules that recognize a binding partner on the cell to be detected. The choice of the targeting moiety will vary depending on the cell that is to be labeled. For example, for detecting a cancer cell, a targeting moiety is selected such that its binding partner is differentially expressed on a cancer cell. A vast number of cancer markers are known in the art. They include without limitation cell surface receptors such as erb2, PDGF receptor, VEGF receptors, a host of intracellular proteins such as phosphatidylinositol 3-kinases, c-abl, raf, ras, as well as a host of nuclear proteins including transcription factors and other nucleic acid binding molecules. In some other embodiments, the cancer marker is Immunoglobulin epsilon Fc receptor II, Alk-1, CD20, EGF receptor, FGF receptor, NGF receptor, EpCam, CD3, CD4, CD11a, CD19, CD22, CD30, CD33, CD38, CD40, CD51, CD55, CD80, CD95, CCR2, CCR3, CCR4, CCR5, CTLA-4, Mucin 1, Mucin 16, Endoglin, Mesothelin receptor, Nogo receptor, folate receptor, CXCR4, insulin-like growth factor receptor, Ganglioside GD3, and alpha or beta Integrins. To differentially label various cell types, targeting moieties recognizing a cell-specific binding partner can be used. For example, there are a host of protein markers differentially expressed on T cells as opposed on B cells or other cells of different lineage. Neuronal markers, muscle cell markers, as well as markers indicative of cells of ectodermal, mesodermal or endodermal origins are also known in the art, all of which can be used depending on the intended applications. The targeting moieties can be antibodies, receptors, cytokines, growth factors, and any other moieties or combinations thereof that are recognized by a binding partner on the cell to be labeled. The cell which is labeled may be labeled intracellularly.

The differentially labeled cells can be imaged by directing exciting wavelength to the cell and detecting emitted fluorescence from the cell, in a number of in-vitro formats, either in solution or immobilized on a substrate.

The labeled cells and/or the intensity of the fluorescence may be detected or quantified by performing flow cytometry. Cells or particles labeled with the compounds of the invention or stained with labeled biomolecules of the invention may also be separated and isolated based on the specific properties of the label using fluorescence activated cell sorting (FACS). Such techniques are known in the art. Briefly, cells are labeled with a subject fluorescent dye and then passed, in a suspending medium, through a narrow dropping nozzle so that each cell is typically in a small droplet. A laser based detector system is used to excite fluorescence and droplets with positively fluorescent cells are given an electric charge. Charged and uncharged droplets are separated as they fall between charged plates and so collect in different tubes. The machine can be used either as an analytical tool, counting the number of labeled cells in a population or to separate the cells for subsequent growth of the selected population. Further sophistication can be built into the system by using a second laser system at right angles to the first to look at a second fluorescent label or to gauge cell size on the basis of light scatter.

Additional guidance for performing fluorescent cell sorting can be found in publications such as the following: Darzynkiewicz, Z., Crissman, H. A. and Robinson, J. P., Eds., Cytometry, Third Edition Parts A and B (Methods in Cell Biology, Volumes 63 and 64), Academic Press (2001); Davey, H. M. and Kell, D. B., "Flow cytometry and cell sorting of heterogeneous microbial populations: the importance of single-cell analyses," Microbiological Rev 60, 641-696 (1996); Givan, A. L., Flow Cytometry: First Principles, Second Edition, John Wiley and Sons (2001); Herzenberg, L. A., Parks, D., Sahaf, B., Perez, O., Roederer, M. and Herzenberg, L. A., "The history and future of the fluorescence activated cell sorter and flow cytometry: a view from Stanford," Clin Chem 48, 1819-1827 (2002); Jaroszeski, M. J. and Heller, R., Eds., Flow Cytometry Protocols (Methods in Molecular Biology, Volume 91), Humana Press (1997); Ormerod, M. G., Ed., Flow Cytometry: A Practical Approach, Third Edition, Oxford University Press (2000); Robinson, J. P., Ed., Current Protocols in Cytometry, John Wiley and Sons (1997); Shapiro, H. M., "Optical measurement in cytometry: light scattering, extinction, absorption and fluorescence," Meth Cell Biol 63, 107-129 (2001); Shapiro, H. M., Practical Flow Cytometry, Fourth Edition, Wiley-Liss (2003); Weaver, J. L., "Introduction to flow cytometry," Methods 21, 199-201 (2000).

Fluorescent compounds of the invention may also be used for fluorescence lifetime imaging (FLIM). FLIM is a useful technique for producing images based on the variation in the fluorescence decay characteristics of a fluorescent sample. It can be used as an imaging technique in confocal microscopy and other microscope systems. The lifetime of the fluorophore signal, rather than its intensity, is used to create the image in FLIM, which has the advantage of minimizing the effect of photon scattering in thick layers of sample. FLIM may be useful for biomedical tissue imaging, allowing to probe greater tissue depths than conventional fluorescence microscopy.

The compounds of the invention may be used in single molecule applications. Removal of ensemble averaging by observing individual molecules of fluorescent group may allow the determination of the mechanism of biological and chemical processes. Such processes may include the translocation of protein motors such as kinesin or myosin, formation, dissolution and translocation of cellular protein complexes and the mechanism of action of DNA or RNA polymerases. In such experiments, the present compounds may be used, for example, to label biomolecules which are attached to a surface such as a microscopy slide or flow chamber. Individual fluorophores may subsequently be observed using total internal reflection fluorescence microscopy.

The present compounds may also be used for the labeling of lipids. Lipids are involved in many biological processes, and the labeling of lipids and lipid rafts may is often a valuable method for studying their properties. Various lipid monolayers and bilayers may be labeled in live cells or artificial systems such as liposomes and micelles. For example, a live cell population may be labeled with a fluorescent conjugate prepared by reacting a compound of the invention and cholera toxin subunit B, which specifically interacts with lipid rafts. Such lipid rafts may then be crosslinked into distinct membrane patches by the use of an anti-cholera toxin antibody, which may be labeled with one of the present compounds.

The labeled polypeptides of the present invention find use as biosensors in prokaryotic and eukaryotic cells, e.g. as calcium ion indicators, as pH indicators, as phorphorylation indicators, as indicators of other ions including without limiting to magnesium, sodium, potassium, chloride and halides. For example, for detection of calcium ion, proteins containing an EF-hand motif are known to translocate from the cytosol to membranes upon binding to calcium ion. These proteins contain a myristoyl group that is buried within the molecule by hydrophobic interactions with other regions of the protein. Binding of calcium ion induces a conformational change exposing the myristoyl group which then is available for the insertion into the lipid bilayer. Labeling such an EF-hand containing protein with a subject fluorescent dye makes it an indicator of intracellular calcium ion concentration by monitoring the translocation from the cytosol to the plasma membrane. Such monitoring can be performed with the use of an optical detector, e.g., a confocal microscope. EF-hand proteins suitable for use in this system include, but are not limited to: recoverin (1-3), calcineurin B, troponin C, visinin, neurocalcin, calmodulin, parvalbumin, and the like.

For use as a pH indicator, a system based on hisactophilins may be employed. Hisactophilins are myristoylated histidine-rich proteins known to exist in Dictyostelium. Their binding to actin and acidic lipids is sharply pH-dependent within the range of cytoplasmic pH variations. In living cells membrane binding seems to override the interaction of hisactophilins with actin filaments. At pH of approximately 6.5 they typically locate to the plasma membrane and nucleus. In contrast, at pH 7.5 they evenly distribute throughout the cytoplasmic space. This change of distribution is reversible and is attributed to histidine clusters exposed in loops on the surface of the molecule. The reversion of intracellular distribution in the range of cytoplasmic pH variations is in accord with a pK of 6.5 of histidine residues. The cellular distribution is independent of myristoylation of the protein. By conjugating the subject fluorescent dye to hisactophilin, the intracellular distribution of the labeled hisactophilin can be followed by laser scanning, confocal microscopy or standard fluorescence microscopy. Quantitative fluorescence analysis can be done by performing line scans through cells (laser scanning confocal microscopy) or other electronic data analysis (e.g., using metamorph software (Universal Imaging Corp) and averaging of data collected in a population of cells.

The subject fluorescent proteins also find use in applications involving the automated screening of arrays of cells by using microscopic imaging and electronic analysis. Screening can be used for drug discovery and in the field of functional genomics: e.g., where the subject proteins are used as markers of whole cells to detect changes in multicellular reorganization and migration, e.g., formation of multicellular tubules (blood vessel formation) by endothelial cells, migration of cells through Fluoroblok Insert System (Becton Dickinson Co.), wound healing, neurite outgrowth; where the proteins are used as markers fused to peptides (e.g., targeting sequences) and proteins that allow the detection of change of intracellular location as indicator for cellular activity, for example: signal transduction, such as kinase and transcription factor translocation upon stimuli, such as protein kinase C, protein kinase A, transcription factor NFkB, and NFAT; cell cycle proteins, such as cyclin A, cyclin B1 and cyclinE; protease cleavage with subsequent movement of cleaved substrate, phospholipids, with markers for intracellular structures such as endoplasmic reticulum, Golgi apparatus, mitochondria, peroxisomes, nucleus, nucleoli, plasma membrane, histones, endosomes, lysosomes, microtubules, actin.

The subject fluorescent proteins also find use in high through-put screening assays. The subject fluorescent proteins are typically more stable than proteins lacking the subject fluorescent dyes. In some aspects, the fluorescent proteins can exhibit a serum half-life of more than 1 hour, 2 hours, 5 hours, or 24 hours or more.

The subject fluorescent proteins can be used as second messenger detectors, e.g., by conjugating the subject fluorescent dyes to specific signaling domains, e.g., calcium binding SH2-, SH3-, PH-, PDZ-domain and etc.

The examples below are for the purpose of illustrating the practice of the invention. They shall not be construed as being a limitation on the scope of the invention or claims.

EXAMPLES

Example 1

Preparation of 2-(anilinovinyl)-1-(5-carboxypentyl)-3,3-dimethyl-5-sulfoindolium, Potassium Salt (Compound No. 1)

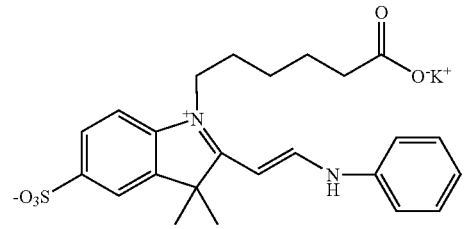

Compound No. 1

A mixture of 1-(5-carboxypentyl)-2,3,3-trimethylindoleninium-5-sulfonate, potassium salt (Bioconjugate Chem. 4, 105 (1993)) (5 g), N,N'-diphenylformamidine (2.3 g) and acetic anhydride (1.1 mL) was heated at 120° C. for 30 minutes. After cooling down to room temperature, the mixture was concentrated to dryness under vacuum and the residue was purified by column chromatography on silica gel (3.5 g).

Example 2

Preparation of 2-(4-anilinobutadienyl)-1-(5-carboxypentyl)-3,3-dimethyl-5-sulfoindolium, Potassium Salt (Compound No. 2)

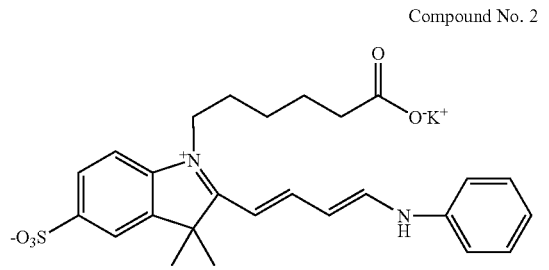

Compound No. 2

A mixture of 1-(5-carboxypentyl)-2,3,3-trimethylindoleninium-5-sulfonate, potassium salt (10 g), malonaldehyde dianil hydrochloride (8 g), Et$_3$N (0.356 mL) in AcOH (40 mL) was heated at 120° C. for 3 hours. After cooling down to room temperature, the mixture was concentrated to dryness under vacuum and the residue was purified by column chromatography on silica gel to dark brown gummy solid (5 g).

Example 3

Preparation of Compound Nos. 3a and 3b

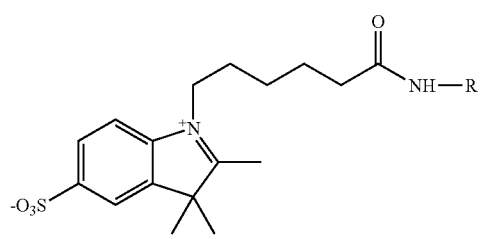

Compound No. 3a R = (CH$_2$CH$_2$O)$_{24}$CH$_3$
Compound No. 3b R = (CH$_2$CH$_2$O)$_{12}$CH$_3$ To a solution of 1-(5-carboxypentyl)-2,3,3-trimethylindoleninium-5-sulfonate, potassium salt (0.1 g) in DMF (1 mL) was added Et$_3$N (0.1 mL) and TSTU (80 mg). The mixture was stirred at room temperature for 1 hour, followed by the addition of Et$_3$N (40 µL) and m-dPEG$_{24}$ amine (0.4 g) (QuantaBiodesign, Powell, Ohio) or m-dPEG$_{12}$ amine (0.2 g) (QuantaBiodesign, Powell, Ohio). The mixture was stirred at room temperature overnight and then concentrated to dryness. The residue was purified by column chromatography on silica gel to give a light brown solid (250 mg for compound No. 3a and 102 mg for compound No. 3b).

Example 4

Preparation of Compound No. 4

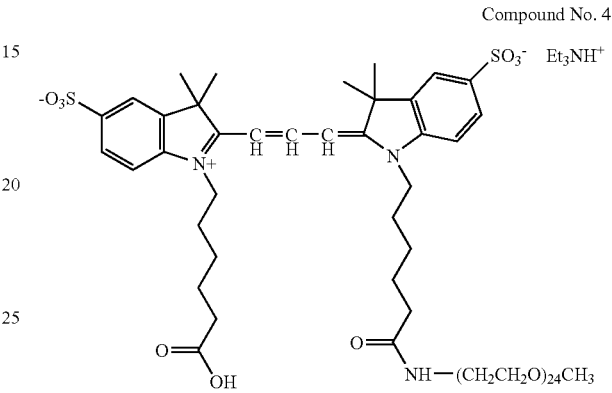

Compound No. 4

A mixture of compound No. 3a (40 mg), compound No. 1 (30 mg), acetic anhydride (15 µL) and Et$_3$N (45 µL) in DMF (1 mL) was stirred at room temperature overnight. The dark red solution was concentrated to dryness under vacuum and the residue was purified by column chromatography on silica gel to give a dark red solid (40 mg).

Example 5

Preparation of Compound No. 5

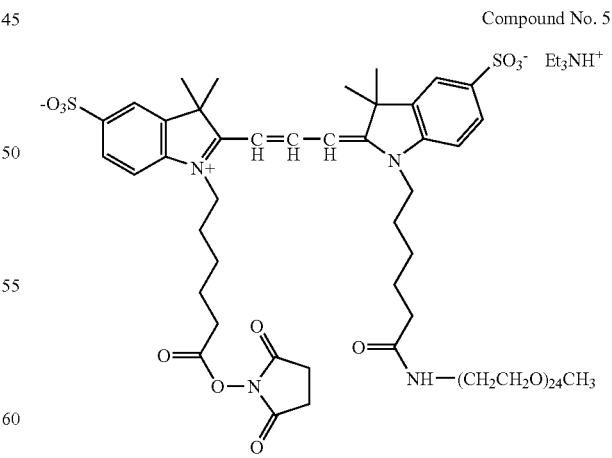

Compound No. 5

A mixture of compound No. 4 (15 mg), Et$_3$N (3.5 µL) and TSTU (3 mg) in DMF (0.2 mL) was stirred at room temperature for 1 hour. Et$_2$O (5 mL) was added and the precipitate (19 mg) was collected by centrifugation.

Example 6

Preparation of Compound No. 6

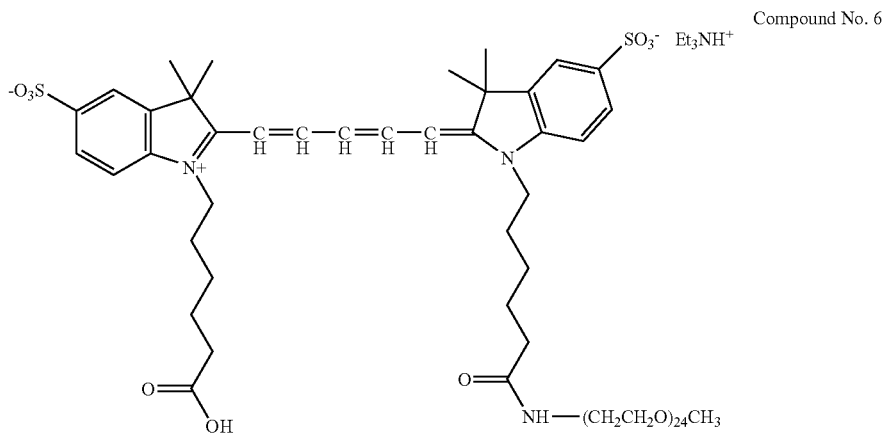

A mixture of compound No. 3a (30 mg), compound No. 2 (20 mg), acetic anhydride (10 μL) and Et₃N (30 μL) in DMF (1 mL) was stirred at room temperature overnight. The dark blue solution was concentrated to dryness under vacuum and the residue was purified by column chromatography on silica gel to give a dark blue solid (20 mg).

Example 7

Preparation of Compound No. 7

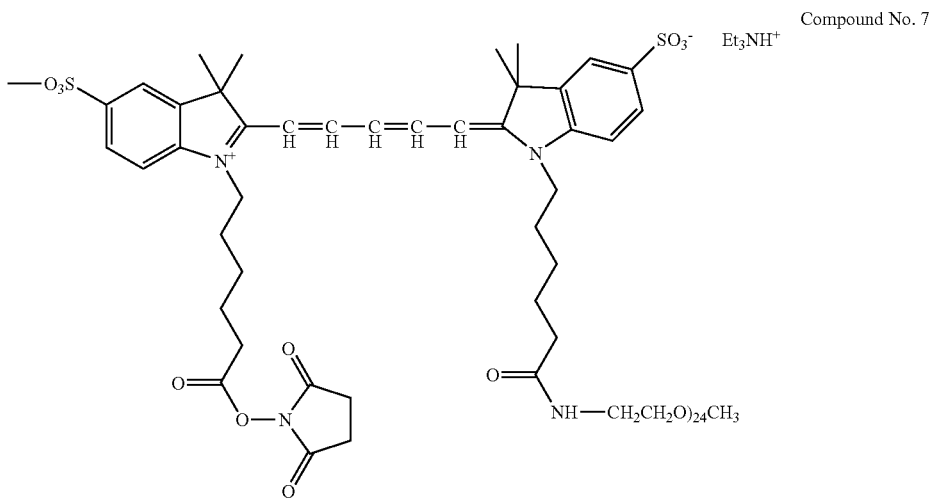

To a solution of compound No. 6 (13 mg) in DMF (0.2 mL) was added Et₃N (3 μL) and TSTU (2.5 mg) and the mixture was stirred at room temperature for 1 hour. Et₂O (2 mL) was added and the precipitate (23 mg) was collected by centrifugation.

Example 8
Preparation of Compound No. 8
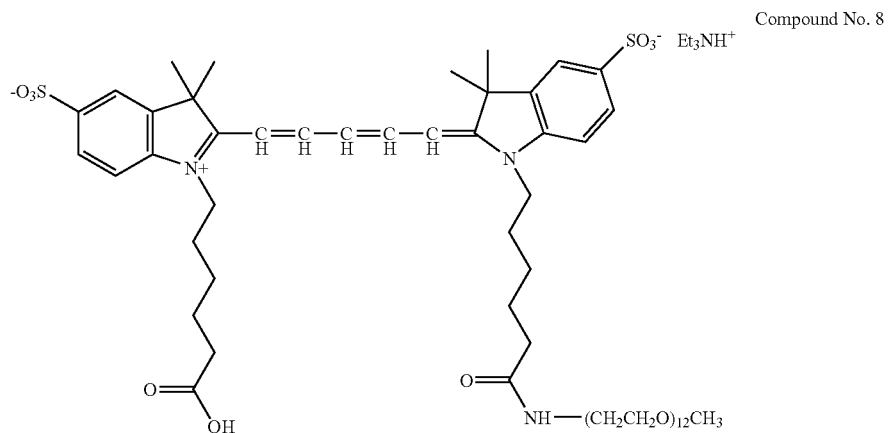
Compound No. 8
Compound 8 (60 mg) was synthesized from compound No. 2 (35 mg) and compound No. 3b (50 mg) according to the preparation of compound No. 6.
Example 9
Preparation of Compound No. 9
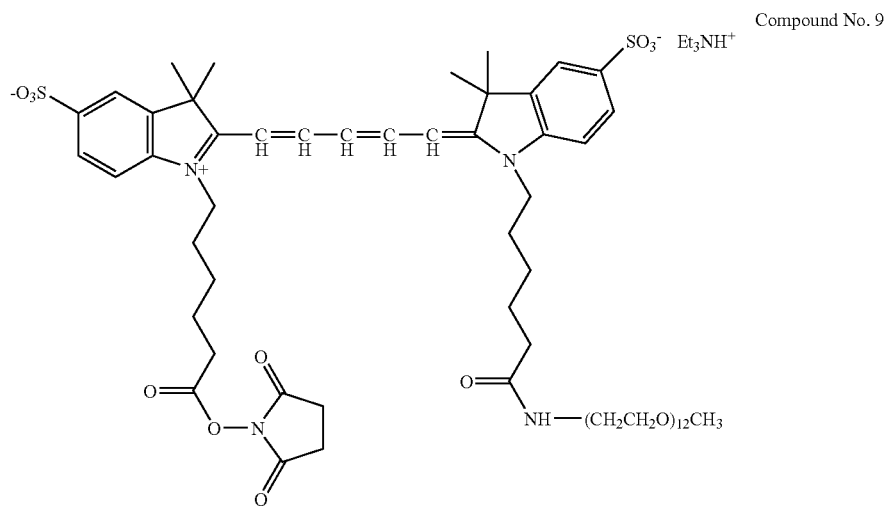
Compound No. 9
Compound No. 9 (10 mg) was synthesized from compound No. 8 (14 mg) according to the preparation of compound No. 7.

Example 10

Preparation of Compound No. 10

Compound No. 10

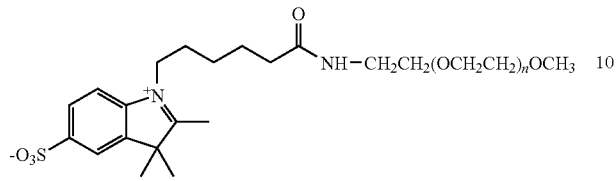

Compound No. 10 (75 mg) was prepared from 1-(5-carboxypentyl)-2,3,3-trimethylindoleninium-5-sulfonate, potassium and mPEG-NH$_2$ (Mwt~2,000) (Laysan Bio. Arab, Ala.) according to the synthesis of compound No. 3.

Example 11

Preparation of Compound No. 11

Compound No. 11

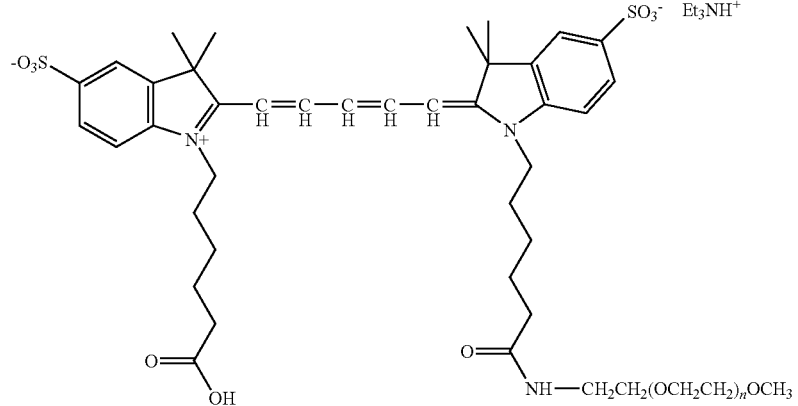

Compound No. 11 (15 mg) was prepared from compound No. 10 (20 mg) and compound No. 2 (6 mg) according to the synthesis of compound No. 6.

Example 12

Preparation of Compound No. 12

Compound No. 12

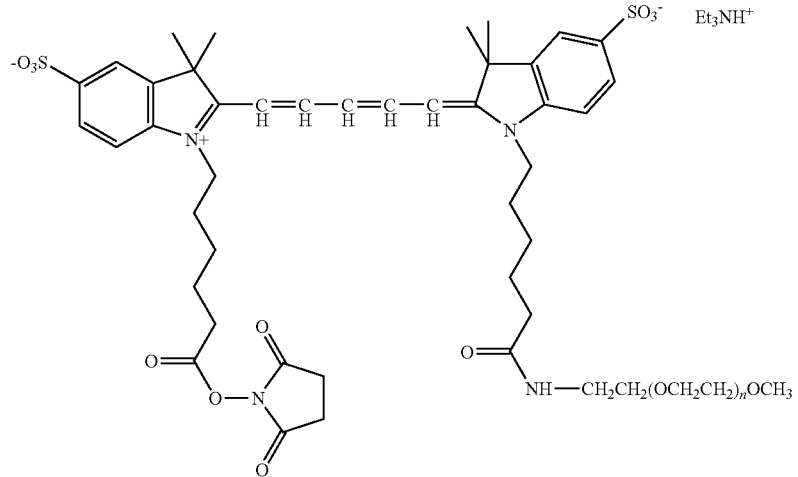

Compound No. 12 (3 mg) was prepared from compound No. 11 (4 mg) according to the synthesis of compound No. 7.

Example 13

Preparation of Compound No. 13

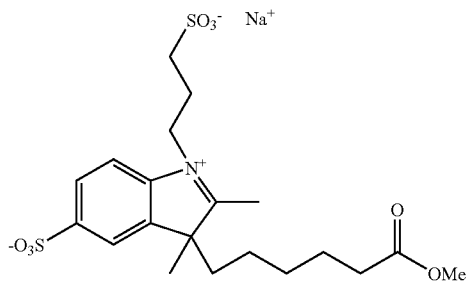

Compound No. 13

A mixture of p-hydrazinobenzenesulfonic acid (5 g), methyl 7-methyl-8-oxononanoate (6 g) (US patent application 2006/0121503 A1) in acetic acid (20 mL) was refluxed gently for 3 hours. After cooling down to room temperature, the mixture was concentrated to dryness and the residue was purified by column chromatography on silica gel to give a reddish brown solid (3 g). The solid was mixed with NaOAc (1 equivalent) in MeOH (100 mL) and the resulting solution was stirred at room temperature for 30 minutes. The solution was concentrated to dryness under vacuum to give a reddish brown solid (3 g).

Example 14

Preparation of Compound No. 14

Compound No. 14

A mixture of compound No. 13 (0.86 g) and 1,3-propanesulftone (0.83 g) was heated at 120° C. for 3 hours. EtOAc (50 mL) was added and the suspension was refluxed gently for 2 hours. After cooling to room temperature, the precipitate (1 g) was collected by suction filtration.

Example 15

Preparation of Compound No. 15

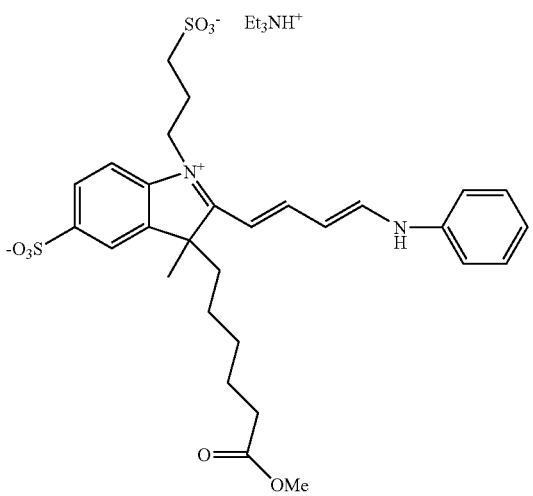

Compound No. 15

A mixture of compound No. 14 (0.8 g), malonaldehyde dianil hydrochloride (0.52 g), Et$_3$N (23 µL) in AcOH (3 mL) was heated at 120° C. for 3 hours. After cooling down to room temperature, the mixture was concentrated to dryness under vacuum and the residue was purified by column chromatography on silica gel to dark red gummy solid (0.5 g).

Example 16
Preparation of Compound No. 16
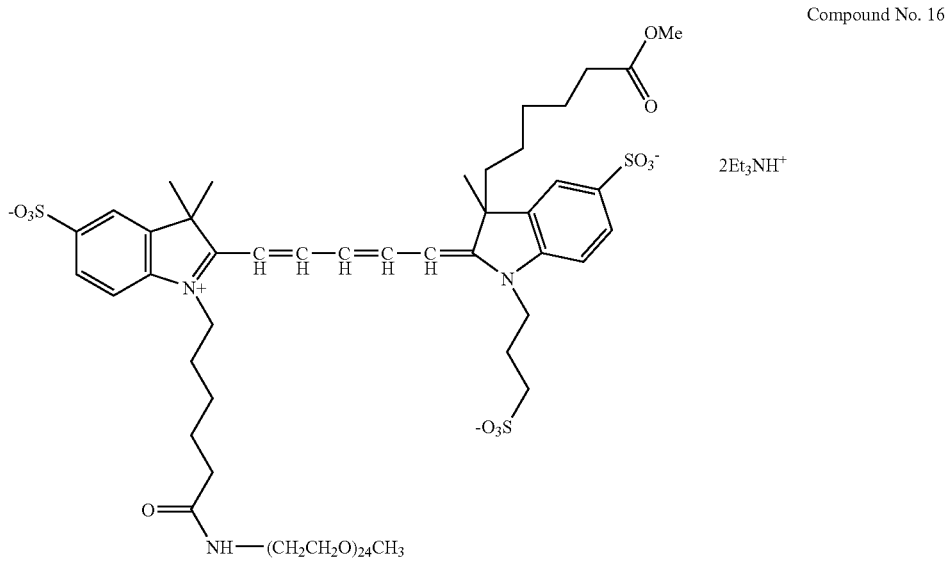
Compound No. 16
Compound No. 16 (80 mg) was prepared from compound No. 15 (50 mg) and compound No. 3a (120 mg) according to the synthesis of compound No. 6.
Example 17
Preparation of Compound No. 17
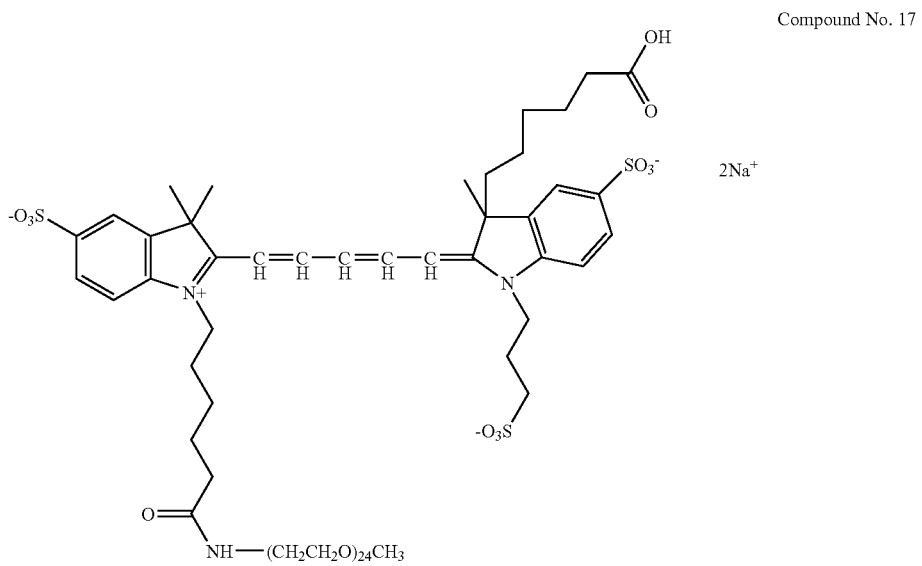
Compound No. 17
To a solution of compound No. 16 (50 mg) in $H_2O$ (2 mL) is added 1 M NaOH (120 μL). The solution was stirred at room temperature for 1 hour and then purified by LH-20 column (35 mg).

Example 18

Preparation of Compound No. 18

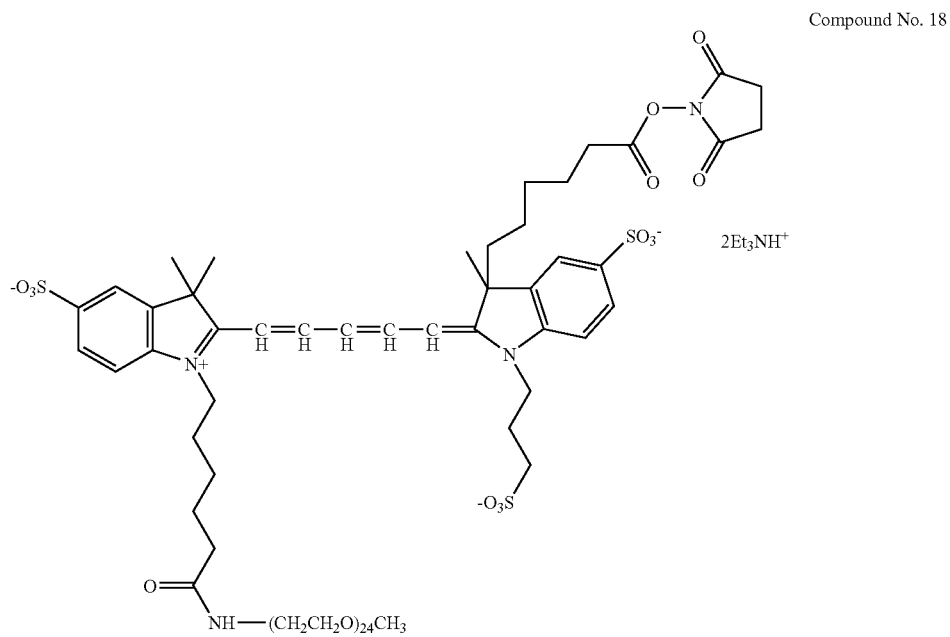

Compound No. 18

Compound No. 18 (5 mg) was prepared from compound No. 17 (4 mg) according to the synthesis of compound No. 7.

Example 19

Preparation of Compound No. 19

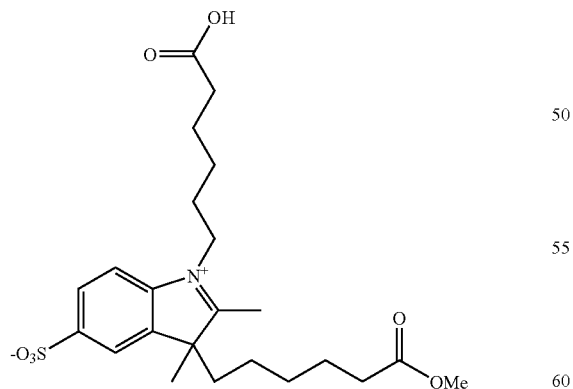

Compound No. 19

A mixture of compound No. 13 (0.6 g) and 6-bromohexanoic acid (0.63 g) was heated at 140° C. for 1 hour. EtOAc (30 mL) was added and the suspension is refluxed gently for 1 hour and the precipitate (0.45 g) was collected by suction filtration.

Example 20

Preparation of Compound No. 20

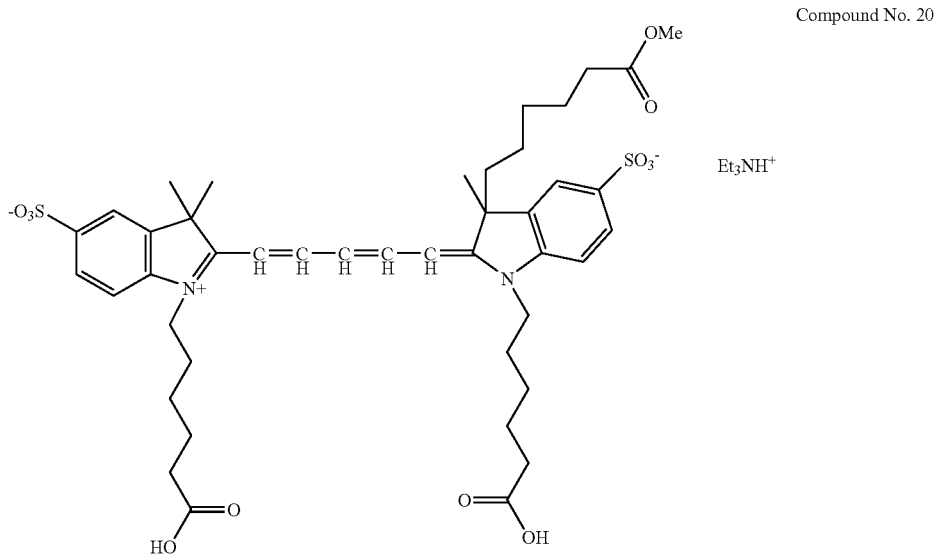

Compound No. 20

A mixture of compound No. 19 (84 mg), compound No. 2 (52 mg), acetic anhydride (32 µL) and Et$_3$N (0.1 mL) in DMF (2 mL) was stirred at room temperature overnight. The solution was concentrated to dryness under vacuum and the residue was purified by column chromatography on silica gel to give dark blue solid (20 mg).

Example 21

Preparation of Compound No. 21

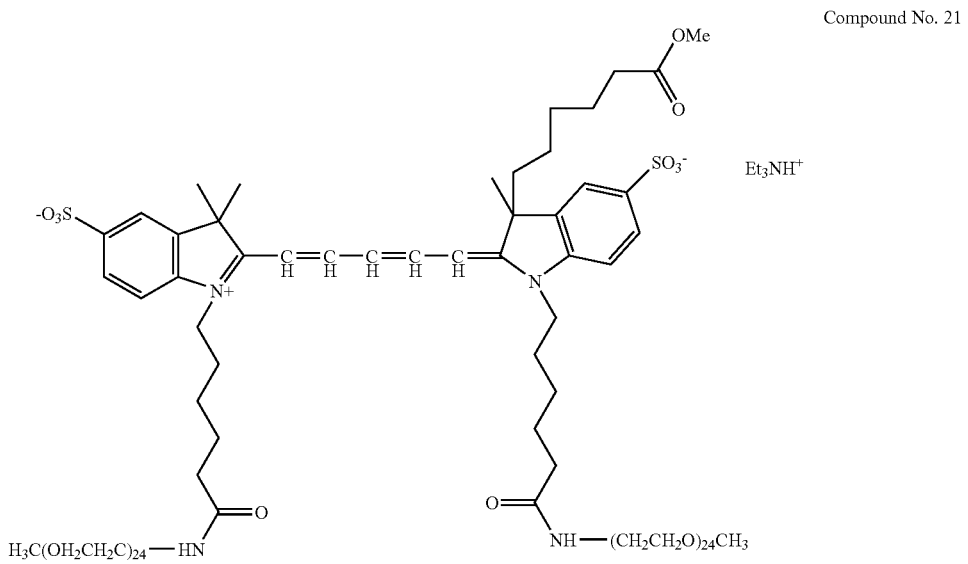

Compound No. 21

Compound No. 21 (17 mg) was prepared from compound No. 20 (9 mg) and m-dPEG$_{24}$ amine (27 mg) according to the synthesis of compound No. 3.

Example 22
Preparation of Compound No. 22
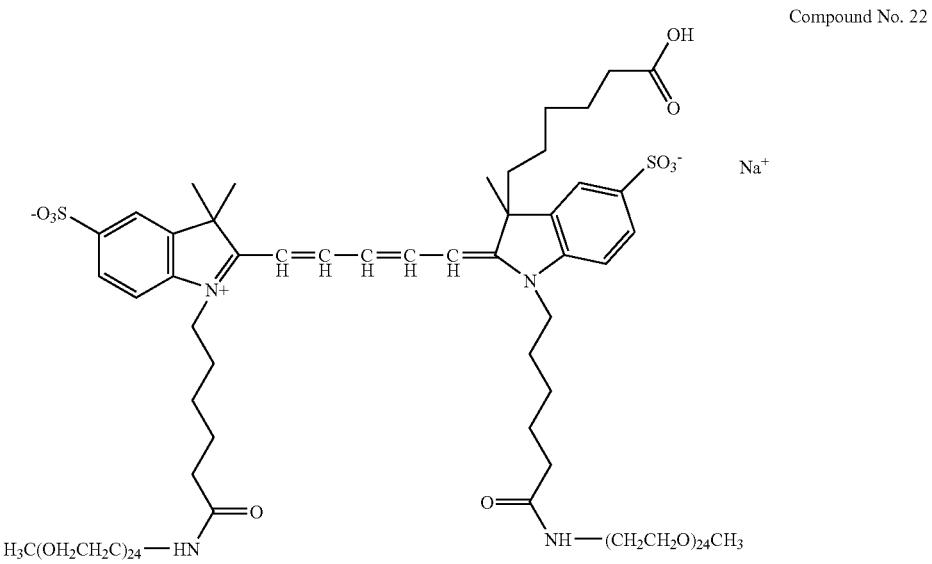
Compound No. 22
To a solution of compound No. 21 (17 mg) in H₂O (0.5 mL) was added 1 M NaOH (0.1 mL) and the solution was stirred at room temperature for 30 minutes. The solution was acidified with 1 N HCl (0.1 mL) and purified by LH-20 column to give a dark blue solid (10 mg) after lyophilization.
Example 23
Preparation of Compound No. 23
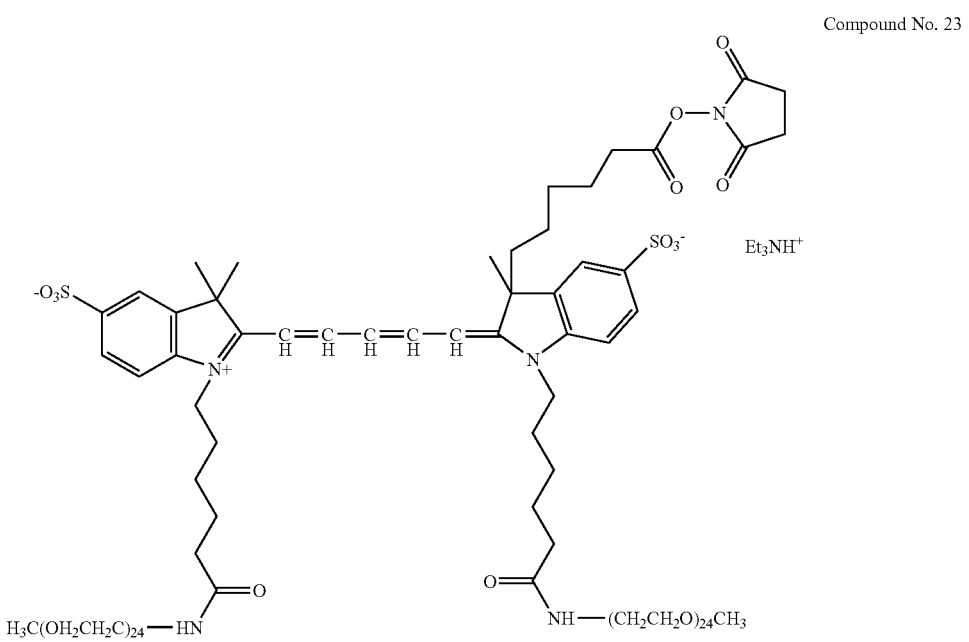
Compound No. 23

Compound No. 23 (4 mg) was prepared from compound No. 22 (6 mg) according to the synthesis of compound No. 7.

Example 24

Preparation of Compound Nos. 24a and 24b

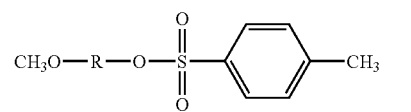

Compound No. 24a: R = —(CH$_2$CH$_2$O)$_{10}$CH$_2$CH$_2$—
Compound No. 24b: R = —(CH$_2$CH$_2$O)$_{23}$CH$_2$CH$_2$—

To a solution of undecaethylene glycol methyl ether (1 g) (Polypure AS, Oslo, Norway) or m-dPEG$_{24}$ alcohol (1 g) (QuantaBiodesign, Powell, Ohio) in CH$_2$Cl$_2$ (5 mL) and pyridine (5 mL) at 0° C. is added p-TsCl (1.1 equivalents) portionwise. The mixture was stirred at 0° C. for 2 hours and then at room temperature overnight. The solution was concentrated to dryness in vacuo and the residue is purified by column chromatography on silica gel to give a colorless oil (1.25 g for compound No. 24a and 1.10 g for compound No. 24b).

Example 25

Preparation of Compound No. 25a and 25b

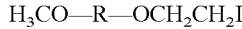

Compound No. 25a: R=—(CH$_2$CH$_2$O)$_{10}$CH$_2$CH$_2$—
Compound No. 25b: R=—(CH$_2$CH$_2$O)$_{23}$CH$_2$CH$_2$—

A mixture of compound No. 24a (1.2 g) or compound No. 24b (1.1 g) and NaI (1.1 equivalent) in acetone (10 mL) was refluxed gently overnight. After cooling down to room temperature the mixture was concentrated to dryness under vacuum and the residue was purified by column chromatography on silica gel to give a colorless solid (1.1 g for compound No. 25a and 1 g for compound No. 25b).

Example 26

Preparation of Compound No. 26

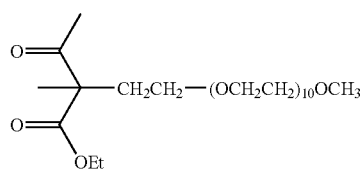

Compound No. 26

A mixture of sodium ethoxide (0.13 g) and ethyl 2-methylacetoacetate (0.28 g) in anhydrous EtOH (5 mL) was stirred at room temperature for 1 hour, followed by the addition of compound No. 25a (0.8 g). The mixture was refluxed gently overnight and the solution was concentrated to dryness under vacuum. The residue was purified by column chromatography on silica gel to give an off-white oil (0.75 g).

Example 27

Preparation of Compound No. 27

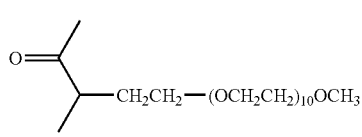

Compound No. 27

To a solution of compound No. 26 (0.7 g) in MeOH (10 mL) was added a solution of NaOH (0.21 g) in H$_2$O (2 mL). The mixture was heated at 60° C. overnight. After cooling down to room temperature, the solution was neutralized with 6M HCl (1 mL). The solution was concentrated to dryness under vacuum and the residue was purified by column chromatography on silica gel to give a colorless oil (0.55 g).

Example 28

Preparation of Compound No. 28

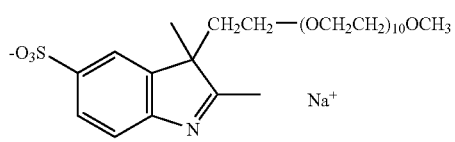

Compound No. 28

A mixture of p-hydrazinobenzenesulfonic acid (100 mg) and compound No. 27 (300 mg) in acetic acid (5 mL) was heated to reflux overnight. After cooling down to room temperature, the mixture was concentrated to dryness and the residue was purified by column chromatography on silica gel a pale brown solid (270 mg). The solid was mixed with NaOAc (1 equivalent) in MeOH (10 mL) and the resulting solution was stirred at room temperature for 30 minutes. The solution was concentrated to dryness under vacuum to give reddish brown solid (280 mg).

Example 29

Preparation of Compound No. 29

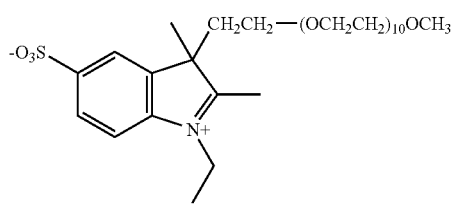

Compound No. 29

A mixture of compound No. 28 (200 mg) and large excess of ethyl iodide (10 mL) was heated to boiling overnight.

EtOAc (20 mL) was added and the suspension was refluxed gently for 1 hour. After cooling to room temperature, the precipitate (250 mg) was collected by suction filtration.

Example 30

Preparation of Compound No. 30

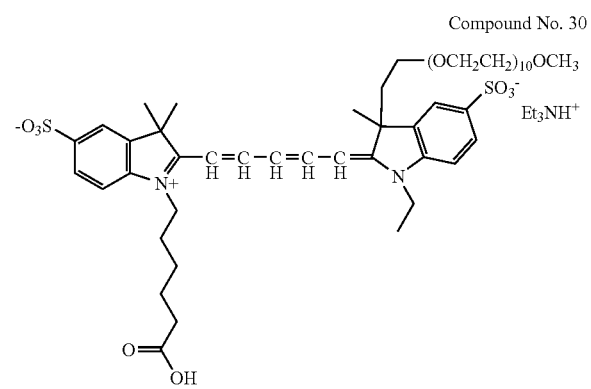

Compound No. 30

Compound No. 30 (55 mg) was prepared from compound No. 29 (100 mg) and compound No. 2 (65 mg) according to the synthesis of compound No. 6.

Example 31

Preparation of Compound No. 31

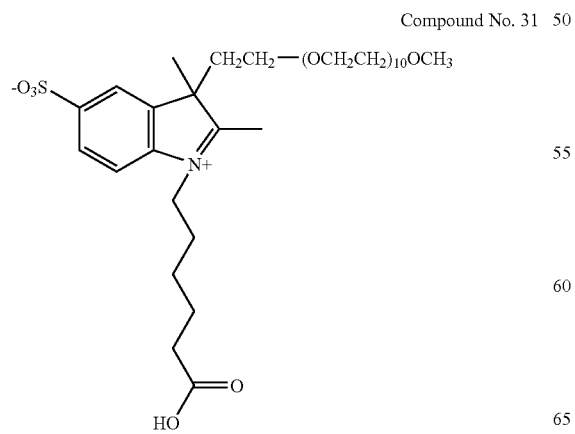

Compound No. 31

Compound No. 31 (120 mg) was prepared from compound No. 30 (200 mg) and 6-bromohexanoic acid (1 g) according to the synthesis of compound No. 19.

Example 32

Preparation of Compound No. 32

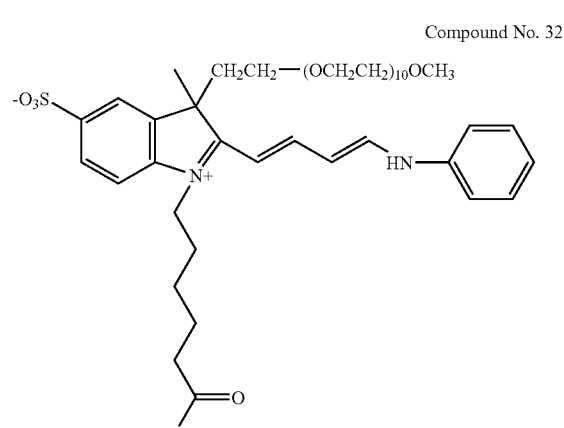

Compound No. 32

Compound No. 32 (75 mg) was prepared from compound No. 31 (100 mg) according to the synthesis of compound No. 2.

Example 33

Preparation of Compound No. 33

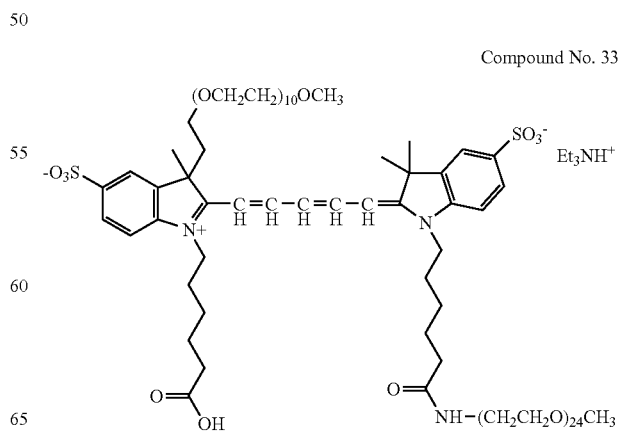

Compound No. 33

Compound No. 33 (7 mg) was prepared from compound No. 32 (30 mg) and compound No. 3a (45 mg). according to the synthesis of compound No. 6.

Example 34

Preparation of Compound No. 34

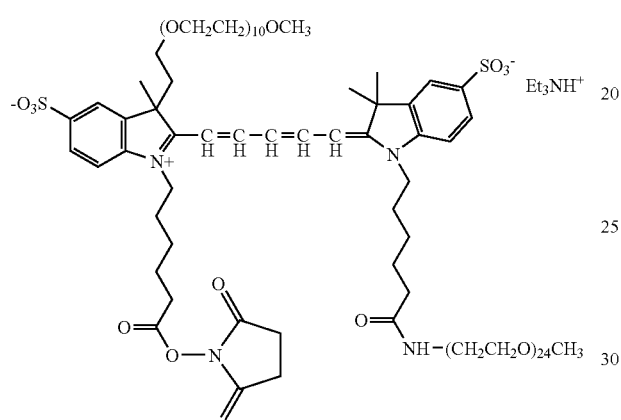
Compound No. 34

Compound No. 34 (3 mg) was prepared from compound No. 33 (5 mg) according to the synthesis of compound No. 7.

Example 35

Preparation of Compound No. 35

Compound No. 35 (7 mg) was prepared from compound No. 32 (30 mg) and compound No. 29 (23 mg) according to the synthesis of compound No. 6.

Example 36

Preparation of Compound Nos. 36a and 36b

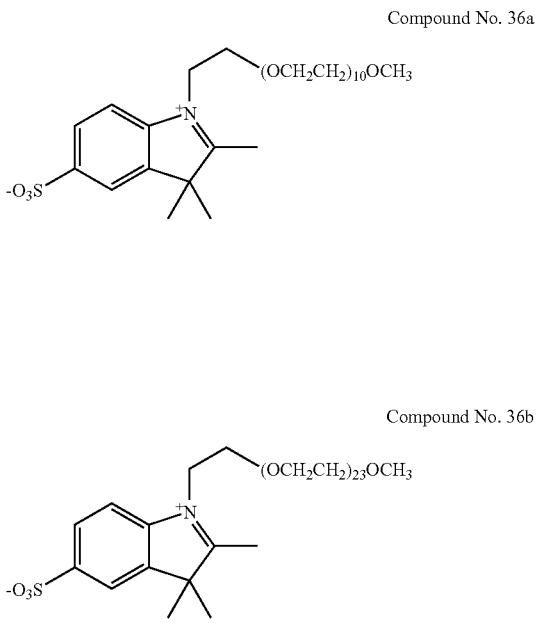
Compound No. 36a

Compound No. 36b

Compound No. 36a (110 mg) and compound No. 36b (100 mg) were each prepared by quaternizing 2,3,3-trimethylindoleninium-5-sulfonate, sodium salt (1 equivalent) with compound No. 25a (600 mg) and compound No. 25b (400 mg), respectively, according to the synthesis of compound No. 19.

Example 37

Preparation of Compound No. 37

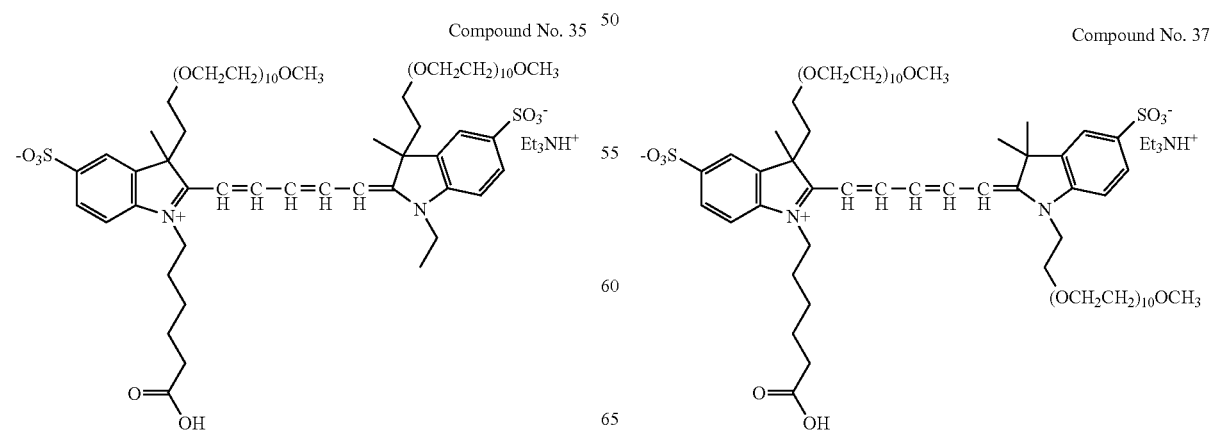
Compound No. 35

Compound No. 37

Compound No. 37 (11 mg) was prepared from compound No. 36a (25 mg) and compound No. 32 (40 mg) according to the synthesis of compound No. 6.

Example 38

Preparation of Compound No. 38

Compound No. 38

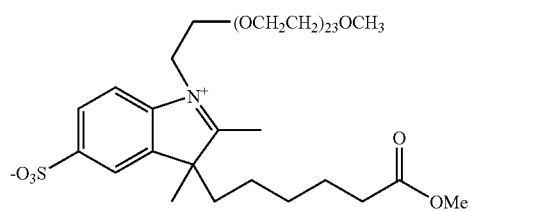

Compound No. 38 (36 mg) was synthesized from compound No. 13 (15 mg) and compound No. 25b (50 mg) according to the preparation of compound No. 19.

Example 39

Preparation of Compound No. 39

Compound No. 39

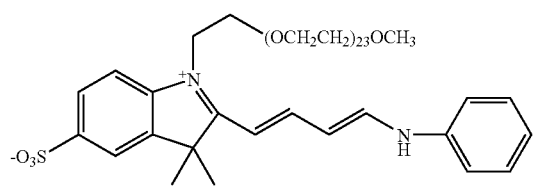

Compound No 39 (70 mg) was synthesized from compound No. 36b (100 mg) according to the preparation of compound No. 2.

Example 40

Preparation of Compound No. 40

Compound No. 40

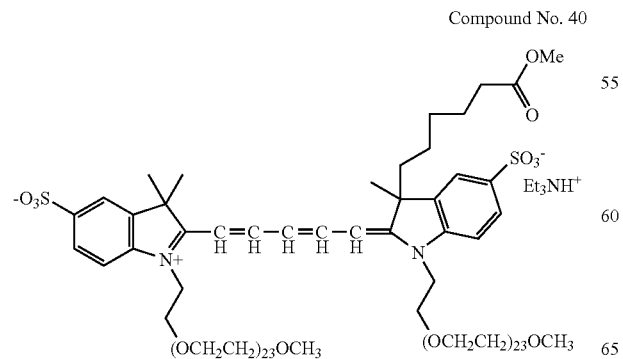

Compound No. 40 (38 mg) was synthesized from compound No. 38 (30 mg) and compound No. 39 (32 mg) according to the preparation of compound No. 6.

Example 41

Preparation of Compound No. 41

Compound No. 41

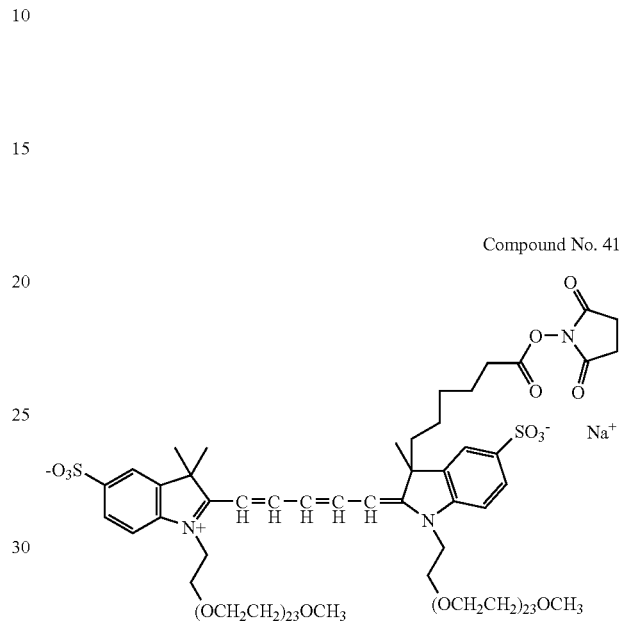

Compound No. 40 (20 mg) was hydrolyzed to give the free acid form (14 mg) according to the synthesis of compound No. 22. The free acid form of the dye was then converted to compound No. 41 (10 mg) according to the preparation of compound No. 23.

Example 42

Preparation of Compound No. 42

Compound No. 42

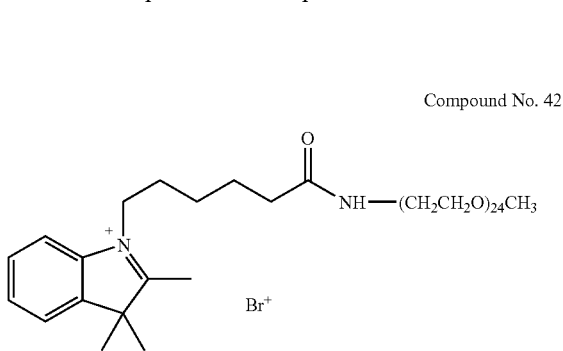

Compound No. 42 (0.19 mg) was synthesized from 1-(5-carboxypentyl)-2,3,3-trimethylindoleninium bromide (0.1 g) and m-dPEG$_{24}$ amine (0.3 g) according to the preparation of compound No. 3b.

Example 43

Preparation of Compound No. 43

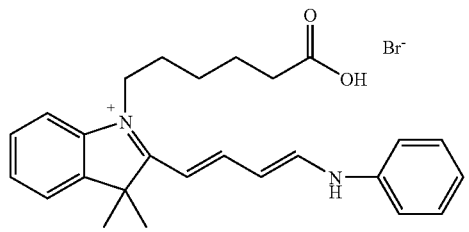

Compound No. 43

Compound No. 43 (0.5 g) was synthesized from 1-(5-carboxypenthyl)-2,3,3-trimethylindoleninium bromide (1 g) and malonaldehyde dianil hydrochloride (0.85 g) according to the preparation of compound No. 2.

Example 44

Preparation of Compound No. 44

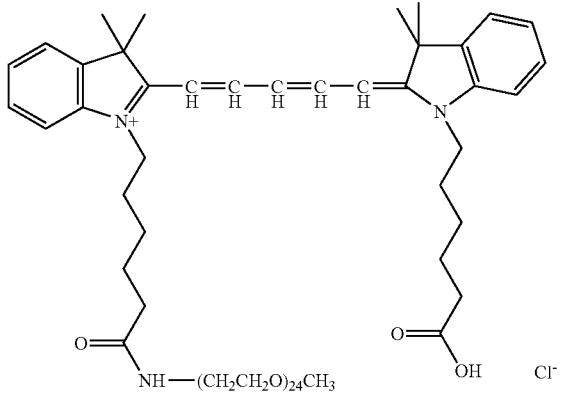

Compound No. 44

Compound No. 44 (25 mg) was prepared from compound No. 42 (40 mg) and compound No. 43 (15 mg) according to the synthesis of compound No. 6.

Example 45

Preparation of Compound No. 45

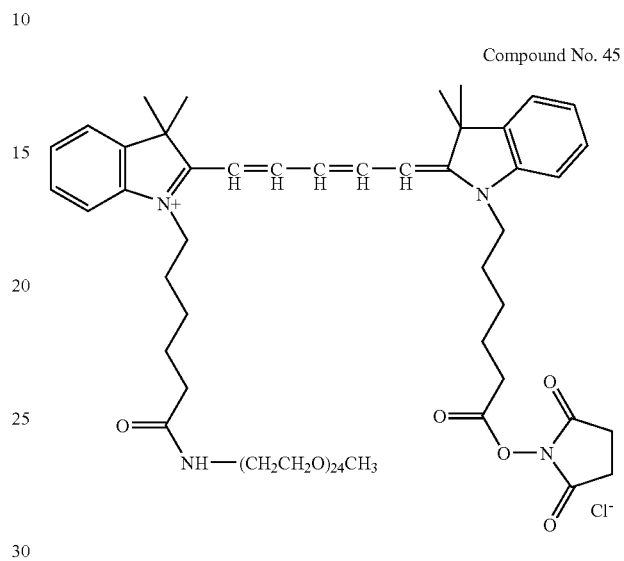

Compound No. 45

Compound No. 45 (20 mg) was prepared from compound No. 44 (25 mg) according to the synthesis of compound No. 7.

Example 46

Preparation of Compound No. 46

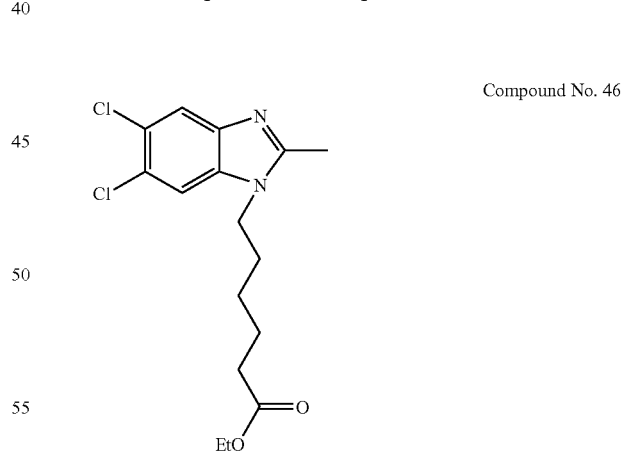

Compound No. 46

To sodium hydride (300 mg) in DMF at 0° C. was added 5,6-dichloro-2-methylbenzoimidazole (500 mg) in one portion. The mixture was stirred at 0° C. for 15 minutes, followed by addition of ethyl 6-bromohexanoate (0.66 mL). The mixture was stirred at 0° C. for another 15 minutes and then at room temperature for 1 hour. The solution was concentrated to dryness under vacuum and the residue was purified by column chromatography on silica gel to give pale brown solid (0.75 g).

Example 47

Preparation of Compound No. 47

Compound No. 47

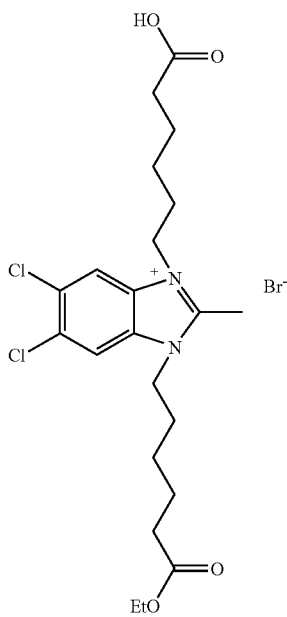

A mixture of compound No. 46 (170 mg) and 6-bromohexanoic acid (200 mg) was heated at 140° C. for 1 hour. EtOAc (20 mL) was added and the suspension was refluxed gently for 30 minutes. After cooling down to room temperature, the precipitate (260 mg) was collected by suction filtration.

Example 48

Preparation of Compound No. 48

Compound No. 48

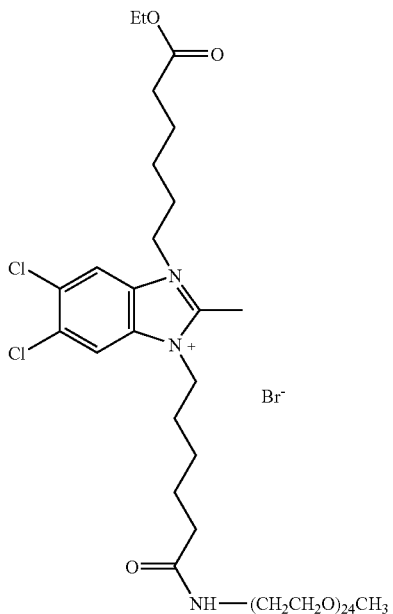

Compound No. 48 (55 mg) was synthesized from compound No. 47 (0.1 g) and m-dPEG24 amine (200 mg) according to the preparation of compound No. 3a.

Example 49

Preparation of Compound No. 49

Compound No. 49

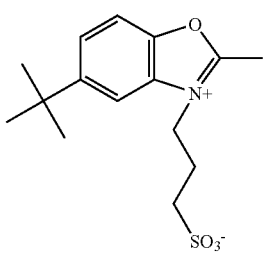

Compound No. 49 (700 mg) was prepared from 2-methyl-6-t-butylbenzooxazole (540 mg) and 1,3-propanesulftone (450 mg) according to the synthesis of compound No. 14.

Example 50

Preparation of Compound No. 50

Compound No. 50

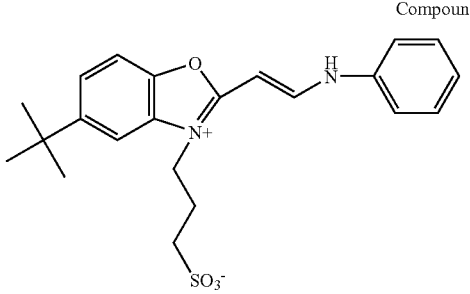

Compound No. 50 (270 mg) was prepared from compound No. 49 (460 mg) and N,N'-diphenylformamidine (340 mg) according to the synthesis of compound No. 1.

Example 51

Preparation of Compound No. 51a

Compound No. 51

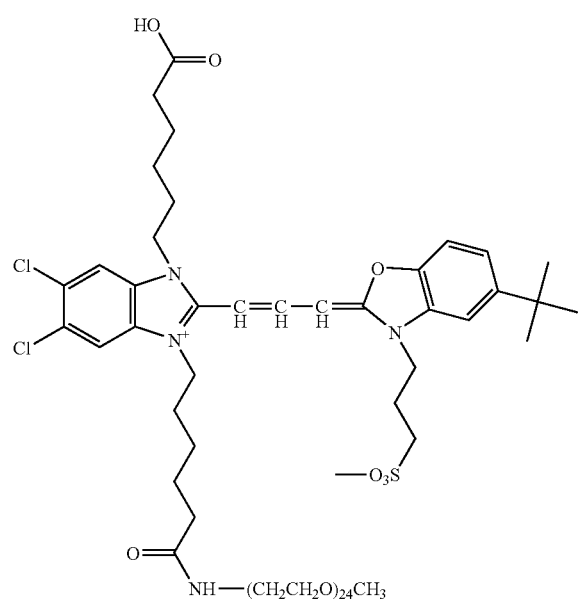

Compound No. 48 (30 mg) and compound No. 50 (10 mg) were coupled to give a cyanine dye ethyl ester intermediate (16 mg) according to the synthesis of compound No. 4. The resulting intermediate was hydrolyzed using 1 M NaOH to give the free acid dye compound No. 51 (10 mg) according to the synthesis of compound No. 22.

Example 52

Preparation of Compound No. 52

Compound No. 52

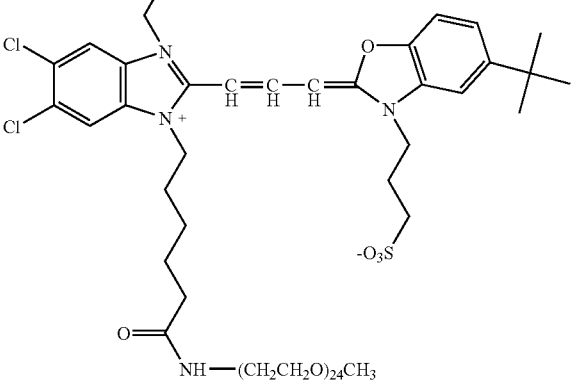

Compound No. 52 (7 mg) was prepared from compound No. 51 (8 mg) according to the synthesis of compound No. 5.

Example 53

Preparation of Compound No. 53

Compound No. 53

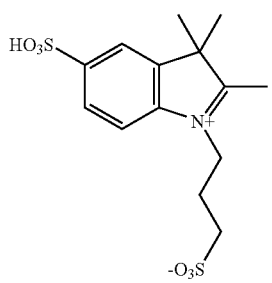

Compound No. 53 (18 g) was prepared from 2,3,3-trimethylindoleninium-5-sulfonate, sodium salt (11 g) (Bioconjugate Chem. 4, 105 (1993)) according to the synthesis of compound No. 49.

Example 54

Preparation of Compound No. 54

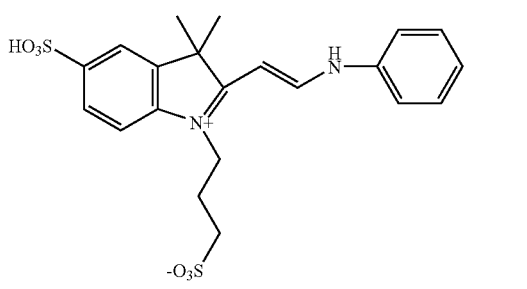

Compound No. 54

Compound No. 54 (2.4 g) was prepared from compound No. 53 (5.7 g) according to the synthesis of compound No. 1.

Example 55

Preparation of Compound No. 55

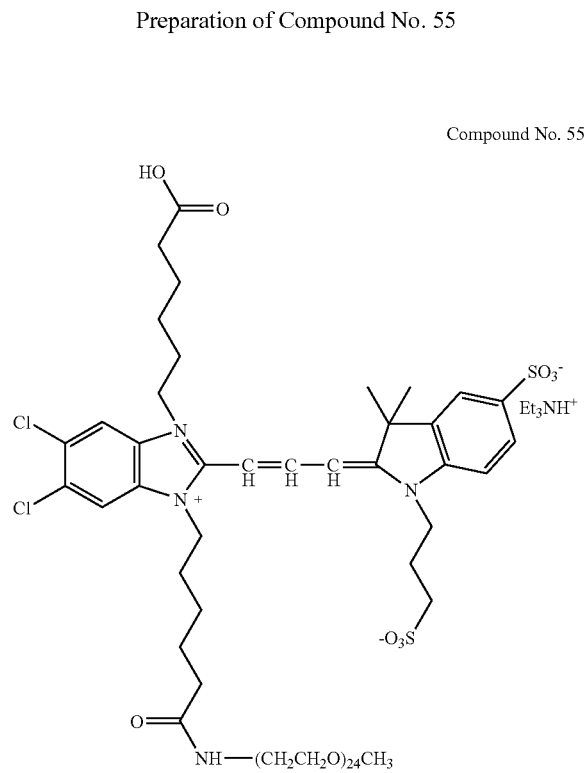

Compound No. 55

Compound No. 54 (19 mg) and compound No. 48 (33 mg) were coupled to give a cyanine dye ethyl ester intermediate (25 mg) according to the synthesis of compound No. 4. Hydrolysis of the intermediate using 1 M NaOH give compound No. 55 (17 mg) according to the synthesis of compound No. 22.

Example 56

Preparation of Compound No. 56

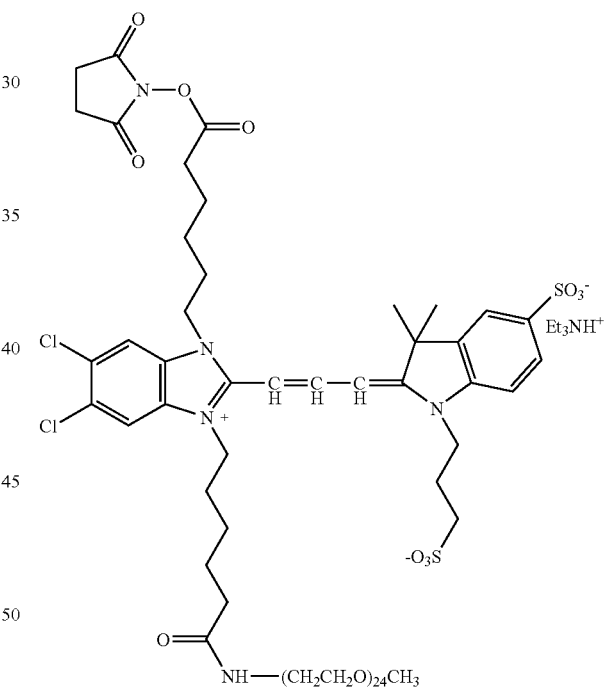

Compound No. 56

Compound No. 56 (6 mg) was prepared from compound No. 55 (10 mg) according to the synthesis of compound No. 5.

Example 57

Preparation of Compound No. 57

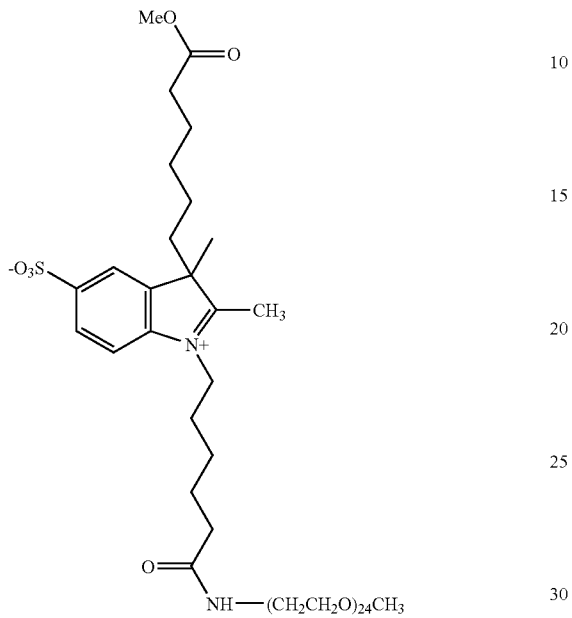

Compound No. 57

Compound No. 57 (55 mg) was synthesized from compound No. 19 (80 mg) and m-dPEG24 amine (100 mg) according to the preparation of compound No. 3a

Example 58

Preparation of Compound No. 58

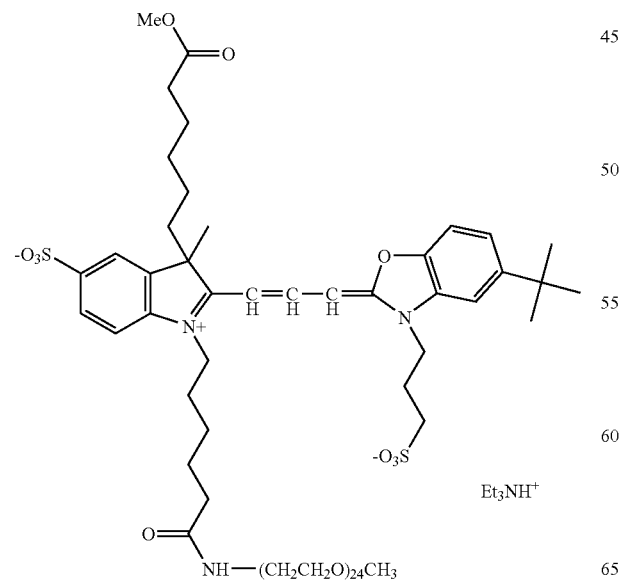

Compound No. 58

Compound No. 58 (8 mg) was prepared from compound No. 57 (20 mg) and compound No. 50 (10 mg) according to the synthesis of compound No. 4.

Example 59

Preparation of 2-(6-anilinohexatrienyl)-1-(5-carboxypentyl)-3,3-dimethyl-5-sulfoindolinium, Inner Salt (Compound No. 59)

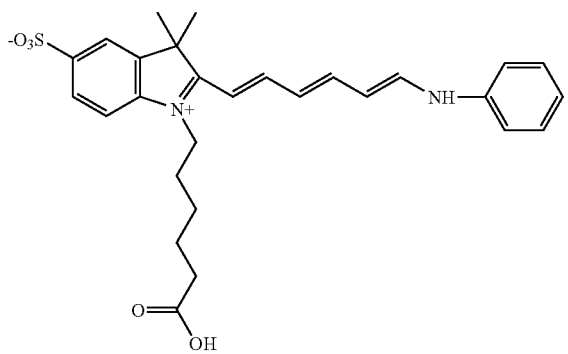

Compound No. 59

Compound No. 59 (4 g) was prepared from 1-(5-carboxypentyl)-2,3,3-trimethylindoleninium-5-sulfonate inner salt (12 g) and glutoconaldehyde dianil hydrochloride (18 g) according to the synthesis of compound No. 2.

Example 60
Preparation of Compound No. 60
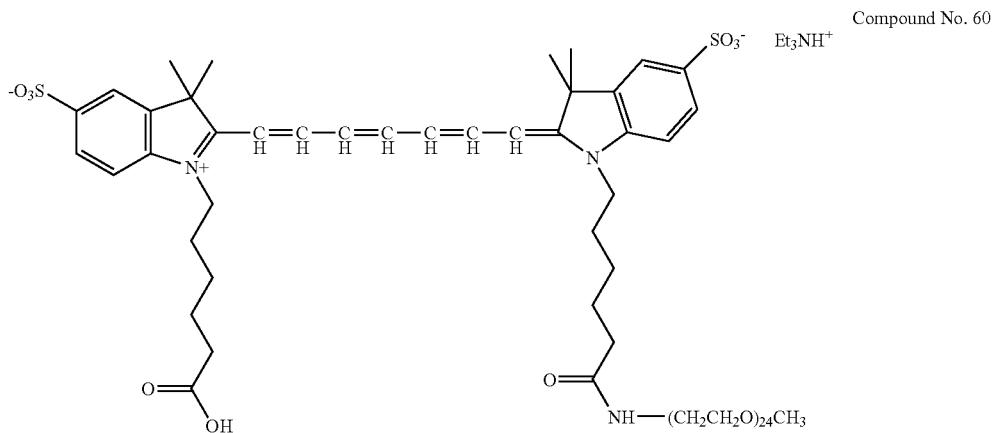
Compound No. 60 (15 mg) was prepared from compound No. 59 (50 mg) and compound No. 3a (50 mg) according to the synthesis of compound No. 6.
Example 61
Preparation of Compound No. 61
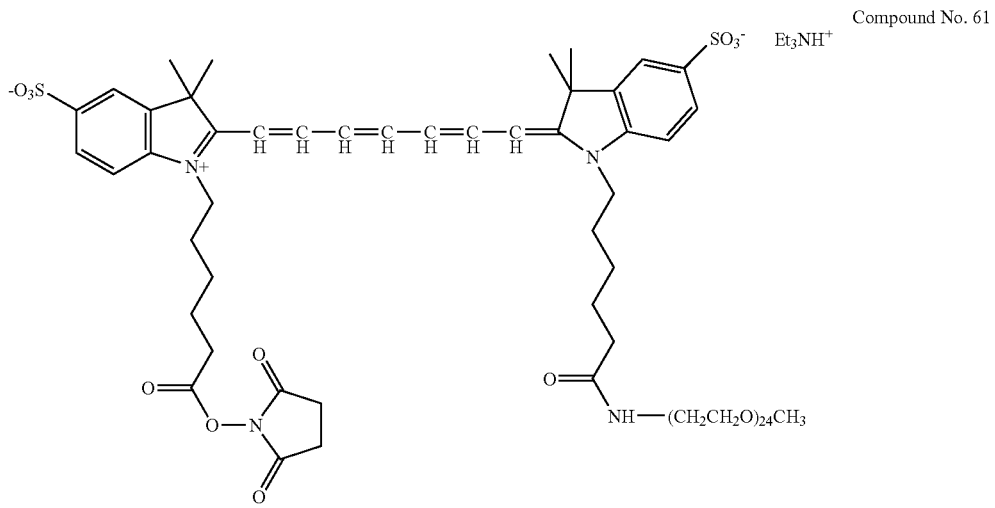
Compound No. 61 (6 mg) was prepared from compound No. 60 (10 mg) according to the synthesis of compound No. 7.

Example 62

Preparation of Compound No. 62

Compound No. 62

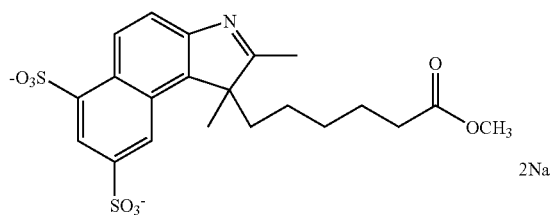

2Na

Compound No. 62 (5.37 g) was prepared from 6-hydrazinonaphthalene 1,3-disulfonate (5.3 g) (Bioconjugate Chem. 7, 356 (1996)) and methyl 7-methyl-8-oxononanoate (3.8 g) according to the synthesis of compound No. 13.

Example 63

Preparation of Compound No. 63

Compound No. 63

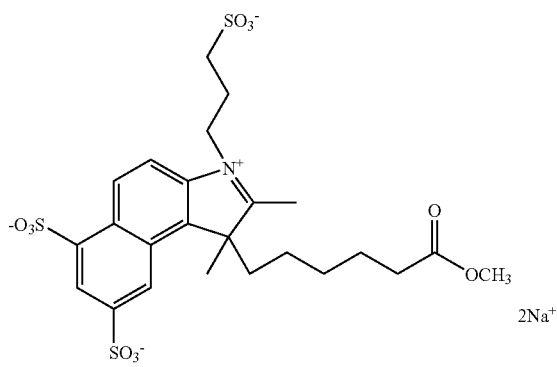

$2Na^+$

Compound No. 63 (15 g) was prepared from compound No. 62 (5.37 g), 1,3-propanesulftone (6 g) and according to the synthesis of compound No. 14.

Example 64

Preparation of Compound No. 64

Compound No. 64

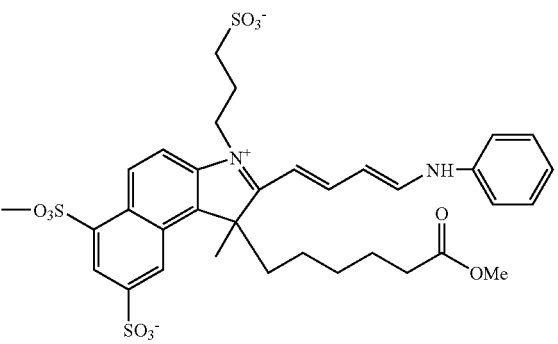

$2\ Et_3NH^+$

Compound No. 64 (1.5 g) was prepared from compound No. 63 (7 g) according to the synthesis of compound No. 2.

Example 65
Preparation of Compound No. 65
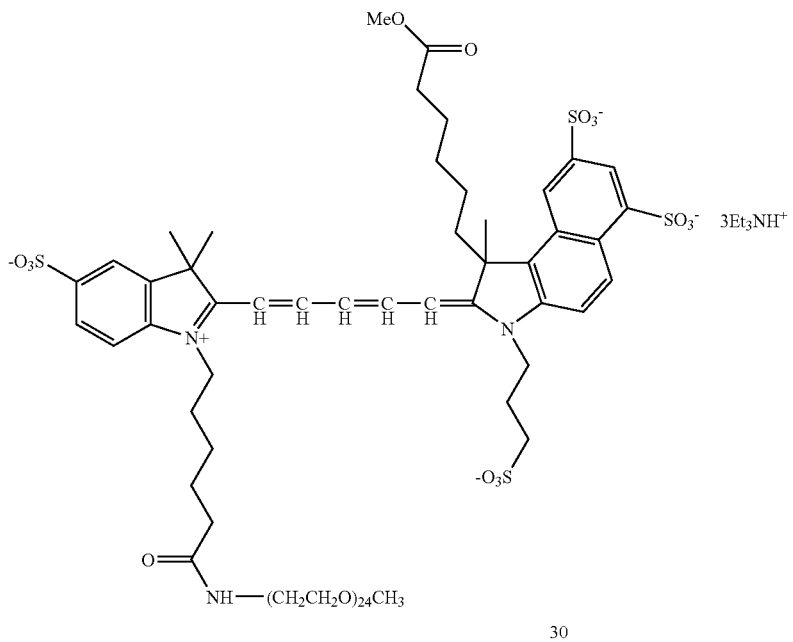
Compound No. 65
Compound No. 65 (17 mg) was prepared from compound No. 64 (60 mg) and compound No. 3a (100 mg) according to the synthesis of compound No. 6.
Example 66
Preparation of Compound No. 66
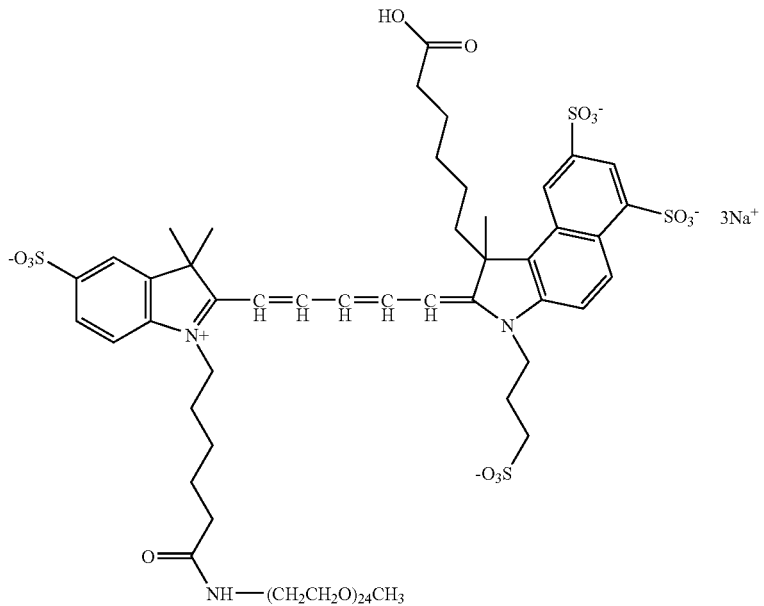
Compound No. 66
Compound No. 66 (6 mg) was prepared from compound No. 72 (15 mg) according to the synthesis of compound No. 17.

Example 67

Preparation Compound No. 67

Compound No. 67

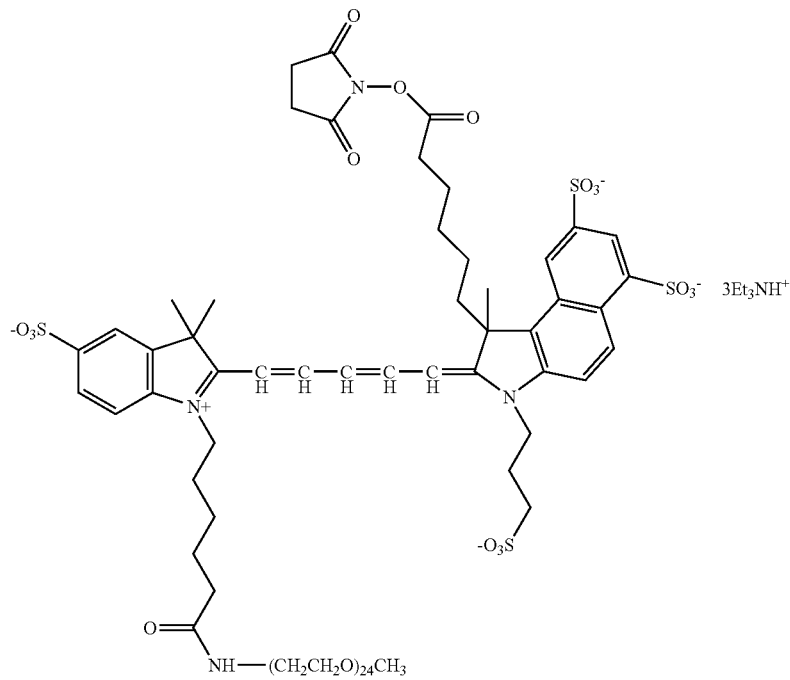

Compound No. 67 (3 mg) was prepared from compound No. 66 (5 mg) according to the synthesis of compound No. 7.

Example 68

Preparation of Compound No. 68

Compound No. 68

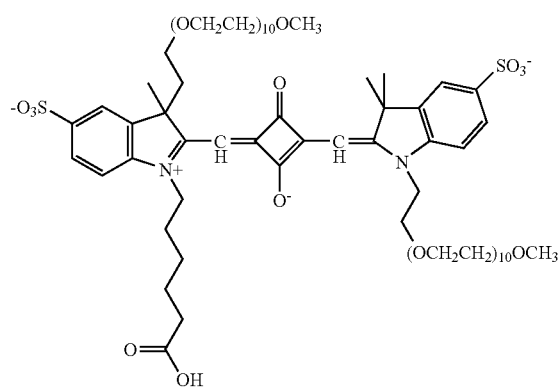

A mixture of compound No. 31 (86 mg), compound No. 36a (76 mg) and squaric acid (12 mg) in 1-butanol:toluene (10 mL, 1:1) was heated to refluxed overnight using a Dean-Stark trap filled with 4 Å molecular sieve. After cooling down to room temperature, the solution was concentrated to dryness under vacuum and the residue was purified by column chromatography on silica gel to give a dark blue solid (8 mg).

Example 69

Preparation of Compound No. 69

Compound No. 69

Compound No. 69 (60 mg) was prepared from compound No. 31 (100 mg) according to the synthesis of compound No. 1.

Example 70

Preparation of Compound No. 70

Compound No. 70

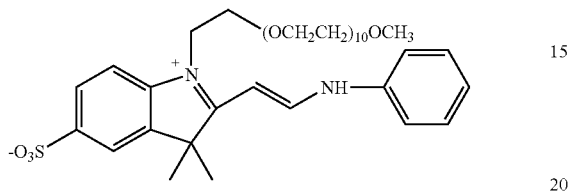

Compound No. 70 (50 mg) was prepared from compound No. 36a (100 mg) according to the synthesis of compound No. 1.

Example 71

Preparation of Compound No. 71

Compound No. 71

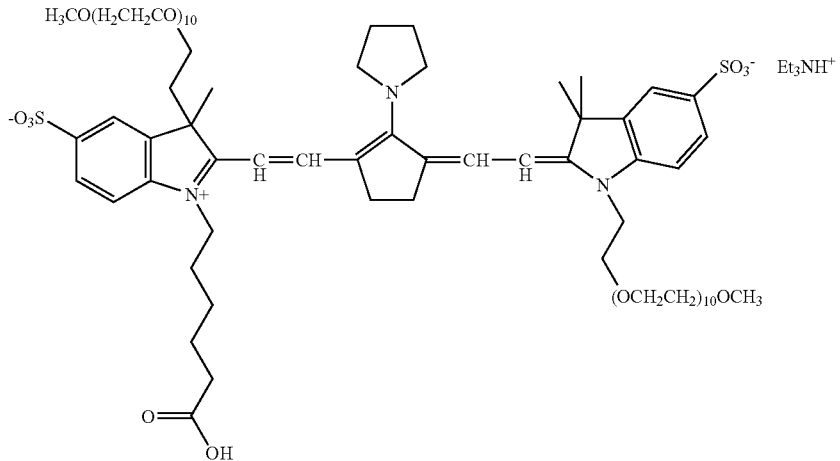

A mixture of compound No. 69 (40 mg), compound No. 70 (36 mg), 3-pyrrolidino-1-cyclopentene (6 mg), acetic anhydride (12 μL) and Et$_3$N (30 μL) in DMF (1 mL) was stirred at room temperature overnight. The solution is concentrated to dryness under vacuum and the residue was purified by column chromatography on silica gel to give greenish solid (10 mg).

Example 72

Preparation of Compound No. 72

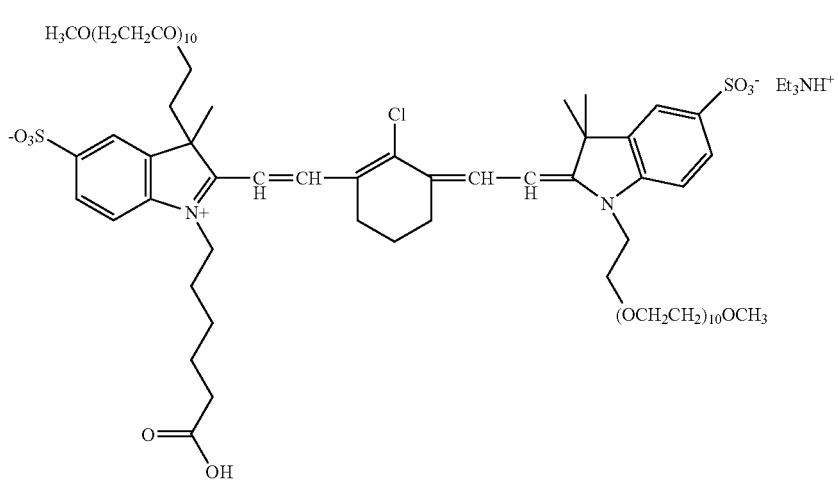

Compound No. 72

A mixture of compound No. 31 (45 mg), compound No. 36a (40 mg), 2-chloro-3-(anilinomethylene)-1-(aniliniummethyl)cyclohex-1-ene (17 mg), acetic anhydride (16 µL) and $Et_3N$ (38 µL) in DMF (1 mL) was stirred at room temperature overnight. The solution was concentrated to dryness under vacuum and the residue was purified by column chromatography on silica gel to give greenish solid (9 mg).

Example 73

Preparation of Compound No. 73

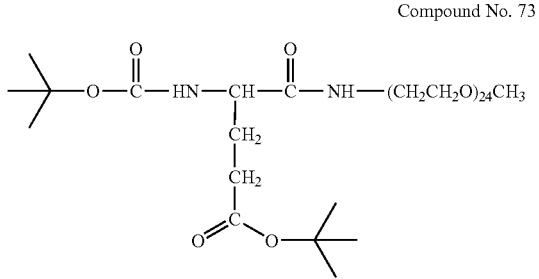

Compound No. 73

To a solution of Boc-Glu(OBut)-OH (30 mg) (Advanced ChemTech, Louisville, Ky.) in DMF (1 mL) was added $Et_3N$ (42 µL) and TSTU (30 mg). The mixture was stirred at room temperature for 3 hours, followed by the addition of m-dPEG$_{24}$ amine (100 mg). The mixture was kept stirring at room temperature overnight and then concentrated to dryness under vacuum. The residue was purified by column chromatography on silica gel to give compound No. 73 as a colorless oil (70 mg).

Example 74

Preparation of Compound No. 74

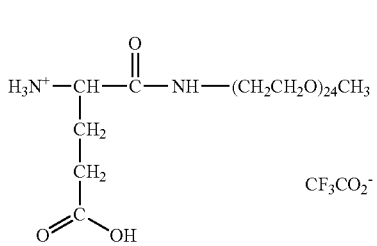

Compound No. 74

To a solution of compound No. 73 (68 mg) in $CH_2Cl_2$ (1 mL) at 0° C. was added TFA (1 mL). The mixture was stirred at 0° C. for 1 hour and then at room temperature overnight. The solution was concentrated to dryness under vacuum to give a colorless oil (68 mg).

Example 75

Preparation of Compound No. 75

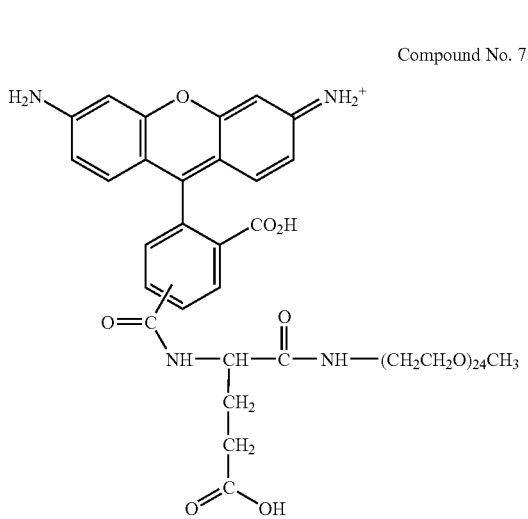

Compound No. 75

To a suspension of 5-(and -6)-carboxyrhodamine 110, succinimidyl ester (14 mg) (Biotium, Hayward, Calif.) in DMF (500 µL) at room temperature was added $Et_3N$ (50 µL) and compound No. 74 (34 mg). The mixture was stirred at room temperature overnight and then concentrated to dryness under vacuum. The residue was purified by LH-20 column (24 mg).

Example 76

Preparation of Compound No. 76

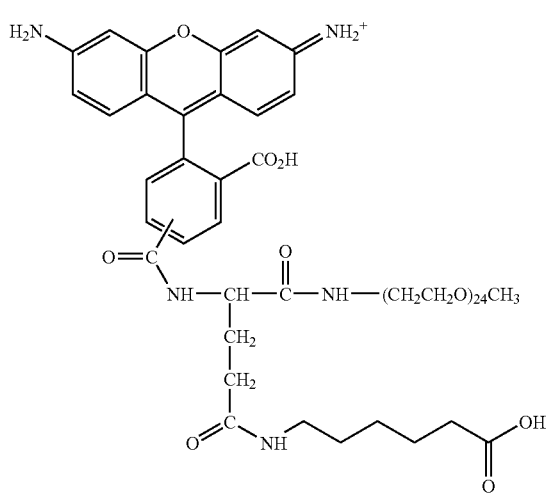

Compound No. 76

To a solution of compound No. 75 (24 mg) in DMF (500 µL) at 0° C. was added $Et_3N$ (10 µL) and TSTU (4.5 mg). The mixture was stirred at 0° C. for 1 hour, followed by the addition of $Et_3N$ (5 µL) and a solution of 6-amino-1-hexanoic acid (4 mg) in $H_2O$ (100 µL). The mixture was stirred at room temperature overnight and then concentrated to dryness under vacuum. The residue was purified by LH-20 column to give a yellow solid (10 mg).

Example 77

Preparation of Compound No. 77

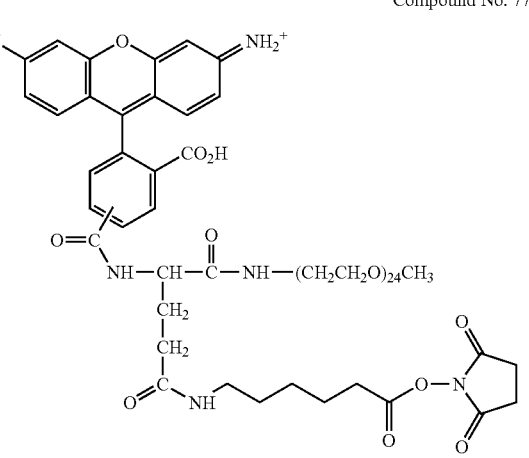

Compound No. 77

To a solution of compound No. 76 (10 mg) in DMF (500 µL) at 0° C. was added $Et_3N$ (3 µL) and TSTU (2 mg). The mixture was stirred at 0° C. for 1 hour and $Et_2O$ (3 mL) was added. The precipitate (5 mg) was collected by centrifugation.

Example 78

Preparation of Compound No. 78

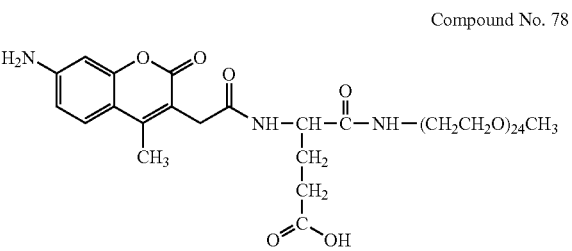

Compound No. 78

To a solution of 7-amino-4-methylcoumarin-3-acetic acid, succinimidyl ester (20 mg, prepared according to U.S. Pat. No. 4,956,480) in DMF (500 µL) was added $Et_3N$ (50 µL) and compound No. 74 (34 mg). The mixture was stirred at room temperature for 2 hours and then concentrated to dryness under vacuum. The residue was purified by LH-20 column (30 mg).

Example 79

Preparation of Compound No. 79

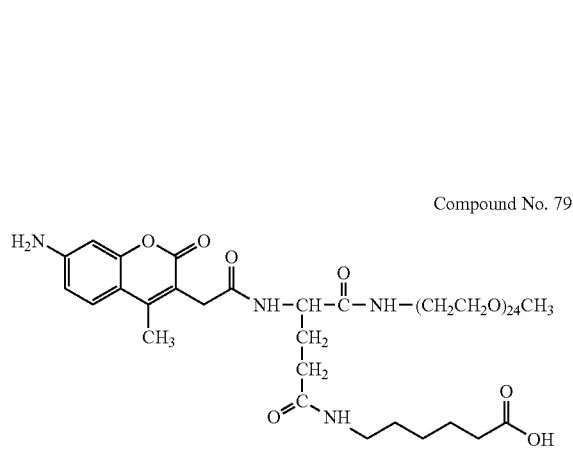

Compound No. 79

Compound 79 (10 mg) was prepared from compound No. 78 (15 mg) according to the synthesis of compound No. 76.

Example 80

Preparation of Compound No. 80

Compound No. 80 (7 mg) was prepared compound No. 79 (10 mg) according to the synthesis of compound No. 77.

Example 81

Preparation of Compound No. 81

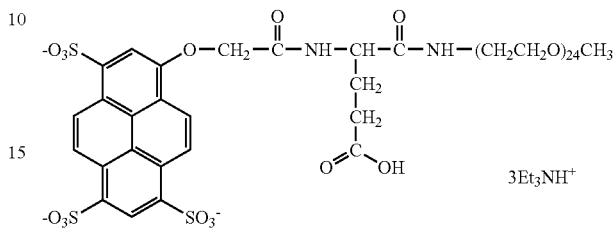

Compound No. 81

Compound No. 81 (12 mg) was prepared from 1,3,6-trisulfo-8-pyrenyloxyacetyl azide, sodium salt (15 mg, U.S. Pat. No. 5,132,432) and compound No. 74 (15 mg) according to the synthesis of compound No. 75.

Example 82

Preparation of Compound 82

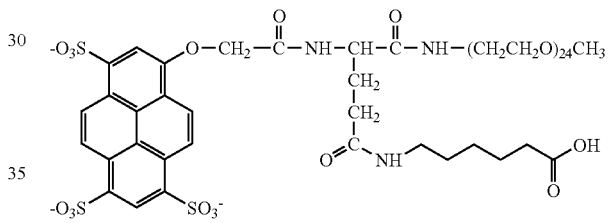

Compound No. 82

Compound No. 80

Compound No. 82 (6 mg) was prepared from compound No. 81 (14 mg) according to the synthesis of compound No. 76.

Example 83

Preparation of Compound No. 83

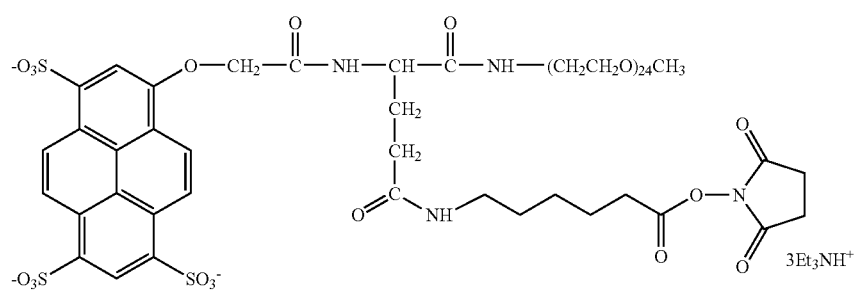

Compound No. 83

Compound No. 83 (5 mg) was prepared from compound No. 82 (5 mg) according to the synthesis of compound No. 77.

Example 84

Preparation of Compound No. 84

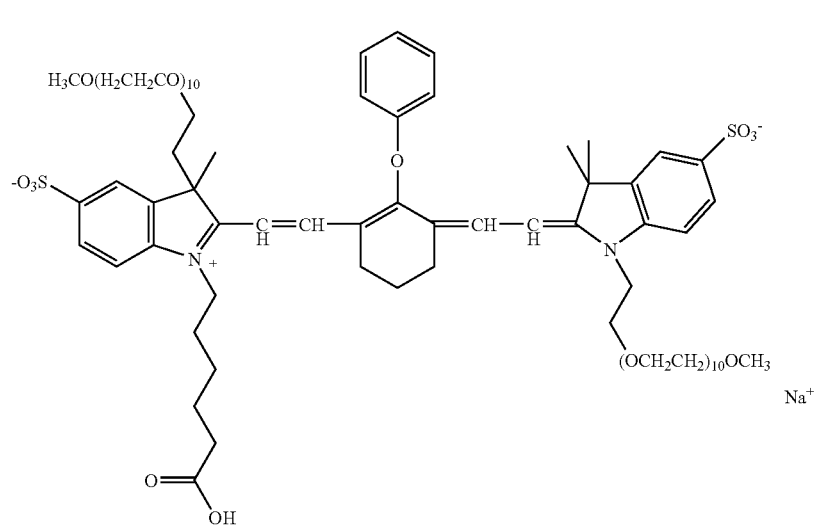

Compound No. 84

A mixture of compound No. 72 (8 mg) and sodium phenoxide (10 mg) was heated at 70° C. overnight and then concentrated to dryness under vacuum. The residue was purified by LH-20 column (3 mg).

Example 85

Preparation of Compound No. 85

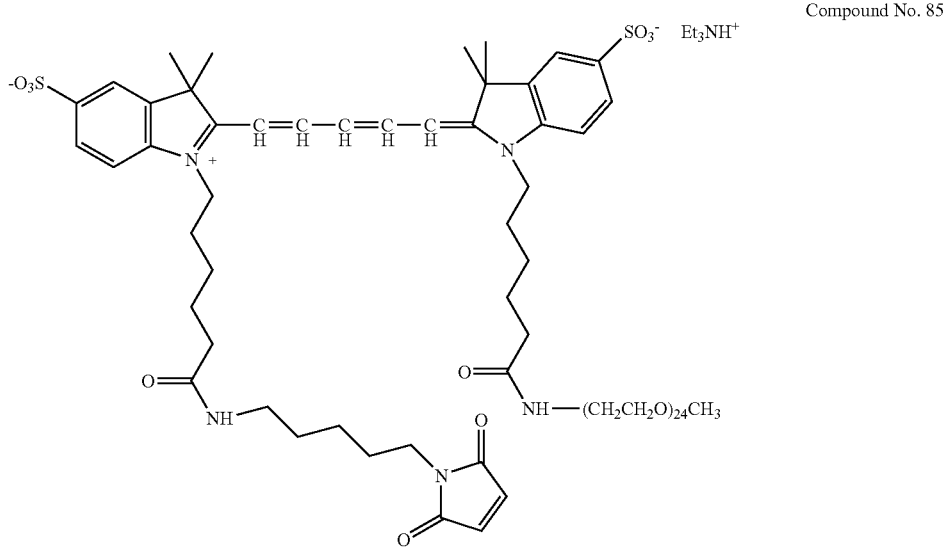

Compound No. 85

To a solution of compound No. 7 (5 mg) in DMF (200 μL) was added Et₃N (5 μL) and N-(5-aminopentyl)maleimide, trifluoroacetate salt (4 mg, Biotium). The mixture was stirred at room temperature for 1 hour and then concentrated to dryness under vacuum. The residue was purified by column chromatography on silica gel (2 mg).

Example 86

Preparation of Compound No. 86

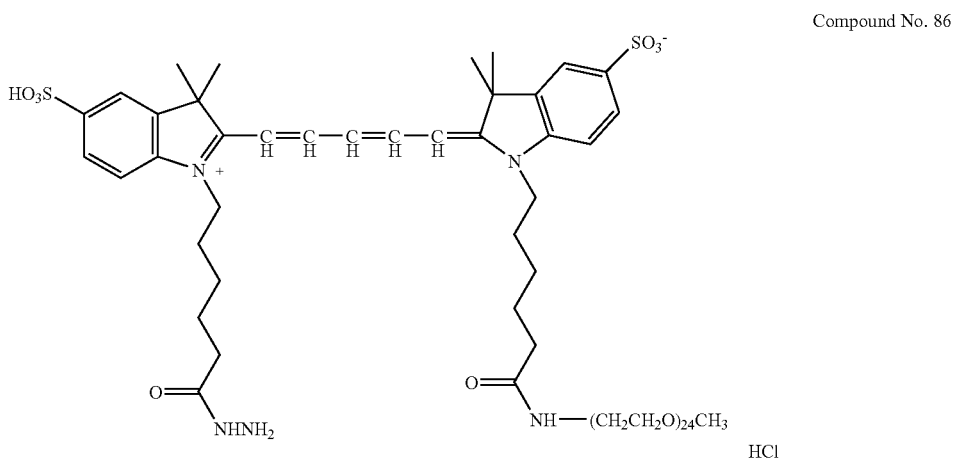

Compound No. 86

To a solution of compound No. 7 (5 mg) in DMF (200 μL) was added anhydrous hydrazine (10 μL). The mixture was stirred at room temperature for 2 hours and then acidified with 1N HCl. The solution was concentrated to dryness under vacuum and the residue was purified by LH-20 column (3 mg).

Example 87
Preparation of Compound No. 87
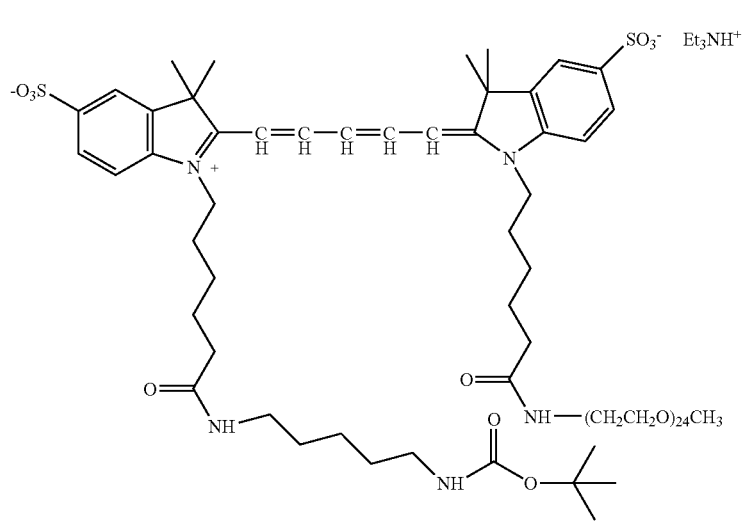
Compound No. 87
Compound No. 87 (5 mg) was prepared from compound No. 7 (10 mg) and mono t-BOC-cadaverine (2 equivalents) according to the synthesis of compound No. 85.
Example 88
Preparation of Compound No. 88
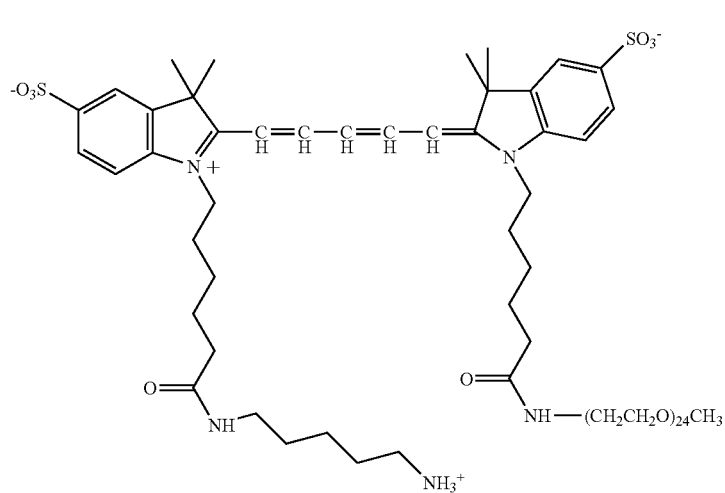
Compound No. 88

To a solution of compound No. 87 (4 mg) in CH$_2$Cl$_2$ (500 µL) at 5° C. was added TFA (250 µL). The mixture was stirred at 5° C. for 30 minutes and then concentrated to dryness under vacuum. The reside was purified by LH-20 column to give a dark blue solid (1.5 mg)

Example 89

Preparation of Compound No. 89

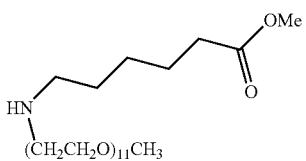

Compound No. 89

A mixture of compound No. 24a (1 g), methyl 6-aminohexanoate (0.32 g) and diisopropylethylamine (0.61 mL) in CH$_3$CN (5 mL) was refluxed gently overnight. After cooling down to room temperature, the solution was concentrated to dryness under vacuum. The residue was purified by silica gel column to give a pale yellow oil (0.4 g).

Example 90

Preparation of Compound No. 90

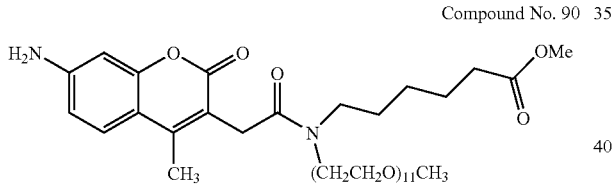

Compound No. 90

To a solution of 7-amino-4-methylcoumarin-3-acetic acid, succinimidyl ester (17 mg) was added Et$_3$N (50 µL) and compound No. 89 (60 mg) in DMF (0.5 mL). The mixture was stirred at room for 30 minutes and then concentrated to dryness under vacuum. The residue was purified by silica gel column (46 mg).

Example 91

Preparation of Compound No. 91

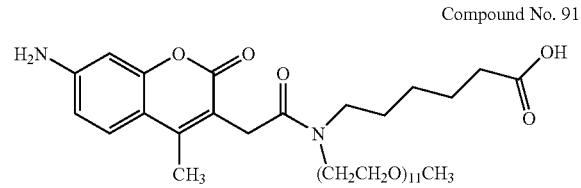

Compound No. 91

To a solution of compound No. 90 (40 mg) in H$_2$O (0.5 mL) was added 1M NaOH solution (0.15 mL). The mixture was stirred at room temperature for 1 hr and then acidified with 1 M HCl (0.15 mL). The aqueous solution was purified by LH-20 column. (35 mg).

Example 92

Preparation of Compound No. 92

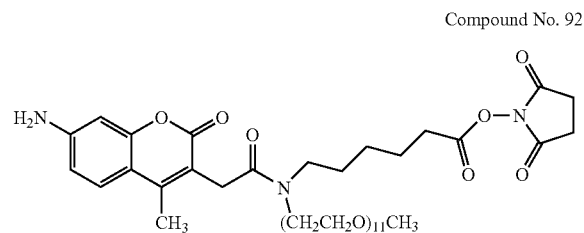

Compound No. 92

Compound No. 92 (30 mg) was prepared from compound No. 91 (34 mg) according to the synthesis of compound No. 80.

Example 93

Preparation of Compound No. 93

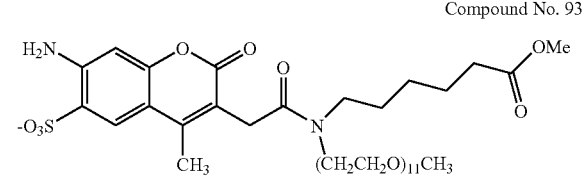

Compound No. 93

Compound No. 93 (40 mg) was prepared from 7-amino-4-methyl-6-sulfocoumarin-3-acetic acid succinimidyl ester (16 mg) (*Bioorg. & Med. Chem. Letters,* 9, 2229 (1999)) according to the synthesis of compound No. 90.

Example 94

Preparation of Compound No. 94

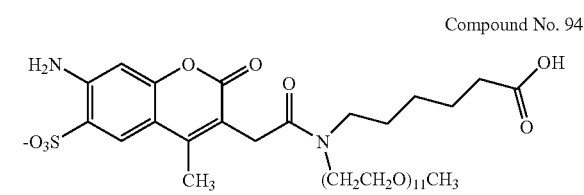

Compound No. 94

Compound No. 94 (20 mg) was prepared from compound No. 93 (35 mg) according to the synthesis of compound No. 91.

Example 95

Preparation of Compound No. 95

Compound No. 95

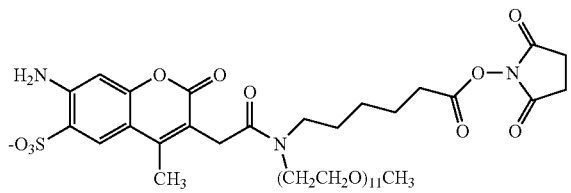

Compound No. 95 (15 mg) was prepared from compound No. 94 (17 mg) according to the synthesis of compound No. 80.

Example 96

Preparation of Compound No. 96

Compound No. 96

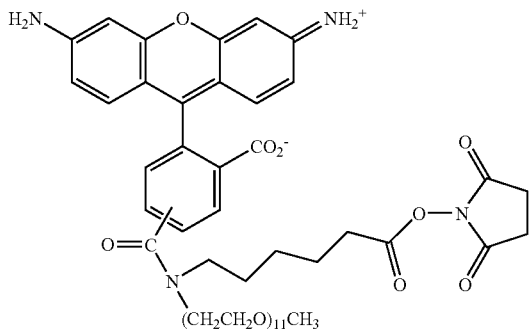

To a mixture of 5-(and -6)-carboxyrhodamine 110, succinimidyl ester (CR110 SE) (60 mg) (Biotium, Hayward, Calif.) and $Et_3N$ (90 µL) in DMF (500 µL) was added compound No. 89 (68 mg). The mixture was stirred at room temperature for 2 days and then concentrated to dryness under vacuum. The residue was redissolved in $H_2O$ (500 µL) and 1N NaOH (400 µL) was added. The mixture was stirred at room temperature overnight and then loaded onto a LH 20 column. Eluting of the LH-20 column with water produced pure free acid form of the rhodamine dye (45 mg). The free acid rhodamine dye (30 mg) was converted to compound No. 96 (22 mg) according to the synthesis of compound No. 80.

Example 97

Preparation of Protein Dye-Conjugates

Fluorescent conjugates of goat anti-mouse IgG (GAM), goat anti-rabbit IgG (GAR), and streptavidin were prepared from the respective proteins and a reactive dye, following published procedures (U.S. Pat. No. 6,974,873; Haugland et al., *Meth. Mol. Biol.* 45, 205 (1995); Haugland et al., *Meth. Mol. Biol.* 45, 223 (1995); Haugland et al., *Meth. Mol. Biol.* 45, 235 (1995); Haugland et al., *Current Protocols in Cell Biology*, 16.5.1-16.5.22 (2000)). Briefly, an antibody or streptavidin at 1 mg/mL in 0.1 mM pH 8.5 sodium bicarbonate buffer was mixed with one of the reactive dye at various ratio of dye molecules/protein molecule. After incubating for about an hour at room temperature, the reaction mixture was separated by gel filtration using Sephadex G-25 equilibrated with PBS (pH 7.4). The various dye molecules/protein ratios used in the labeling reactions produced protein conjugates with different degree of dye labeling (DOL) as listed in Table 7 below for each dye/protein pair.

TABLE 7

List of selected antibody and streptavidin conjugates prepared according to the invention

| Protein | Dye | Degree of Labeling (DOL) |
|---|---|---|
| Streptavidin | Compound No. 5 | 2.8; 3.8; 4.6; 7.8; 9.1; 9.4; 10.6 |
| Goat anti-mouse IgG | Compound No. 5 | 1.1; 1.7; 2.9; 3.7; 4.9; 5.8; 7.4; 7.6 |
| Goat anti-rabbit IgG | Compound No. 41 | 1.4; 1.9; 3.0; 5.2; 6.1; 7.1; 9.3 |
| Goat anti-mouse IgG | Compound No. 41 | 1.1; 1.7; 2.7; 3.9; 4.8; 5.8; 6.6; 7.3 |
| Goat anti-mouse IgG | Compound No. 67 | 1.7; 3.5; 4.9; 6.2; 8.3 |
| Goat anti-mouse IgG | Compound No. 92 | 1.7; 4.9; 7.2; 8.6 |
| Goat anti-mouse IgG | Compound No. 96 | 1.35; 1.87; 2.69; 3.49; 4.20 |

The fluorescence of the conjugates was measured using a JACSO fluorescence spectrophotometer and was then plotted against the DOL to give FIGS. 4-7.

Example 98

Preparation of a Phalloidin Dye-Conjugate

To aminophalloidin (1 mg) and compound Nos. 5, 7 and 23 (1.5 equivalents) in DMF (200 µL) was added N,N-diisopropylethylamine (3 equivalents) and the mixture was stirred at room temperature overnight. The solution was concentrated to dryness under vacuum and the residue was purified by column chromatography by LH-20 column (1.5 mg). The product is an effective stain for F-actin filaments in fixed-cell preparations.

Example 99

Preparation and Use of a Fluorescent α-Bungarotoxin Dye-Conjugate

To a solution of α-bungarotoxin (1 mg) in 0.1 M sodium bicarbonate (25 µL) was added compound No. 7 (1.5 equivalents) in one portion and the mixture was stirred at room temperature for 2 hours. The product was purified by G-25 size exclusion column and then by reverse-phase HPLC. Staining of acetylcholine receptors and detection of their resulting fluorescence, although detected at longer wavelength, was comparable to that obtained with Texas Red α-bungarotoxin conjugate.

Example 100

Preparation of Aminodextran-Dye Conjugate

To a solution of 70000 MW aminodextran with an average of 13 amino groups in 0.1M sodium bicarbonate (400 µL) is added compound No. 7 so as to give a dye/dextran of about 12. After 6 hours the conjugate is purified on SEPHADEX G-50 with water as eluent. Typically 4-6 moles of dye are conjugated to 70000 MW dextran.

Example 101

Preparation of Dye-Bacteria Conjugates

Heat killed *Escherichia coli* are suspended in pH 8-9 buffer (10 mg/mL) and then incubated with 0.5-1.0 mg/mL of an amine-reactive dye such as compound No. 7. After 30-60 minutes the labeled bacteria are centrifuged and washed several times with buffer to remove any free dye. The labeled bacteria is analyzed by flow cytometry.

Example 102

Preparation of Nucleotide-Dye Conjugates

To a solution of 5-(3-aminoallyl)-2-deoxyuridine 5'-triphosphate (2 mg, Sigma Chemical) in $H_2O$ (100 µL) is added compound No. 7 or compound No. 23 in DMF and triethylamine (5 µL). The mixture is stirred at room temperature for 3 hours and then concentrated to dryness in vacuo. The residue is purified by preparative HPLC. The product fractions are lyophilized to give a dark blue nucleotide conjugate. Alternatively, fluorescent dye-conjugates of deoxyuridine 5'-triphosphate are prepared from 5-(3-amino-1-propynyl)-2'-deoxyuridine 5'-triphosphate or by treating a thiolated nucleotide or a thiophosphate nucleotide with a thiol reactive dye of the invention such as compound No. 85.

Additionally, 2'-(or 3')-2-aminoethylaminocarbonyladenosine 5'-triphosphate is reacted with slight excess of compound No. 7 and following the precipitation with ethanol, the ribose-modified product is purified by preparative HPLC. Additional nucleotides conjugates with the dyes of invention can readily prepared by someone skilled in the art following the published procedures such as Nimmakayalu M. et al., *Biotechniques*, 2000, 28, 518; Muhlegger K. et al., *Biol. Chem.* Hoppe Seyler, 1990, 371, 953; Giaid A. et al. *Histochemistry*, 1989, 93, 191.

Example 103

Preparation of an Oligonucleotide Dye-Conjugate

To a 5'-amine-modified, 18-base M13 primer sequence (100 µg) in $H_2O$ (4 µL) is added a solution of compound No. 7 (500 µg) in 0.1M sodium borate pH=8.5 buffer (200 µL). The mixture is stirred at room temperature overnight and 3 volumes of cold ethanol are added. The mixture is cooled to −20° C., centrifuged, the supernatant is decanted, the pellet is rinsed with ethanol and then dissolved in $H_2O$ (100 µL). The labeled oligonucleotide is purified by preparative HPLC. The desired peak is collected and evaporated to give the fluorescent oligonucleotide.

Example 104

Flow Cytometry Analysis of Cells Extracellularly Stained with Dye-Antibody Conjugates One million Jurkat cells per sample were stained with 0.25 µg mouse anti-human CD3 (BD Biosciences) followed by 1 µg of goat anti-mouse IgG labeled with compound No. 41 at the DOL shown in FIG. 8 (Example 96). Flow cytometry was performed on a Beckman Coulter FC-500 using CXP software. Noise represents average fluorescence intensity from cells stained with only goat anti-mouse-compound No. 41 conjugate as background control. Signal represents average fluorescence intensity from cells stained with CD3 and goat anti-mouse-compound No. 41.

Example 105

Flow Cytometry Analysis of Cells Intracellularly Stained with Dye-Antibody Conjugates One million Jurkat cells were fixed, permeabilized, and incubated with 0.25 µg mouse anti-human CD3 antibody (BD Biosciences). The CD3 antibody was followed by incubation with 1 µg goat anti-mouse IgG conjugated AlexaFluor647 (DOL 3.1) or compound No. 41 (DOL 3.9) (Example 96). About 10,000 cells from each sample were analyzed on a BD FACS Calibur flow cytometer and fluorescence was detected in the FL4 channel.

Example 106

Labeling β-Galactosidase with a Thiol Reactive Dye

A solution of β-galactosidase, a protein rich in free thiol groups, is prepared in PBS buffer (1 mg in 200 µL) and then treated with a solution of thiol reactive compound No. 85 (5 mg) in DMF (100 µL). Unreactive dye is removed by centrifugation using Nanosep centrifugal device. The degree of substitution by the dye is estimated using the method cited in Example 96.

Example 107

Photostability Comparison Among Compound No. 96 Alexa Fluor 488 and Fluorescein

Actin filaments were stained with phalloidin labeled with compound No. 96, Alexa Fluor 488 or fluorescein (the phalloidin conjugates were prepared from aminophalloidin and the succinimidyl ester form of the dyes using the procedure described in Example 98). After washing, each stained sample was continuously illuminated and the fluorescence intensity was monitored by taking measurement every 5 seconds. The relative fluorescence vs. time for each sample was plotted (FIG. 11). For a long time, fluorescein had been the dye of choice for green fluorescence color because the dye's absorption peak well matches with the 488 nm argon laser line. However, fluorescein undergoes photobleaching very quickly, limiting its use for microscopy studies. Alexa Fluor 488 from Molecular Probes, Inc. was developed as a superior alternative because of its exceptional photostability. FIG. 11 demonstrates that compound No. 96 of the invention is more photostable than Alexa Fluor 488.

Example 108

Measuring the Serum Half-Life of a Labeled Biomolecule of the Invention

The in vivo serum half-life of a labeled biomolecule of the invention may be measured, for example, after injection of a labeled biomolecule into catheterized rats, for example as described by [Pepinsky, R. B., et al. (2001) J Pharmacol Exp Ther, 297: 1059-66]. The plasma concentration of the biomolecule is then measured in extracted blood samples. Such samples may be withdrawn at various time points depending on the time course studied. The concentration of the labeled biomolecule may be measured using a variety of methods, including fluorescence measurements and/or biochemical techniques such as ELISA or Western Blots. The stabilizing effect of a fluorescent group of the invention may be measured by comparing the stability of the labeled biomolecule of the invention relative to a corresponding biomolecule lacking said dye.

Example 109

Measurement and Comparison of Aggregation Behavior of an Antibody Labeled with a Dye of the Invention and the Same Antibody Labeled with Other Commercially Available Dyes A set of goat anti-mouse IgG conjugates were prepared by labeling a portion of goat anti-mouse IgG with one of three near IR dyes. Additionally for each dye, separate portions were labeled at one of several different degree of labeling (DOL), to observe the absorption spectra for aggregation behavior as the concentration of dye molecules on the antibody is increased with increased degree of labeling. The dyes utilized were Cy7® dye, Alexa Fluor 750® (AF750®) dye, and a dye of the invention, Dye No. 29 (Table 3). FIG. 12A shows the absorption spectra of the conjugate formed from labeling goat anti-mouse IgG with Cy7® dye at 4 different DOL (1.2 to 3.4 dye molecules per antibody). FIG. 12B shows the absorption spectra of the conjugate formed from labeling goat anti-mouse IgG with Alexa Fluor 750® (AF750®) dye at four different DOL (2.2 to 5.9 dye molecules per antibody). FIG. 12C shows the absorption spectra of the conjugate formed from labeling goat anti-mouse IgG with Dye No. 29 (Table 3), at six different DOL (1.1 to 7.4 dye molecules per antibody). All spectra were taken at room temperature in PBS 7.4 buffer. The spectra of both Cy7® dye- and AF750® dye-labeled conjugates (A and B) display a double peak characteristic of dye aggregation while the spectra of Compound No. 29-labeled conjugates (C) show substantially a single peak, indicating a substantial lack of dye aggregation.

Example 110

Measurement and Comparison of Fluorescent Signal of an Antibody Labeled with a Dye of the Invention and the Same Antibody Labeled with Other Commercially Available Dyes which Lack a Water Soluble Polymer Group A set of goat anti-mouse IgG conjugates were prepared by labeling a portion of goat anti-mouse IgG with one of three near IR dyes. Additionally for each dye, separate portions were labeled at one of several different degree of labeling (DOL), to observe the fluorescent output as the concentration of dye molecules on the antibody is increased with increased degree of labeling. The dyes utilized were: a dye of the invention, Dye No. 29 (Table 3) Cy7® dye, and Alexa Fluor 750® (AF750®) dye. The Cy7® dye and Alexa Fluor 750® (AF750®) dye do not have a water soluble polymer group. FIG. 13 shows total fluorescence vs. degree of labeling (DOL) for Dye 29, Alexa Fluor 750® (AF750®) dye and Cy7® dye, at identical protein concentrations in pH 7.4 PBS buffer, when excited at 735 nm. The data shows that, compared to AF750® dye and Cy7® dye, the fluorescent group of Dye 29 has higher fluorescence quantum yield over a wide degree of labeling and has less fluorescence quenching when the antibody is at higher degrees of labeling.

Example 111

Measurement and Comparison of the Fluorescent Signal Arising from Intracellular Staining of Jurkat Cells with Goat Anti-Mouse IgG Labeled with Three Near-IR Dyes A set of goat anti-mouse IgG labeled conjugates were prepared from labeling a portion of goat anti-mouse IgG with one of Dye No. 29 (Table 3), Alexa Fluor 750® dye or Cy7® dye. Jurkat cells were first labeled with mouse anti-human CD3 antibody and then stained with one of the three labeled secondary antibodies, which all have a similar degree of labeling. To measure the background fluorescence from each labeled secondary antibody, the cells were also stained directly with each of the fluorescent secondary antibody without the primary antibody (dark columns). FIG. 14 shows the relative fluorescence levels of the Jurkat cells stained with goat anti-mouse IgG labeled with Dye No. 29 (Table 3), Alexa Fluor 750® dye and Cy7® dye, respectively, as measured by flow cytometry. The results demonstrate that cells stained with antibody conjugate of this invention are significantly brighter and have excellent signal-to-noise ratio.

Example 112

Determination and Comparison of Photostability for Three Near IR Dyes

FIG. 15 compares the photostability of three near-IR dyes: Compound No. 29 of Table 3, Alexa Fluor 750® (AF750®) dye and Cy7® dye. Solutions of the three dyes at 5 µM dye concentration were exposed to sun light for ½ hour. Absorption spectra of the solutions were recorded before and after the photolysis. The results show the near-IR dye of the invention is significantly more stable than both AF750® dye and Cy7® dye.

Example 113

Measurement and Comparison of the Fluorescent Signal Arising from Intracellular Staining of Jurkat Cells with Goat Anti-Mouse IgG Labeled with APC-Alexa Fluor 750® Tandem Dye or Dye 29 (Table 3)

FIGS. 16A and B show the relative fluorescence levels of Jurkat cells stained intracellularly with an antibody labeled with APC-Alexa Fluor 750® tandem dye or Dye 29 (Table 3). FIG. 16A is a graphical representation showing the relative fluorescence levels of Jurkat cells stained with indicated amount of either goat anti-mouse IgG labeled with compound No. 29 (DOL=3.5) or a commercially available goat anti-mouse IgG labeled with an APC-AF750® tandem dye (Invitrogen), as measured by flow cytometry. The cells were first labeled with mouse anti-human CD3 antibody and then stained with one of the two labeled secondary antibodies. To measure the background fluorescence from each labeled secondary antibody, the cells were also stained directly with the fluorescent secondary antibody without the primary antibody (darkened columns). FIG. 16B shows the signal-to-noise ratios of the stainings from FIG. 16A. Flow cytometry experiments were performed on a BD LSR II equipped with a 633 nm laser and 780/60 nm PMT detector. The results demonstrate that Dye No. 29 gives excellent fluorescent signal with very little background while the APC-AF750® tandem dye showed significant nonspecific staining. Dye No. 29 has very little absorption at 633 nm whereas the tandem dye has nearly maximal absorption at the laser wavelength due to the donor dye APC. Because tandem dyes such as APC-AF750® dyes are much more difficult and thus expensive to manufacture than a simple dye such as Dye No. 29, near-IR dyes of the invention are particularly advantageous for flow cytometry analysis using a 633 nm or longer wavelength excitation source.

Example 114

Determination of Total Fluorescence as a Function of Degree of Labeling for Goat Anti-Mouse IgG Conjugates of Three Near-IR Dyes with Similar Wavelengths FIG. 17 shows the total fluorescence vs. degree of labeling (DOL) for goat anti-mouse IgG conjugates of a dye of the invention, Dye No. 31 (Table 3), Dylight™ 800 Dyefrom Thermo Fisher, and IRDye 800® CW dye from Li-Cor Biosciences, all of which have similar wavelengths. The data show that Dye No. 31 is significantly brighter than the other two dyes over a wide range of DOL.

Example 115

Determination of Fluorescent Signal as a Function of Degree of Labeling and Comparison of Fluorescent Quenching and Signal-to-Noise for Goat Anti-Mouse IgG Conjugates of Three Near IR Dyes FIG. 18 shows the relative fluorescence levels of Jurkat cells stained with goat anti-mouse IgG antibodies labeled with Dye No. 31 (Table 3), Dylight™ 800 dye from Thermo Fisher and IRDye 800® CW dye from Li-Cor Biosciences, respectively, as measured by flow cytometry. To assess the fluorescence quenching of the three near-IR dyes, the antibody was labeled with each dye at several different degrees of labeling (DOL) as indicated. The cells were first labeled with mouse anti-human CD3 antibody and then stained with one of the labeled secondary antibodies. To measure the background fluorescence from each labeled secondary antibody, the cells were also stained directly with each of the fluorescent secondary antibodies without the primary antibody (isotype, dark columns). The results show that Dye No. 31 is significantly brighter than both Dylight™ 800 dye and IRDye 800® CW dye over a wide range of DOL. Also importantly, Dye No. 31 produced much better signal-to-noise ratio than the other two dyes.

Example 116

Measurement and Comparison of Fluorescence Quantum Yield for Four Spectrally Similar Near IR Dyes FIG. 19 is a plot of total fluorescence vs. degree of labeling (DOL) for goat anti-mouse IgG conjugates of a near-IR dye of the invention, Dye No. 32 (Table 3), and three spectrally similar near-IR fluorescent groups, Cy5.5® dye from GE Healthcare, Alexa Fluor 680® (AF680) dye from Invitrogen and Dylight™ 680 from Thermo Fisher, respectively. Fluorescence measurements were made in pH 7.4 PBS buffer using 660 nm excitation. The data shows that, compared to Cy5.5®, Alexa Fluor 680® and Dylight™ 680, the fluorescent group of the invention has higher fluorescence quantum yield over a wide degree of labeling.

Example 117

Measurement and Comparison of Relative Fluorescent Signal from Jurkat Cells Intracellularly Stained by Goat Anti-Mouse IgG Antibodies Labeled Individually with Four Different Near IR Dyes FIGS. 20A and B show data related to the relative fluorescence level of Jurkat cells stained with goat anti-mouse IgG antibodies labeled individually with four different near IR dyes. FIG. 20A shows the relative fluorescence levels of Jurkat cells stained with goat anti-mouse IgG antibodies labeled with Dye No. 32 (Table 3), Cy5.5® dye from GE Healthcare, Dylight™ 680 dye from Thermo Fisher or Alexa Fluor 680® (AF680®) dye from Invitrogen, as measured by flow cytometry. To assess the fluorescence quenching of the three near-IR dyes, each portion of goat anti-mouse IgG antibody was labeled with one dye at one of two different degree of labeling (DOL) as indicated to form a set of eight antibodies. The cells were first labeled with mouse anti-human CD3 antibody and then stained with one of the labeled secondary antibodies. To measure the background fluorescence from each labeled secondary antibody, the cells were also stained directly with each of the fluorescent secondary antibodies without the primary antibody (isotype, dark columns). FIB. 20B is a plot of signal-to-noise ratio (S/N) for the staining results in FIG. 20A. The data show that conjugates labeled with Dye No. 32 are much brighter and more specific in staining than conjugates prepared from the other three commercial near-IR dyes.

Example 118

Preparation of Dye 29

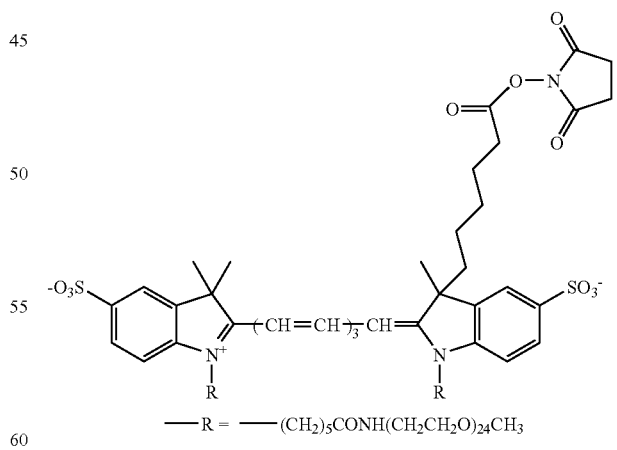

Dye 29 (Table 3)

Dye 29 was prepared in 4 steps from common intermediates used in previous examples herein. Compound No. 19 (84 mg), compound No. 59, and sodium acetate (4 equivalents) were combined in a mixture of acetic acid (2 mL) and acetic anhydride (1 mL). The resulting mixture is heated at 120° C. for 20 min to form the intermediate compound No. 29a.

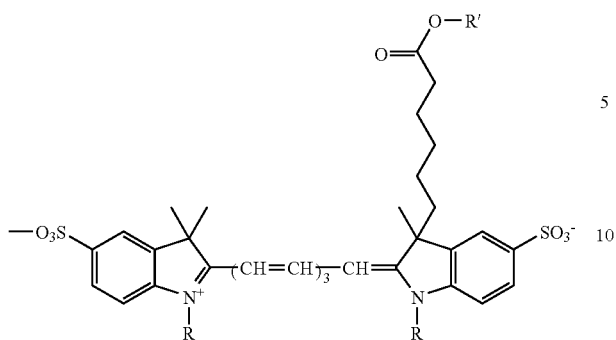

Compound No. 29a:  R = —(CH₂)₅CO₂H;  R' = —CH₃.

Compound No. 29b:  R = —(CH₂)₅CONH(CH₂CH₂O)₂₄CH₃;
R' = —CH₃.

Compound No. 29c:  R = —(CH₂)₅CONH(CH₂CH₂O)₂₄CH₃;
R' = —H.

The solvent was distilled off under vacuum. The product was purified by Sephadex LH-20 using water as the eluent. Compound No. 29a (30 mg) was converted to the peggylated intermediate compound No. 29b by following the procedure to make compound No. 21 (Example 21). The methyl ester intermediate compound No. 21b (18 mg) was hydrolyzed to the free acid compound No. 29c by following the procedure to make compound No. 22 (Example 22). Compound No. 29c (5 mg) was activated to the final product Dye 29 using TSTU and triethylamine as described for compound No. 23 in Example 23.

Example 118

Preparation of Dye 31

Dye 31

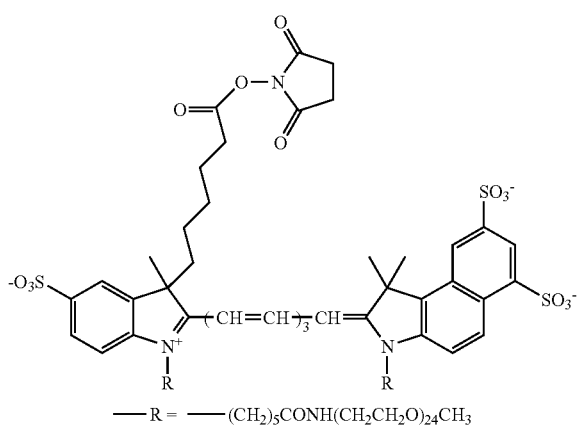

—R = —(CH₂)₅CONH(CH₂CH₂O)₂₄CH₃

Dye 31 was prepared in 4 steps from common intermediates used in previous examples herein. Compound No. 19 (12 g) was first treated with glutoconaldehyde dianil hydrochloride (18 g) and Et₃N (0.5 mL) in AcOH (40 mL) at 120° C. for 3 hours. After cooling down to room temperature, the mixture was concentrated to dryness under vacuum and the residue was purified by column chromatography on silica gel to give compound No. 31a as a red brown gummy solid (3 g).

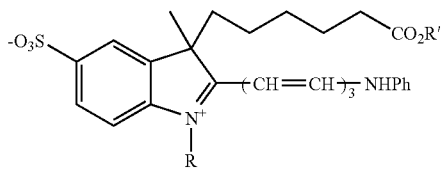

Compound No. 31a: R = —(CH₂)₅CO₂H; R' = —CH₃.

The above intermediate (1 g) was coupled to N-(5-carboxypentyl)-1,3,3-trimethylbenzindolenium-6,8-dilsulfonate (1 equivalent) (Bioconjugate Chem. 7, 356 (1996)) to give compound No. 31b (80 mg) using the condition to make compound No. 29a in Example 109.

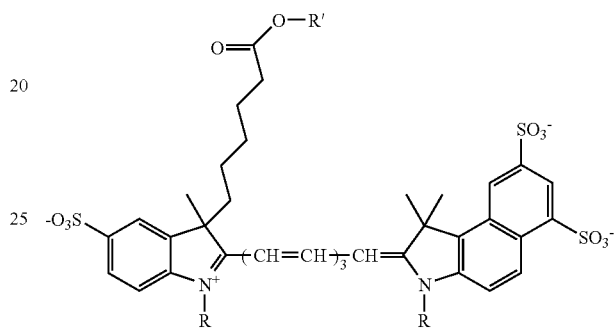

Compound No. 31b: R = —(CH₂)₅CO₂H; R' = —CH₃
Compound No. 31c: R = —(CH₂)₅CONH(CH₂CH₂O)₂₄CH₃;
R□ = —CH₃
Compound No. 31d: R = —(CH₂)₅CONH(CH₂CH₂O)₂₄CH₃;
R□ = —H Compound No. 31b (25 mg) was converted to compound No. 31c (60 mg), followed by hydrolysis to the free acid compound No. 31d using the procedures described in Example 109. Finally, the free acid dye compound No. 31d (10 mg) was activated to Dye 31 using TSTU and triethylamine (Example 109).

Example 120

Preparation of Dye 32

Dye 32

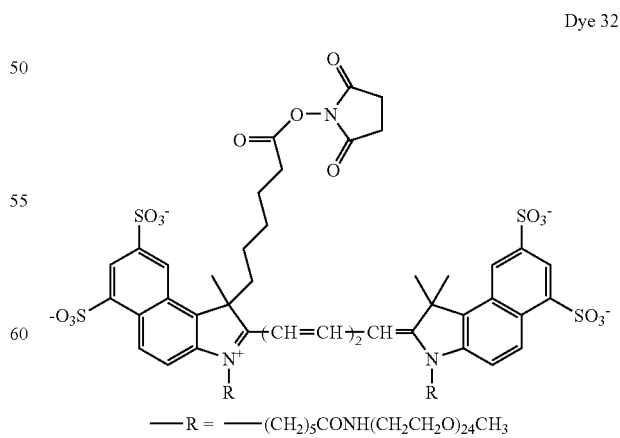

—R = —(CH₂)₅CONH(CH₂CH₂O)₂₄CH₃

Dye 32 was prepared using sulfonated benzindolium intermediates and procedures similar to those used for preparing compound No. 23 (Example 23). Briefly, N-(5-carboxypentyl)-1,3,3-trimethylbenzindolenium-6,8-dilsulfonate (Example 110) (5 g) was reacted with malonaldehyde dianil hydrochloride (5 g), Et₃N (0.5 mL) in AcOH (50 mL) was heated at 120° C. for 3 hours. After cooling down to room temperature, the mixture was concentrated to dryness under vacuum and the residue was purified by column chromatography on silica gel to compound No. 32a as an orange red gummy solid (2.5 g).

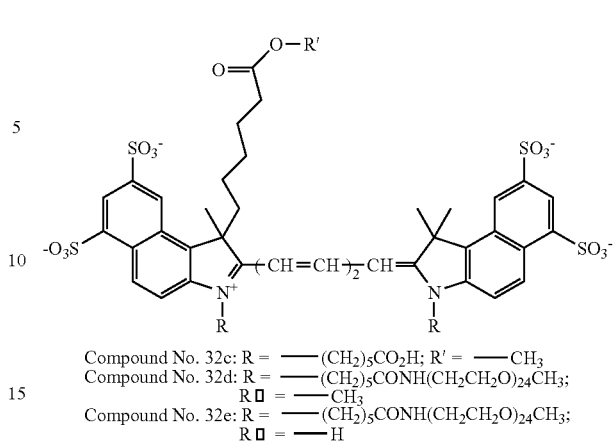

Compound No. 32c: R = —(CH₂)₅CO₂H; R' = —CH₃
Compound No. 32d: R = —(CH₂)₅CONH(CH₂CH₂O)₂₄CH₃;
R□ = —CH₃
Compound No. 32e: R = —(CH₂)₅CONH(CH₂CH₂O)₂₄CH₃;
R□ = —H Procedures for the steps leading from compound No. 32c to compound No. 32e are analogous to those used for preparing compound No. 23 (Example 23).

What is claimed is:
1. A compound of any one of the formulae:

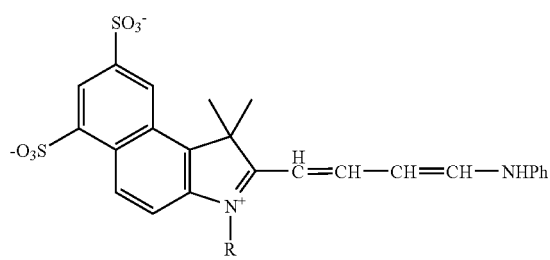

Compound No. 32a: R = —(CH₂)₅CO₂H

Compound No. 62 (Example 62) (5 g) was thoroughly mixed with 6-bromohexanoic acid (1.5 equivalent) and then heated at 95° C. for 24 h to form the benzindolium intermediate compound No. 32b:

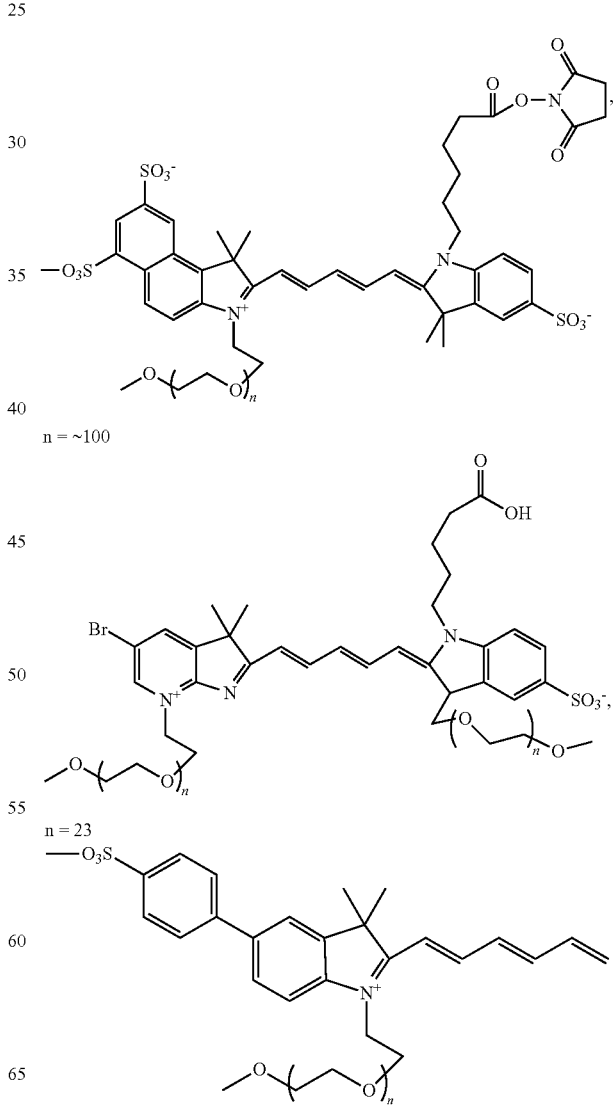

n = ~100 n = 23

Compound No. 32b

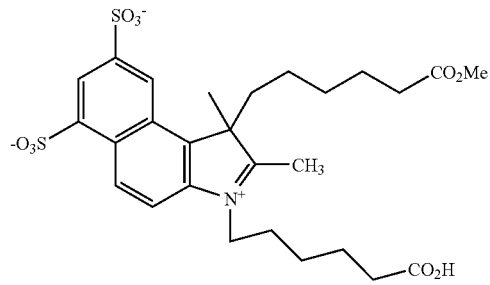

Compound No. 32a and compound No. 32b were coupled to form the cyanine methyl ester intermediate compound No. 32c, which is subsequently peggylated to form compound No. 32d, followed by hydrolysis to form the free acid compound No. 32e and final conversion to the succinimidyl ester Dye 32.

217
-continued
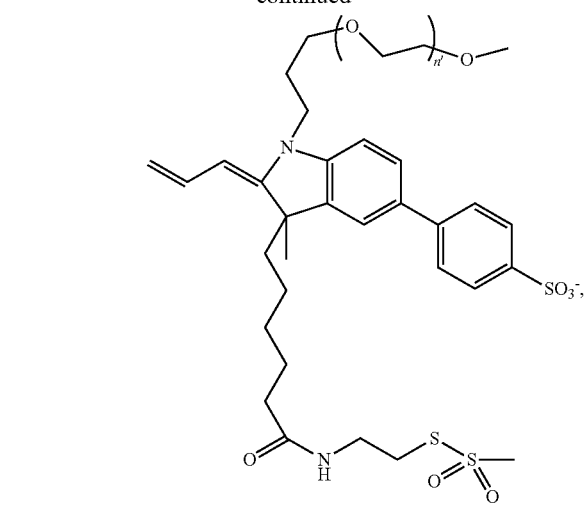
n = 23
n' = 11
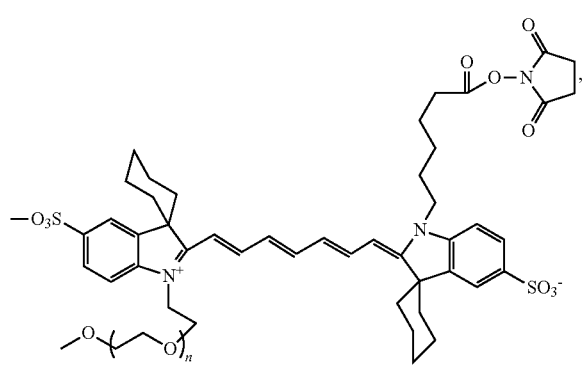
n = 23
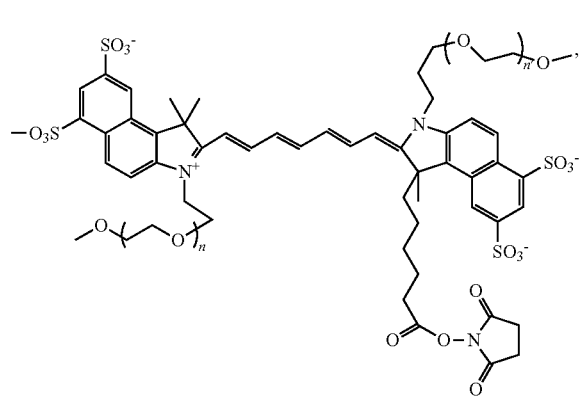
n = 23
n' = 11
218
-continued
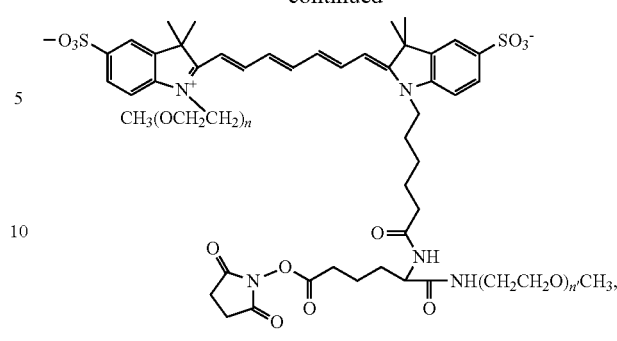
n = 12
n' = 24
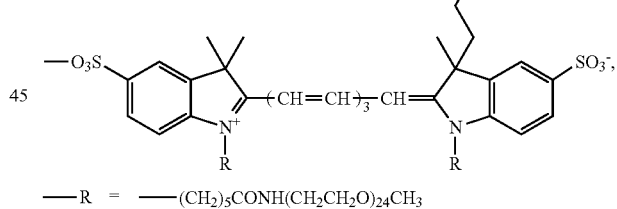
n = 24
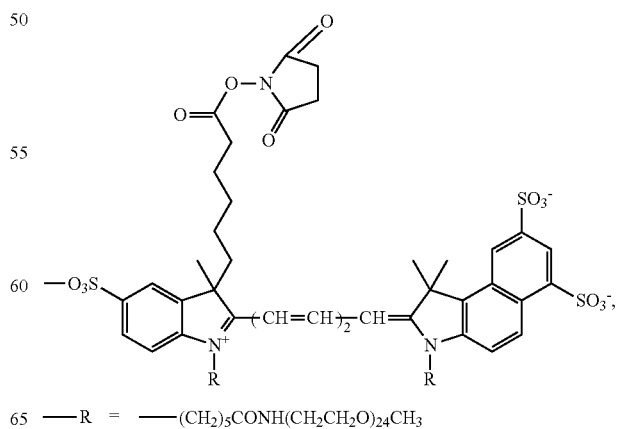

-continued

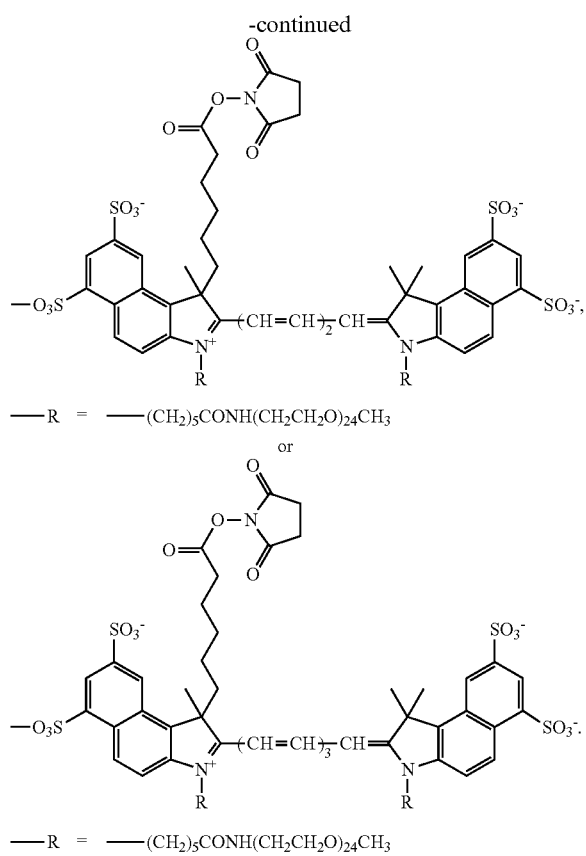

2. A kit comprising:
i) the compound of claim 1; ii) a buffer; iii) materials or devices for purifying conjugation products; and iv) instructions instructing the use of the compound.

3. A biomolecule having an amine, a thiol, a hydroxyl, or an aldehyde functional group comprising a label having a structure of a Formula of claim 1, wherein the at least one reactive moiety of the Formula has undergone a reaction which attaches the label to the biomolecule.

4. The biomolecule comprising a label of claim 3 wherein the biomolecule comprises a polynucleotide.

5. The biomolecule comprising a label of claim 3 wherein the biomolecule comprises a polypeptide.

6. The biomolecule of claim 5, wherein the polypeptide further comprises an antigen binding site.

7. The biomolecule of claim 5, wherein the polypeptide is a whole immunoglobulin.

8. The biomolecule of claim 5, wherein the polypeptide is a Fab fragment.

9. An immunoglobulin having an amine, a thiol, a hydroxyl, or an aldehyde functional group labeled with a compound of claim 1.

10. The immunoglobulin of claim 9, wherein the immunoglobulin retains binding specificity to a target upon conjugation to the fluorescent compound.

11. The immunoglobulin of claim 10, wherein the immunoglobin is an antibody that binds specifically to an antigen on a cancer cell.

12. The immunoglobin of claim 11 wherein the antibody binds to erb2.

13. An immunoglobin having an amine, a thiol, a hydroxyl, or an aldehyde functional group comprising a label having a structure of a Formula of claim 1 wherein the at least one reactive moiety of the Formula has undergone a reaction which attaches the label to the immunoglobin, wherein the immunoglobin is an antibody that binds specifically to an antigen on a cancer cell.

14. The immunoglobin of claim 13 wherein the antibody binds to erb2.

15. A polypeptide having an amine, a thiol, a hydroxyl, or an aldehyde functional group labeled with a fluorescent compound, the polypeptide exhibiting a serum half-life no shorter than that of a corresponding polypeptide that lacks the fluorescent compound, wherein the fluorescent compound is a compound of claim 1.

16. A method of preparing a labeled biomolecule comprising reacting a compound of claim 1 and a substrate biomolecule under conditions sufficient to effect crosslinking between the compound and the substrate biomolecule.

17. The method of claim 16, wherein the substrate biomolecule is a polypeptide, a polynucleotide, a carbohydrate, a lipid or a combination thereof.

18. The method of claim 17, wherein the substrate biomolecule is a polynucleotide.

19. A method of labeling a polypeptide comprising: forming a complex that comprises the polypeptide and a binding agent, wherein the binding agent comprises a fluorescent label having a structure of formula of claim 1 wherein the at least one reactive moiety of the Formula has undergone a reaction which attaches the label to the binding agent.

20. The method of claim 19 wherein the binding agent is an antibody.

21. The method of claim 20 wherein the complex comprises (a) a primary antibody that binds to the polypeptide, and (b) the binding agent which functions as a secondary antibody exhibiting binding capability to the primary antibody.

22. The method of claim 21, wherein the labeling occurs on a solid substrate.

23. The method of claim 21 that labels a polypeptide intracellularly.

24. The method of claim 21, wherein the complex yields a signal to noise ratio greater than about 100, wherein the signal to noise ratio is calculated by the formula:

(fluorescent signal from a complex comprising the polypeptide bound by a primary antibody which in turn is bound to the binding agent)/(fluorescent signal from a mixture of the polypeptide, an isotype control primary antibody and the binding agent).

25. The method of claim 21, wherein the complex yields a signal to noise ratio greater than about 250, wherein the signal to noise ratio is calculated by the formula:

(fluorescent signal from a complex comprising the polypeptide bound by a primary antibody which in turn is bound to the binding agent)/(fluorescent signal from a mixture of the polypeptide, an isotype control primary antibody and the binding agent).

26. The method of claim 21, wherein the complex yields a signal to noise ratio greater than about 270, wherein the signal to noise ratio is calculated by the formula:

(fluorescent signal from a complex comprising the polypeptide bound by a primary antibody which in turn is bound to the binding agent)/(fluorescent signal from a mixture of the polypeptide, an isotype control primary antibody and the binding agent).

27. A method for labeling a cell within a population of cells whereby the cell is differentially labeled relative to neighboring cells within the population, the method comprising contacting the cell with a biomolecule of claim 3, wherein the biomolecule comprises a targeting moiety that binds to a binding partner that is indicative of the cell, and thereby differentially labeling the cell relative to neighboring cells within the population.

28. The method of claim 27, further comprising the step of imaging the cell, the imaging step comprising:
  i) directing exciting wavelength to the cell; and
  ii) detecting emitted fluorescence from the cell.

29. The method of claim 27, wherein the labeling takes place in vitro.

30. The method of claim 27, wherein the labeling takes place in vivo.

\* \* \* \* \*